United States Patent
Kim et al.

(10) Patent No.: US 9,259,590 B2
(45) Date of Patent: Feb. 16, 2016

(54) TUBE-STRUCTURED BATTERY TO BE INSERTED INTO LIVING BODY

(75) Inventors: Ki-Won Kim, Gyeongsangnam-do (KR); Tae-Hyeon Nam, Gyeongsangnam-do (KR); Jou-Hyeon Ahn, Gyeongsangnam-do (KR); Hyo-Jun Ahn, Gyeongsangnam-do (KR); Gyu-Bong Cho, Gyeongsangnam-do (KR); Jung-Pil Noh, Gyeongsangbuk-do (KR); Chang-Joon Kim, Gyeongsangnam-do (KR); Mei-Yu Zhang, Gyeongsangnam-do (KR); Se-Kyo Chung, Gyeongsangnam-do (KR); Dong-Woo Kang, Gyeongsangnam-do (KR); Kwon-Koo Cho, Gyeongsangnam-do (KR); Ho-Suk Ryu, Gyeongnam (KR)

(73) Assignee: Industry-Academic Cooperation Foundation Gyeongsang National University (KR)

( * ) Notice: Subject to any disclaimer, the term of this patent is extended or adjusted under 35 U.S.C. 154(b) by 436 days.

(21) Appl. No.: 13/635,244

(22) PCT Filed: Nov. 5, 2010

(86) PCT No.: PCT/KR2010/007823
§ 371 (c)(1),
(2), (4) Date: Sep. 14, 2012

(87) PCT Pub. No.: WO2011/115349
PCT Pub. Date: Sep. 22, 2011

(65) Prior Publication Data
US 2013/0026969 A1 Jan. 31, 2013

(30) Foreign Application Priority Data

Mar. 17, 2010 (KR) .................. 10-2010-0023848
Oct. 20, 2010 (KR) .................. 10-2010-0102361
Nov. 1, 2010 (KR) .................. 10-2010-0107507
Nov. 4, 2010 (KR) .................. 10-2010-0109222
Nov. 4, 2010 (KR) .................. 10-2010-0109227

(51) Int. Cl.
*H01M 8/16* (2006.01)
*A61N 1/378* (2006.01)
*H01M 2/02* (2006.01)

(52) U.S. Cl.
CPC ........... *A61N 1/3785* (2013.01); *H01M 2/0202* (2013.01); *H01M 8/16* (2013.01); *H01M 2/022* (2013.01); *Y02E 60/527* (2013.01)

(58) Field of Classification Search
CPC ...... A61N 1/3785; H01M 2/022; H01M 8/16; Y02E 60/527
USPC ........................................ 320/103
See application file for complete search history.

(56) References Cited

U.S. PATENT DOCUMENTS 3,941,135 A * 3/1976 von Sturm et al. ............. 607/35
2001/0025187 A1 * 9/2001 Okada ......................... 606/200

(Continued)

FOREIGN PATENT DOCUMENTS

| JP | 07-265442 | 10/1995 |
| KR | 1020070092777 | 9/2007 |
| KR | 10-2009-0040797 | 4/2009 |

*Primary Examiner* — Vuthe Siek
*Assistant Examiner* — Aric Lin
(74) *Attorney, Agent, or Firm* — Blank Rome LLP; Michael C. Greenbaum; Jamie B. Tesfazion

(57) ABSTRACT

A tube-structured battery to be inserted into a living body is provided. The tube-structured battery includes: a biofuel battery part which generates electric energy by using biofuel in the blood passing through an internal space of the tube structure; a transformer circuit part which adjusts a voltage or current density by using the generated electric energy; and a secondary battery part which is charged with the electric energy by using the adjusted voltage or current density to store the electric energy, wherein the tube-structured battery is inserted into the living body or a blood vessel of the living body.

20 Claims, 181 Drawing Sheets

(56) References Cited

U.S. PATENT DOCUMENTS

| | | |
|---|---|---|
| 2002/0025469 A1* | 2/2002 | Heller .................. 429/43 |
| 2004/0101741 A1 | 5/2004 | Minteer et al. |
| 2006/0134178 A1 | 6/2006 | Doisaki |
| 2006/0289834 A1 | 12/2006 | Doisaki |
| 2007/0059565 A1 | 3/2007 | Siu et al. |
| 2008/0213631 A1* | 9/2008 | Krishnamoorthy et al. ...... 429/2 |
| 2009/0036939 A1* | 2/2009 | Singh et al. .................. 607/5 |
| 2010/0298720 A1* | 11/2010 | Potkay .................. 600/485 |

* cited by examiner

FIG. 52
(a)
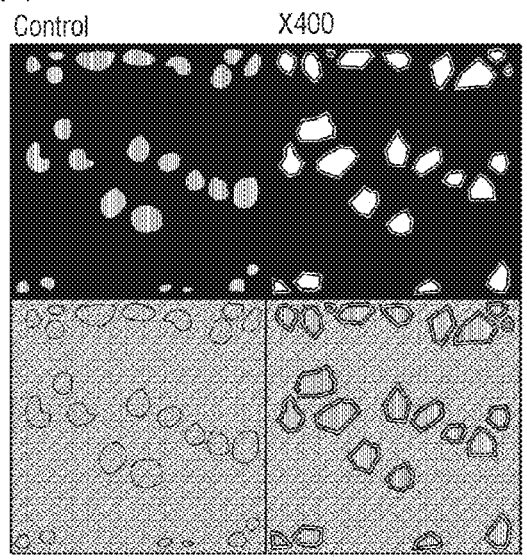
(b)
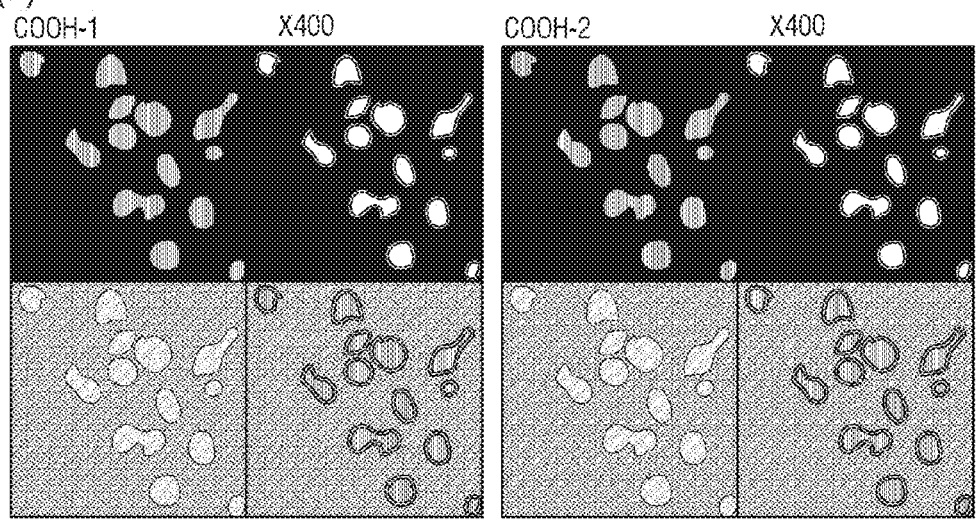

* p < 0.05

* p < 0.05

FIG. 68
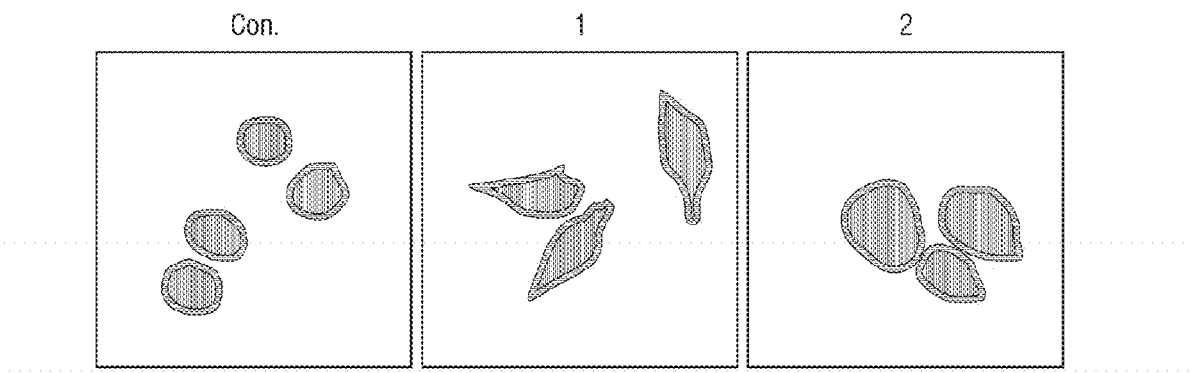
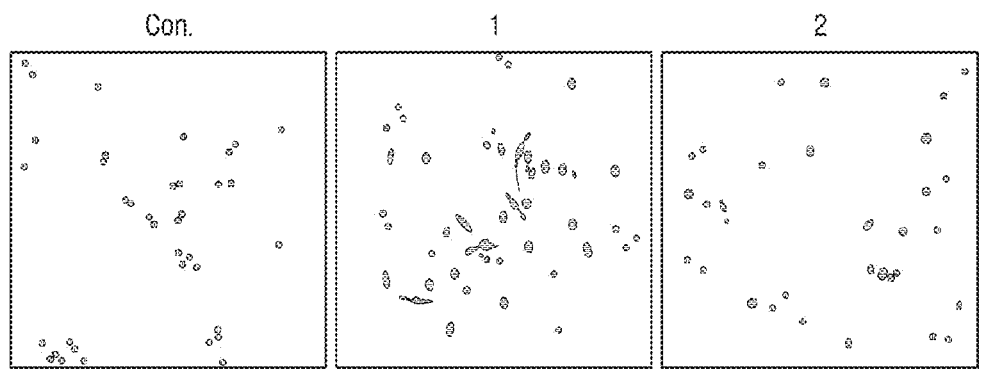

FIG. 71
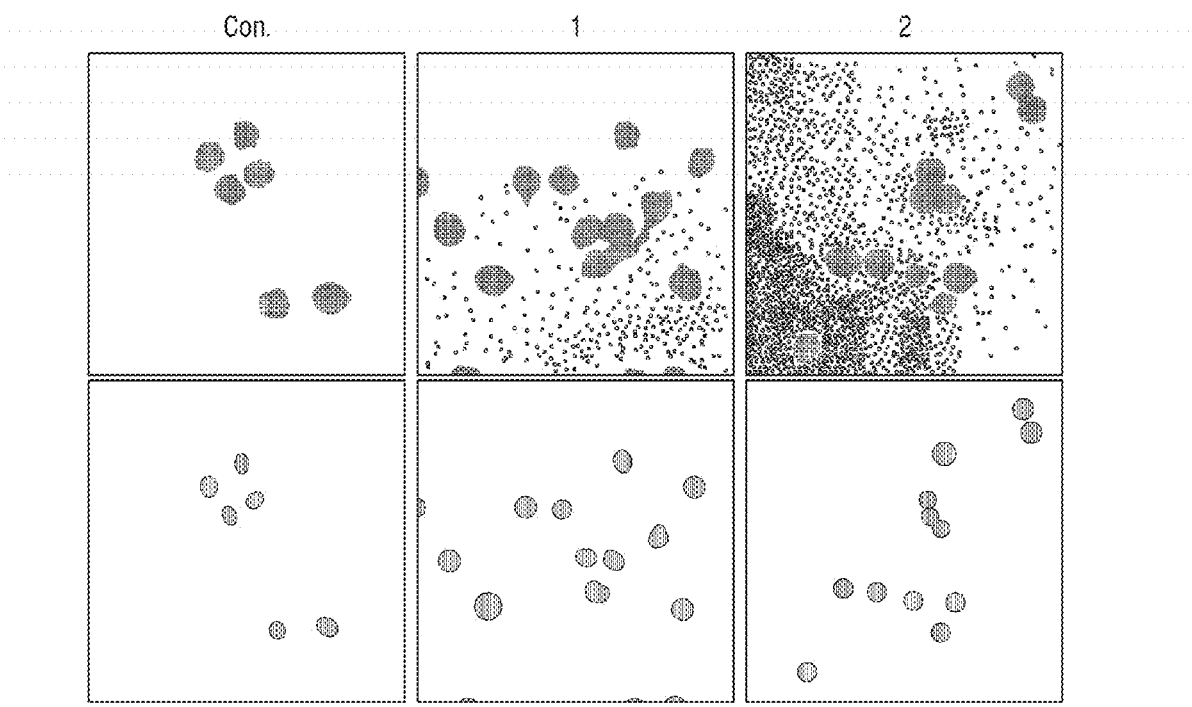
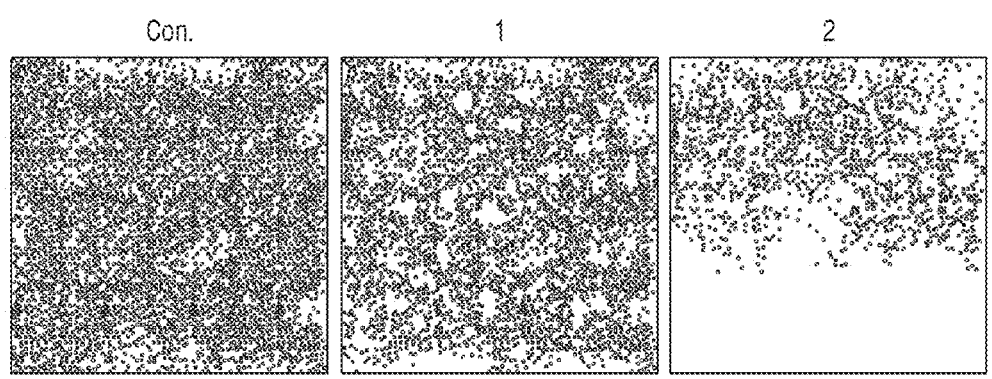

FIG. 178
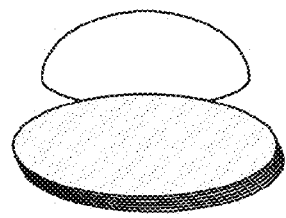
PCU
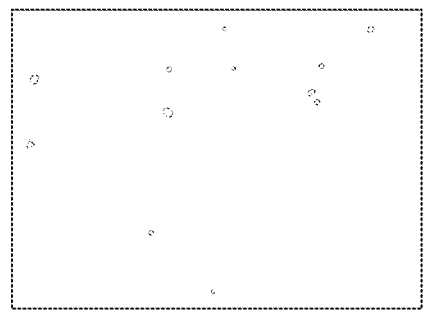
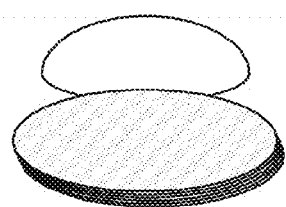
PCU/CNT = 1:5
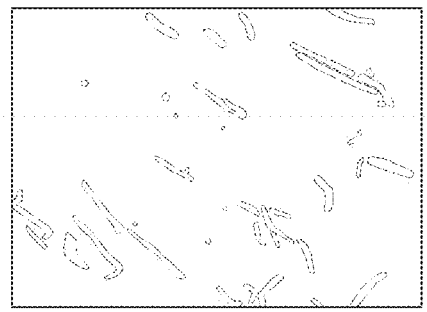
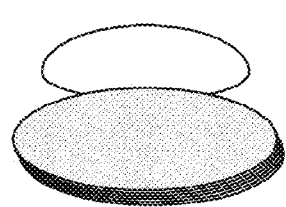
PCU/CNT = 1:10
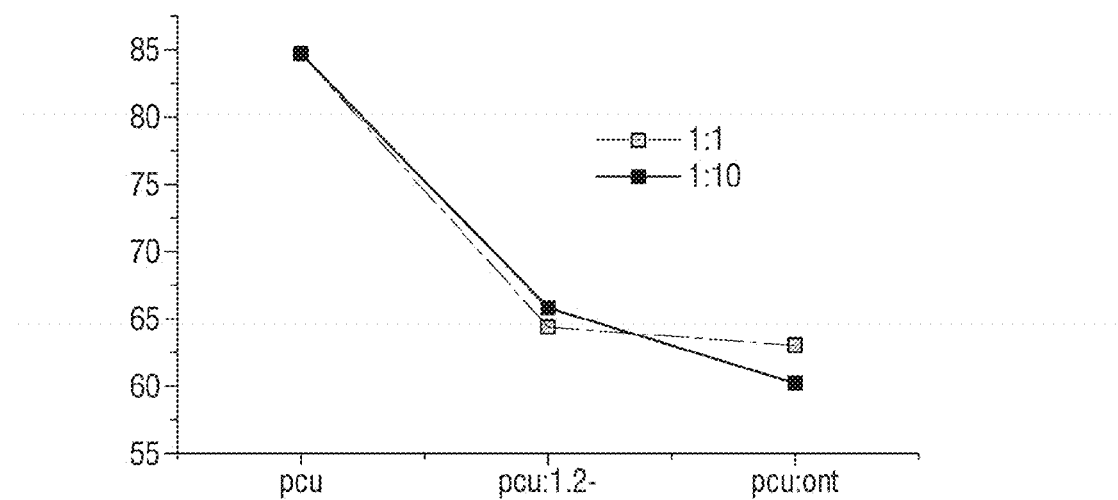

FIG. 180
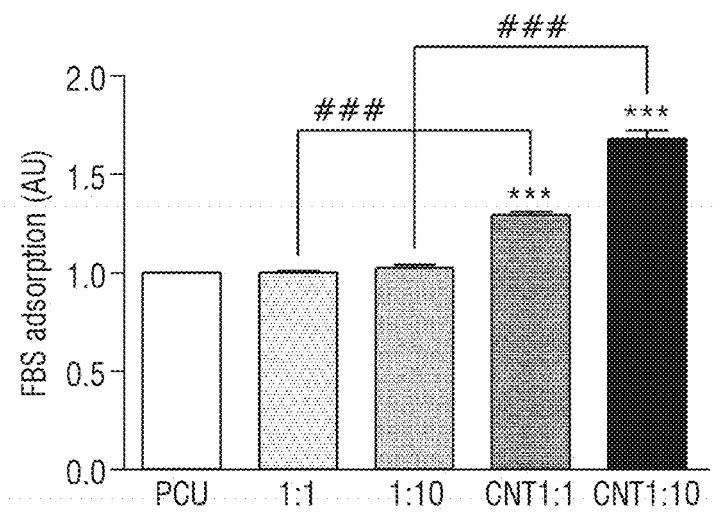
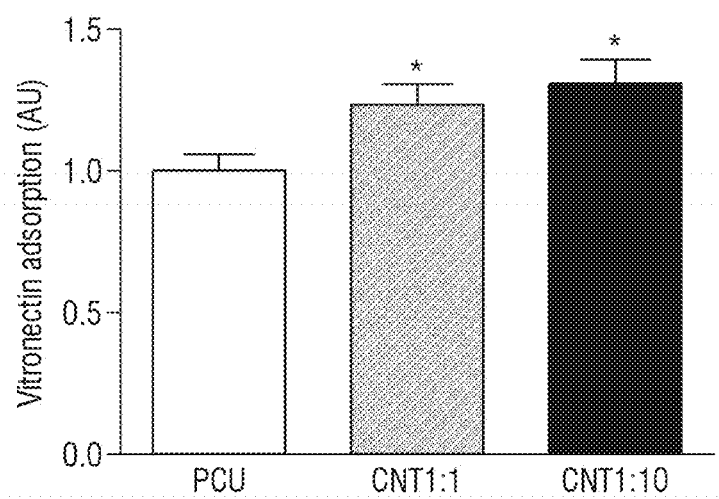

TUBE-STRUCTURED BATTERY TO BE INSERTED INTO LIVING BODY

This Application is a U.S. National Phase of PCT/KR2010/007823, filed Nov. 5, 2010 and claims priority under 35 U.S.C. §119 from Korean Patent Application Nos. 10-2010-0023848, 10-2010-0102361, 10-2010-0107507, 10-2010-0109222, and 10-2010-0109227, respectively filed on Mar. 17, 2010, Oct. 20, 2010, Nov. 1, 2010, Nov. 4, 2010, and Nov. 4, 2010, in the Korean Intellectual Property Office, the disclosure of which is incorporated herein by reference in its entirety.

BACKGROUND

1. Field

The present general inventive concept generally relates to a battery to be inserted into a living body, and more particularly, to a tube-structured battery to into a blood vessel of a living body.

2. Description of the Related Art

Living body implantable medical devices, such as an artificial heart, a pacemaker, a video pill, a diagnostic medical center, a drug infusion pump, etc., assist a patient to be diagnosed and cured. However, since the living body implantable medical devices have large sizes to give burdens to patients, many patients who have been implanted with the living implantable medical devices complain of inconveniences of wearing sensations.

Therefore, many efforts to reduce the sizes of the living body implantable medical devices have been made. However, since a volume of a primary battery occupying a considerable portion between about 20 v % and about 60 v % in these devices is great, remarkably reducing the sizes of the medical devices is limited.

In particular, a life of primary battery ends after a predetermined time, and thus an implanted device is to be periodically replaced through a surgical operation.

A living body implantable secondary battery has been developed and commercialized. As a charging method of the secondary battery, there is a method of charging the secondary battery by using an external radio frequency (RF) or a method of charging the secondary battery by wire through a terminal exposed to the outside. This method causes a continuous charging, and the charging method using the terminal exposed to the outside causes inconveniences to patients. Also, the charging method using the RF causes a safety problem.

According to a report, a size of a device which does not give repulsion toward wearing sensations to patients and does not give pains to the patients when implanting the device is 0.5 cm (length)×500 μm (width)×200 μm (thickness). Therefore, a size of a battery used as power of the device is to be reduced in an ultra-small size. In this case, a capacity of the battery is also reduced and thus cannot be used for a long time.

In order to solve this problem, there have appeared a micro-sized living body implantable biofuel battery which generates electricity from Glucose existing in a living body.

The biofuel battery has a micro-size but oxidizes the Glucose of the living body to self-generate the electricity and thus continuously supplies electricity to a device implanted into the living body. However, voltage and current densities generated from the electricity are very low, and thus it is impossible to apply the living body implantable biofuel battery as an enough power source to supply power to a living body implantable device. Also, in consideration of convenience of a user, a micro-sized biofuel battery to be inserted into a blood vessel is requested.

SUMMARY

Exemplary embodiments address at least the above problems and/or disadvantages and other disadvantages not described above. Also, the exemplary embodiments are not required to overcome the disadvantages described above, and an exemplary embodiment may not overcome any of the problems described above.

The exemplary embodiments provide a tube-structured battery to be inserted into a living body or a blood vessel.

The exemplary embodiments also provide a method of efficiently fixing enzyme in an electrode of a tube-structured battery to be inserted into a living body or a blood vessel The exemplary embodiments also provide efficient processing of toxicity generated due to an exposure of a tube-structured battery into a blood vessel or a living body.

The exemplary embodiments also provide a method of initially driving a transformer circuit unit for boosting a voltage generated from a tube-structured battery to be inserted into a living body or a blood vessel and efficiently charging the tube-structured battery with the generated voltage through the transformer circuit unit.

The exemplary embodiments also provide various types of secondary battery parts of a tube-structured battery to be inserted into a living body or a blood vessel.

According to an aspect of the exemplary embodiments, there is provided a tube-structured battery to be inserted into a living body, including: a biofuel battery part which generates electric energy by using biofuel in the blood passing through an internal space of the tube structure; a transformer circuit part which adjusts a voltage or current density by using the generated electric energy; and a secondary battery part which is charged with the electric energy by using the adjusted voltage or current density to store the electric energy, wherein the tube-structured battery is inserted into the living body or a blood vessel of the living body.

The biofuel battery part, the transformer circuit part, and the secondary battery part may constitute a fusion battery part. The tube-structured battery may further include a support part which has the tube structure and supports the fusion battery part.

The tube-structured battery further include: a transreflective layer which encloses a surface of the biofuel battery part and selectively passes the biofuel of the blood.

The tube-structured battery may further include: a biocompatible coating layer which encloses at least an area of the tube-structured battery contacting the blood or the living body.

The tube-structured battery may further include: a fixing part which comprises at least one fixing member for fixing the tube-structured battery into the blood or the living body The biofuel battery part may include: an electrode; and an enzymatic area in which at least one enzyme is fixed on a side of the electrode.

If the biofuel of the blood is attached to the at least one enzyme, the biofuel battery part may generate the electric energy.

The electrode may form a 3-dimensional (3D) nanostructure.

The biofuel battery part may further include a current collector. The electrode may form a 3D nanostructure along with the current collector.

The biofuel battery part may further include a current collector. The electrode may form a single body along with the current collector.

The enzymatic area may include a plurality of enzymatic layers forming a multilayered structure.

The transformer circuit part may include: a coil which, if a current is applied, generates a magnetic field; a rigid body which increases the generated magnetic field; and a controller which adjusts a current applied to the coil, wherein the rigid body has a tube structure whose both ends are opened, and the coil encloses the rigid body having the tube structure.

The transformer circuit part may include: a boost type power converter which boosts a voltage generated by the biofuel battery part and supplies the boosted voltage to the secondary battery part; and an initial driver circuit which applies control power to the boost type power converter to control initial driving of the boost type power converter.

The transformer circuit part may include: a boost type power converter which boots a voltage generated by the biofuel battery part and supplies the boosted voltage to the secondary battery part; a maximum power point tracking circuit which calculates a charging current command for maximum power point tracking by using a current flowing into the biofuel battery part and the generated voltage; and a charging current control circuit which controls the boost type power converter to track the charging current command charging the secondary battery part.

The tube-structured battery may perform a toxicity treatment or a biocompatibility treatment with respect to at least one area of the tube-structured battery contacting the blood or the living body.

The fusion battery part may have a flat plate structure. A side of the flat plate structure and an other side of the flat plate structure facing the side may be fixed by the support part.

The support part may include an opening formed in an area of a side of the tube structure, and the fusion battery part is inserted into the opening.

The support part may have a polygonal pillar shape whose internal cross-section is circular and outer cross-section is polygonal. At least one of the biofuel battery part, the transformer circuit part, and the secondary battery part constituting the fusion battery part may be disposed on a side of the polygonal pillar.

The biofuel battery part may be disposed in the blood vessel, and at least one of the transformer circuit part and the secondary battery part may be disposed outside the blood vessel.

According to another aspect of the exemplary embodiments, there is provided a tube-structured artificial vessel including: a biofuel battery part which generates electric energy by using biofuel of the blood passing through an internal space of the tube structure; a transformer circuit part which adjusts a voltage or current density by using the generated electric energy; and a secondary battery part which is charged with the electric energy by using the adjusted voltage or current.

According to various exemplary embodiments of the present general inventive concept, a tube-structured battery to be inserted into a living body may be provided in various types according to arrangements and structures of a biofuel battery part, a transformer circuit part, and a secondary battery part.

According to various exemplary embodiments of the present general inventive concept, an enzyme may be fixed in a multilayer to an electrode of the tube-structured battery to increase a loading amount of the enzyme per unit area of the electrode in order to increase an amount of generated power.

Also, an active site of the enzyme may be masked in the fixing step to increase an reactivity between an enzyme and a substrate of the fixing enzyme in order to improve efficiency of the battery.

According to various exemplary embodiments of the present general inventive concept, cytotoxicity may be reduced in materials such as a carbon nanotube, etc. constituting the electrode of the tube-structured battery.

According to various exemplary embodiments of the present general inventive concept, the transformer circuit part constituting the tube-structured battery may be initially driven. Also, power generated by the biofuel battery part may efficiently charge the secondary battery part at a maximum power point.

According to various exemplary embodiments of the present general inventive concept, the secondary battery part may be realized as various types such as a natrium battery, an alkali battery, a lithium battery, etc. Also, positive and negative pore electrodes constituting the secondary battery part may be provided, and the secondary battery part may provide a 3D nanostructure along with an all-in-one electrode and current collector device.

BRIEF DESCRIPTION OF THE DRAWINGS

The above and/or other aspects will be more apparent by describing certain exemplary embodiments with reference to the accompanying drawings, in which:

FIG. 52 is a view illustrating test data checked with a fluorescence microscope when macrophagocyte uptakes a single walled carbon nanotube into a cell, wherein blue fluorescence denotes a dyed nucleus in a cell, red fluorescence denotes a dyed action in the cell, a black part in the cell denotes a single walled carbon nanotube into which the cell up-taken, (a) denotes a captured control cell which does not treat the single walled carbon nanotube, (b) denotes a result of up-taking the single walled carbon nanotube (denoted by COOH-1) dispersed by the conventional method, and (c) denotes a result of up-taking the single walled carbon nanotube (denoted by COOH-2) dispersed by the dispersing method of the present general inventive concept;

FIG. 68 is a view illustrating a result of dying actin with a fluorescent material and then observing the actin to check cytoskeleton of macrophagocyte (Con: control group, 1: when treating titanium, 2: when treating nano-processed titanium, red: actin, and blue: nucleus);

FIG. 71 is a view illustrating a result of checking an expression degree of iNOS protein of macrophagocyte by using green;

FIG. 178 is a view illustrating nano-scale surface roughness of a coating layer fabricated by changing a synthesis ratio between CNT and PCU, wherein a lower graph illustrates changes in a surface tension with respect to a synthesis of a carbon nanotube (y denotes a measured value (angle)), and the surface roughness increases with an increase in the carbon nanotube, thereby increasing the surface tension;

FIG. 180 is a view illustrating an adsorption degree of protein with respect to a synthesis ratio between weights of CNT and PCU in a coating layer of the present general inventive concept, wherein roughness of a nano surface more affects the adsorption of the protein than surface energy, the protein is more adsorbed with an increase in the carbon nanotube, a lower graph illustrating an adsorption degree of vitronectin with respect to a synthesis ratio of a coating layer, and the protein is more adsorbed with an increase in a ratio of the carbon nanotube.

DETAILED DESCRIPTION OF THE EXEMPLARY EMBODIMENTS

Figure 1:
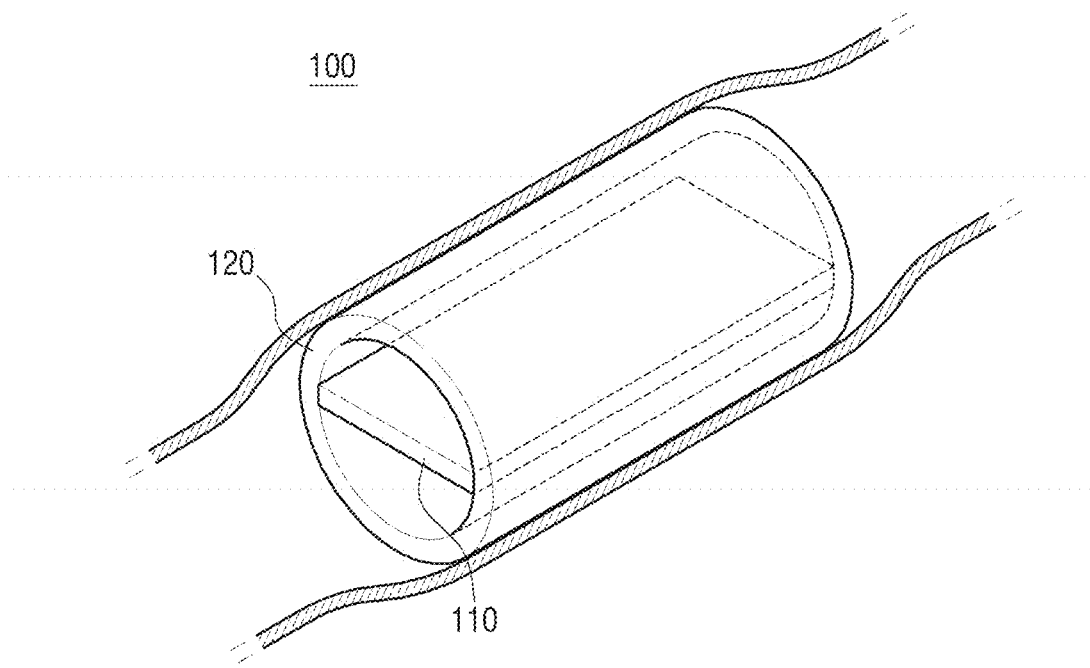
FIG. 1 is a view illustrating a tube-structured battery to be inserted into a living body according to an exemplary embodiment of the present general inventive concept.

Exemplary embodiments are described in greater detail with reference to the accompanying drawings.

In the following description, the same drawing reference numerals are used for the same elements even in different drawings. The matters defined in the description, such as detailed construction and elements, are provided to assist in a comprehensive understanding of the exemplary embodiments. Thus, it is apparent that the exemplary embodiments can be carried out without those specifically defined matters. Also, well-known functions or constructions are not described in detail since they would obscure the exemplary embodiments with unnecessary detail.

In detail, various exemplary embodiments are drawn according to a shape of a tube-structured battery to be inserted into a living body. Also, various exemplary embodiments are drawn according to a method of fixing enzyme in an electrode of a biofuel battery part constituting the tube-structured battery, a method of treating toxicity of the biofuel battery part, and a method of treating biocompatibility. In addition, various exemplary embodiments related to initial driving and maximum power point tracking are drawn from a transformer circuit part constituting the tube-structured battery. Moreover, various exemplary embodiments are drawn according to types and shapes of an electrode and a current collector of a secondary battery part constituting the tube-structured battery

[Shape of Tube-Structured Battery to be Inserted into Living Body]

[Tube-Structured Battery to be Inserted into Living Body According to First Exemplary Embodiment]

FIG. 1 is a view illustrating a tube-structured battery to be inserted into a living body according to an exemplary embodiment of the present general inventive concept.

Referring to FIG. 1, a tube-structured battery 100 to be inserted into a living body includes a fusion battery part 110 and a support part 120.

The fusion battery part 110 and the support part 120 are included in a blood vessel.

The fusion battery part 110 generates electric energy by using biofuel of blood passing through an internal space of the support part 120, adjusts a voltage or current density of the electric energy, and charges and stores the electric energy.

The fusion battery part 110 may have a flat plate structure in which a biofuel battery part, a transformer circuit part, and a second battery part are arranged side by side.

Here, biofuel may be at least one of glucose, pyruvic acid, lactic acid, and amino acid of the blood.

The support part 120 has an empty cylindrical structure or tube structure whose both ends are opened and fixes the fusion battery part 110 therein to allow the blood to pass through the internal space.

The tube-structured battery 100 generates electric energy by using the biofuel of the blood, converts and stores the electric energy, and supplies the electric energy to a device (not shown) implanted into the living body.

The tube-structured battery 100 is moved into a particular part of a blood vessel through a micro-catheter or a transfer tube or is positioned in a particular part of the blood vessel or the living body through a surgical operation.

Since the tube-structured battery 100 is inserted into the blood vessel of the living body, the fusion battery part 110 and the support part 120 are coated with a biocompatibility coating layer including a high biocompatibility material.

The tube-structured battery 100 is inserted into the blood vessel of the living body, and thus at least one component constituting the tube-structured battery 100 may be realized as a flexible circuit, a flexible device, a flexible layer, or the like.

The tube-structured battery 100 supplies the electric energy to various types of electronic devices such as an artificial internal organ, a sensor, etc. The tube-structured battery 100 uses a Micro Electro Mechanical Systems (MEMS) technology, further a Nano Electro Mechanical Systems (NEMS) technology.

Both ends of the tube-structured battery 100 are opened, and cavities having the opened ends has polygonal cross-sections. However, in order not to disturb a blood circulation in the blood and to well absorb an original material of the living body, the cavities having the opened ends may have circular or elliptical cross-sections. Here, the cross-section may be a surface cut between both openings of the tube-structured battery 100.

Reacting electrodes of the biofuel battery part and the secondary battery part may have sizes smaller than micro-sizes to increase reaction efficiency for generating electrons. The electrodes of the biofuel battery part and the secondary battery part may be fabricated by using a wet growth (sol-gel, electrolysis, electroless deposition or a dry growth (chemical evaporation, physical evaporation).

An anode of the electrode of the secondary battery part may be formed of a lithium metallic oxide and include metal Co, Ni, Mn, Fe, or a phosphoric acid-based material. A cathode of the electrode of the secondary battery part may use a material causing a reversible reaction with lithium, a material reversibly forming a compound with lithium metal, one selected from a group consisting of C, Na, K, Rb, Cs, Fr, Be, Mg, Ca, Sr, Ba, Ra, Ti, Ag, Zn, Cd, Al, Ga, In, Si, Ge, Sn, Pb, Sb, Ni, Bi, and combinations thereof, oxide thereof, or nitride thereof. The cathode may also be formed of an electrode active material including the above-mentioned materials and a lithium alloy. In addition, the cathode may be formed of a material whose a lithium secession (decomposition) reaction is 2.5 V (Li/Li+) or less based on a lithium electrode.

Liquid electrolyte or solid electrolyte may be used as electrolyte of the secondary battery part. Lithium salt, such as hexafluorophosphoric acid lithium, tetrafluorophosphoric acid lithium, tetrafluoroborate lithium, or the like, may be mixed with propylene carbonate, ethylene carbonate, diethyl carbonate, methyl ethyl carbonate, γ-butyrolactone, or the like to be used the liquid electrolyte.

Fluoride resin such as poly(vinylidene), tetrafluoroethylene polymer, or the like, celluosics such as methyl-celluose, carboxy-methyl-celluose, or the like, a polyvinyl-based material such as polyvinyl alcohol or the like, and lithium salt may be mixed to be used the solid electrolyte. Li—P—O—N-based or sulfur-based solid electrolyte may be used the solid electrolyte.

The tube-structured battery 100 may be applied in various fields such a device to be inserted into a living body selected from at least one of a drug infusion pump, a nano-robot to be inserted into a human body, an active drug transfer system, a pacemaker, a nerve stimulator, a biosensor, and a biochip.

For example, a size of a currently marketed external insulin infusion pump for curing diabetes is sharply reduced to fabricate an internal insulin infusion pump by using the tube-structured battery 100.

Also, the tube-structured battery 100 may be used as a power source of an implantable medical device which is currently used and a power source of an implantable robot which will be developed in the future to be used for diagnoses and surgeries.

Differently shown in FIG. 1, the secondary battery part of the fusion battery part 110 may be disposed outside the blood vessel. In this case, the secondary battery part may be coated with a bioprotective layer or a biocompatible coating layer.

Detailed structure and operation principle of the fusion battery part 110 will be described in more detail with reference to FIGS. 2 through 11.

Figure 2:
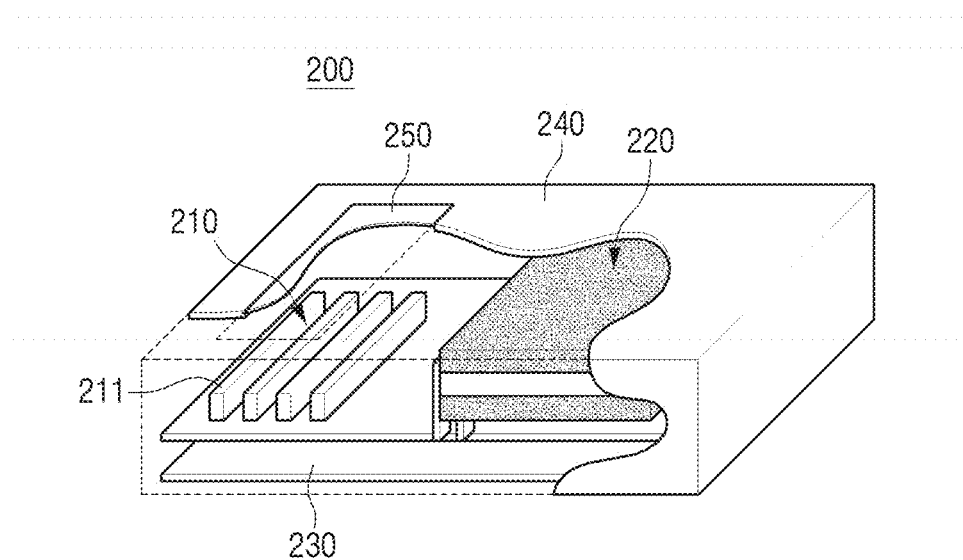
FIG. 2 is a view illustrating a fusion battery part according to an exemplary embodiment of the present general inventive concept.

FIG. 2 is a view illustrating a fusion battery part according to an exemplary embodiment of the present general inventive concept.

Referring to FIG. 2, a fusion battery part 200 includes a biofuel battery part 210, a secondary battery part 220, a transformer circuit part 230, and a biocompatible coating layer 240.

The biofuel battery part 210 has a stack structure in which unit fuel batteries 211 are connected to one another in series or may use several pairs of electrodes, which are connected to one another in series, to raise a voltage.

Also, the secondary battery part 220 may be a thin film battery or a nano-electrode having a small amount of active material to be charged at a low current. The biofuel battery part 210 and the secondary battery part 220 may be connected to each other by using the transformer circuit part 230 which adjusts voltage and current densities of the fusion battery part 200.

Since the fusion battery part 200 is to be used in a living body, the fusion battery part 200 may be enclosed by the biocompatible coating layer 240 including a high biocompatible material. In particular, the secondary battery part 220 or a capacitor (not shown) may be completely blocked from a material of the living body.

Since a voltage generated by the biofuel battery part 210 is generally lower than or equal to 1V, electric energy generated by the biofuel battery part 210 is insufficient to be applied to an electronic device in the living body. Therefore, the transformer circuit part 230 boosts the voltage generated by the biofuel battery part 210 to transform the current density into a form usable in the electronic device in the living body. The transformer circuit part 230 may not boost the voltage but may adjust the current density to transform the current density into a form usable in the electronic device in the living body.

The biocompatible coating layer 240 may be formed by any currently used method. In particular, polylactic acid (PLA), poly-β-hydroxybutyrate, chitosan, or silicon may be used as a coating layer material having a high biocompatibility.

In order to increase strength and a damp proof property of a coated layer, a material selected from a group consisting of metal such as titanium or nickel, a ceramic material such as zirconia or the like, and combinations thereof may be first coated, and then a material having a high biocompatibility may be coated.

However, since the biofuel battery part 210 self-generates the electric energy by using fuel in the living body, a transreflective layer 250 may be formed in an area of the biocompatible coating layer 240 to pass the fuel of the living body through the biofuel battery part 210. An electrode of the biofuel battery part 210 may be degenerated by protein or the like in the living body, and thus the transreflective layer 250 may pass only the fuel of the living body.

The transreflective layer 250 may include a material selected from the group consisting of cellulose, polymethylmethacrylate (PMMA), polysulfone, poly(ethylene-convinylaceate, and combinations thereof.

Figure 3:
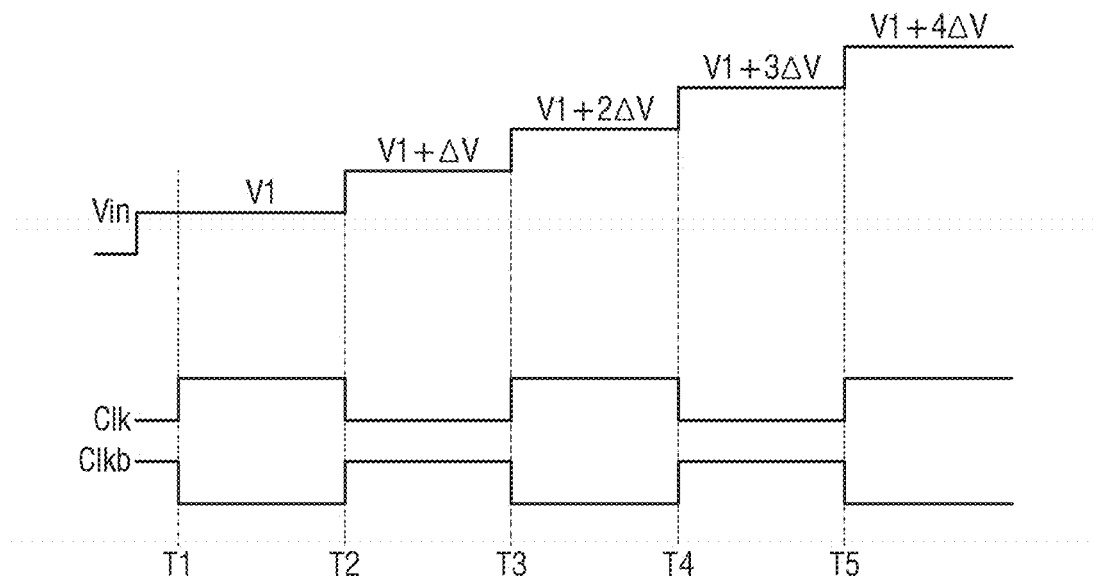
FIG. 3 is a view illustrating a transformer circuit unit according to an exemplary embodiment of the present general inventive concept.

FIG. 3 is a view illustrating a transformer circuit part according to an exemplary embodiment of the present general inventive concept.

As shown in FIG. 3, the transformer circuit part 230 includes five PMOS transistors M1 through M5, five capacitors C1 through C5, five CMOS transistors CM1 through CM5. Each of the five CMOS transistor CM1 through CM5 includes one NMOS transistor MN1-5 and one PMOS transistor MP1-5. In the present exemplary embodiment, the five CMOS transistors CM1 through CM5 are included. However, the appropriate number of CMOS transistors is used to adjust an input voltage Vin to an output voltage Vout in a predetermine range.

A clock signal clk and an inverted clock signal clkb may be generated from an oscillator (not shown) of the transformer circuit part 230. Also, a necessary voltage of the oscillator may operate in a range of a voltage input from the biofuel battery part 210.

Gate electrodes of the PMOS transistors M1 through M5 are respectively connected to nodes at which the NMOS transistors and the PMOS transistors of the CMOS transistors CM1 through CM5 are connected to one another. The input voltage Vin is input into a source electrode of the PMOS transistor M1, and the output voltage Vout is charged into the capacitor C5.

The transformer circuit part 230 uses the clock signal clk and the inverted clock signal clk as control signals to boost the input voltage Vin. The inverted clock signal clk is applied to the NMOS transistors MN2 and MN4 constituting the CMOS transistors CM2 and CM4 and gate electrodes of the CMOS transistors MP2 and MP4 and. The clock signal clk is applied to the NMOS transistors MN1, MN3, and MN5 constituting the PMOS transistors MP1, MP3, and MP5 and gate electrodes of the PMOS transistors MP1, MP3, and MP5.

An end of the capacitor C1 is connected to a drain electrode of the NMOS transistor MN3, and the inverted clock signal clk is applied to an other end of the capacitor C1. An end of the capacitor C1 is connected to drain electrodes of the NMOS transistors MN3 and MN4, and the clock signal clk is applied to an other end of the capacitor C2. An end of the capacitor C3 is connected to drain electrodes of the NMOS transistors MN4 and MN5, and the inverted clock signal clk is applied to an other end of the capacitor C3. An end of the capacitor C4 is connected to the drain electrode of the NMOS transistor MN5, and the inverted clock signal clk is applied to an other end of the capacitor C4. The capacitor C5 is connected between a drain electrode of the PMOS transistor MP5 and ground, and the output voltage Vout is determined by the voltage charged into the capacitor C5.

A voltage boosting process will now be described in detail with reference to FIG. 4.

Figure 4:
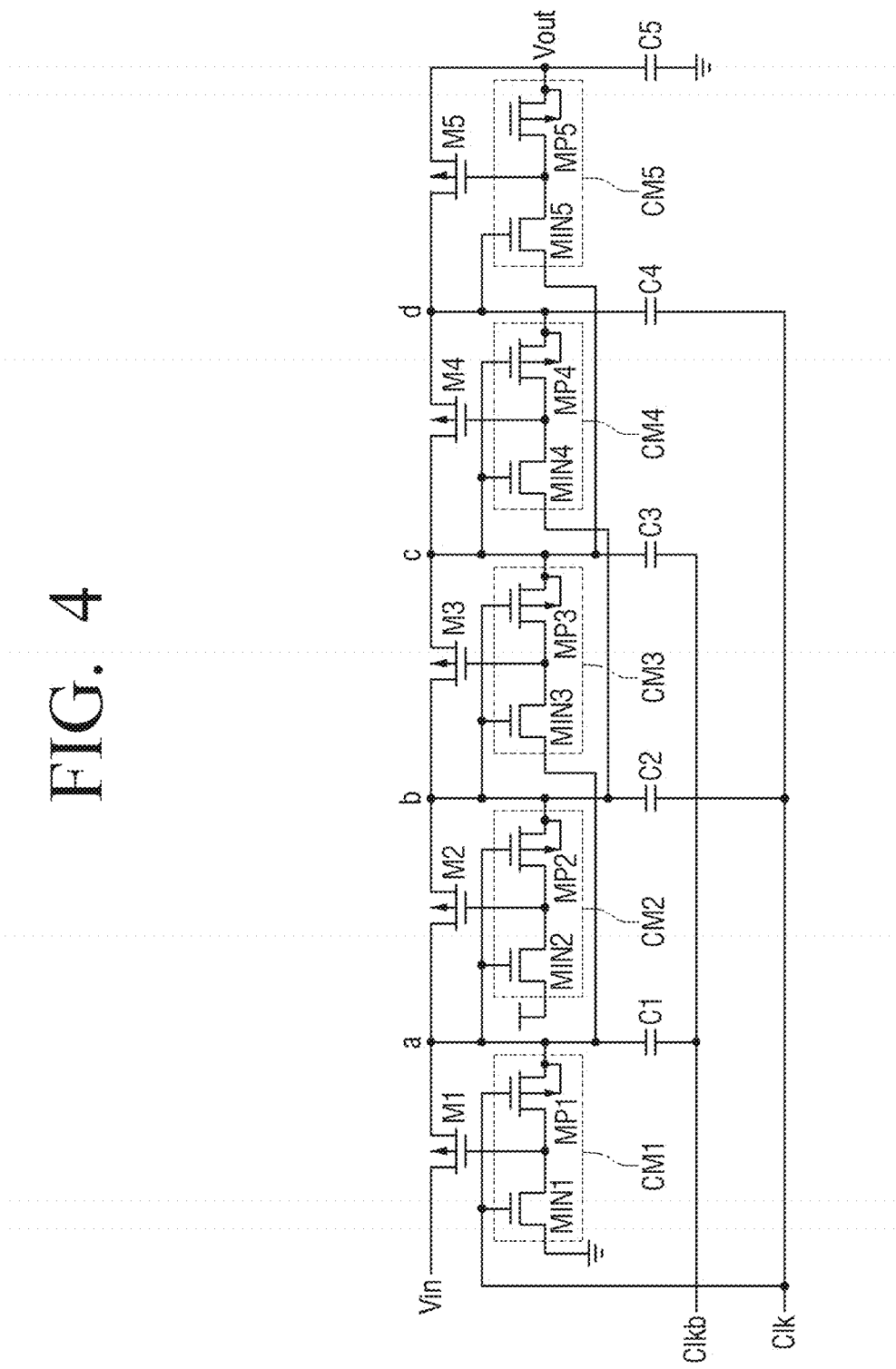
FIG. 4 is a view illustrating a boosting process performed by the transformer circuit unit of FIG. 3 according to a clock signal and an inverted clock signal.

FIG. 4 is a view illustrating a voltage boosting process performed by the transformer circuit part 230 of FIG. 3 according to a clock signal and an inverted clock signal.

If the clock signal clk is on a high level, and the inverted clock signal clk is on a low level at a time T1, the NMOS transistor MN1 is turned, and thus the PMOS transistor M1 is turned on.

The high level of the clock signal clk and the inverted clock signal clk are enough levels to turn on the NMOS transistors MN1 through MN5 and the PMOS transistors M1 through M5 and MP1 through MP5. If the PMOS transistor M1 is turned on, a voltage of contact point a is equal to the input voltage Vin. Here, a voltage on a low level is applied to the other end of the capacitor C1, and thus both ends of the capacitor C is charged with a voltage (hereinafter Δreferred to as a first voltage V1) corresponding to a difference between the input voltage Vin and the low level. The low level is a ground voltage, and the first voltage V1 and the input voltage Vin have the same level.

If the inverted clock signal clk is on a high level, and the clock signal clk is on a low level at a time T2, the voltage of the other end of the capacitor C1 increases from a low level to a high level. Therefore, the voltage of the contact point a increases by the increased voltage (hereinafter referred to ΔV). Then, the voltage of the contact point a has a voltage level (V1+ΔV). Here, a voltage VDD is set to a low level voltage so that a difference between the voltage VDD and the voltage (V1+ΔV) is higher than a threshold voltage of the NMOS transistor MN2. Therefore, the NMOS transistor MN2 is turned on, and thus the voltage VDD having the low level is applied to the gate electrode of the PMOS transistor M2, thereby turning on the PMOS transistor M2. Then, the voltage of the contact point a becomes the voltage (V1+ΔV), and the voltage having the low level is applied to the other end of the capacitor C2. Therefore, both ends of the capacitor C2 is charged with the voltage (V1+ΔV).

If the inverted clock signal clk is on a low level, and the clock signal clk is on a high level at a time T3, the voltage of the other end of the capacitor C2 increases from the low level to the high level. Therefore, the voltage of the contact point a increases by the increased voltage ΔV. Then, a voltage of a contact point b is on a voltage level v Then, the voltage of the contact point b becomes a voltage level V1+2ΔV. Here, the NMOS transistor MN3 is turned on by the voltage V1+2ΔV having a high level, a difference between voltages of the gate electrode and the source electrode of the PMOS transistor M3 becomes a voltage ΔV, and the voltage ΔV is set to be higher than an absolute value of a threshold voltage of the PMOS transistor M3. Therefore, the PMOS transistor M3 is turned. Here, a voltage of a contact point c becomes the voltage V1+2ΔV. Since the voltage V1+2ΔV is applied to the end of the capacitor C3, and a low level is applied to the other end of the capacitor C3, both ends of the capacitor C3 is charged with the voltage V1+2ΔV.

If the inverted clock signal clk is on a high level, and the clock signal clk is on a low level at a time T4, the voltage of the other end of the capacitor C3 increases from a low level to a high level. Therefore, the voltage of the contact point c increases by the increased voltage ΔV. Then, the voltage of the contact point c becomes a voltage level V1+3ΔV. Here, the NMOS transistor MN4 is turned on by the voltage V1+3ΔV on the high level, and a voltage difference between the gate electrode and the source electrode of the PMOS transistor M4 becomes the voltage ΔV, thereby turning on the PMOS transistor M4. Here, a voltage of a contact point d becomes the voltage V1+3ΔV. The voltage V1+3ΔV is applied to the end of the capacitor C4, and a low level voltage is applied to the other end of the capacitor C4. Therefore, the both ends of the capacitor C4 are charged with the voltage V1+3ΔV.

If the inverted clock signal clk is on a low level, and the clock signal clk is on a high level at a time T5, the voltage of the other end of the capacitor C4 increases from the low level to the high level. Therefore, the voltage of the contact point d increases by the increased voltage ΔV. Then, the voltage of the contact point d becomes a voltage V1+4ΔV. The NMOS transistor MN5 is turned on by the voltage V1+4ΔV having the high level, and a voltage difference between the gate electrode and the source electrode of the PMOS transistor M becomes the voltage ΔV, thereby turning on the PMOS transistor M5. Here, the voltage of the end of the capacitor C5 becomes the voltage V1+4ΔV. The voltage of the other end of the capacitor C5 is a ground voltage, and thus the output voltage is determined as the voltage V1+4ΔV. According to this method, the transformer circuit part 230 boosts the input voltage Vin to increase the output voltage Vout up to the voltage level V1+4ΔV.

As a result, the input voltage may be boosted and output through this process.

Figure 5:
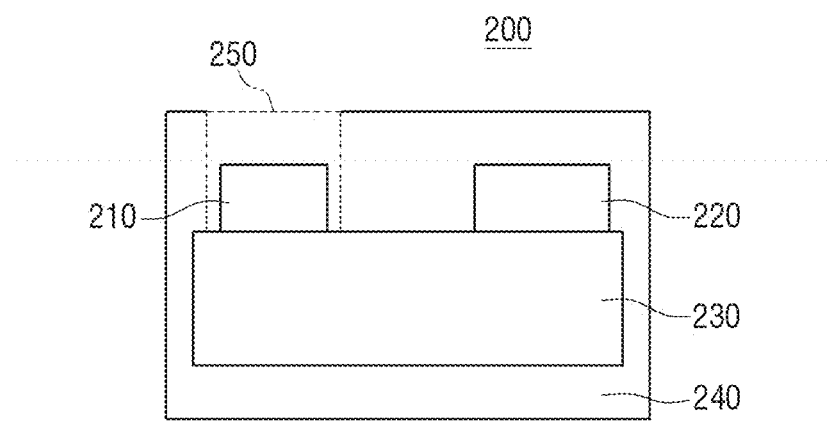
FIGS. 5 through 7 are views illustrating a fusion battery part according to an exemplary embodiment of the present general inventive concept.
Figure 6:
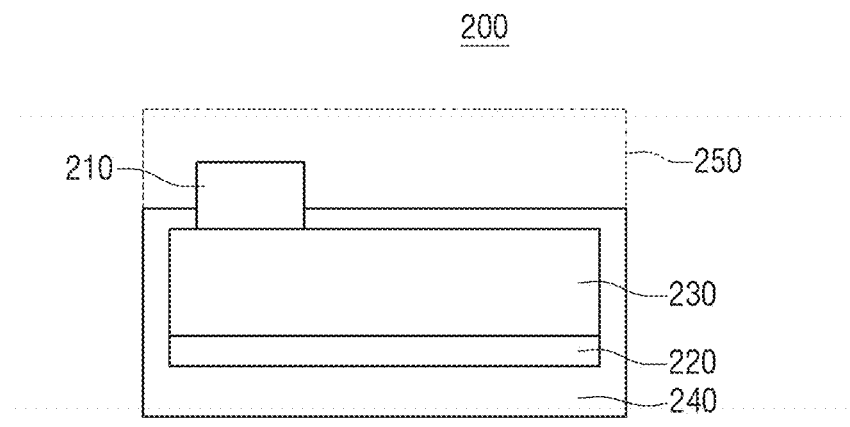
Figure 7:
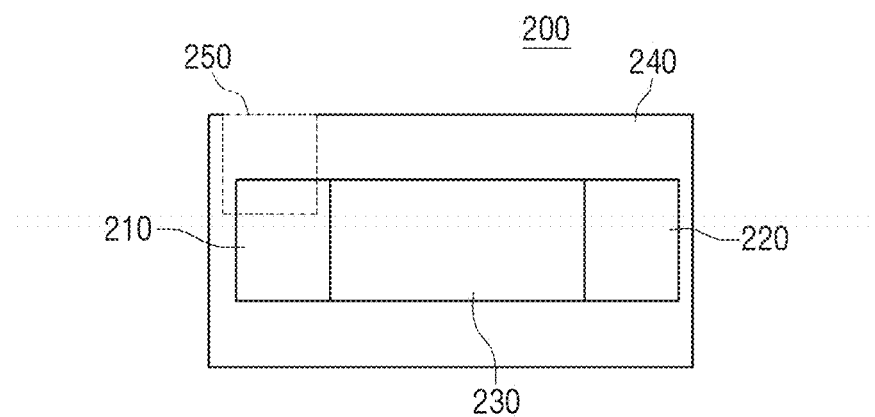

FIGS. 5 through 7 are views illustrating a fusion battery part according to an exemplary embodiment of the present general inventive concept. FIGS. 5 through 7 respectively illustrating various types of fusion battery parts according to connection positions of a biofuel battery part, a secondary battery part, and a transformer circuit part.

Referring to FIG. 5, in order to fabricate a fusion battery part 200, a transformer circuit part 230 is formed as a single layer, and a biofuel battery part 210 and a secondary battery part 220 are formed together as single layers on the transformer circuit part 230.

The transformer circuit part 230 may be formed on a substrate such as silicon or the like by using a CMOS process or the like. A passivation layer is coated between the transformer circuit part 230 and the biofuel battery part 210 or the secondary part 220 for an electric insulation, and only a passage charged with electricity may be filled with metal such as aluminum or the like.

The substrate may be formed of a material such as a polyimide or the like to secure flexibility, and the substrate, the transformer circuit part 230, and the fusion battery part 200 may be flexible.

A biocompatible coating layer 240 is formed at an edge of the fusion battery part 200, and the biofuel battery part 210 is enclosed by a transreflective layer 250 through which fuel in a living body passes.

Referring to FIG. 6, in order to fabricate the fusion battery part 200, the secondary battery part 220 is formed as a single layer underneath the transformer circuit part 230 which is a single layer. The biofuel battery part 210 is formed as a single layer is formed on the transformer circuit part 230. Also, the biocompatible coating layer 240 is formed at the edge of the fusion battery part 200, and the biofuel battery part 210 is enclosed by the transreflective layer 250 through which the fuel in the living body passes.

Referring to FIG. 7, in order to fabricate the fusion battery part 200, the transformer circuit part 230 is formed on the single layer, and the biofuel battery part 210 and the secondary battery part 220 are formed together on the above-described single layer and are connected to the transformer circuit part 230. The biocompatible layer 240 is formed at the edge of the fusion battery part 200, and the biofuel battery part 210 is enclosed by the transreflective layer 250 through which the fuel in the living body passes.

Figure 8:
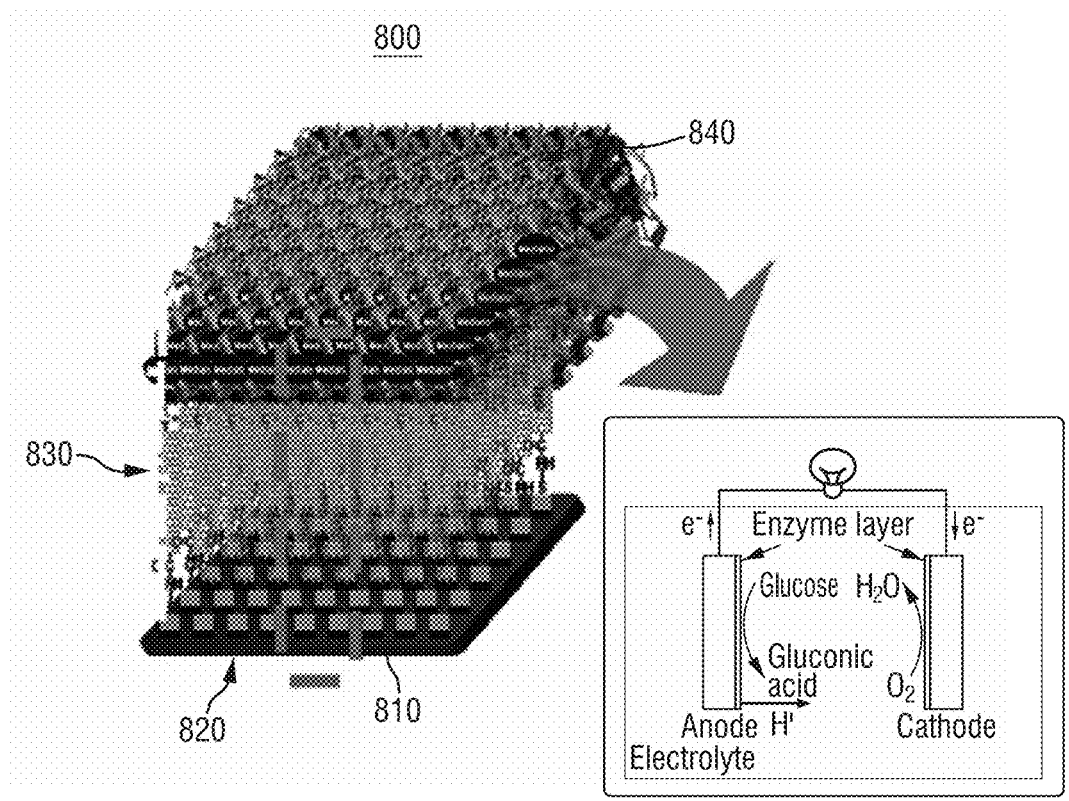
FIG. 8 is a view illustrating a biofuel battery part according to an exemplary embodiment of the present general inventive concept.

FIG. 8 is a view illustrating an electrode of a biofuel battery part according to an exemplary embodiment of the present general inventive concept.

Referring to FIG. 8, in order to fabricate an electrode 800 of the biofuel battery part 210, a nanoparticle seed 820 is formed of metal or the like on a current collector 810, a carbon nanotube 830 is grown, and enzyme 840 is fixed to the carbon nanotube 830.

However, the enzyme 840 may be formed on all types of conductive nanotubes or conductive nanowires.

Anode enzyme, such as a glucose oxidizing enzyme, a pyruvate oxidizing enzyme, a lactic acid oxidizing enzyme, amino acid oxidizing enzymet, or the like, is fixed to fabricate the anode. A cathode enzyme, such as laccase, bilirubin oxidizing enzyme, or the like, is fixed to fabricate a cathode.

Figure 9:
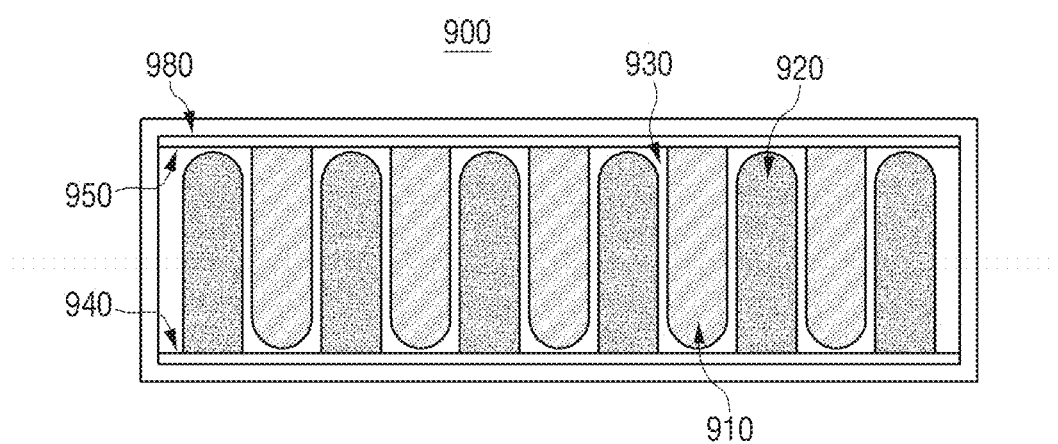
FIG. 9 is a view illustrating a nano-structure secondary battery part according to an exemplary embodiment of the present general inventive concept.

FIG. 9 is a view illustrating a nanostructure secondary battery part according to an exemplary embodiment of the present general inventive concept. Referring to FIG. 9, a nanostructure anode 910 formed on an anode current collector 940 is disengaged from a nanostructure cathode 920 formed on a cathode current collector 950. Therefore, a secondary part 900 having a small size, a high energy density, and a nanostructure is fabricated.

A general type of secondary battery or a capacitor may be used as the secondary battery part 900. However, in order to perform charging at a low current density of the biofuel battery part 210, the secondary battery part 900 may be a thin film type electrode or a 3D nano type electrode.

An electrode active material may be coated on a nanotube such as a carbon nanotube or the like or a nanowire or may be formed in a nanotube or nanowire form in order to constitute the 3D nano type electrode.

FIGS. 10 through 13 are views respectively illustrating a method of improving an enzyme constituting a fusion battery part to increase an electron transfer speed and a generated current density.

Referring to FIG. 8B, if an active site of an enzyme engaging in generating an electron is hidden in the enzyme, a transfer speed is reduced, and thus generation lacks.

Referring to FIG. 10A, an unnecessary part of the enzyme covering the active site of the enzyme is trimmed to allow an electron generating active site to contact an electrode surface in order to increase an electron transfer speed.

Referring to FIG. 11B, the enzyme is disorderedly arranged on the electrode surface when the enzyme is fixed, and thus the generation lacks.

Referring to FIG. 11A, a his-tag or a cysteine amino acid reside is expressed in a particular position of an enzyme protein surface. The enzyme is regularly arranged on the electrode surface through the his-tag or the cysteine amino acid reside to increase an accumulation of the enzyme.

Figure 12:
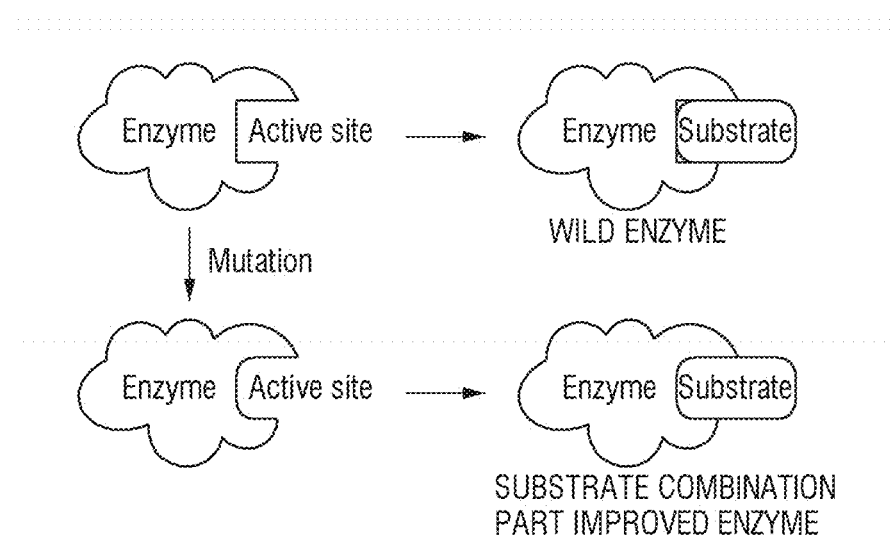

FIG. 12 illustrates a method of modifying a character combination part of an enzyme to increase a character affination in order to increase a reaction speed of a character of the enzyme.

Figure 13:
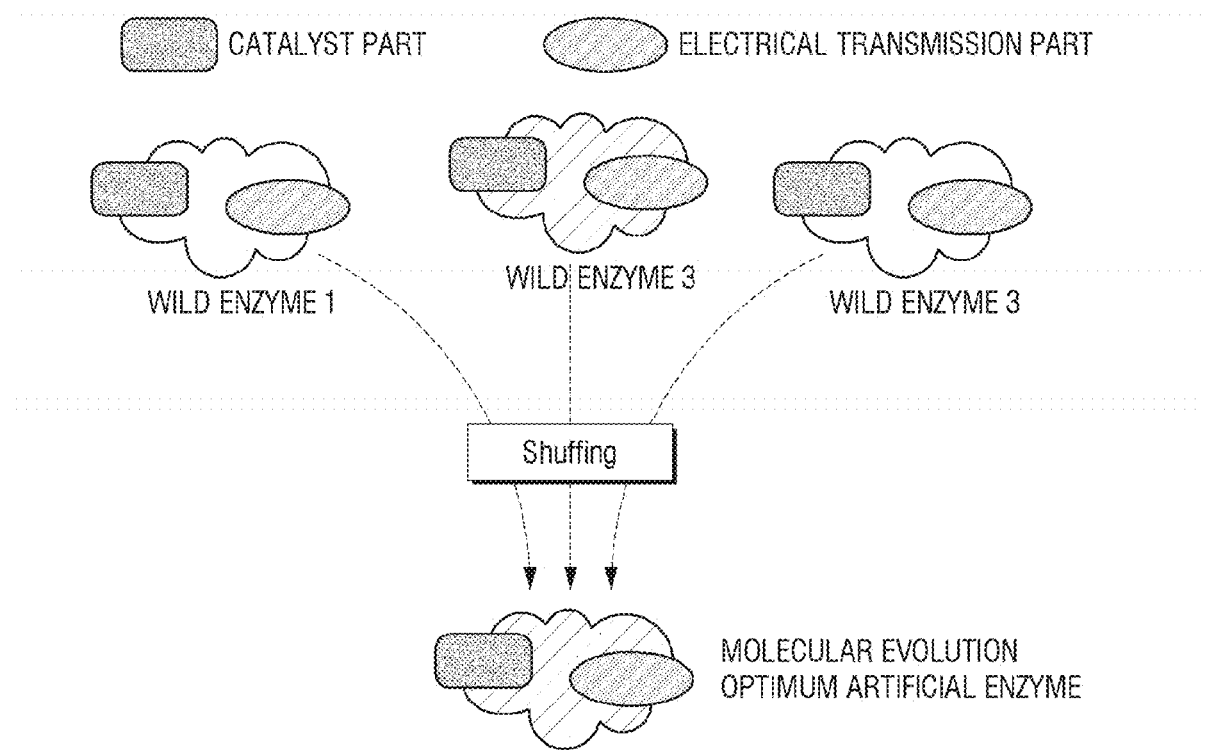

FIG. 13 illustrates a method of combining a catalyst site participating in generating electrons of enzymes having similar functions with an electron transfer site by using a family DNA shuffling technique, which is a kind of molecular evolution technique, in order to fabricate an artificial enzyme having an optimum catalyst site and an optimum electron transfer sit which are appropriate for a biofuel battery.

[Biofuel Battery to be Inserted into Living Body According to Modified Exemplary Embodiment of First Exemplary Embodiment]

Figure 14:
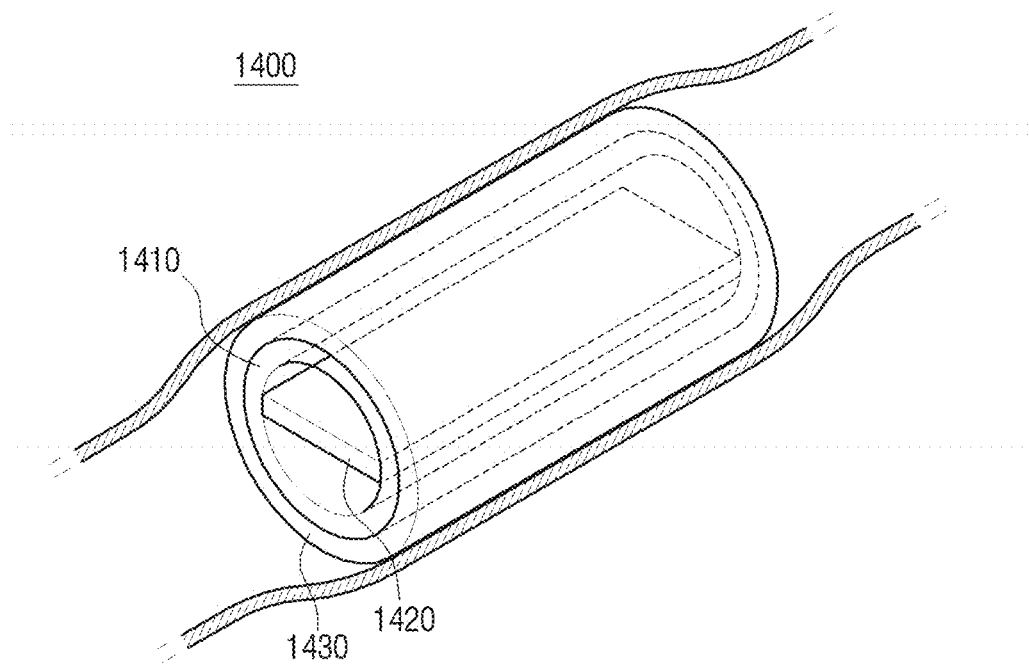
FIG. 14 is a view illustrating a tube-structured battery to be inserted into a living body according to another exemplary embodiment of the present general inventive concept.

FIG. 14 is a view illustrating a battery to be inserted into a living body according to a modified exemplary embodiment of the first exemplary embodiment.

Referring to FIG. 14, a battery 1400 to be inserted into a living body includes a biofuel battery part 1410, a transformer circuit part 1420, and a secondary battery part 1430.

The biofuel battery part 1410 generates electric energy by using biofuel in the blood passing through a tube-structured internal space whose both ends are opened.

The transformer circuit part 1420 adjusts a voltage or current density of the generated electric energy.

The secondary battery part 1430 is charged with the electric energy having the adjusted voltage or current density to store the electric energy.

The battery 1400 may include a transreflective layer (not shown) which encloses a surface of the biofuel battery part 1410 through which the biofuel of the blood passes and which selectively passes the biofuel of the blood. Therefore, the battery 1400 allows glucose of the blood to react with an enzyme of the biofuel battery part 1410.

The biofuel battery part 1410 has a tube structure having two opened ends or a tube structure, is connected to the transformer circuit part 1420 in the internal space of the biofuel battery part 1410, and is connected to the secondary battery part 1430 outside the biofuel battery part 1410. The transformer circuit part 1420 forms a flat plate structure. The secondary battery part 1430 forms a tube type structure which encloses the biofuel battery part 1410 outside the biofuel battery part 1410.

The battery 1400 of FIG. 14 performs a function of a support part in which the biofuel battery part 1410 and the secondary battery part 1430 fix the transformer circuit part 1420. The battery 1400 may further include a tube-structured support part (not shown) which encloses the secondary battery part 1430 outside the secondary battery part 1430.

Differently from the battery 1400 of FIG. 14, the secondary battery part 1430 of the battery 1400 may be arranged outside a blood vessel. In this case, the secondary battery part 1430 may be coated with a bioprotective layer.

The biofuel battery part 1410, the transformer circuit part 1420, and the secondary battery part 1430 of the battery 1400 may be coated with the bioprotective layer.

Differently from the battery 100 of FIG. 1 in which the fusion battery part 110 including a biofuel battery part, a transformer circuit part, and a secondary battery part has a flat plate type structure, only the transformer circuit part 1420 of the battery 1400 of FIG. 14 may have a flat plate type structure. Therefore, the transformer circuit part 1420 of the battery 1400, which is not easily fabricated in a tube structure, may be easily fabricated. Also, the battery 1400 may increase a contact area between the biofuel battery part 1410 and a biomaterial of the blood.

The contents of FIGS. 2 through 15 may be equally applied to the battery 1400 of FIG. 14, and thus repeated descriptions will be omitted.

[Battery to be Inserted into Living Body According to Modified Exemplary Embodiment of First Exemplary Embodiment]

Figure 15:
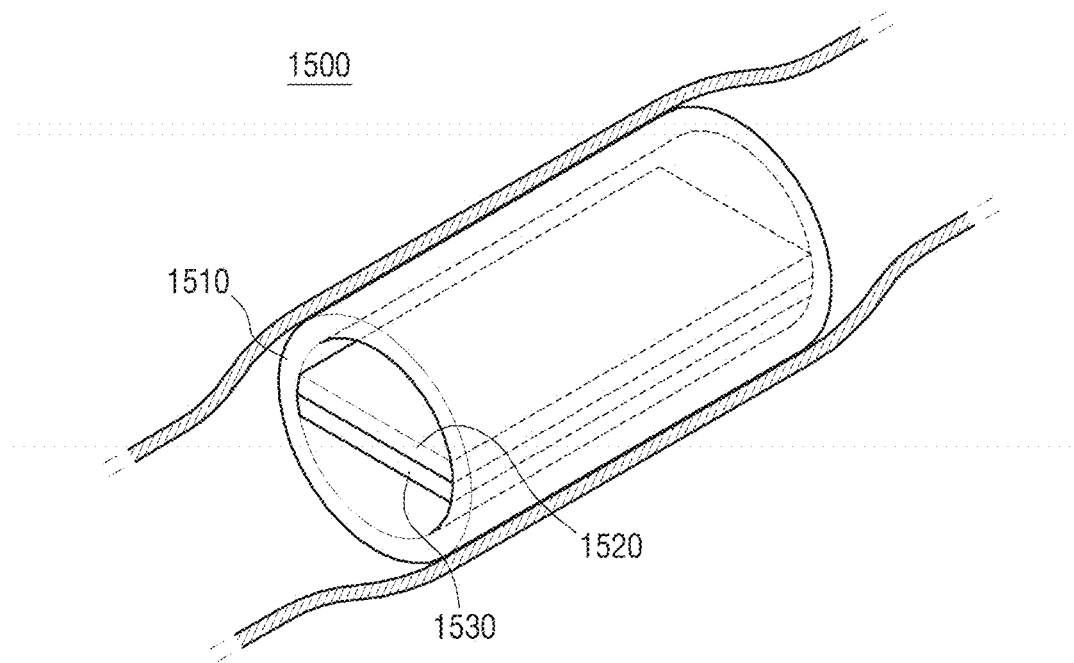
FIG. 15 is a view illustrating a tube-structured battery to be inserted into a living body according to another exemplary embodiment of the present general inventive concept.

FIG. 15 is a view illustrating a battery to be inserted into a living body according to a modified exemplary embodiment of the first exemplary embodiment of the present general inventive concept.

Referring to FIG. 15, a battery 1500 to be inserted into a living body includes a biofuel battery part 1510, a transformer circuit part 1520, and a secondary battery part 1530.

The biofuel battery part 1510 generates electric energy by using biofuel of the blood passing through an internal space having a tube structure whose both ends are opened.

The transformer circuit part 1520 adjusts a voltage or current density of the generated electric energy.

The secondary battery part 1530 is charged with the electric energy having the adjusted voltage or current density to store the electric energy.

The battery 1500 may further include a transreflective layer which is arranged at an end of an empty tube type structure having two opened ends and selectively passes biofuel of the blood.

The biofuel battery part 1510 has a tube structure having two opened ends and is connected to the transformer circuit part 1520 and the secondary battery part 1530 in the internal space of the biofuel battery part 1510. The transformer circuit part 1520 and the secondary battery part 1530 contact each other and respectively form flat plate type structures.

The battery 1500 of FIG. 15 may perform a function of a support part in which the biofuel battery part 1510 fixes the transformer circuit part 1510. The battery 1500 may further include a tube-structured support part (not shown) which encloses the biofuel battery part 1510 outside the biofuel battery part 1510.

Differently from the battery 1500 of FIG. 15, the secondary battery part 1530 of the battery 1500 may be arranged outside a blood vessel. In this case, the secondary battery part 1530 may be coated with a bioprotective layer.

The biofuel battery part 1510, the transformer circuit part 1520, and the secondary battery part 1530 of the battery 1500 may be coated with the bioprotective layer.

The battery 1400 of FIG. 14 in which only the transformer circuit part 1420 has the flat platetype structure, the transformer circuit part 1520 and the secondary battery part 1530 of the battery 1500 of FIG. 15 may have flat platetype structures. Therefore, a diameter of the biofuel battery part 1510 may increase, and thus the battery 1500 may further increase a contact area between the biofuel battery part 1510 and a biomaterial of the blood.

The contents of FIGS. 2 through 13 may be equally applied to the battery 1500 of FIG. 15, and thus repeated descriptions will be omitted.

[Battery to be Inserted into Living Body According to Second Exemplary Embodiment]

Figure 16:
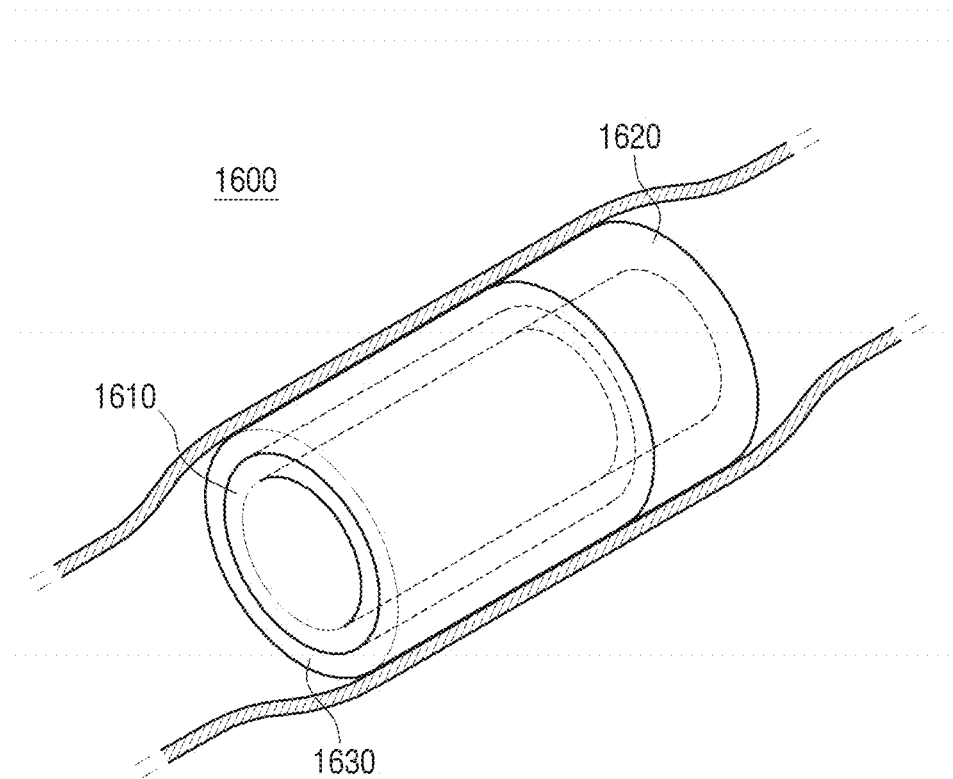
FIG. 16 is a view illustrating a tube-structured battery to be inserted into a living body according to another exemplary embodiment of the present general inventive concept.

FIG. 16 is a view illustrating a battery to be inserted into a living body according to a second exemplary embodiment of the present general inventive concept.

Referring to FIG. 16, a battery 1600 to be inserted into a living body includes a biofuel battery part 1610, a transformer circuit part 1620, and a secondary battery part 1630.

The biofuel battery part 1610 generates electric energy by using biofuel of the blood passing through a tube-structured internal space whose both ends are opened.

The transformer circuit part 1620 adjusts a voltage or current density of the generated electric energy.

The secondary battery part 1630 is charged with the electric energy having the adjusted voltage or current density to store the electric energy.

The battery 1600 may further include a transreflective layer which is arranged at an end of an empty tube structure having two opened ends and selectively passes biofuel of the blood.

The battery 1600 includes the biofuel battery part 1610 which is positioned in an innermost part of the tube structure and the secondary battery part 1630 which has a tube structure and encloses the biofuel battery part 1610.

The transformer circuit part 1620 may be connected to the biofuel battery part 1610 and the secondary battery par 130 on sides of the biofuel battery part 1610 and the secondary battery part 1630 which are formed side by side.

Differently from FIG. 16, the battery 1600 may include a new biofuel battery part (not shown) and a new secondary part (not shown) which have the same structures as the biofuel battery part 1610 and the secondary battery part 1630 and are connected to the transformer circuit part 1620 on an other side of the transformer circuit part 1620.

Therefore, the transformer circuit part 1620 may control a voltage or current density by using electric energy generated from the biofuel battery part 1610 or the new biofuel battery part.

However, the battery 1600 is not limited to the above-described contents. The transformer circuit part 1620 may be connected to the new biofuel battery part and the new secondary part in series on sides of the new biofuel battery part and the new secondary battery part, and a new transformer circuit part (not shown) may be connected to the new biofuel battery part and the new secondary part on other sides of the new biofuel battery part and the new secondary battery part.

[Battery to be Inserted into Living Body According to Modified Exemplary Embodiment of Second Exemplary Embodiment]

Figure 17:
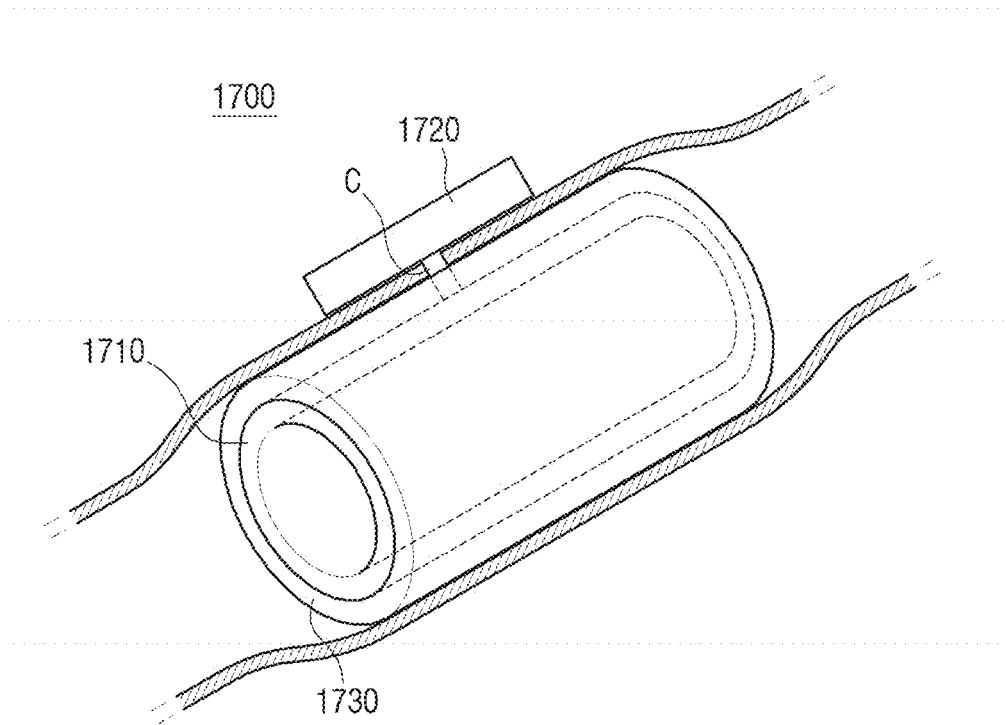
FIG. 17 is a view illustrating a tube-structured battery to be inserted into a living body according to another exemplary embodiment of the present general inventive concept.

FIG. 17 is a view illustrating a battery to be inserted into a living body according to a modified exemplary embodiment of the second exemplary embodiment of the present general inventive concept.

Referring to FIG. 17, a battery 1700 to be inserted into a living body includes a biofuel battery part 1710, a transformer circuit part 1720, and a secondary battery part 1730.

The biofuel battery part 1710 generates electric energy by using biofuel of the blood passing through an internal space having a tube structure whose both ends are opened.

The transformer circuit part 1720 adjusts a voltage or current density of the generated electric energy.

The secondary battery part 1730 is charged with the electric energy having the adjusted voltage or current density to store the electric energy.

The battery 1700 may further include a transreflective layer which is arranged at an end of an empty tube structure having two opened ends and selectively passes the biofuel of the blood.

The biofuel battery part 1710 and the secondary battery part 1730 of the battery 1700 may be arranged in a blood vessel.

The transformer circuit part 1720 may be arranged outside the blood vessel. For example, the transformer circuit part 1720 may have a flat platetype structure outside the blood vessel. The transformer circuit part 1720 may be connected to the biofuel battery part 1710 through a connection part C. The single connection part C is shown in FIG. 7 but is not limited thereto. Also, the transformer circuit part 1720 may be coated with a biocompatible coating layer.

Differently from FIG. 17, in the battery 1700, only the biofuel battery part 1710 may be arranged in the blood vessel, and the transformer circuit part 1720 and the secondary battery part 1730 may be arranged outside the blood vessel.

[Battery to be Inserted into Living Body According to Third Exemplary Embodiment]

Figure 18:
FIG. 18 is a view illustrating a tube-structured battery to be inserted into a living body according to another exemplary embodiment of the present general inventive concept.

FIG. 18 is a view illustrating a battery to be inserted into a living body according to a third exemplary embodiment of the present general inventive concept.

Referring to FIG. 18, a battery 1800 to be inserted into a living body includes a fusion battery part 1810 and a support part 1820.

The fusion battery part 1810 and the support part 1820 are included in a blood vessel.

The fusion battery part 1810 generates electric energy by using biofuel of the blood passing through an internal space of the support part 1820, adjusts a voltage or current density of the generated electric energy, and charges and stores the electric energy.

As shown in FIG. 2, the fusion battery part 1810 may include the biofuel battery part 210, the secondary battery part 220, the transformer circuit part 230, the biocompatible coating layer 240, and the transreflective layer 250. The contents described with reference to FIGS. 2 through 13 may be equally applied.

The support part 1820 may be formed a flexible material and may have a tube structure having two opened ends.

An opening may be formed in an area of a side of the support part 1820, and the fusion battery part 1810 may be inserted into (attached to) the opening of the support part 1820. Therefore, the fusion battery part 1810 may generate the electric energy by using the biofuel of the blood passing through the internal space of the support part 1820.

The battery 1800 may further include a transreflective layer which is arranged at an end of an empty tube structure whose both ends are opened and selectively passes the biofuel of the blood.

Alternatively, since the fusion battery part 1810 is inserted into (attached to) the opening of the support part 1820, a transreflective layer may be further included on a side (a side contacting the biofuel) of the fusion battery part 1810 to selectively pass the biofuel of the blood.

In detail, the transreflective layer 250 of FIG. 2 may be arranged to contact the biofuel of the blood passing through an inner part of the tube structure of the support part 1820. In this case, the fusion battery part 1810 may have various structures as shown in FIGS. 5 through 7.

The support part 1820 may be arranged in the blood vessel, and the fusion battery part 1810 may be inserted into the living body outside the blood vessel.

[Battery to be Inserted in Living Body According to Modified Exemplary Embodiment of Third Exemplary Embodiment]

Figure 19:
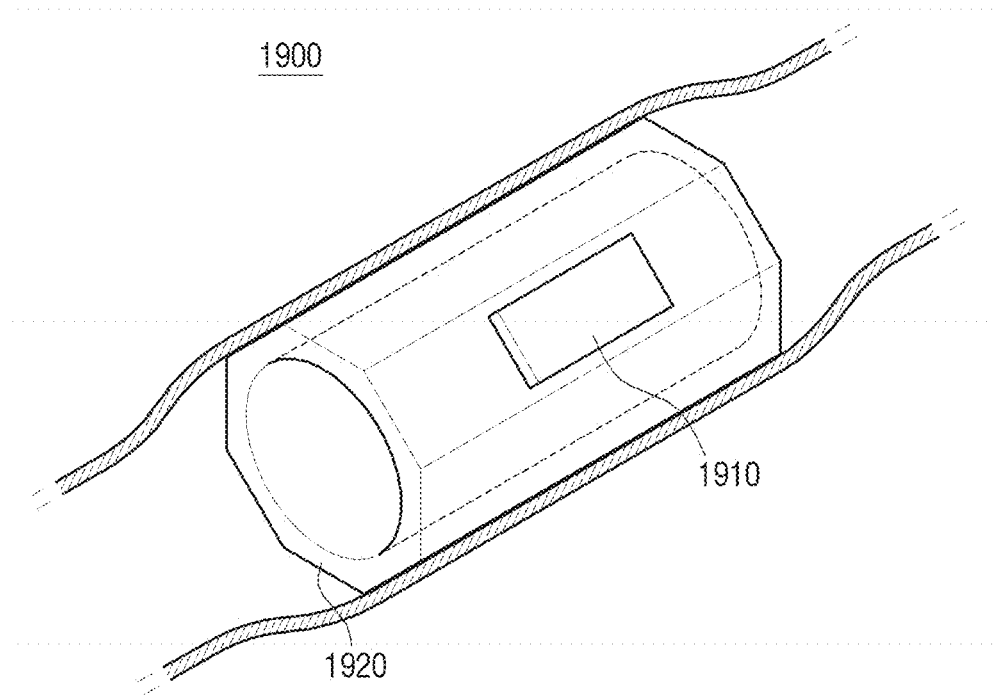
FIG. 19 is a view illustrating a tube-structured battery to be inserted into a living body according to another exemplary embodiment of the present general inventive concept.

FIG. 19 is a view illustrating a battery to be inserted into a living body according to a modified exemplary embodiment of the third exemplary embodiment of the present general inventive concept.

Referring to FIG. 19, a battery 1900 to be inserted into a living body includes a fusion battery part 1910 and a support part 1920.

In the battery 1900, an inner cross-section of the support part 1920 may have a circular shape like an inner cross-section of the support part 1820 of FIG. 18. However, an outer cross-section of the support part 1920 may have a polygonal shape differently from an outer cross-section of the support part 1820 of FIG. 18. Therefore, the battery 1900 having a tube structure may have a polygonal pillar shape.

In this case, the fusion battery part 1920 may be inserted into (attached to) a side of the support part 1920 in a flat plateform.

The battery 1900 may operate equally with the battery 1800 of FIG. 18.

Differently from FIG. 19, the support part 1920 may be arranged in a blood vessel, and the fusion battery part 1910 may be inserted into a living body outside the blood vessel.

[Battery to be Inserted into Living Body According to Another Modified Exemplary Embodiment of Third Exemplary Embodiment]

Figure 20:
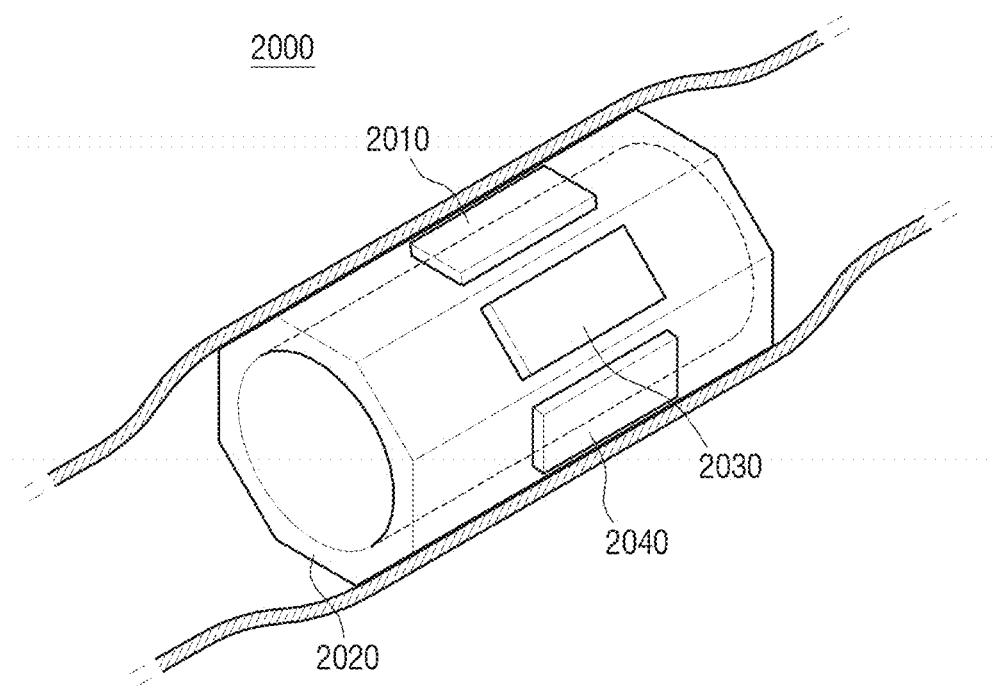
FIG. 20 is a view illustrating a tube-structured battery to be inserted into a living body according to another exemplary embodiment of the present general inventive concept.

FIG. 20 is a view illustrating a battery to be inserted into a living body according to another modified exemplary embodiment of the third exemplary embodiment of the present general inventive concept.

Referring to FIG. 20, a battery 2000 to be inserted into a living body may operate equally with the battery 1900 of FIG. 19.

Differently from the battery 1900 of FIG. 19, in the battery 2000, a biofuel battery part 2010, a transformer circuit part 2030, and a secondary battery part 2040 may be respectively arranged on surfaces of a support part 2020. The biofuel battery part 1810, the transformer circuit part 1830, and the secondary battery part 2040 may constitute a fusion battery part.

[Battery to be Inserted into Living Body According to Modified Exemplary Embodiment of Third Exemplary Embodiment]

Figure 21:
FIG. 21 is a view illustrating a tube-structured battery to be inserted into a living body according to another exemplary embodiment of the present general inventive concept.

FIG. 21 is a view illustrating a battery to be inserted into a living body according to another modified exemplary embodiment of the third exemplary embodiment of the present general inventive concept.

Referring to FIG. 21, a battery 2100 to be inserted into a living body may operate equally with the battery 1900 of FIG. 19.

However, differently from FIG. 19, in the battery 2100, a biofuel battery part 2110, a transformer circuit part 2130, and a secondary battery part 2140 are arranged on a side of a support part 2120. The biofuel battery part 2110, the transformer circuit part 2130, and the secondary battery part 2140 constitute a fusion battery part.

[Battery to be Inserted into Living Body According to Fourth Exemplary Embodiment]

Figure 22:
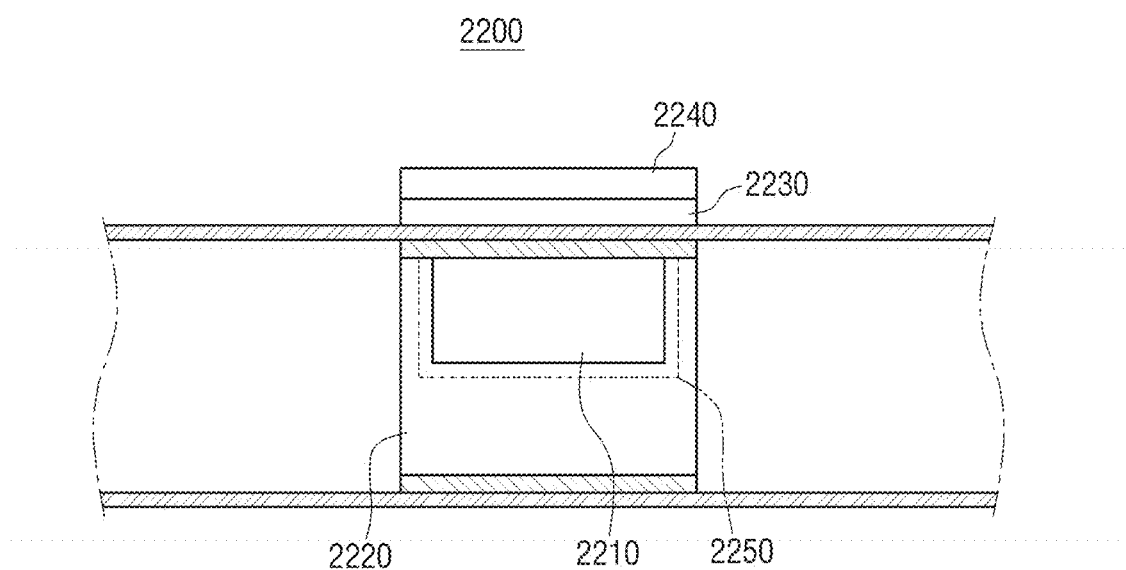
FIG. 22 is a view illustrating a tube-structured battery to be inserted into a living body according to another exemplary embodiment of the present general inventive concept.

FIG. 22 is a view illustrating a battery to be inserted into a living body according to a fourth exemplary embodiment of the present general inventive concept.

Referring to FIG. 22, a battery 2200 to be inserted into a living body includes a biofuel battery part 2210, a support part 2220, a transformer circuit part 2230, a secondary battery part 2240, and a transreflective layer 2250.

The biofuel battery part 2210, the support part 2220, and the transreflective layer 2250 may be included in a blood vessel, but the transformer circuit part 2230, and the secondary battery part 2240 may be inserted into a living body outside the blood vessel.

The biofuel battery part 2210 generates electric energy by using biofuel of the blood passing through an internal space of the support part 2220. The biofuel battery part 2210 is attached to an area of the support part 2220 having a tube structure to be fixed to the support part 2220. The biofuel battery part 2210 protrudes in a central direction of the tube structure on an inner surface of the support part 2220 having the tube structure and may have various shapes besides a shown hexahedron.

The biofuel battery part 2210 is enclosed by the transreflective layer 2250. The biofuel battery part 2210 selectively passes biofuel of the blood such as glucose or the like by using the transreflective layer 2250.

The support part 2220 may be formed of a flexible material and may have a tube structure having two opened ends.

The support part 2220 may have an opening in an area of a side thereof, and the biofuel battery part 2210 and the transformer circuit part 2230 are connected to each other through the opening of the support part 2220. In this case, the biofuel battery part 2210 and the transformer circuit part 2230 may be directly connected to each other or may be connected to each other through a connection member (not shown).

The transformer circuit part 2230 is inserted into the living body outside the blood vessel and adjusts a voltage or current density of electric energy generated by the biofuel battery part 2210.

The secondary battery part 2240 is connected to the transformer circuit part 2230 outside the blood vessel and is charged with the electric energy having the adjusted voltage or current density to store the electric energy.

The transformer circuit part 2230 and the secondary battery part 2240 may have flat plate shapes. Differently from FIG. 22, the transformer circuit part 2230 and the secondary battery part 2240 may be formed as single layers not as dual layers.

In the battery 2200, the biofuel battery part 2210 may be fixed into the blood vessel by the support part 2220 having the tube structure, and the biofuel battery part 2210 may be coated with the transreflective layer 2210. In this case, shapes, structures, arrangement positions, etc. of the transformer circuit part 2230 and the secondary battery part 2240 may be variously changed.

Differently from FIG. 22, the battery 220 may be an artificial vessel or only the support part 2220 of the battery 2200 may be an artificial vessel.

[Battery to be Inserted into Living Body According to Fifth Exemplary Embodiment]

Figure 23:
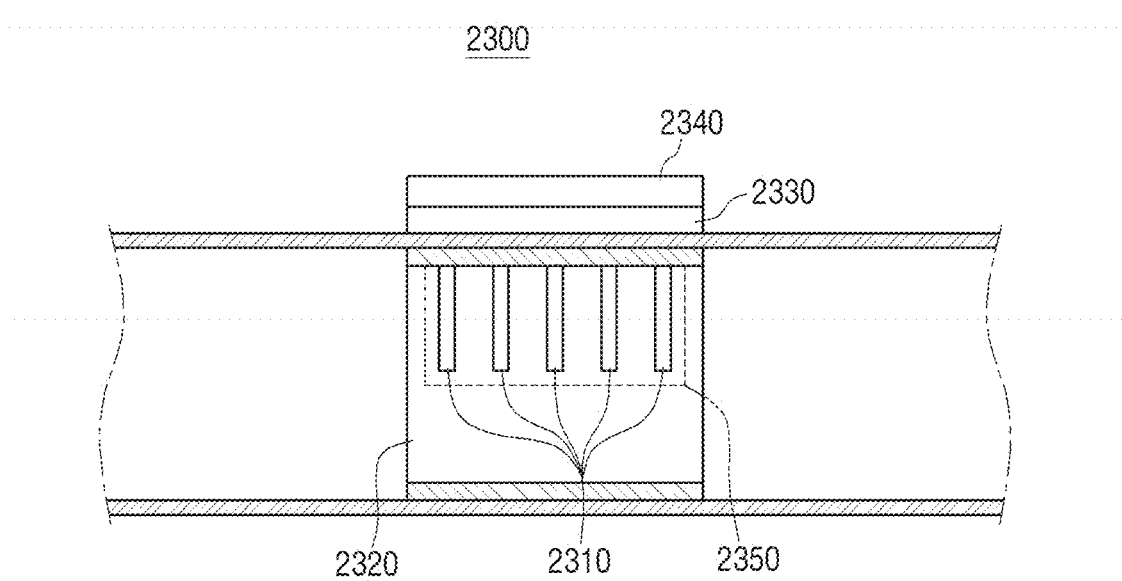
FIG. 23 is a view illustrating a tube-structured battery to be inserted into a living body according to another exemplary embodiment of the present general inventive concept.

FIG. 23 is a view illustrating a battery to be inserted into a living body according to a fifth exemplary embodiment of the present general inventive concept.

Referring to FIG. 23, a battery 2300 to be inserted into a living body includes a biofuel battery part 2310, a support part 2320, a transformer circuit part 2330, a secondary battery part 2340, and a transreflective layer 2350.

The battery 2300 may operate equally with the battery 2200 of FIG. 22.

However, in the battery 2300, the biofuel battery part 2310 has a different shape from the biofuel battery part 2210 of FIG. 22.

In detail, the biofuel battery part 2310 includes a plurality of probes and generates electric energy from biofuel of the blood passing through an internal space of the support part 2320 by using the plurality of probes.

Here, the probes refer to a plurality of protruding structures of at least one of an anode and a cathode constituting the biofuel battery part 2310.

The biofuel battery part 2310 is enclosed by the transreflective layer 2350. The biofuel battery part 2310 selectively passes the biofuel of the blood such as glucose by using the transreflective layer 2350.

Differently from FIG. 23, the battery 2300 may be realized as an artificial vessel or only the support part 2320 of the battery 2300 may be realized as an artificial vessel.

Descriptions of the battery 2300 overlapping those of the battery 2200 of FIG. 22 will be omitted hereinafter.

[Battery to be Inserted into Living Body According to Sixth Exemplary Embodiment]

Figure 24:
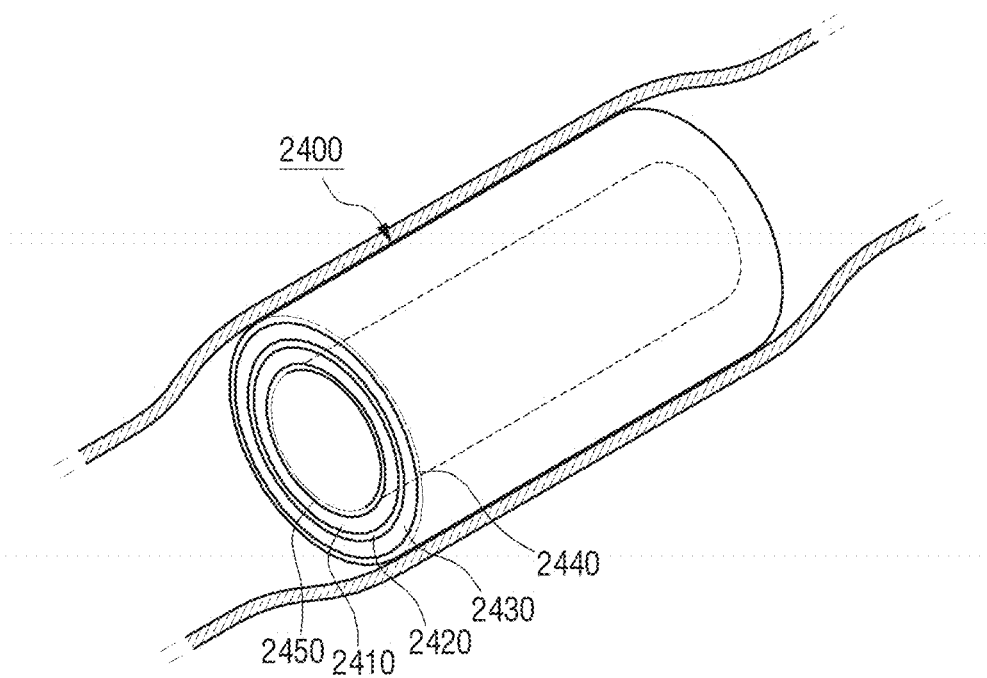
FIG. 24 is a view illustrating a tube-structured battery to be inserted into a living body according to another exemplary embodiment of the present general inventive concept.

FIG. 24 is a view illustrating a tube-structured battery to be inserted into a living body according to a sixth exemplary embodiment of the present general inventive concept. Referring to FIG. 24, a tube-structured battery 2400 to be inserted into a living body includes a biofuel battery part 2410, a transformer circuit part 2420, a secondary battery part 2430, and a biocompatible coating layer 2440.

The biofuel battery part 2410 has a tube structure having a cavity whose both ends are opened and generates electric energy by using the blood passing through the cavity.

The transformer circuit part 2420 forms a tube structure, which encloses the biofuel battery part 2410, outside the biofuel battery part 2410 and adjusts a voltage or current density by using the generated electric energy.

The secondary battery part 2430 forms a tube structure, which encloses the transformer circuit part 2420, outside the transformer circuit part 2420 and is charged with the electric energy by using the adjusted voltage or current density to store the electric energy. If an electronic device (not shown) in a living body requires electric energy, the secondary battery part 2420 supplies the charged electric energy to the electronic device to be discharged.

The secondary battery part 2430 may be realized as a chargeable or dischargeable secondary battery part or may be realized by using one or more capacitors.

The biocompatible coating layer 2440 may be a thin film which encloses an outer surface of the secondary battery part 2430.

The transreflective layer 2450 is coated on an inner surface of the biofuel battery part 2410. The transreflective layer 2450 is a very thin film. If the transreflective layer 2450 is arranged, a diameter of a cavity of the tube-structured battery 2400 may be reduced.

The biofuel battery part 2410, the transformer circuit part 2420, the secondary battery part 2430, and the biocompatible coating layer 2440 may be respectively formed as single layers.

In the tube-structured battery 2400, the biofuel battery part 2410, the transformer circuit part 2420, and the secondary battery part 2430 are highly integrated to provide a fusion battery.

Figure 25:
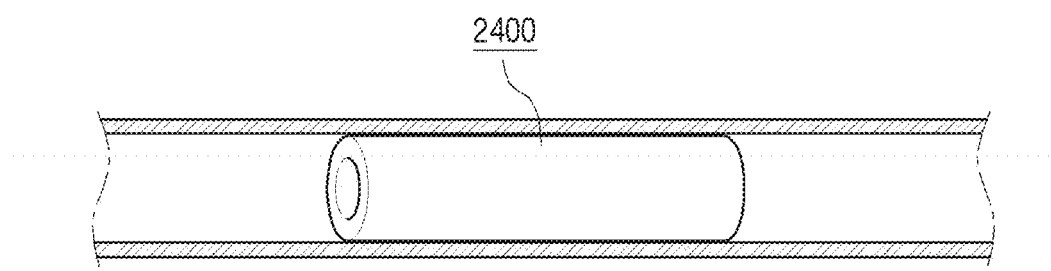
FIGS. 25 through 27 are views illustrating the tube-structured battery of FIG. 24 arranged in a blood vessel, according to various exemplary embodiments of the present general inventive concept.
Figure 26:
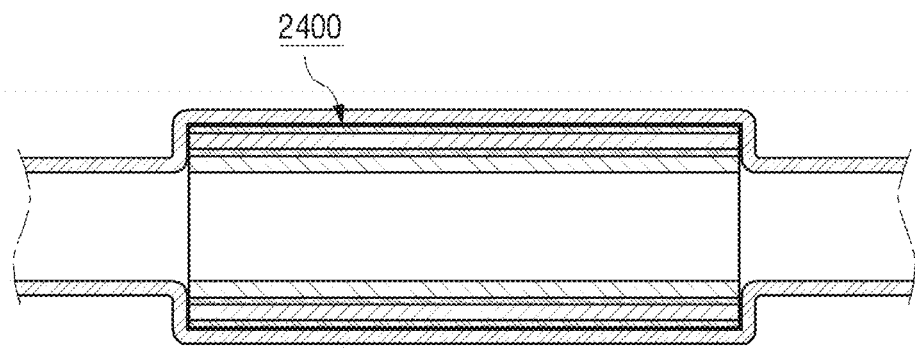
Figure 27:
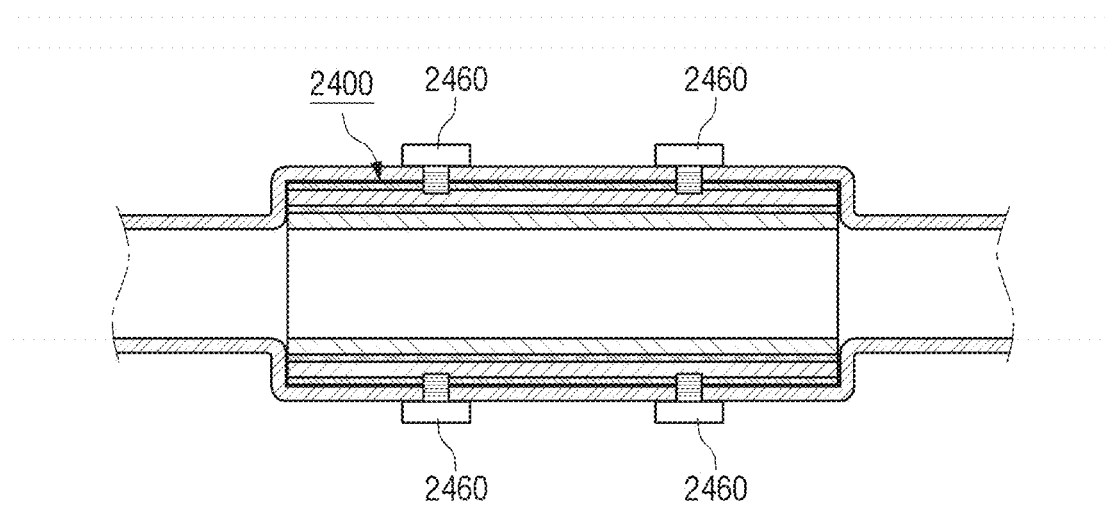

FIGS. 25 through 27 are views illustrating the tube-structured battery 2400 of the sixth exemplary embodiment arranged in a blood vessel, according to various exemplary embodiments of the present general inventive concept.

Referring to FIG. 25, the tube-structured battery 2400 does not extend an adjacent vessel but is inserted into the adjacent vessel. Here, an external diameter of the tube-structured battery 2400 is equal to a diameter of the blood vessel. In other words, the diameter of the cavity of the biofuel battery part 2410 may be smaller than the diameter of the blood vessel.

Referring to FIG. 26, the tube-structured battery 2400 extends the adjacent vessel to be inserted into the adjacent vessel. The tube-structured battery 2400 extends the diameter of the blood vessel of the living body to fix the blood vessel of the living body.

In detail, as shown in FIG. 26, the diameter of the cavity of the biofuel battery part 2410 is equal to the diameter of the blood vessel. Therefore, a problem of accumulating a thrombus around the tube-structured battery 2400 is solved.

IF the diameter of the blood vessel of the living body of the tube-structured battery 2400 extends, the diameter of the cavity of the biofuel battery part 2410 may be smaller or greater than the diameter of the blood vessel differently from FIG. 26.

IF the biofuel battery part 2410 further includes the transreflective layer 2450, the diameter of the cavity of the transreflective layer 2450 may be equal to the diameter of the blood vessel. However, since the transreflective layer 2450 is very thin, an internal diameter of the biofuel battery part 2410 may be nearly equal to an internal diameter of the transreflective layer 2450.

FIG. 27 illustrates a structure further including a fixing part 2460 in FIG. 26. As shown in FIG. 27, the tube-structured battery 2400 further includes the fixing part 2460 having at least one fixing member which is to fix the tube-structured battery 2400 to a particular part of the blood vessel.

As shown in FIG. 27, the fixing part 2460 combines fasteners into the secondary battery part 2430 of the tube-structured battery 2400 to attach the tube-structured battery 2400 to the particular part of the blood vessel. Also, a magnet is attached onto an outer wall of the blood vessel to fix the tube-structured battery 2400 to the particular part of the blood vessel. Alternatively, the tube-structured battery 2400 may be pre-attached to an artificial vessel through the fixing part 2460 and then implanted into the blood vessel.

Various exemplary embodiments may be drawn from the tube-structured battery 2400 according to the sixth exemplary embodiment of the present general inventive concept according to arrangements of the biofuel battery part 2410, the transformer circuit part 2420, and the secondary battery part 2430.

For example, the secondary battery part 2430 may be arranged as a single layer on an outermost side, and the biofuel battery part 2410 and the transformer circuit part 2420 may be arranged together on a single layer on an inner side.

As another example, the transformer circuit part 2420 may be arranged as a single layer on an outermost side, and the biofuel battery part 2410 and the secondary battery part 2430 may be arranged together on a single layer on an inner side.

As another example, the biofuel battery part 2410, the transformer circuit part 2420, and the secondary battery part 2430 may be arranged together on a single layer.

According to the above-described examples, the tube-structured battery 2400 having various shapes may be formed. However, the tube-structured battery 2400 of FIG. 24 may the best absorb biofuel since a surface area of the biofuel battery part 2410 contacting the blood is the widest.

[Battery to be Inserted into Living Body According to Another Modified Exemplary Embodiment of Sixth Exemplary Embodiment]

Figure 28:
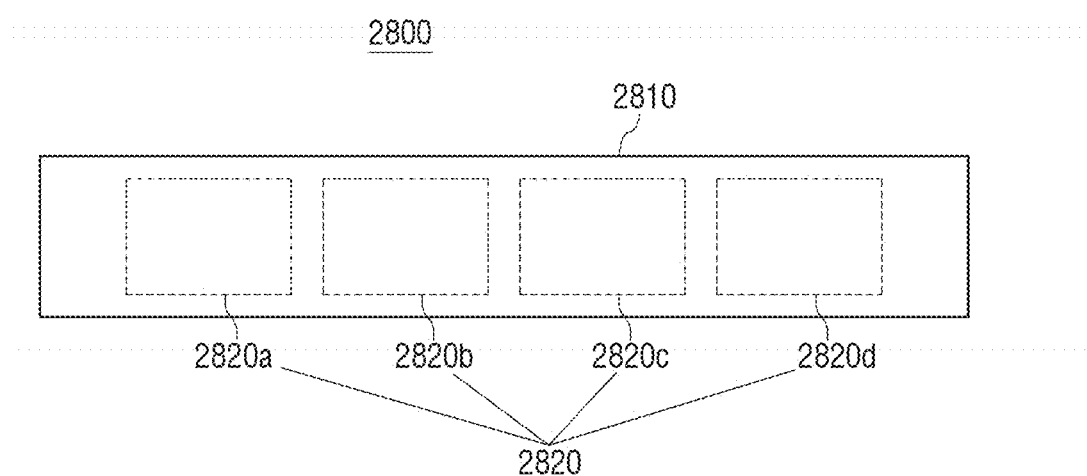
FIGS. 28 and 29 are views illustrating tube-structured batteries to be inserted into a living body according to other exemplary embodiments of the present general inventive concept.
Figure 29:
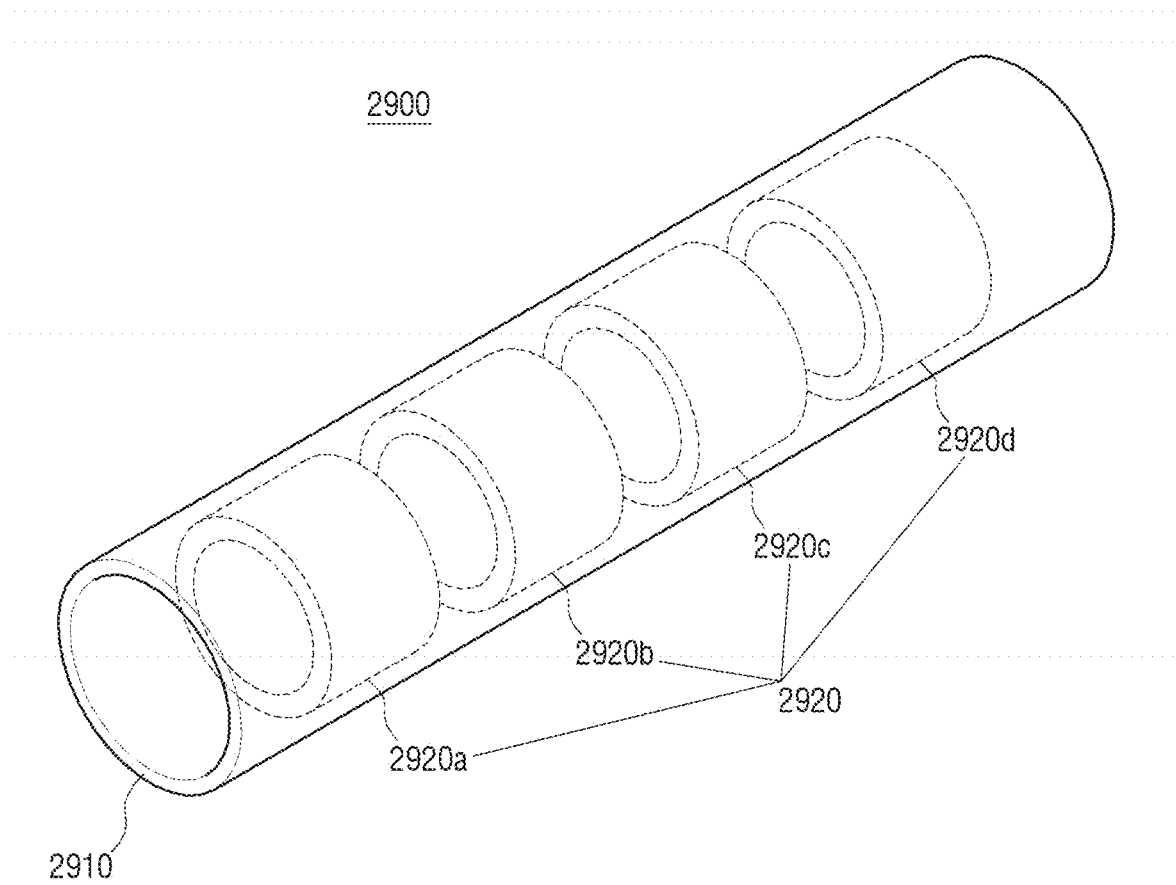

FIGS. 28 and 29 are views illustrating a battery to be inserted into a living body according to another modified exemplary embodiment of the sixth exemplary embodiment of the present general inventive concept.

Referring to FIG. 28, a battery 2800 to be inserted into a living body includes a coating part 2810 and a plurality of cells 2820.

The coating part 2810 has a tube structure whose both ends are opened.

The plurality of cells 2820 are arranged in series from an end of the coating part 2810 to an other end of the coating part 2810.

Therefore, the battery 2800 boosts a voltage by using the plurality of cells 2820 arranged in series in a longitudinal direction in the coating part 2810.

FIG. 29 illustrates the battery 2800 of FIG. 28 in more detail. Each of a plurality of cells (one of the plurality of cells 2820a, 2820b, 2820c, and 2820d) has a tube structure having a cavity whose both ends are opened and includes a biofuel battery part which generates electric energy by using the blood passing through the cavity, a transformer circuit part which is arranged outside the biofuel battery part to adjust a voltage or current density by using the generated electric energy, and a secondary battery part which is arranged outside the transformer circuit part to be charged with the electric energy by using the adjusted voltage or current density in order to store the electric energy. The battery 2800 may be inserted into a blood vessel of a living body.

For the descriptive convenience, the biofuel battery part, the transformer circuit part, and the secondary battery part are shown without being separated from one another in FIGS. 28 and 29.

Referring to FIGS. 28 and 29, if each of the plurality of cells 2820 generates a voltage of 1V, and four cells are connected to one another in series, the voltage of 1V may be boosted to a voltage of 4V.

The number of the plurality of cells 2820 is 4 in FIGS. 28 and 29 but is not limited thereto.

An operation of each of the plurality of cells (one of the cells 2820a, 2820b, 2820c, and 2820d) has been described in detail, and thus repeated description will be omitted.

[Battery to be Inserted into Living Body According to Seventh Exemplary Embodiment]

Figure 30:
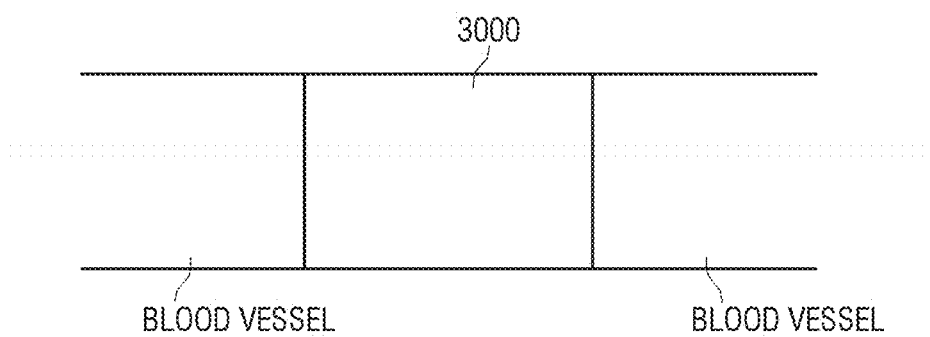
FIG. 30 is a view illustrating a tube-structured battery to be inserted into a living body according to another exemplary embodiment of the present general inventive concept.

FIG. 30 is a view illustrating a battery to be inserted into a living body according to a seventh exemplary embodiment of the present general inventive concept.

Referring to FIG. 30, an artificial vessel 3000 has a tube structure having a cavity whose both ends are opened and includes a biofuel battery part which generates electric energy by using the blood passing through the cavity, a transformer circuit part which adjusts a voltage or current density by using the generated electric energy, a secondary battery part which is charged with the electric energy by using the adjusted voltage or current density to store the electric energy, and a coating part which encloses an outer surface of the secondary battery part.

Here, the coating part may be a biocompatible coating layer which is formed of at least one of ployglycolide (PG), ployglycolic acid (PGA), polylactide (PL), polylactic acid (PLA), polycaprolactone (PCL), poly(ethylene terephthalate) (PET), expanded poly(tetrafluoroethylene) (ePTFE), and polyurethane (PU).

The artificial vessel 3000 does not generate toxicity in a living body, minimizes thrombopoiesis, and does not cause infection, inflammation, and an immune reaction in a peridesm. Also, the artificial vessel 3000 may endure contraction and expansion and may not be deformed or changed.

As shown in FIG. 30, an area of a blood vessel of a living body may be removed, and then the artificial vessel 3000 may be implanted. For the implantation, a bypass operation or a direct operation may be applied.

Referring to FIG. 30, the artificial vessel 3000 may be a battery to be inserted into a living body.

[Battery to be Inserted into Living Body According to Another Modified Exemplary Embodiment of Seventh Exemplary Embodiment]

Figure 31:
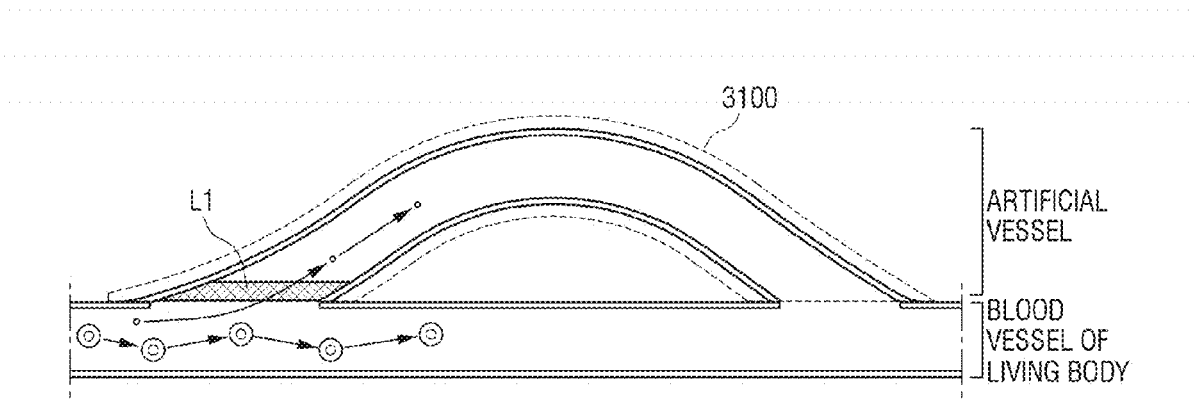
FIG. 31 is a view illustrating a tube-structured battery to be inserted into a living body according to another exemplary embodiment of the present general inventive concept.

FIG. 31 is a view illustrating a battery to be inserted into a living body according to another modified exemplary embodiment of the seventh exemplary embodiment of the present general inventive concept.

Referring to FIG. 31, a battery 3100 to be inserted into a living body is connected to a blood vessel of the living body in parallel to diverge a flow of the blood in the blood vessel of the living body. The battery 3100 may be realized as an artificial vessel. In detail, the whole artificial vessel may be the battery 3100. However, differently from the battery 3100 of FIG. 31, a part of the artificial vessel may be realized as a battery to be inserted into a living body.

First and second areas of the blood vessel of the living body are opened and then are connected to the artificial vessel having a tube structure to insert the battery 3100 into the living body.

A transreflective layer L1 is included at an end of a tube structure of the battery 3100 connected to the blood vessel of the living body. Therefore, if a battery as described according to the first through sixth exemplary embodiments is applied as the battery 3100, the battery 3100 may not include a transreflective layer of the battery of the first through sixth exemplary embodiments.

The transreflective layer L1 selectively passes only biofuel of the blood such as glucose or the like but does not pass white blood cells or red blood cells.

Therefore, the biofuel of the blood such as the glucose or the like may pass through the battery 3100, and the white or red blood cells may pass through the blood vessel of the living body. Therefore, the battery 3100 may efficiently use the biofuel of the living body.

The transreflective layer L1 may be realized as a hydrophilic filter into which cells of the blood do not penetrate. An external material in the blood may not be adsorbed onto the transreflective layer L1 according to shear stress caused by the blood flow.

The transreflective layer L1 may be formed at an end or an other end of the battery 3100 in consideration of types (artery or vein) of blood vessel and may be formed at a front end of a blood circulation.

[Battery to be Inserted into Living Body According to Another Modified Exemplary Embodiment of Seventh Exemplary Embodiment]

Figure 32:
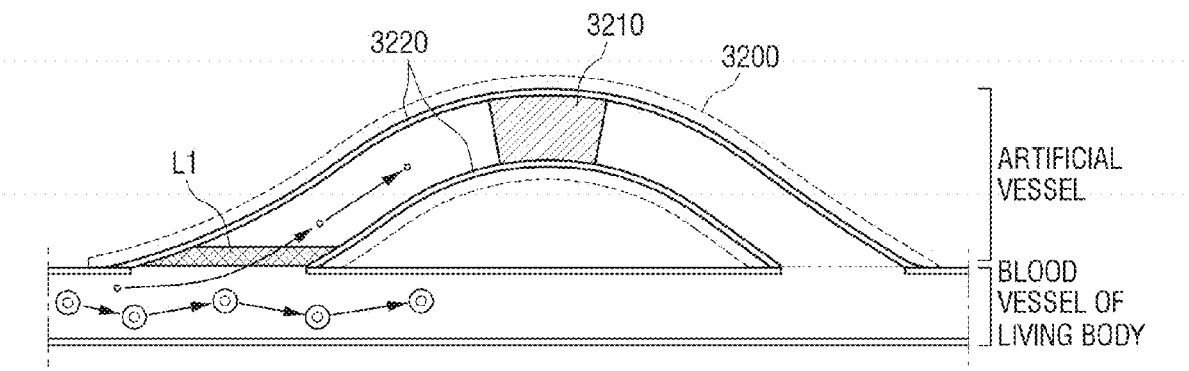
FIG. 32 is a view illustrating a tube-structured battery to be inserted into a living body according to another exemplary embodiment of the present general inventive concept.

FIG. 32 is a view illustrating a battery to be inserted into a living body according to another modified exemplary embodiment of the seventh exemplary embodiment of the present general inventive concept.

Referring to FIG. 32, a battery 3200 to be inserted into a living body is inserted into a part of an artificial vessel 3220, and a transreflective layer L1 is formed at an end of the artificial vessel 3220. The battery 3200 may perform the same operation as the battery 2200 of FIG. 22.

Differently from FIG. 32, the transreflective layer L1 may not be formed at the end of the artificial layer 3220 but may be formed at an end of the battery 3200.

A battery to be inserted into a living body and have various structures as described in the first through sixth exemplary embodiments may be applied as the battery 3200.

Repeated descriptions of the battery 3200 of FIG. 32 will be omitted hereinafter.

[Battery to be Inserted into Living Body According to Another Modified Exemplary Embodiment of Seventh Exemplary Embodiment]

Figure 33:
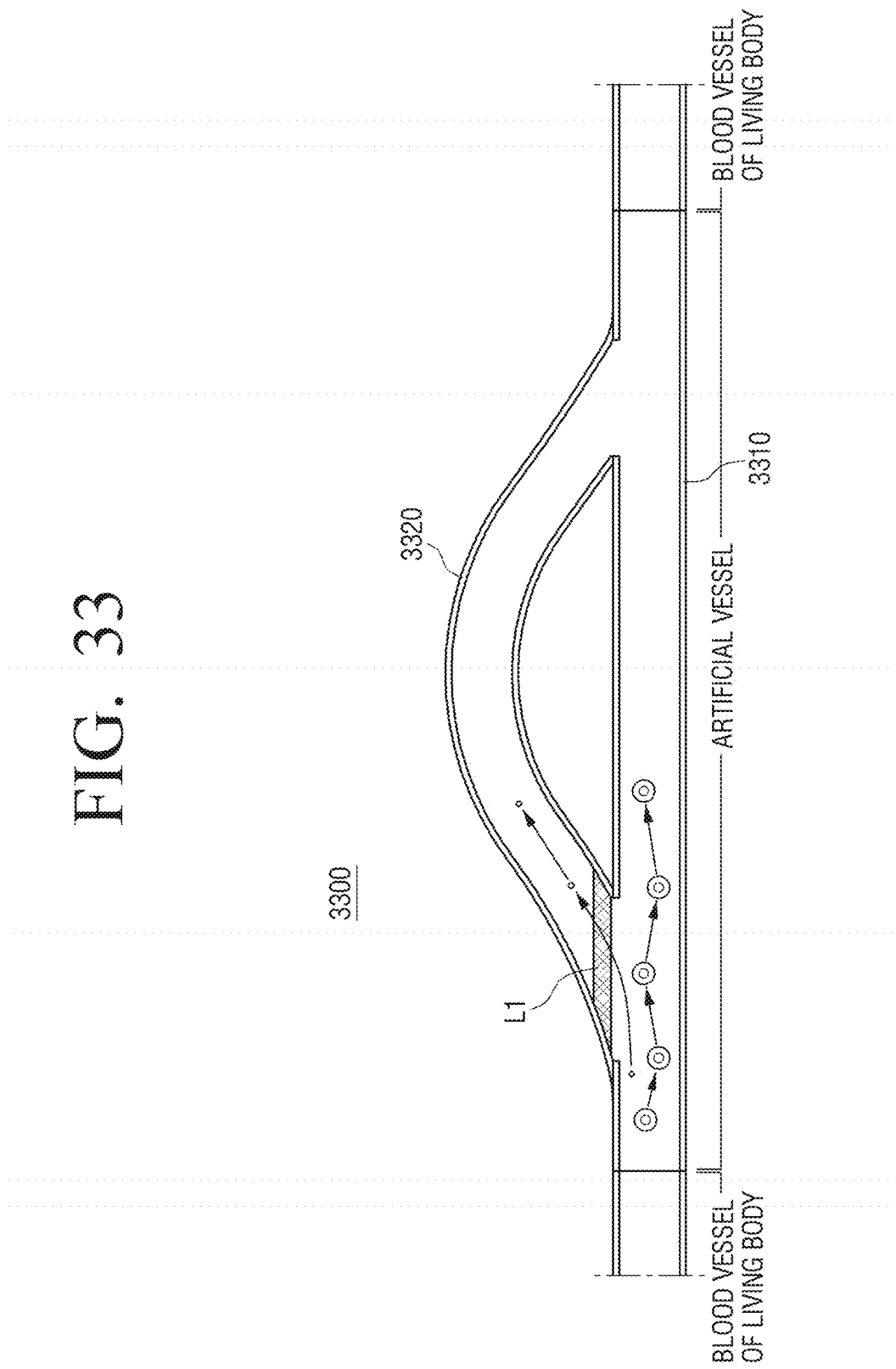
FIG. 33 is a view illustrating a tube-structured battery to be inserted into a living body according to another exemplary embodiment of the present general inventive concept.

FIG. 33 is a view illustrating a battery to be inserted into a living body according to another modified exemplary embodiment of the seventh exemplary embodiment of the present general inventive concept.

Referring to FIG. 33, a blood vessel of the living body and an artificial vessel 3300 are connected to each other, and the artificial vessel 3300 includes first and second artificial vessels 3310 and 3320.

The second artificial vessel 3320 is connected to the first artificial vessel 3310 in parallel. Therefore, the blood flowing into the first artificial vessel 3310 diverges into the first and second artificial vessels 3310 and 3320.

At least one of the first and second artificial vessels 3310 and 3320 may be realized as a battery (not shown) to be inserted into a living body. In this case, the battery may be a battery to be inserted into a living body and have various structures as described in the first through sixth exemplary embodiments.

Alternatively, a battery to be inserted into a living body may be installed in a part of at least one of the first and second artificial vessels 3310 and 3320. In this case, the battery (not shown) may be the battery to be inserted into the living body and have the various structures as described in the first through sixth exemplary embodiments.

However, in the artificial vessel 3300, the first and second artificial vessels 3310 and 3320 are connected to each other in parallel but are not limited thereto. A plurality of artificial vessels may be connected to one another in parallel.

The battery described in FIG. 33 may operate equally with the batteries of FIGS. 31 and 32, and thus repeated descriptions will be omitted hereinafter.

The contents related to the artificial vessel or the battery to be inserted into the living body shown in FIGS. 30 through 33 may be applied to the battery described in the first through sixth exemplary embodiments.

[Example of Structure of Transformer Circuit Part]

Figure 34:
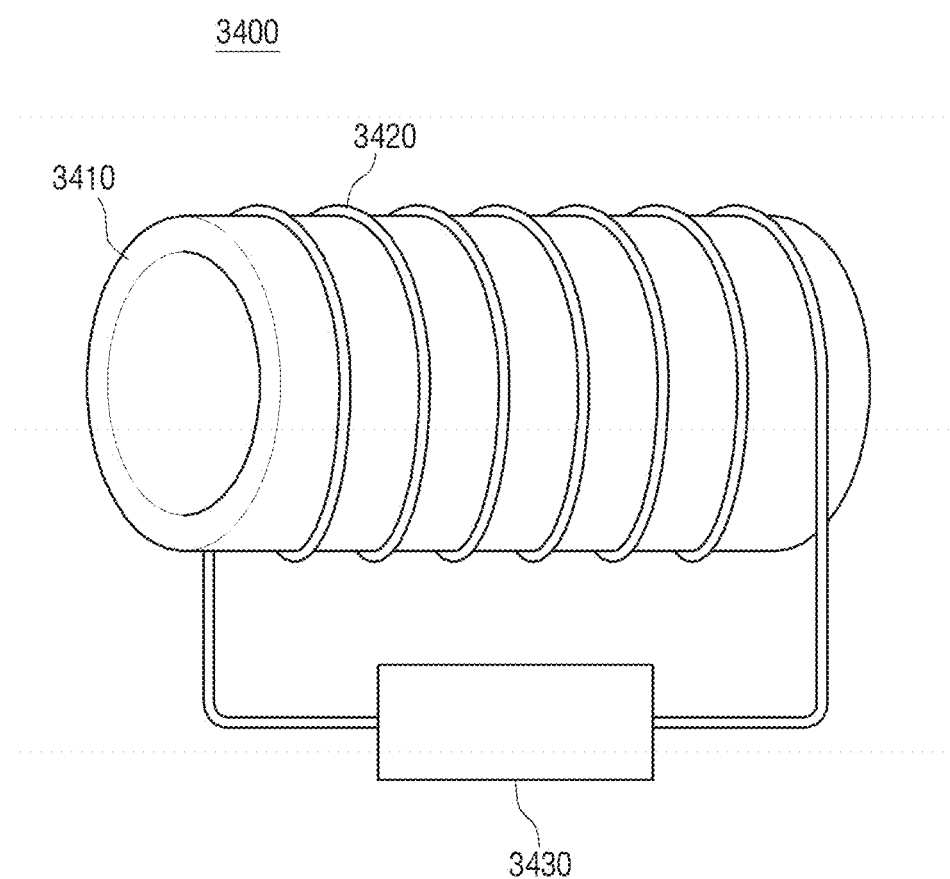
FIG. 34 is a view illustrating a transformer circuit unit according to an exemplary embodiment of the present general inventive concept.

FIG. 34 is a view illustrating a structure of a transformer circuit part according to an exemplary embodiment of the present general inventive concept.

In order to realize a transformer circuit part in a battery to be inserted into a living described in the first through seventh exemplary embodiments, various types of functional devices may be attached onto and packaged onto a substrate or various types of functional devices may be integrated on a chip. The transformer circuit part may be realized in a flat plate shape.

Since the battery to be inserted into the living body has a tube structure, a transformer circuit part 3400 may be realized as a coil which encloses an outer surface of the battery having the tube structure as shown in FIG. 34.

Referring to FIG. 34, the transformer circuit part 3400 includes a coil 3410, a ferromagnetic body 3420, and a controller 3430.

The coil 3410 forms a magnetic field if a current is applied. The ferromagnetic body 3410 has a tube structure whose both ends are opened and further increases the magnetic field formed by the coil 3410. The controller 3420 applies the current or generates a voltage for operating the transformer circuit part 3400.

The contents of the transformer circuit part 3400 related to FIG. 34 may be applied to the battery described in the first through seventh exemplary embodiments.

[Example of Biofuel Battery Part]

Figure 35:
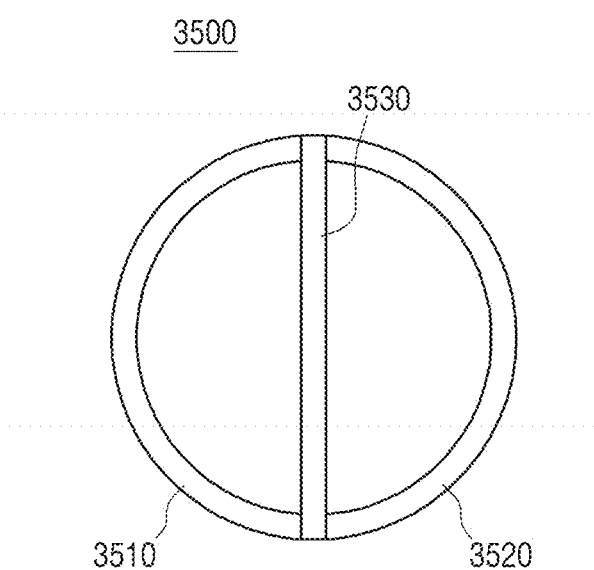
FIG. 35 is a view illustrating a structure of a biofuel battery part according to an exemplary embodiment of the present general inventive concept.

FIG. 35 is a view illustrating a biofuel battery part according to an exemplary embodiment of the present general inventive concept.

Referring to FIG. 35, a biofuel battery part 3500 includes a cathode part 3510, an anode part 3520, and a separator 3530.

The cathode part 3510 collects electrons from the blood flowing through an opening.

The anode part 3520 receives the collected electrons from the cathode part 3510.

The cathode part 3510 and the anode part 3520 may be formed of a material such as graphite felt, porous carbon, platinum, glasslike carbon, or the like.

The separator 3530 separates the cathode part 3510 and the anode part 3520 from each other on an inner side of the transformer circuit part (not shown). The separator 3530 may be formed of glass wool including stoma, glass bead, graphite felt, sand, or the like.

As will be described later with reference to FIG. 36, the biofuel battery part 3500 may include the cathode part 3510 and the anode part 3520 without the separator 3530.

Figure 36:
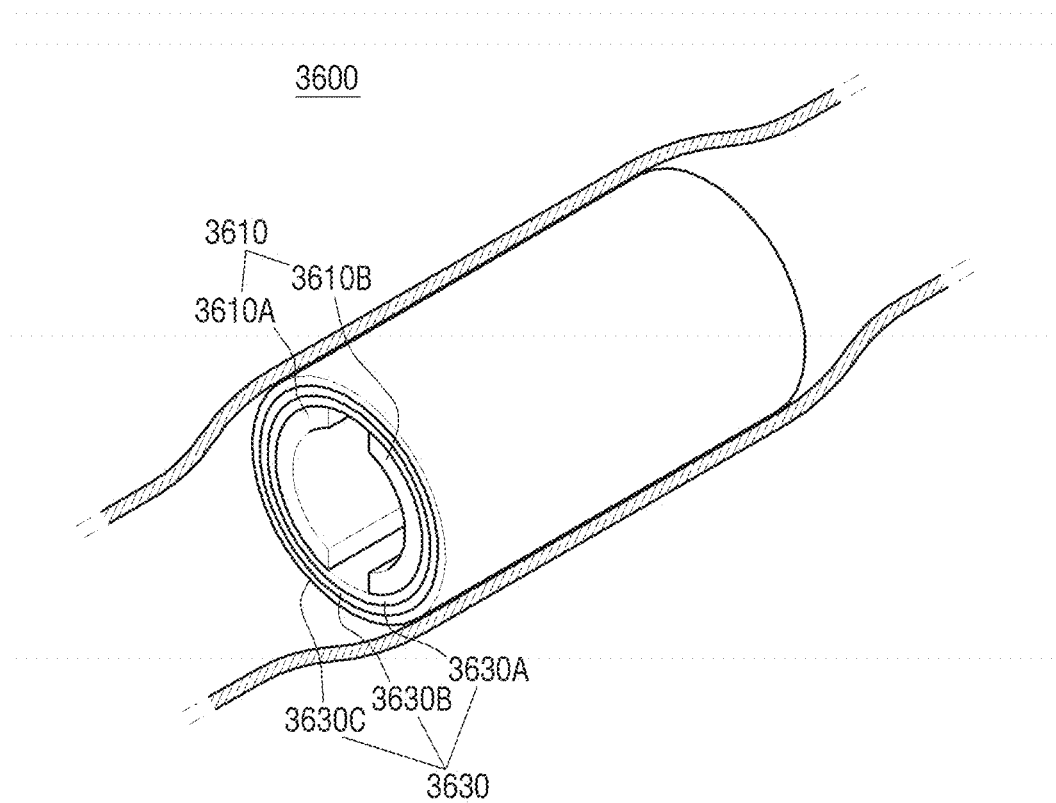
FIG. 36 is a view illustrating detailed structures of a biofuel battery part and a secondary battery part according to an exemplary embodiment of the present general inventive concept.

FIG. 36 is a view illustrating detailed structures of a biofuel battery part and a secondary battery part according to an exemplary embodiment of the present general inventive concept.

Referring to FIG. 36, a battery 3600 to be inserted into a living body includes a biofuel battery part 3610 and a secondary battery part 3630. For the descriptive convenience, a transformer circuit part is omitted. The biofuel battery part 3610 and the secondary battery part 3630 have tube structures.

The biofuel battery part 3610 has a structure in which an anode 3610A and a cathode 3610B separate from each other. However, if the anode 3610A and the cathode 3610B separate from each other, the biofuel battery part 3610 is not limited to the shown structure but may have various structures.

The secondary battery part 3630 includes a cathode 3630A, an electrolyte, and an anode 3630 which have tube structures. In detail, the secondary battery part 3630 has a structure in which the cathode 3630A, the electrolyte 3630B, and the anode 3630B sequentially enclose the biofuel battery part 3610. However, for the descriptive convenience, the description of a current collector constituting the secondary battery part 3630 will be omitted.

The contents related to the biofuel battery part 3610 and the secondary battery part 3630 of FIG. 36 may be applied to the batteries of FIGS. 14, 16, and 17 including a biofuel battery part and a secondary battery part having tube structures.

Figure 37:
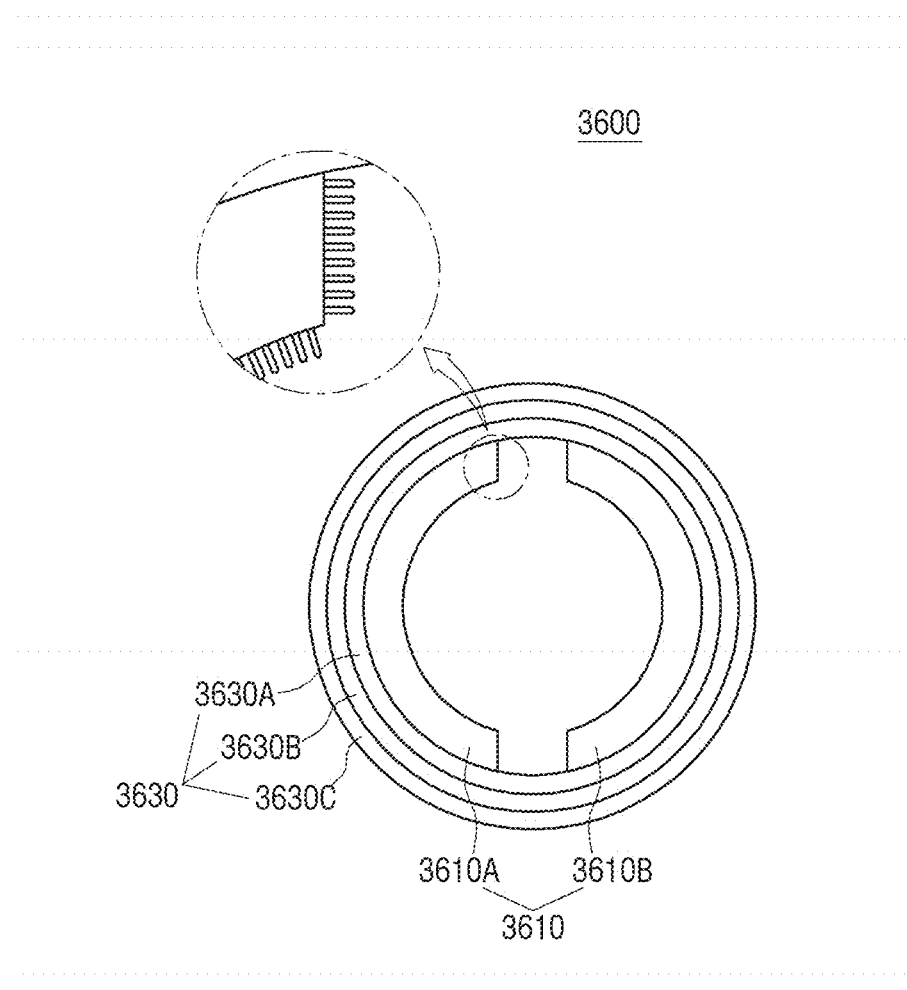
FIG. 37 is a view illustrating the biofuel battery part of FIG. 36 in detail.

FIG. 37 is a view illustrating the biofuel battery part of FIG. 36 in more detail.

Referring to FIG. 37, an area of the biofuel battery part 3610, through which the blood passes, is enclosed by a transreflective layer. Therefore, the biofuel battery part 3610 selectively passes only biofuel of the blood.

Figure 10:
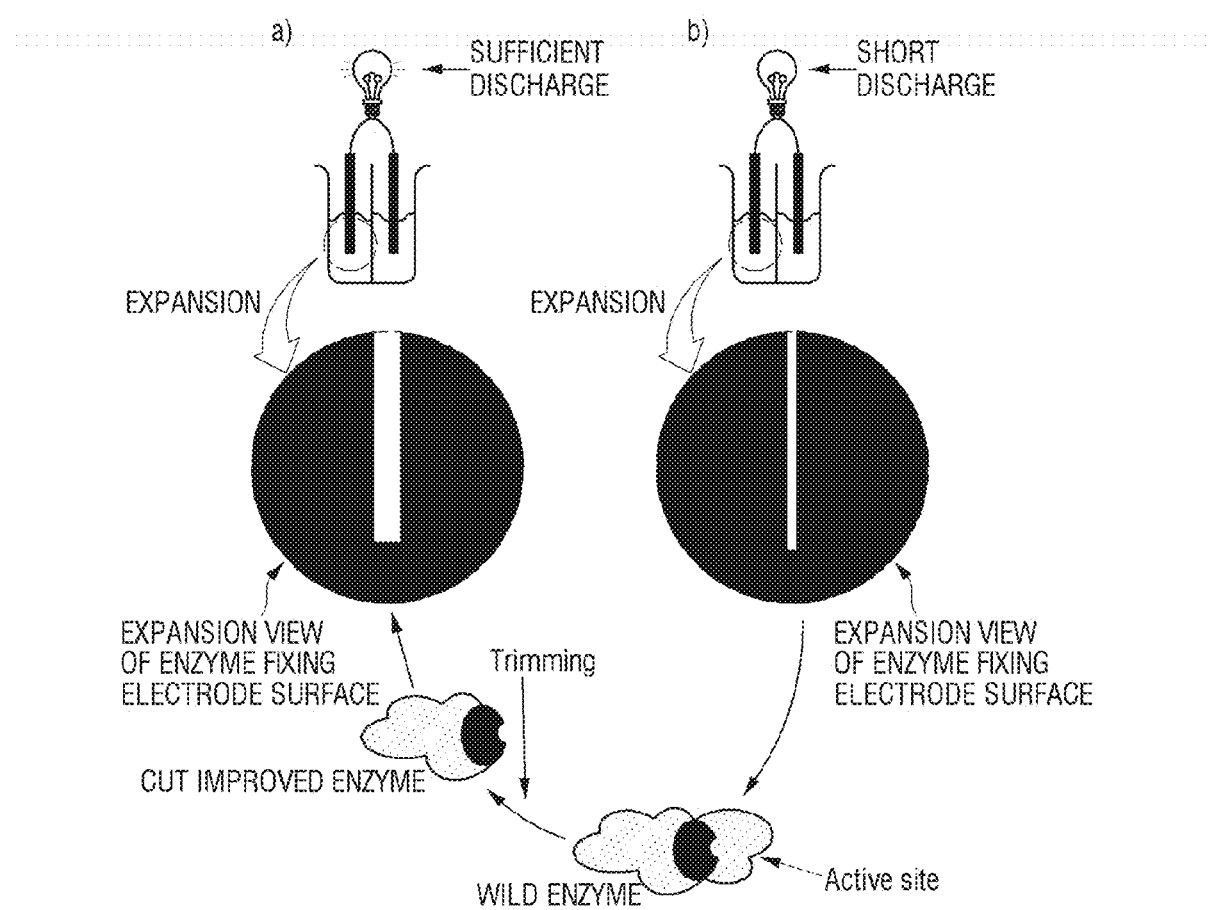
FIGS. 10 through 13 are views illustrating a method of improving enzyme constituting a fusion battery part to increase an electron transmission speed and a generated current density
Figure 11:
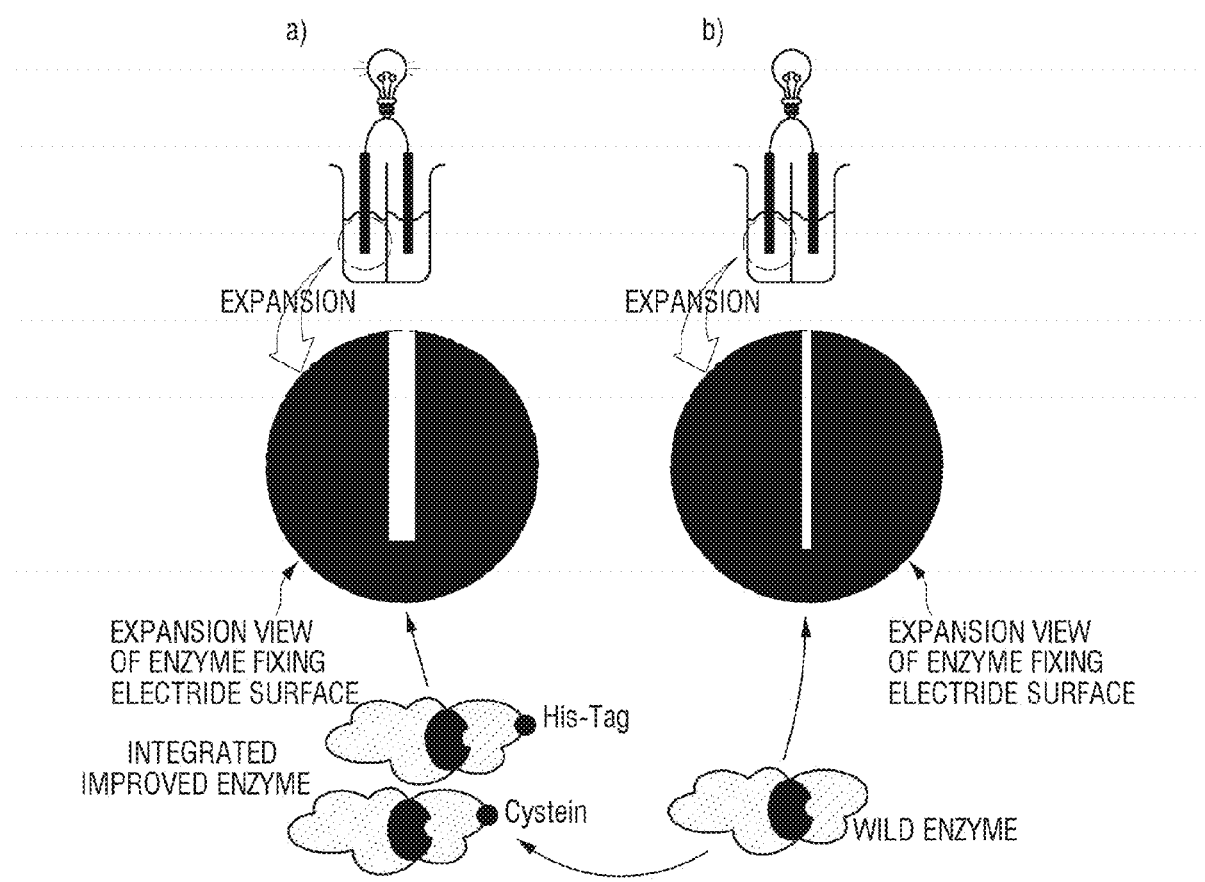

As shown in FIG. 37, a plurality of protrusions are formed on a surface of at least one of the anode 3610A and the cathode 3610 of the biofuel battery part 3610. An enzyme is fixed to the plurality of protrusions as shown in FIGS. 10 and 11.

Therefore, an area, in which the biofuel, such as glucose, having selectively passed through the transreflective layer enclosing the biofuel battery part 3610 reacts with an enzyme, may increase.

Differently from FIG. 37, the biofuel battery part 3610 may have a structure in which an enzyme is fixed to a carbon nanotube as shown in FIG. 8.

The contents related to the biofuel battery part 3610 of FIG. 37 may be applied to the battery to be inserted into the living body described in the first through seventh exemplary embodiments.

Figure 38:
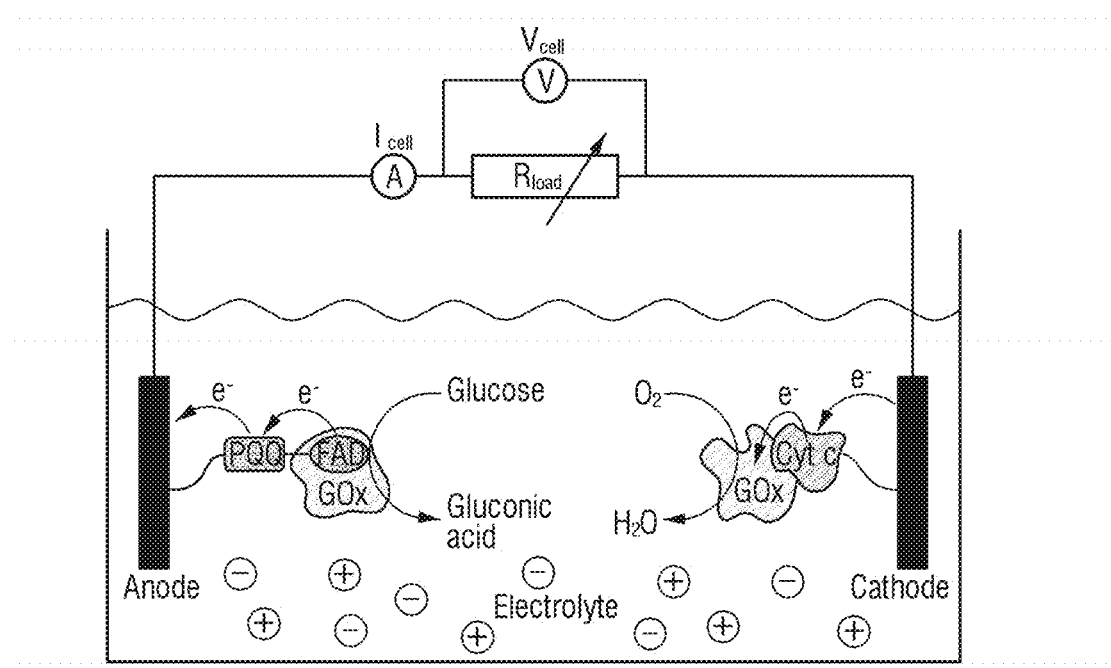
FIG. 38 is a view illustrating an operation of generating electric energy through a biofuel battery part.

FIG. 38 is a view illustrating an operation principle of generating electric energy from a biofuel battery part.

Glucose of the blood may be changed into a gluconic acid to discharge electrons, and the discharged electrons may be collected at an anode of the biofuel battery part. The electrons collected at the anode are transmitted to a cathode through an electric wire. The cathode returns at least one of cytochrome c and cytochrome oxidase to water by using the transmitted electrons. This process may be repeatedly performed to generate electric energy from the biofuel battery part.

The glucose is used as an example of the biofuel in FIG. 38 but is not limited thereto. The biofuel battery part does not include a separator in FIG. 38 but may include the separator.

The operation principle f generating the electric energy from the biofuel battery part related to 38 may be applied to the battery to be inserted into the living body described in the first through seventh exemplary embodiments.

In various exemplary embodiments of the present general inventive concept, various techniques of the semiconductor packaging field may be applied for a connection between a biofuel battery part and a secondary battery part, a connection between the biofuel battery part and a transformer circuit part, and a connection between the transformer circuit part and the secondary battery part.

For example, various techniques, such as a method of simply stacking elements to connect connection terminals of the elements to one another, a method of performing a thermal treatment after the above connection, a method of connecting the connection terminals of the elements to one another by using a wiring technique, a method of connecting the elements to one another by using minute wires, bead balls, connectors, etc., and a method of patterning connection lines of the elements, may be applied.

[Fixing Enzyme to Electrode of Biofuel Battery Part]

With reference to the descriptions related to FIG. 8, in order to fabricate the electrode 800 of the biofuel battery part 210, the nanoparticle seed 820 is formed of metal or the like on the current collector 810, the carbon nanotube 830 is grown, and the enzyme 840 is fixed to the carbon nanotube 830. In this case, a method of fixing the enzyme to the carbon nanotube 830 will be described in detail hereinafter. The method of fixing the enzyme to the electrode of the biofuel battery part may be applied to both a case where the electrode of the biofuel battery part is an anode and a case where the electrode of the biofuel battery part is a cathode.

Figure 39:
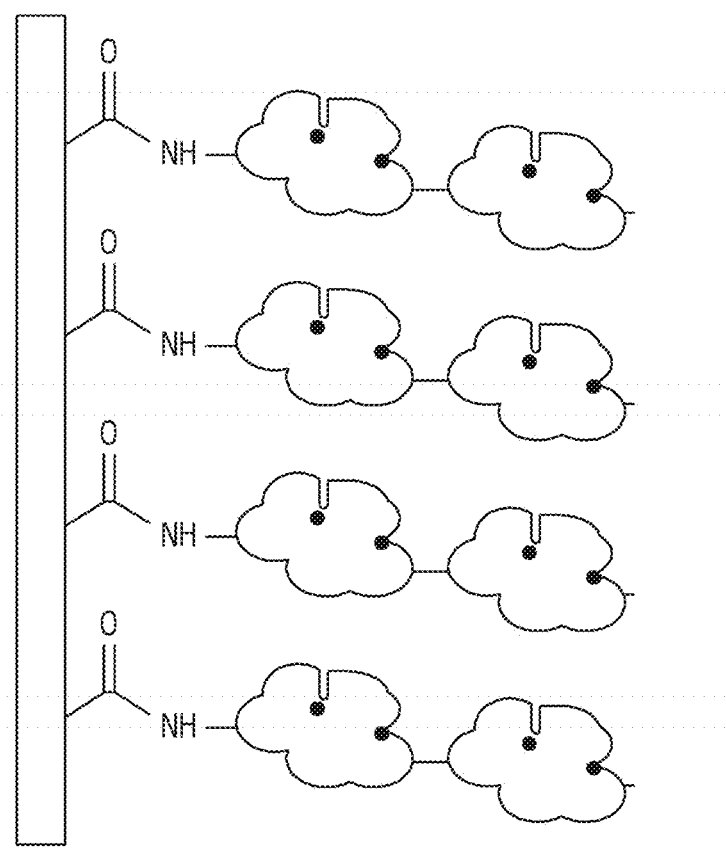
FIG. 39 is a view illustrating an electrode of an enzymatic biofuel battery according to an exemplary embodiment of the present general inventive concept.

FIG. 39 illustrates an electrode of an enzymatic fuel battery according to an exemplary embodiment of the present general inventive concept. Hereinafter, the electrode of the enzymatic fuel battery refers to an electrode of a biofuel battery part.

As shown in FIG. 39, an electrode of a biofuel battery according to the present general inventive concept includes: an electron conductor; a first enzymatic layer which includes an enzyme fixed to the electron conductor and an electron transfer medium; and a second enzymatic layer which includes an enzyme combined with the enzyme of the first enzymatic layer and an electron transfer medium. A substrate which particularly reacts to the enzymes is attached to active sites of the enzymes of the first and second enzymatic layers to mask the active sites of the enzymes.

The electron conductor is a material which conducts electrons and thus may be formed of a material having high electrical conductivity. In particular, an appropriate electron conductor includes carbonaceous materials, in detail, a carbon fiber, carbon paper, carbon black, carbon powder, a single walled carbon tube, a double walled carbon tube, and a carbon nanotube array.

According to an electrode according to an exemplary embodiment of the present general inventive concept, the electron conductor is a porous carbon material. The porous carbon material has conductivity and a high specific surface area in terms of porous characteristic. Therefore, an enzyme is highly loaded per unit area, and thus a reaction area increases. In detail, the porous carbon material is a carbon nanotube and includes a single walled carbon nanotube (SWCNT) or a multi walled carbon nanotube (MWCNT).

Figure 44:
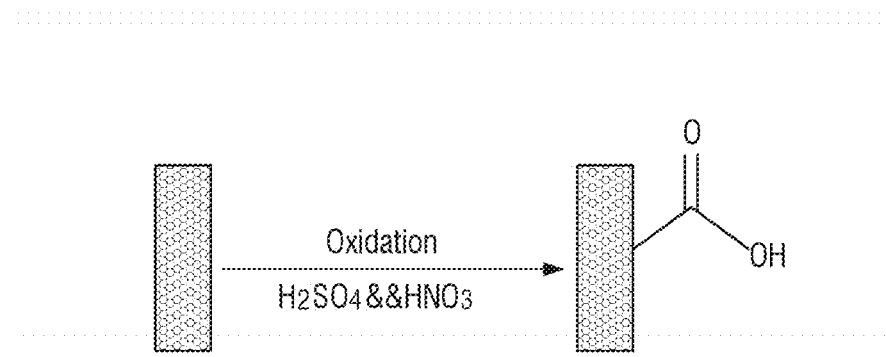
FIG. 44 is a schematic view illustrating a CNT modified mechanism.

The CNT used for the electrode of the enzymatic fuel battery according to the present general inventive concept is modified to introduce carboxyl (—COOH). A carbon material such as CNT has not reactivity and thus is not directly combined with protein enzyme. Therefore, in order to fix the enzyme, a function group is to be added to increase reactivity with the enzyme. A well-known ionic functionalizing method may be used to introduce carboxyl into CNT. In detail, a method of treating an acid solution including a mixture of nitride acid and sulfuric acid by volume of 1:3 is used (M. A. Hamon). FIG. 44 schematically illustrates a CNT reforming mechanism introducing carboxyl.

If carboxyl is introduced into CNT according to the above-described method, the carboxyl reacts with amino group of N-terminal of protein enzyme to fix enzyme through a amide combination.

Figure 45:
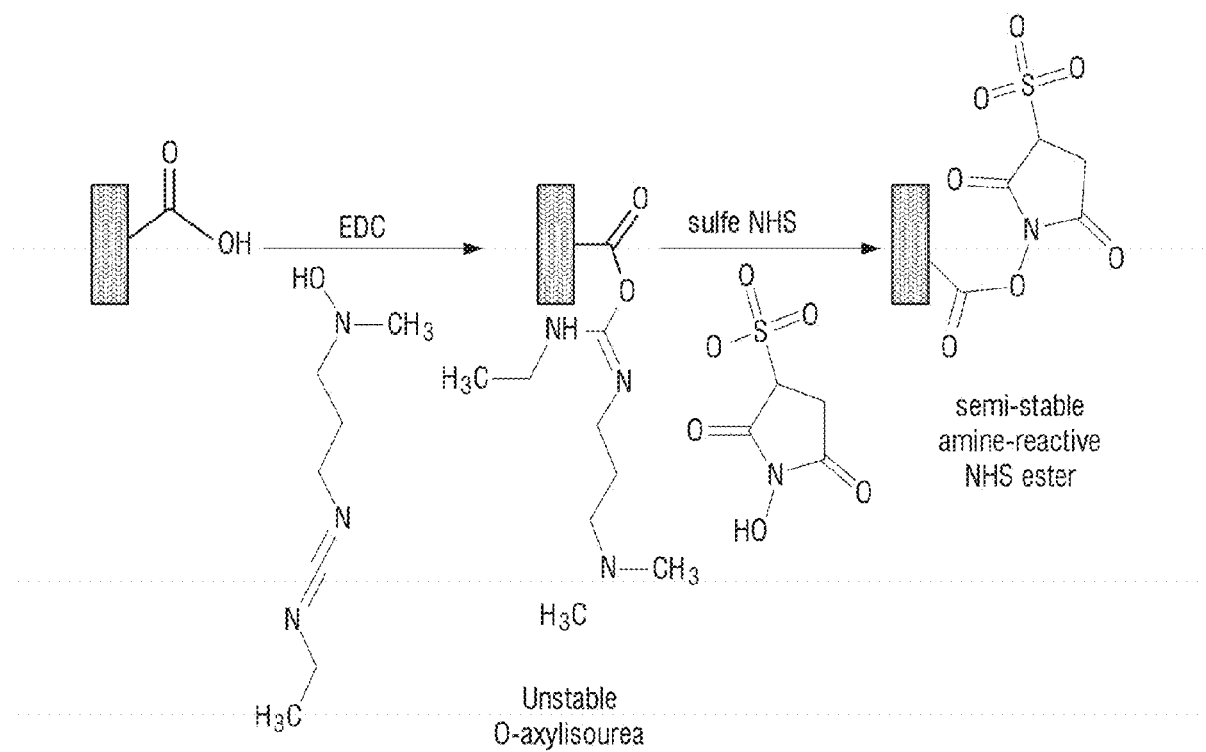
FIG. 45 is a view illustrating a mechanism of a mediated reaction using EDC and NHS.

A linker material may be used to increase reactivity of the amide combination between the carboxyl of the CNT and the amino group of the N-terminal of the enzyme. Examples of the linker material include N-ethyl-N'-(3-dimethylaminopropyl)-carbodiimide (EDC), dicyclohexylcarbodiimid (DCC), disisopropycarbodiimid) (DIC), etc. The reactivity may be induced by EDC. The reactivity may be inducted by a reaction using EDC and N-hydroxy-succinidide (NHS). FIG. 45 schematically illustrates a mechanism of a mediated reaction using EDC and NHS.

According to a detailed exemplary embodiment of the present general inventive concept, the electrode may be used as an anode which oxidizes a substrate to generate free electrons and supplies electrons to an electric circuit through an electron conductor. In the present general inventive concept, the anode refers to an electrode which includes oxidoreductase catalysing oxidation of the substrate. The oxidizing electrode supplies electrons to the electric circuit through the oxidization of the substrate.

The oxidoreductase refers to an enzyme which catalyses a transfer of electrons from a reductant, i.e., a hydrogen or electron donor, to an oxidant, i.e., a hydrogen or electron acceptor. The oxidoreductase may be referred to as a donor: acceptor oxidoreductase but is commonly referred to as a donor dehydrogenase or an acceptor reductase. In particular, if oxygen is an acceptor, the oxidoreductase is referred to as a donor oxidase.

According to an aspect of the present general inventive concept, the oxidoreductase of the oxidizing electrode may be any oxidoreductase which oxidizes a substrate to supply electrodes but is not limited thereto. Therefore, the oxidoreductase of the oxidizing electrode may be one or more selected from the group consisting of glucose oxidase, glucose dehydrogenase, alcohol dehydrogenase aldehyde dehydrogenase, CHCH dehydrogenase, lactate dehydrogenase, lactose dehydrogenase, pyruvate dehydrogenase, formate dehydrogenase, and formaldehyde dehydrogenase. A type of the enzyme may vary according to a type of substrate to be used as fuel of an enzymatic fuel battery. The substrate of the enzyme is an organic compound such as sugar, carbohydrate, organic acid, alcohol, fatty acid, hydrocarbon, ketone, aldehyde, amino acid, protein, and nucleic acid.

According to a detailed exemplary embodiment of the present general inventive concept, the oxidoreductase of the oxidizing electrode may be glucose oxidase. The glucose oxidase oxidizes glucose with gluconolactone and discharges electrons.

Also, the glucose oxidase is an electron transfer medium to which flavin adenine dinucleotide biomolecules are attached per enzyme 1 molecule in each active site of an enzyme.

The electron transfer medium is a compound which is used to transfer electrons generated through oxidization of a substrate to an electron conductor and accepts or provides electrons. In the present general inventive concept, a cofactor of an enzyme may be used as the electron transfer medium may be used. The cofactor may have an oxidative form for accepting electrons to form a reduced form, and the reduced form may provide electrons to generate an oxidative form. The cofactor used as the electron transfer medium is diffused or inserted into a fixed enzyme. A cofactor (FAD/ or $FADH_2$), such as nicotinamide adenine dinucleotide phosphate (NADP), nicotinamide adenine dinucleotide (NAD), flavin adenine dinucleotide (FAD), or the like, may be used as an electron transfer medium. According to an exemplary embodiment of the present general inventive concept, if the fixed enzyme is glucose oxidase, the electron transfer medium is FAD based on the environment of an organism and may exist as FAD+ or $FADH_2$ in the enzyme. As described above, in the FAD, two molecules are attached around an active site of the glucose oxidase. In the case of NADP or NAD, the cofactor is to be added when fabricating the electrode of the enzymatic biofuel battery. However, the case of FAD is attached to a main enzyme such as glucose oxidase in a natural state. Therefore, when fabricating an electrode according to the present general inventive concept, a process of adding FAD to glucose oxidase is not required. Glucose oxidase used in an exemplary embodiment which will be described hereinafter is a wild enzyme which is originated from *aspergillus niger* which is mold and to which FAD is attached and is on the market (product by SIGMA-ALDRICH company).

Figure 46:
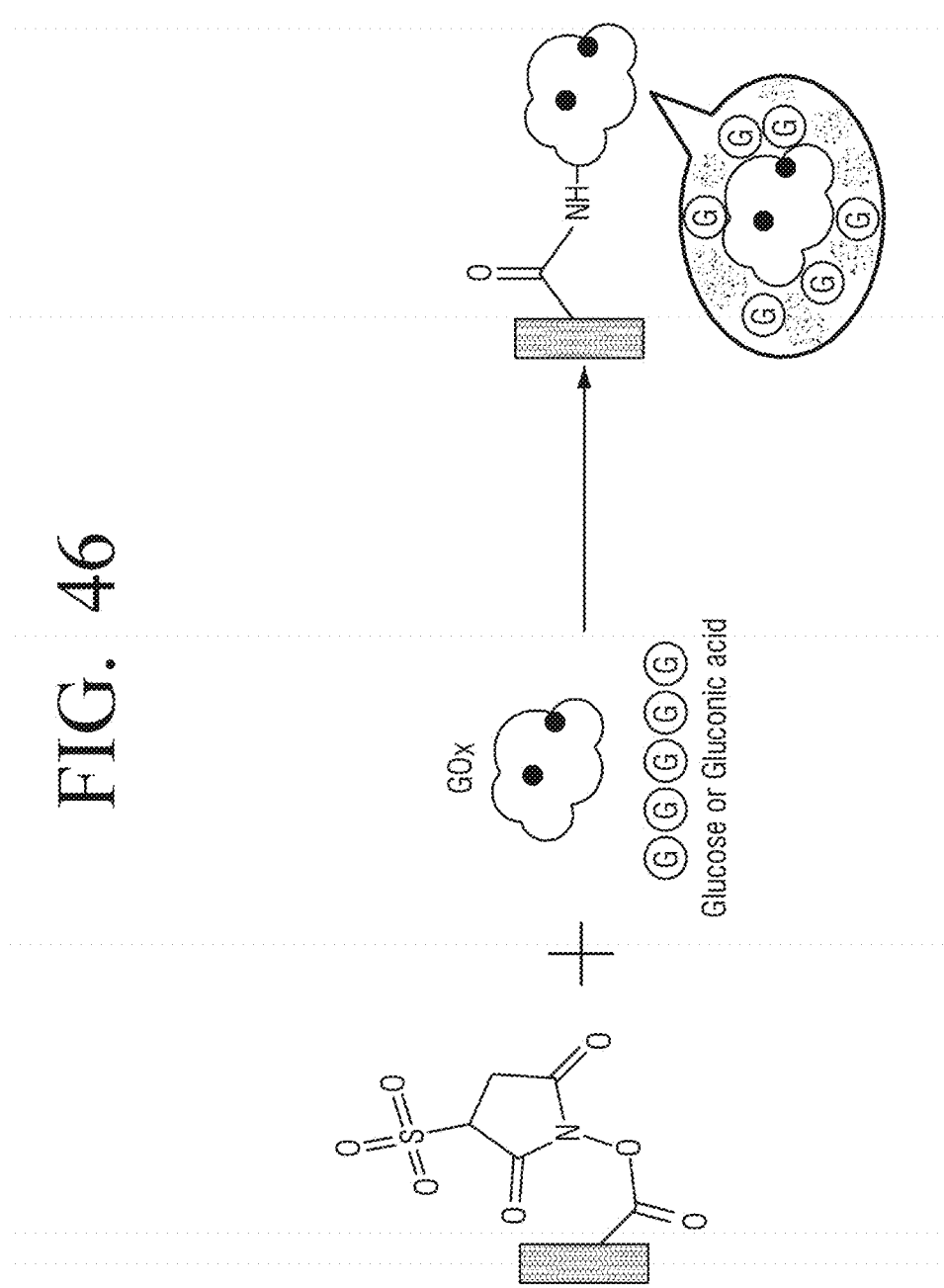
FIG. 46 is a view illustrating a reaction mechanism for fixing a first enzymatic layer in an electronic conductor.

In the electrode of the enzymatic fuel battery according to the present general inventive concept, an enzyme fixed to an electron conductor is formed of a plurality of dual or enzymatic layers. In the present general inventive concept, the enzyme combined with the electron conductor is referred to as a first enzyme, and an enzymatic layer formed of the first enzyme is referred to as a first enzymatic layer. The first enzyme is the above-mentioned oxidase. In detail, the first enzyme may be a glucose enzyme. The first enzyme of the first enzymatic layer may be fixed through a amide combination between an amino acid of an N-terminal of the first enzyme and carboxyl induced into the electron conductor. FIG. 46 schematically illustrates a reaction mechanism of fixing a first enzymatic layer to an electron conductor.

Fixing of the first enzyme is induced by a reforming reaction using EDC and NHS together to increase a reactivity of the amide combination as described above.

In an electrode of a fuel battery according to the present general inventive concept, a second enzymatic layer is combined with the first enzymatic layer. The second enzymatic layer is an enzymatic layer including a second enzyme combined with the first enzyme of the first enzymatic layer. The enzyme may be the oxidizing enzyme. The second enzyme may be equal to or different from the first enzyme. However, the second enzyme may perform the same function as the first enzyme and thus may be equal to the first enzyme.

Figure 47:
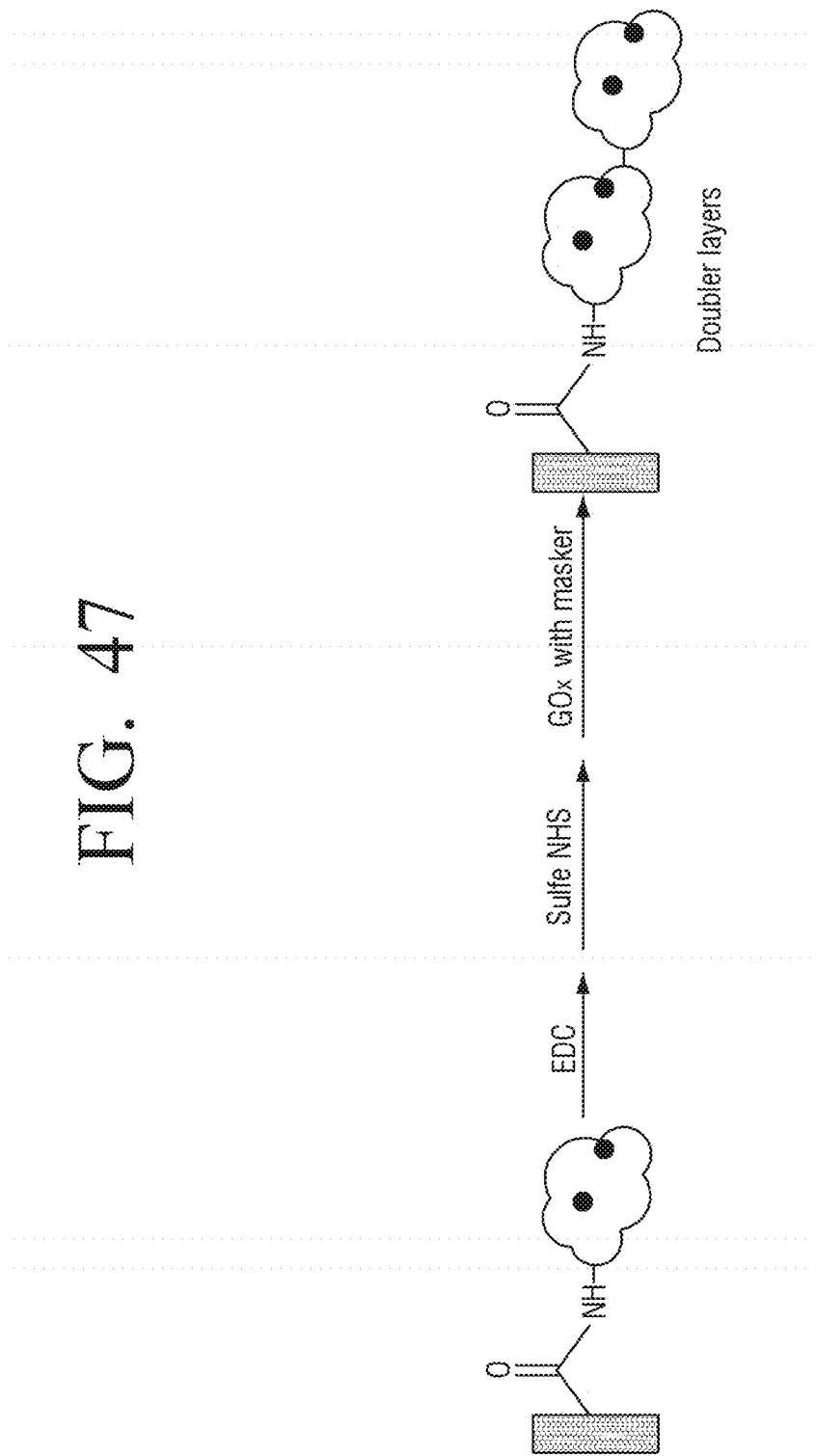
FIG. 47 is a schematic view illustrating a reaction mechanism for forming a second enzymatic layer.

A method of forming the second enzymatic layer will now be described. The electrode having the first enzymatic layer is treated with EDC and NHs to form an intermediate in which carboxyl of the first enzyme is activated. Here, if the second enzyme is added, the amide combination between the activated carboxyl of the intermediate of the first enzyme and the amino acid of the second enzyme is formed. FIG. 47 illustrates the mechanism.

In an electrode according to the present general inventive concept, a dual enzymatic layer as described above is formed in an electron conductor. Therefore, an amount of an enzyme loaded per unit area is increased more than in a well-known electrode. As a result, an amount of power generated per unit area of a battery is increased.

Figure 40:
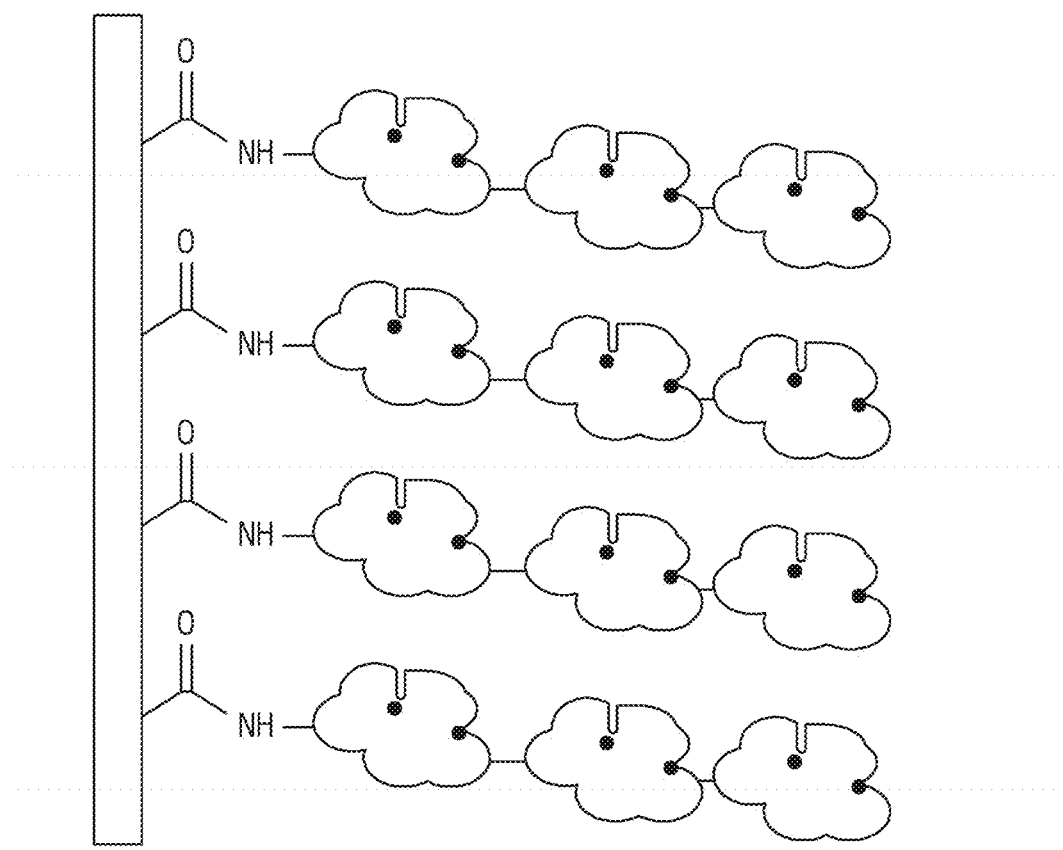
FIG. 40 is a schematic view illustrating an electrode of a biofuel battery having a three-layered enzymatic layer according to another exemplary embodiment of the present general inventive concept.

The detailed method is not described, a plurality of triple or more enzymatic layers may be formed by using a method of combining an enzyme and an enzyme as described above (refer to FIG. 40). In an electrode according to an exemplary embodiment of the present general inventive concept, if a glucose oxidate is used, the substrate is glucose.

Before the first enzyme of the first enzymatic layer is fixed to the electrode, a substrate particularly reacting with the enzyme is attached to an active site of each enzyme to mask the active site. An electron conductor used in an electrode according to the present general inventive concept generates carboxyl and easily reacts with an amino group existing in an active site of an enzyme. If the amino group of the active site of the enzyme reacts with and is combined with the carboxyl of the electron conductor, oxidization efficiency of a fuel substrate is deteriorated. Therefore, in order to prevent this, when the enzyme is fixed to the electron conductor, a masking material is to protect an active site so that the amino group of the active site of the enzyme does not react with carboxyl of CNT.

The masking material is to have a high combination ability with the active site and is to separate from the active site after a predetermine time in order to generate electrons through oxidization of glucose. A material appropriately selected according to a type of an enzyme may be used as the masking material. If the fixed enzyme is a glucose oxidase, glucose or gluconic acid which is attachable to the active site of the glucose oxidase may be used.

Figure 41:
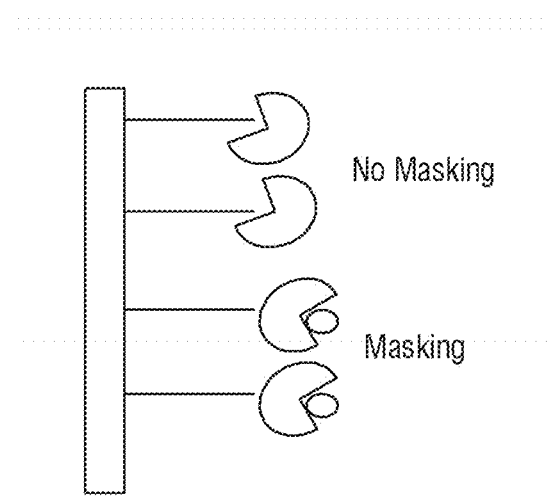
FIG. 41 is a schematic view illustrating orientations of an active site of enzyme fixed in an electrode before and after masking, according to an exemplary embodiment of the present general inventive concept.

If the active site of the enzyme is masked, the active site of the enzyme is oriented opposite to the electron conductor combined with the enzyme. Therefore, enzymes of the first enzymatic layer may be prevented from being directly combined with CNT of the electron conductor in order to solve a problem of deteriorating oxidization efficiency of the enzyme (refer to FIG. 41).

Like the first enzyme, the second enzyme masks the active site thereof with the substrate to improve a performance of the electrode. As will be described in detail in an exemplary embodiment below, the masking of the second enzyme may be performed simultaneously in a process of forming the second enzymatic layer through a combination with the first enzyme. A masking material of the second enzyme may be particularly combined with the second enzyme and may separate from the second enzyme after a predetermined time. In an electrode according to another exemplary embodiment of the present general inventive concept, a second enzyme is a glucose oxidase. Therefore, a masking material of a second enzyme may be glucose. Alternatively, instead of the glucose, a gluconic acid may be used along with the glucose.

A schematic method of fabricating an electrode of a fuel battery according to the present general inventive concept includes: reforming a carbon material, which is an electron conductor, to introduce carboxyl into the carbon material; fixing a first enzyme to the electron conductor to form a first enzymatic layer; and combining a second enzyme with the first enzyme to form an enzymatic layer.

Before fixing the first enzyme to the electron conductor to form the first enzymatic layer and combining the second enzyme with the first enzyme to form the enzymatic layer, a substrate may be attached to active sites of the first and second enzymes to mask the active sites.

When fixing the first enzyme to the electron conductor to form the first enzymatic layer, the reformed electron conductor and the first enzyme may be induced into a linker material in order to improve a reactivity between the reformed electron conductor and the first enzyme.

As described above in detail, in an electrode of an enzymatic fuel battery, an oxidoreductase is fixed as a dual or more layer to an electron conductor. However, those skilled in the art may easily create that an enzyme, such as bilirubin oxidase, peroxidase, or laccase, capable of reducing a substrate may be fixed as a dual or more layer to an electron conductor to be used as a cathode.

Exemplary Embodiment of Fixing Enzyme

An electrode of a fuel battery and a method of fabricating the electrode according to an exemplary embodiment of the present general inventive concept will now be described in detail.

Exemplary Embodiment 1 of Fixing Enzyme (1) Reformation of CNT-Introduction of Carboxyl MWCNT of 10 mg is put into an acid solution of 4 ml (sulfuric acid:nitric acid=3:1, volumetric ratio), gets ultrasonic waves for 3 hours in an ultrasonic cleaner, passes through a 0.2 μl filter, and is collected. This is cleaned with distilled water of 20 ml three times and then dried at a temperature of 60° C. to generate carboxyl.

(2) Attaching of Linker Material

Distilled water of 20 ml is put into MWCNT collected in the step 1, and then ultrasonic waves are applied for 10 minutes in the ultrasonic cleaner in order to improve a dispersion degree. The MWCNT is agitated in a magnetic agitator, an MES buffer (pH=6.1) is added (final concentration, 50 mM), NHS is added (final concentration, 1 mg/mL), and EDC is added (final concentration, 1 mg/ml). The mixture is agitated for 30 minutes at a room temperature, passes through a 0.2 μm filter, and is cleaned with distilled water three times to obtain MWCNT to which an amine-reactive NHS ester is added.

(3) Forming of First Enzymatic Layer and Masking of First Enzyme

Figure 43:
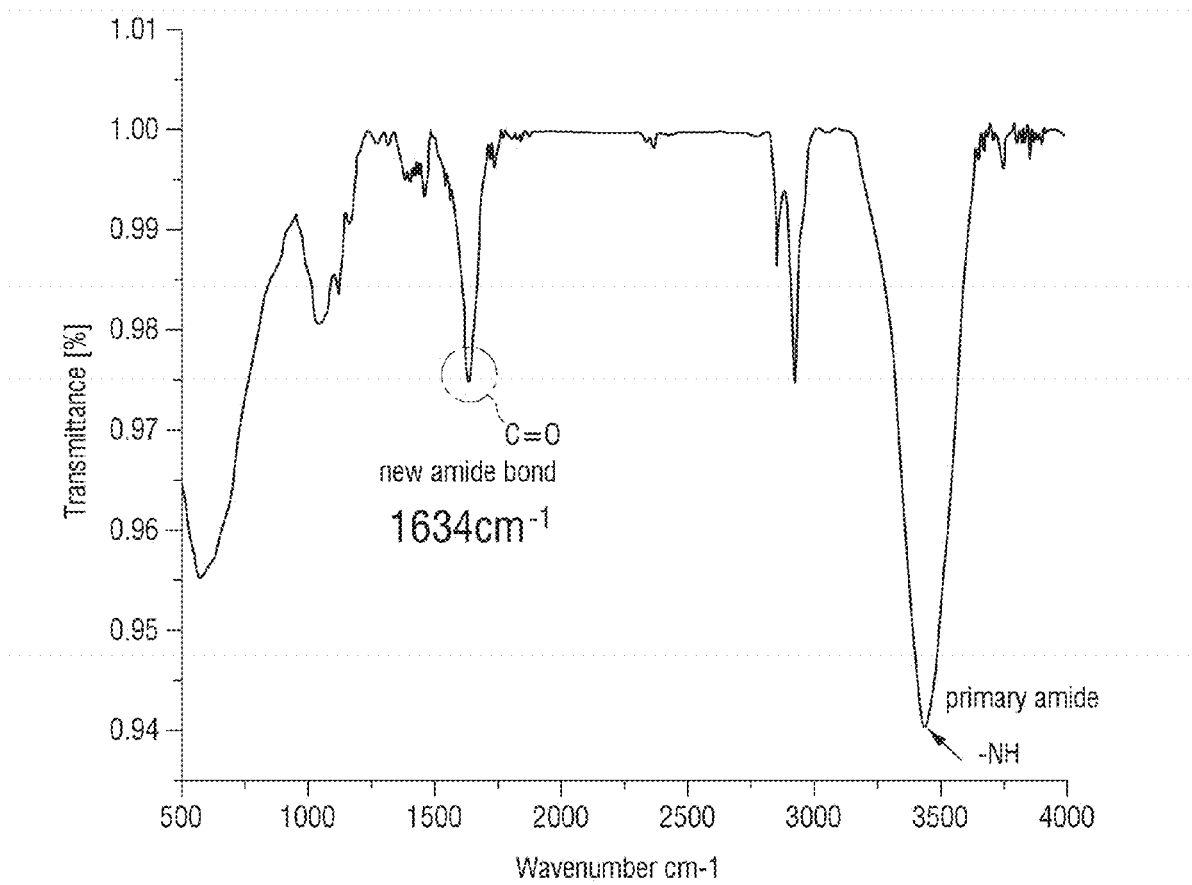
FIG. 43 is a FT-IR graph illustrating a glucose oxidizing enzyme fixed in an MWCNT.

Glucose oxidase of 30 mg is added into glucose solution or gluconic acid solution of 30 ml having saturated concentration of 3M and then is agitated for 30 minutes at a room temperature. The glucose oxidase is G6125 (product by Sigma-Aldrich) on the market, is a wild enzyme originated from *aspergillus niger*, and includes FAD of 2 molecules which is added per enzyme 1 molecule. In this process, an active site of the glucose oxidase is saturated in glucose or gluconic acid. The MWCNT to which the linker collected in the step 2 is added is added and then agitated for 3 hours at a room temperature. This passes through 0.2 μm filter and is cleaned with distilled water three times to obtain the MWCNT to which the glucose oxidase is added. As shown in FIG. 43, it is checked through FT-IR that glucose oxidase is fixed to MWCNT.

(4) Forming of Second Enzymatic Layer and Masking of Second Enzyme

MWCNT to which the glucose oxidase collected in the third step is fixed is put into distilled water of 20 ml, is agitated in a magnetic agitator, and an MES buffer (pH 6.1) (final concentration, 50 mM), NHS (final concentration 1 mg/ml), and EDC (final concentration, 1 mg/ml) are added. The mixture is agitated for 30 minutes at a room temperature, passes through 0.2 μm filter, and is cleaned with distilled water three times. This is added to a glucose solution of saturated concentration of 3M or a gluconic acid solution of 30 ml to which glucose oxidase (G6125 by Sigma-Aldrich) of 30 mg is added and then is agitated for 3 hours at a room temperature. In this process, a newly introduced glucose oxidase newly is combined with a single layered glucose oxidase to obtain MWCNT with which a multilayered glucose oxidase is combined. Also, an active site of the glucose oxidase is saturated in glucose or glucose acid.

Comparison Example 1 of Fixing of Enzyme

MWCNT to which amine-reactive NHS ester is added is obtained according to the same method as the first exemplary embodiment of fixing the enzyme. The MWCNT to which the amine-reactive NHS ester (G6125 by Sigma-Aldrich) is added is added to solution of 30 ml including glucose oxidase of 30 mg and then agitated for 3 hours at a room temperature. This passes through 0.2 μm filter and is cleaned with distilled water three times to obtain MWCNT to which glucose oxidase is attached.

Comparison Example 2 of Fixing Enzyme

MWCNT to which glucose oxidase is attached is obtained according to the same method as the comparison example 1. The MWCNT is put into distilled water of 20 ml, is agitated in a magnetic agitator, and an MES buffer (pH 6.1) (final concentration, 50 mM), NHS (final concentration 1 mg/ml), and EDC (final concentration 1 mg/ml) are added. The mixture is agitated for 30 minutes at a room temperature, passes through 0.2 μm filter, and is cleaned with distilled water three times. This is put into solution of 30 ml including glucose oxidase (G6125 by Sigma-Aldrich) of 30 mg and agitated for 3 hours at a room temperature. Therefore, MWCNT which which a multilayered glucose oxidase is combined is obtained. An oxidase of each layer does not perform a masking process.

Comparison Example 3 of Fixing Enzyme

Only the steps (1) through (3) of the exemplary embodiment 1 of fixing the enzyme are performed to obtain the MWCNT with which the single layered glucose oxidase is combined.

Comparison Test of Electric Characteristic of Enzymatic Electrode According to Exemplary Embodiment 1 of Fixing Enzyme and Comparison Examples 1 Through 3 of Fixing Enzyme A surface of a gold electrode is rubbed with sandpaper, cleaned with distilled water, and attached on a surface of a MWCNT electrode to which glucose oxidase collected in the exemplary embodiment 1 and the comparison examples 1 through 3 is fixed and which is cleaned by using silver/epoxy resin of about 1 mg. The electrode is dried for 1 hour at a room temperature in a vacuum oven, and the surface of the electrode is covered with a dialysis membrane (MW cutoff=12, 000-14,000) and fixed with an O-ring. A current amount which is generated with changes in a voltage at a room temperature is measured by using a potentiostat (CH instrument). An electrode cell is filled with a solution of 6 mM in which KCL of 20 mM and glucose of 10 mM are added to a potassium phosphate butter (pH 0.7) of 100 mM and KCL of 20 mM, and then three electrodes are immersed into the solution.

One of four types of enzymatic electrodes of the exemplary embodiment 1 and the comparison examples 1 through 3 is used as a working electrode, a counter electrode is formed of platinum wire, and a reference electrode is formed of Ag/AgCl. A scan speed is 50 mV/s.

Test Result

Figure 42:
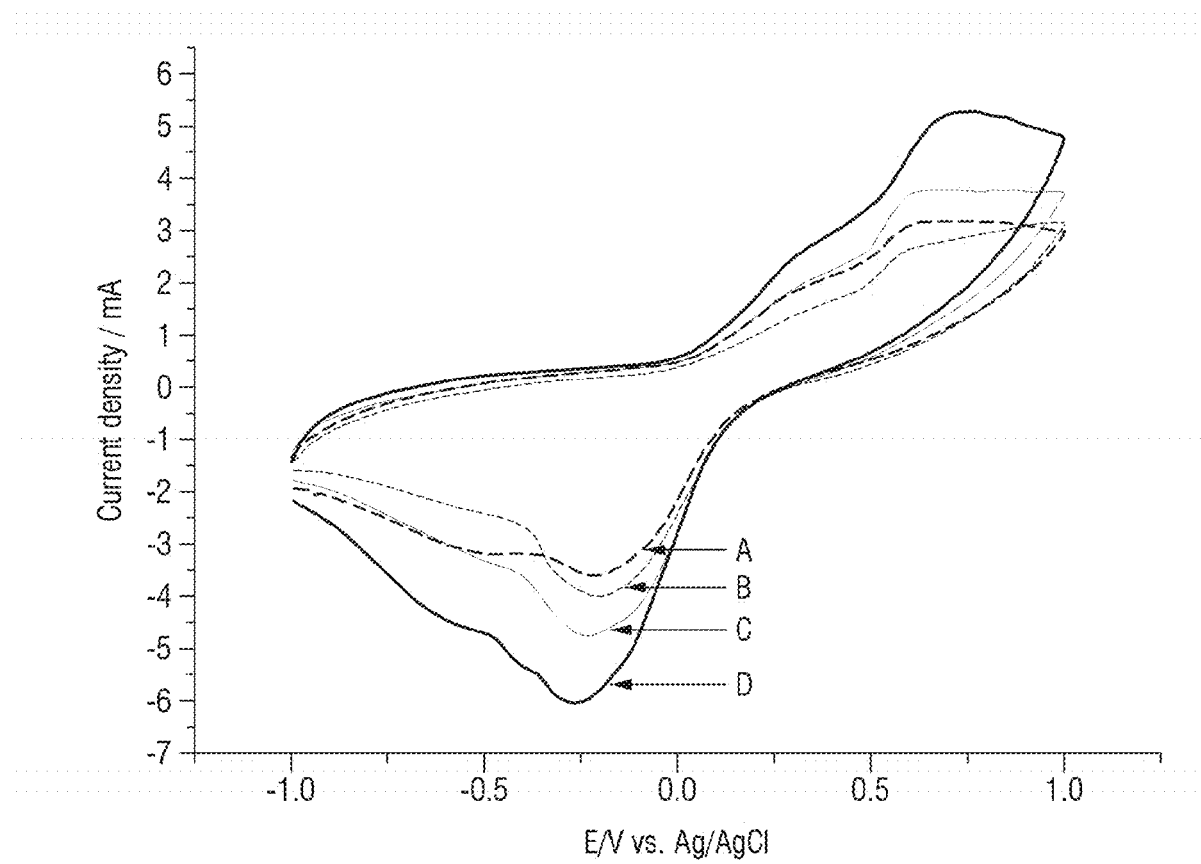
FIG. 42 is a graph illustrating an electrochemical performance of an electrode of a enzymatic biofuel battery by using a glucose oxidation, i.e., a current density with respect to changes in a voltage, according to an exemplary embodiment of the present general inventive concept.

FIG. 42 is a graph illustrating four cyclic volt-ammogram respectively the above electrodes. As shown in FIG. 42, a generated current peak appears between 300 mV and 370 mV, and this denotes a redox potential of $PDA/FDAH_2$. As this value is great, an amount of electron (electricity) increases per unit area and unit time, thereby increasing an electrode performance. Values of electrodes fabricated by the above four methods (of the exemplary embodiment 1 and the comparison examples 1 through 3) are compared with one another. In the case of electrodes to which single layered are attached, electrodes fabricated by fixing enzymes through masking show higher numerical values. According to this method, an electrode of the exemplary embodiment 1 of fixing the multi-layered enzyme shows the highest numerical value compared to an electrodes of the comparison examples 1 through 3. According to the present result, an enzyme fabricating method suggested in the present general inventive concept is much higher than an existing suggested method.

An electrode of an enzymatic fuel battery according to the present general inventive concept has an effect of increasing an amount of power generated with an increase in a loaded amount of enzyme per unit area of the electrode caused by fixing an enzyme as a multilayer. Also, the electrode has an effect of masking an active site of the enzyme in a fixing step to increase a reactivity between the fixed enzyme and a substrate in order to increase efficiency of the enzymatic fuel battery.

[Treating Toxicity of Biofuel Battery Part]

Hereinafter, a method of treating toxicity of a carbon nanotube of a biofuel battery aprt contacting the blood or a living body in consideration of biocompatibility of a battery to be inserted into the living body will be described. However, the toxicity treating method is not limited to the biofuel battery part but may applied to all of the battery exposable to the living body or the blood or an artificial vessel and elements. For the descriptive convenience, the toxicity treating method will be divided into a first toxicity treatment, a second toxicity treatment, and a third toxicity treatment.

[First Toxicity Treatment]

The present general inventive concept provides a method of fabricating a dispersible carbon nanotube, including: (i) mixing a carbon nanotube with a strong acid solvent to introduce a functional group including oxygen onto a surface of the carbon nanotube; (ii) treating the carbon nanotube in the solvent with ultrasonic waves; and (iii) consecutively repeating the two steps.

The carbon nanotube used in the present general inventive concept refers to a carbon material which has a tube shape formed through rolling of a hive-shaped flat plate type carbon tube formed through a combination between one carbon atom and three carbon atoms, a diameter between 1 nm and 100 nm, and a high aspect ratio having a length between tens of nm and dozens of μm. The carbon nano tube includes several types of carbon nanotubes and is classified into a multi-walled nanotube (MWCNT) formed of two or more walls according to the number of walls enclosing a longitudinal direction on its axis and a single-walled nanotube (SWCNT) formed of only one wall. The carbon nanotube include all these types in the present general inventive concept but may be a single-walled carbon nanotube. A diameter of a carbon nanotube useable in the present general inventive concept may be between 1 nm and 30 nm but may be between 1 nm and 20 nm, i.e., between 1 nm and 5 nm.

The term "strong acid solvent" used in the present general inventive concept includes a sulfuric acid, a nitric acid, a hydrochloric acid, or a mixture of one or more thereof and may be a mixture of a sulfuric acid and a nitric acid at a predetermined ratio.

The term "functional group including oxygen" used in the present general inventive concept may be any functional group which includes oxygen and is for functionalizing. The functional group may a functional group including a carbonyl group (—C=O), hydroxyl group (—OH), or a carboxyl group (—COOH). The functional group may be a carboxyl group required in a process of loading various types of drugs.

The step (i) of the fabricating method of the present general inventive concept may be a step of mixing the carbon nanotube with the strong acid solvent to chemically oxidize the functional group including the oxygen on a tip part and a surface of the carbon nanotube in order to introduce a functional group such as —C=O, —COOH, —OH, or the like. Here, a fundamental force between the carbon nanotube and water molecules increases in the solvent through this surface functionalization, the carbon nanotube is charged with negative electricity to generate an electrostatic repulsive force. Therefore, van der Waals force between carbon nanotubes is overcome to obtain a carbon nanotube solution. In this acid treating process, an open tip may be formed.

According to an exemplary embodiment of the present general inventive concept, the step (i) may include a step of agitating the carbon nanotube for 15 minutes to 45 minutes at a speed between 250 RPM and 320 RPM at a room temperature in a mixture of a sulfuric acid and a nitric acid at a ratio of 3:1.

In the fabricating method of the present general inventive concept, the step (ii) includes a step of sonicating the carbon nanotube in the solvent. The sonicating may be performed in a frequency range between 20 KHz and 25 KHz, i.e., in a frequency range between 20 KHz and 22 KHz for 80 minutes to 120 minutes, i.e., for 90 minutes to 110 minutes. If the sonicating is performed for 80 minutes or less, dispersibility may be lowered. Although the sonicating is performed for 120 minutes or more, a dispersion degree does not greatly increase.

In the fabricating method of the present general inventive concept, the step (iii) includes a step of consecutively repeating the steps (i) and (ii). In other words, after the steps (i) and (ii) are performed, the steps (i) and (ii) are sequentially repeated. In this case, repeating may be performed from one time to three times or may be one time.

In a conventional fabricating method, only the step (i) is performed, and thus a degree of surface functionalization caused by an acid functional group does not reach an optimum degree and weakens as time goes on. However, the steps (i) and (ii) of the present general inventive concept are added to noticeably improve the dispersibility in the solvent. Also, if a carbon nanotube is dispersed by using only a conventional sonicating step, the carbon nanotube is dispersible. However, stability of colloid decreases with an increase in a concentration of a solution dispersing the carbon nanotube, and thus the colloid agglomerates. In the present general inventive concept, functionalization of a surface of a carbon nanotube affects an interaction between the carbon nanotube and a liquid media to improve this disadvantage. In consideration of An effect of an activity or functionality degree on the dispersion of the carbon nanotube, chemical oxidization for a predetermined time in a strong acid and sonication are combined and then repeated in order to maximize a synergy effect in both the conventional dispersing method and the dispersing method of the present general inventive concept.

Also, in the conventional dispersing method, the carbon nanotube is to be mixed with the strong acid and then agitated for 14 hours to 24 hours. Therefore, a large amount of time is required to fabricate a carbon nanotube having a desired dispersion degree. However, according to the dispersing method of the present general inventive concept, a carbon nanotube having the same standard dispersion degree is simply obtained.

The carbon nanotube dispersed in water according to the conventional fabricating method agglomerates after a week goes on, and thus precipitate is accumulated on the bottom. However, according to the fabricating method of the present general inventive concept, the dispersed carbon is completely dispersed in water without agglomerating after a week goes on (refer to FIG. 5). Therefore, a dispersion degree is noticeably improved by using a simple method without using an additional organic solvent such as a dispersant, compared to a conventional well-known functionality introducing method The method of fabricating the dispersible carbon nanotube according to the present general inventive concept may further include sonicating, diluting, filtering, and drying steps besides the above-described steps. According to an exemplary embodiment of the present general inventive concept, the fabricating method of the present general inventive concept may include sonicating, strong acid treating, sonicating, diluting, filtering, and drying steps.

According to another aspect of the present general inventive concept, there is provided a dispersible carbon nanotube fabricated according to the fabricating method. The dispersible carbon nanotube of the present general inventive concept has high dispersibility in water than a conventional carbon nanotube.

According to another aspect of the present general inventive concept, there is provided a method of fabricating a compound of a carbon nanotube whose cytotoxicity is relieved and a drug, including: (i) mixing a carbon nanotube with a strong acid solvent to introduce a functional group including oxygen onto a surface of the carbon nanotube; (ii) sonicating the carbon nanotube in the strong acid solvent; (iii) consecutively repeating the steps (i) and (ii).

The descriptions of the steps of the method of fabricating the dispersible carbon nanotube are applied to the steps of the method of fabricating the compound.

According to an in vivo test in which single-walled carbon nanotubes are injected into a mouse and a rat, it is reported that inflammation and pneumonocyte damage may occur (Lam et al., 2004; Warheit et al., 2004). As it is known that carbon nanotube have cytotoxicity, various researches related to this have been made. In particular, it is observed that a cohesion state of carbon nanotube may be related to cytotoxicity (Peter Wick et lo, Toxicology Letter 168, 2007). The present inventor has checked a result of cytotoxicity of macrophagocyte of a carbon nanotube and that the result of the cytotoxicity varies according to variation in dispersibility (refer to FIG. 53). Therefore, when a carbon nanotube is used as a carrier of an anticancer medicine and a drug, the carbon nanotube is to be fabricated to reduce a cytotoxicity effect of the carbon nanotube in order to reduce a side effect of toxicity of a human body. Therefore, the present general inventive concept provide a fabricating method for improving biocompatibility of a compound of a carbon nanotube and a drug in order to solve this problem.

According to an exemplary embodiment of the present general inventive concept, in order to check effects of a single-walled carbon nanotube dispersed by the conventional method and a single-walled carbon nanotube dispersed by the fabricating method of the present general inventive concept on cytotoxicity, cytotoxicity of macrophagocyte which is immunocyte is tested. According to the result of this test, cytotoxicity is much fewer in the fabricating method of the present general inventive concept than in the conventional method (refer to FIG. 53). Therefore, a carbon nanotube which is fabricated by the fabricating method of the present general inventive concept and has improved dispersibility is used as a carrier to more reduce cytotoxicity when being combined with a drug than in the conventional method. Therefore, a compound of a carbon nanotube having high biocompatibility and a drug may be fabricated.

Figure 54:
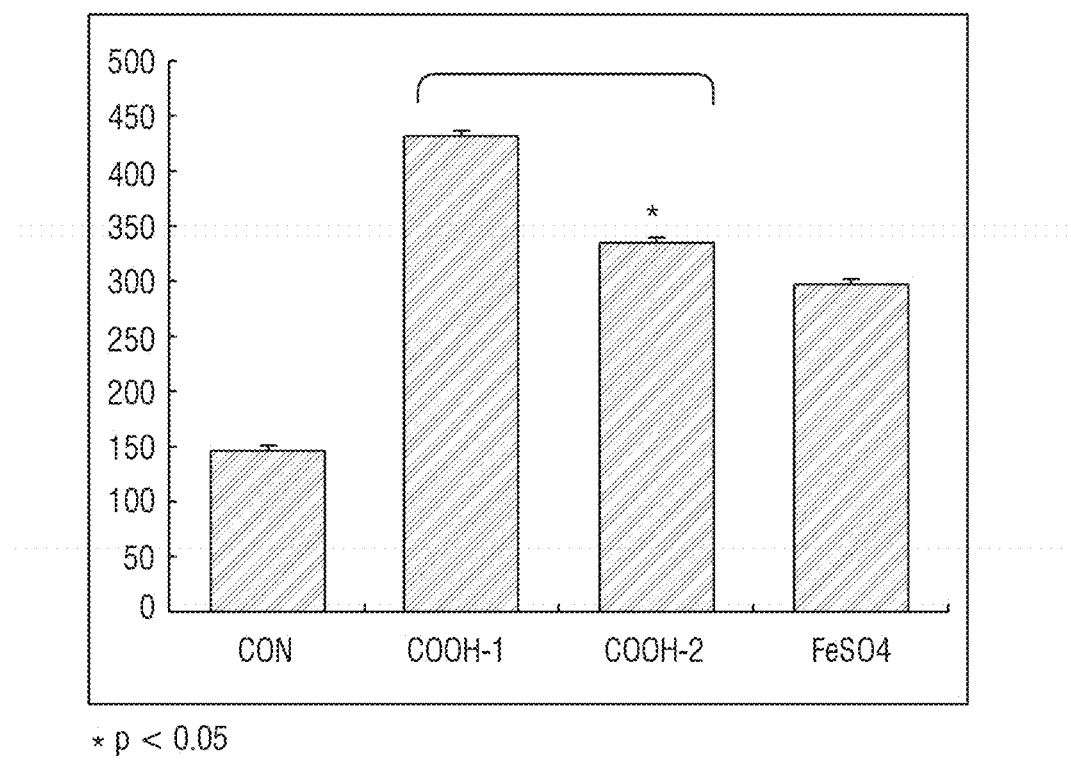
FIG. 54 is a view illustrating results of measuring reactive oxygen species (ROS) according to dispersion degrees of single walled carbon nanotubes which are modified into COOH by method 1 and method 2 and have different dispersion degrees ($*p<0.5$), wherein FeS04 is used as a positive control.

The present inventor measures reactive oxygen species (ROS) in relation to a difference in the cytotoxicity with respect to dispersibility of a carbon nanotube. According to the measurement result, a single-walled carbon nanotube reformed into a carboxyl group according to the present general inventive concept induces the smaller number of ROSs than a single-walled carbon nanotube dispersed according to the conventional method. Therefore, cytotoxicity of the carbon nanotube is reduced (refer to FIG. 54).

The term "carbon nanotube-drug compound" used in the present general inventive concept refers to a compound in which a carbon nanotube is chemically or physically combined with a drug. The chemical combination refers to a chemical combination through a chemical reaction, and the physical combination is a concept including a physical fixation such as adsorption, cohesion, entanglement, entrapment, or the like and a non-chemical fixation which occurs through an electric interaction such as a van der Waals combination or through an action of the electric interaction with the physical fixation.

According to an exemplary embodiment of the present general inventive concept, the carbon nanotube of the compound may operate as a carrier which assists the drug in reaching a target part of a living body. The carbon nanotube may be combined with polysaccharide, protein, or polymer in order to induce a complementary chemical combination such a particular combination between an acceptor and a ligand or a particular combination between an antigen and an antibody in order to be combined with protein or a protein drug. The combination includes a covalent bond and a noncovalent bond. A carbon nanotube introducing an acid functional group of the present general inventive concept may additionally chemically and secondarily combine various materials based on the acid functional group in order to be easily combined with a drug.

The term "drug" or "protein drug" used in the present general inventive concept has medical vitality and includes a polypeptide, a protein, growth factors, such as BMP, VEGF, FGF, PDGF, etc., chemokine, a substrate protein outside a cell, and all types of anticancer drugs. Examples of the anticancer drugs include docetaxel, cisplatin, camptothecin, paclitaxel, tamoxifen, anasterozole, gleevec, 5-FU, floxuridine, leuprolide, flutamide, zoledronate, doxorubicin, vincristine, gemcitabine, streptozocin, carboplatin, topotecan, celecoxib, valdecoxib, nimesulide, cortisone, etc. but are not limited thereto.

Fabricating of Single-Walled Carbon Nanotube Having Functional Group as Carboxyl Group Fabricating of Single-Walled Carbon Nanotube According to Conventional Method In order to compare the conventional method with a result of a method of the present general inventive concept, carbon nanotube dispersed by the conventional method is fabricated.

Figure 48:
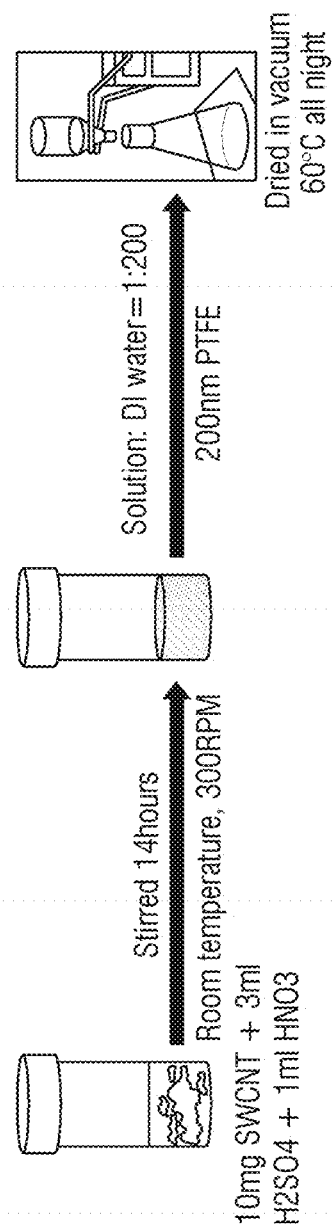
FIG. 48 is a schematic view illustrating a conventional method (referred to as a first method) of dispersing a carbon nanotube by using a strong acid

A single wall carbon nanotube (hereinafter referred to as SWCNT) (purified singlewall nanotube purchased from SES research Inc. (Huoston, Tex. 77092 USA) Lot QS-0552 catalog #900-1351:diameter is 1-5 nm) of 10 mg is put into a mixture (H2SO4: 97%, HNO3:60.0-62.0%) of H2SO4 of 3 ml and HNO3 of 1 ml, agitated for 14 hours at a room temperature at a speed of 300 RPM, and diluted with distilled water (SWCNT/distilled water=1 mg/20 ml). The diluted solution is filtered by using 0.2 μm membrane filter, and powder sticking to filter paper is dried at a temperature of 60° C. in a vacuum state all night to fabricate a single walled carbon nanotube reformed into a carboxyl group. A process of fabricating the single walled carbon nanotube according to the conventional method is illustrated in FIG. 48.

For the comparison, the conventional method is referred to as a first method, and a carbon nanotube fabricated by the first method is marked with COOH-1.

Fabricating of Single Walled Carbon Nanotube According to the Present General Inventive Concept SWCNT (purified singlewall nanotube purchased from SES research Inc. (Huoston, Tex. 77092 USA) Lot QS-0552 catalog #900-1351:diameter is 1-5 nm) of 10 mg is put into a mixture (H2SO4: 97%, HNO3:60.0-62.0%) of H2SO4 of 3 ml and HNO3 of 1 ml and is agitated for 30 minutes at a speed of 300 RPM. The SWCNT is sonicated for 99 minutes by using an ultrasonic machine (220V/60 Hz, ultrasonic frequency: 20 KHz). When the sonicating process is performed, a temperature is increased from about 20° C. to 70° C. The SWCNT is agitated form 30 minutes at a speed of 300 RPM at a room temperature and sonicated for 99 minutes by using an ultrasonic machine (220V/60 Hz, ultrasonic frequency: 20 KHz). The sonicated solution is diluted with distilled water (SWCNT/distilled water=1 mg/20 ml) and filtered by using 0.2 μm membrane filter. Powder sticking to filter paper is dried at a temperature of 60° C. in a vacuum state all night to obtain a single walled carbon nanotube reformed into more many carboxyl groups.

Figure 49:
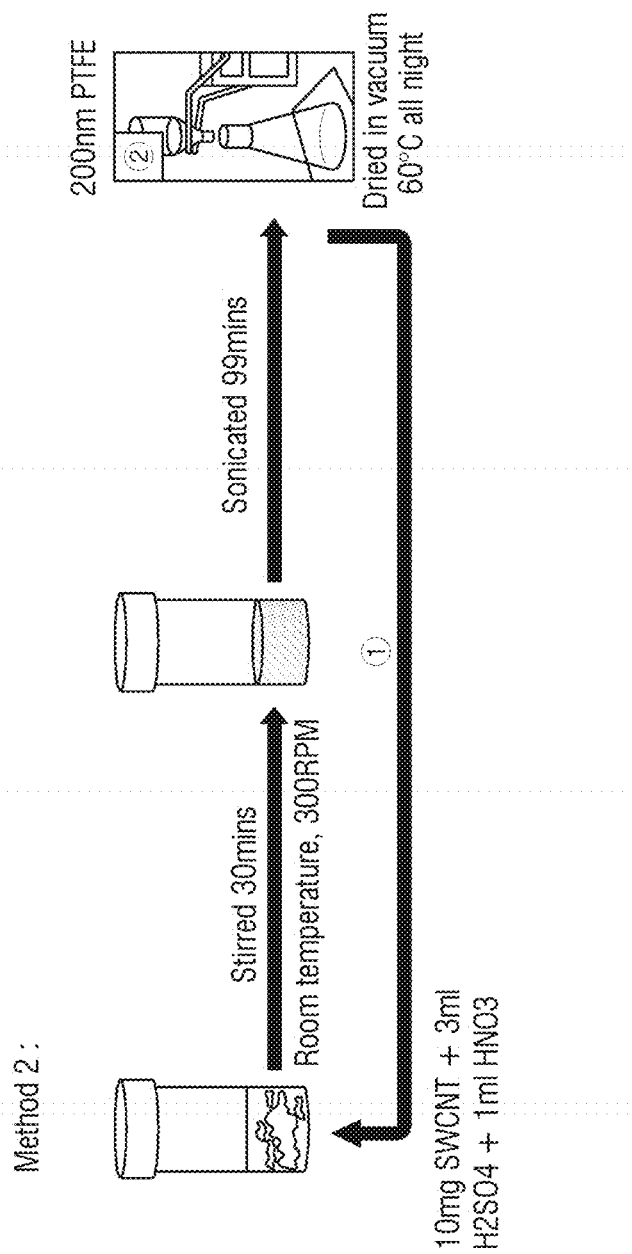
FIG. 49 is a schematic view illustrating a dispersing method (referred to as a second method) of the present general inventive concept, wherein (1) illustrates a process of performing string for 30 minutes and performing an ultrasonication for 99 minutes, and (2) illustrates a process performed after the process (1)

For the comparison, the dispersing method of the present general inventive concept is referred to as a second method, and a carbon nanotube fabricated by the second method is marked with COOH-2 (refer to FIG. 49).

Figure 50:
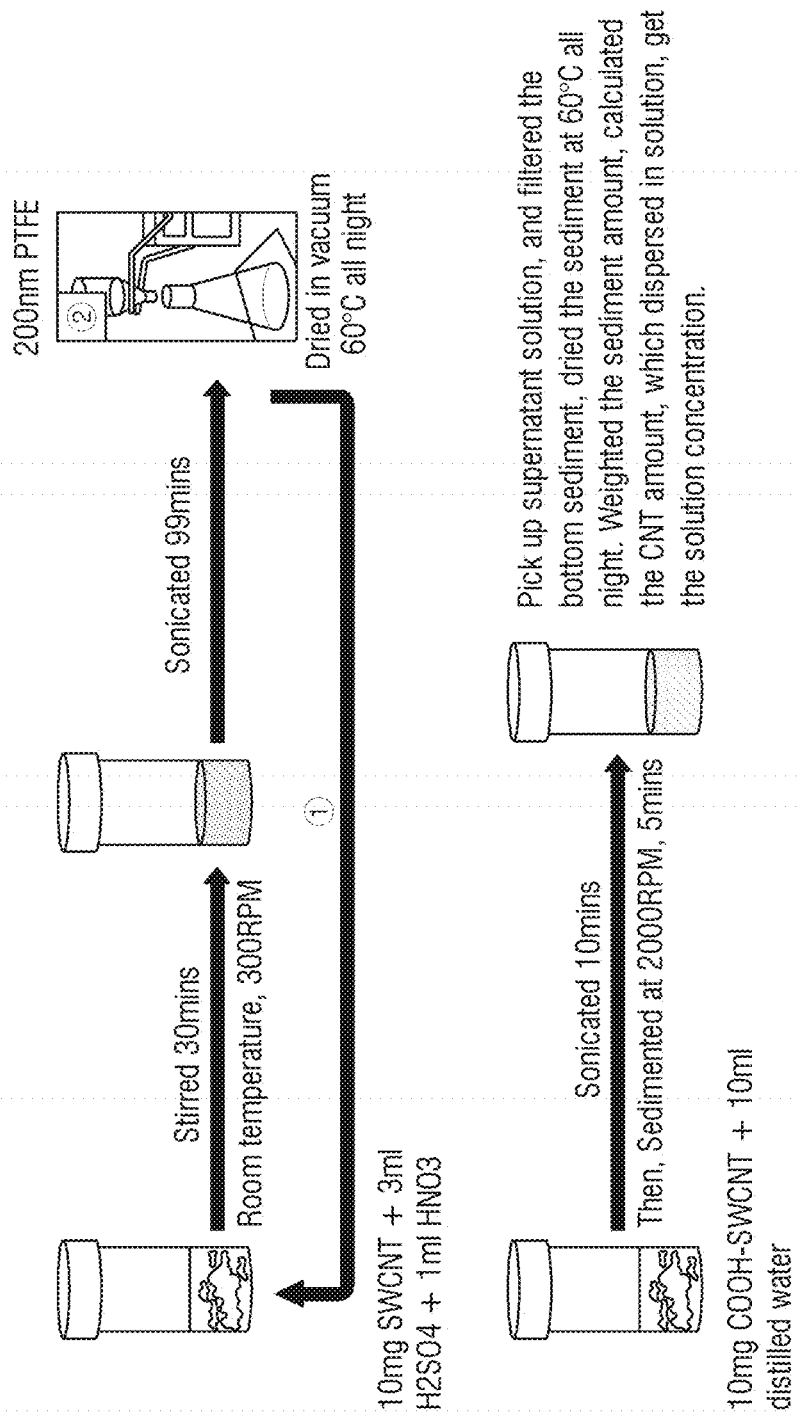
FIG. 50 is a view illustrating a dispersing method of the present general inventive concept and a process of dispersing a single walled carbon nanotube fabricated by the dispersing method in distilled water to measure a dispersion degree.

In order to compare dispersion degrees in distilled water (pH=7) according to the first and second methods, 10 ml of each of carbon nanotubes COOH fabricated by the first and second methods and having functional groups is mixed with distilled water of 10 ml, sonicated for 10 minutes, and deposited for 5 minutes at a speed of 2000 RPM. A supernatant is collected to filter precipitate on the bottom and dry the precipitate at a temperature of 60° C. all night. An amount of precipitate is measured, and an amount of CNT dispersed in the solution is calculated to obtain a concentration of the solution. A process of measuring a dispersion degree according to the second method is illustrated in FIG. 50.

Figure 51:
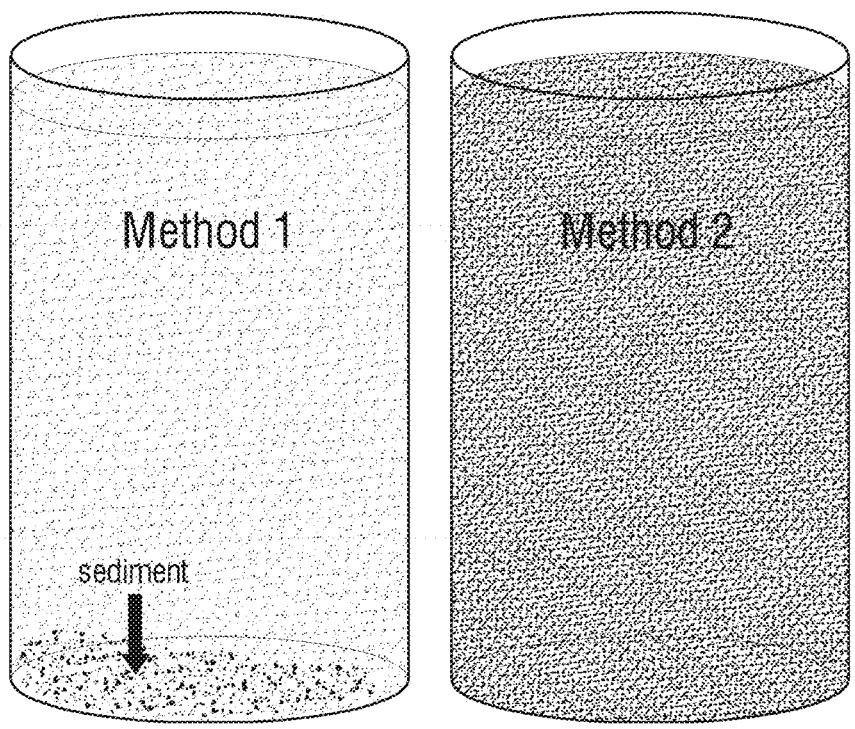
FIG. 51 is a view illustrating dispersion degrees of a carbon nanotube in water after a week according to the conventional method and the dispersing method of the present general inventive for a first toxicity treatment, wherein the left illustrates a result of the conventional method (method 1), and the right illustrates the dispersing method of the present general inventive concept (method 2)

As a result, the carbon nanotube fabricated by the first method agglomerates after a week, and thus precipitate is accumulated. However, the reformed carbon nanotube fabricated by the second method and having the COOH functional group does not agglomerates on the bottom but is completely dispersed in water (refer to FIG. 51). Therefore, according to the dispersing method of the present general inventive concept, the carbon nanotube is reformed into more many carboxyl groups and thus has a high dispersion degree than in the conventional dispersing method.

Test for Checking Uptake of SWCNT in Cell

Macrophagocyte is put into a 4-well plate to be incubated for 4 hours and then stabilized. SWCNT-COOH-1 and SWCNT-COOH-2 are treated in a concentration of 10 ug/ml and incubated for 24 hours. The SWCNT-COOH-1 and the SWCNT-COOH-2 are cleaned two times by using PBS and then fixed by using paraformaldehyde of 3.7%. The SWCNT-COOH-1 and the SWCNT-COOH-2 are cleaned by using PBS and then dyed by using fluorescent phalloidin conjugate solution (50 ug/ml, actin dyeing reagent). The SWCNT-COOH-1 and the SWCNT-COOH-2 are dyed with DAPI (nucleus dying reagent) and cleaned one time by PBS, and a sample is mounted on a slide used for microscope and observed by using LSM 5 exciter (Carl Zeiss, Jena, Germany).

As a result, how the SWCNT is up-taken into the cell is checked, and an action (Red fluorescence-marked with a horizontal line) and a nucleus (Blue fluorescence-marked with a vertical line) are dyed together and observed through a microscope in order to check a definite distribution of the SWCNT in the cell. Differences between uptakes of macrophagocytes of SWCNT-COOH-1 and SWCNT-COOH-2 samples are not great (refer to FIG. 52).

Test for Cytotoxicity of Macrophagocyte with Respect to Dispersion Degree of SWCNT-COOH Macrophagocyte is put into a 96-well plate and stabilized for 4 hours, and SWCNT-COOH-1 and SWCNT-COOH-2 are treated according to concentrations (0.1 ug/ml, 1 ug/ml, 10 ug/ml) in triplicate (n=3) and incubated for 24 hours. H2O2 is used as a positive control.

After 24-hour reaction, each 20 ul of an MTT solution (5 mg/ml) is put into each well and incubated for 2 hours. A supernatant liquid is removed, and DMSO of 100 ul is put, and formazan crystal generated by an MTT reaction is well melted. An absorbance is measured in 570 nm with an Anthos 2010 spectrophotometer.

Figure 53:
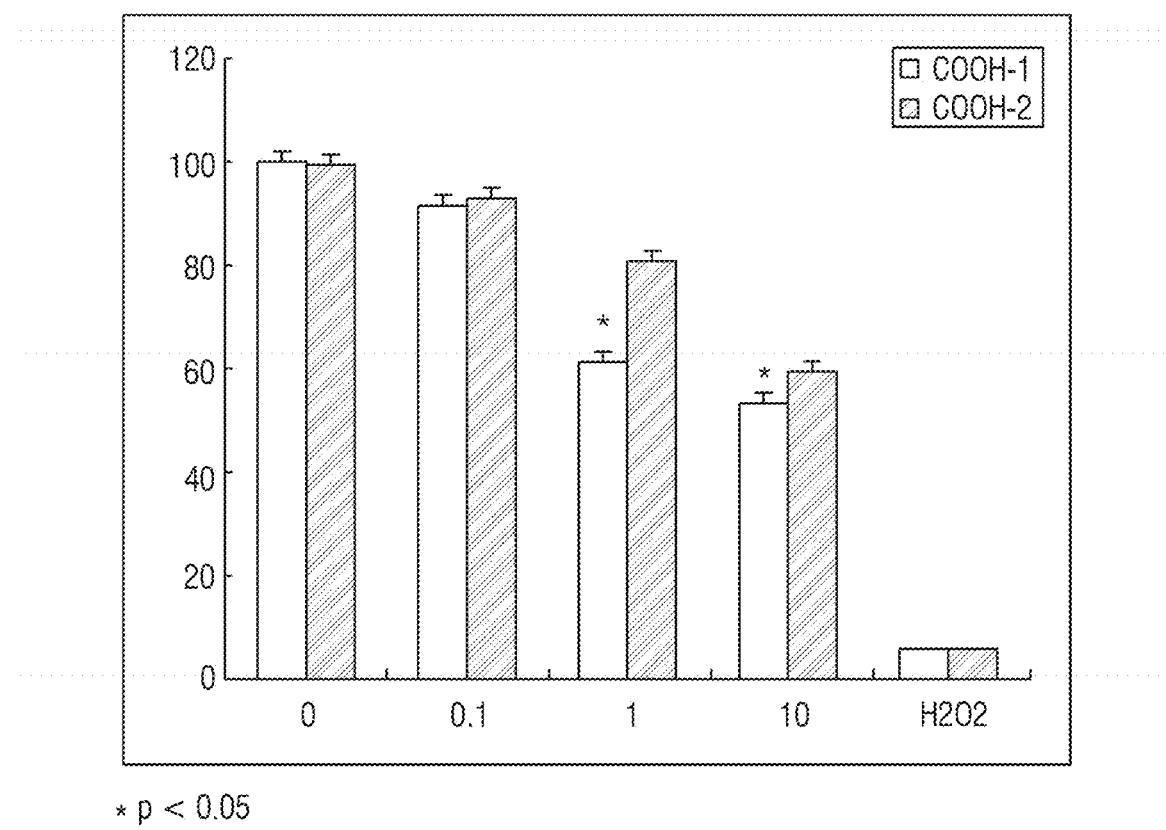
FIG. 53 is a view illustrating a test result of cytotoxicity (MTT) of macrophagocyte appearing when treating single walled carbon nanotubes which are modified into COOH by method 1 and method 2 and have different dispersion degrees, according to concentrations of 0.1 ug/ml, 1 ug/ml, and 10 ug/ml, wherein H2O2 is used as a positive control.

As a result, as shown in FIG. 53, when COOH-1 and COOH-2 fabricated to have different dispersion degrees are compared with a comparison group, both COOH-1 and COOH-2 depend on concentrations and thus kill cells. When COOH-1 and COOH-2 are compared with each other, COOH-2 have much low cytotoxicity than COOH-1 in concentrations of 1 ug/ml and 10 ug/ml. Therefore, COOH-2 fabricated to have a high dispersion degree shows weaker toxicity in macrophagocyte which is an immunocyte.

Test for Measuring Reactive Oxygen Species (ROS) with Respect to Dispersion Degree of SWCNT-COOH Macrophagocyte is put into a black 96-well plate and stabilized for 4 hours, and then SWCNT-COOH-1 and SWCNT-COOH-2 are treated in a concentration of 10 ug/ml in quadruple (n=4) and incubated for 12 hours. F2SO4 is used as a positive control. After a 12-hour reaction, a DHR fluorescent material is put into each well in a concentration of 10 uM and dyed for 1 hour. After dyeing, SWCNT-COOH-1 and SWCNT-COOH-2 are cleaned with PBS two times, and then PBS of 100 ul is put. This is measured in wavelengths of excitation 480 nm and emission 525 nm with a fluorescent plate reader.

According to a result of measuring ROSs causing an oxidative stress and thus causing cytotoxicity, COOH-1 generates more many ROSs than COOH-2 (*p<0.05). According to this result, COOH-2 generate less ROSs than COOH-1 and thus less shows cytotoxicity than COOH-1 (refer to FIG. 54).

[Second Toxicity Treatment]

A carbon nanomaterial of the present general inventive concept may be a carbon nanotube or a nanofiber. The carbon nanomaterial may be a carbon nanotube. The carbon nanomaterial may be a multiwalled carbon nanotube (mwCNT).

The carbon nanotube mostly exists in a bundle in a synthesis step. There is required a technique for cutting a carbon nanotube rope or bundle existing in a tangled state into appropriate sizes appropriate for a composite with a polymer to divide the carbon nanotube rope or bundle into individual carbon nanotubes in order to realize a stable nanodispersion state in a polymer matrix. Overcoming phase separation, cohesion, and low dispersibility and adhesiveness in the polymer matrix is the most important requirement in a nanocompound material.

The carbon nanotube is to be dispersed in an aqueous solution or an organic solvent. Since a hydrophobic property of the carbon nanotube and a mutual attraction between molecules are very great, a selection of a dispersant is to be importantly considered.

The dispersant is a kind of surfactant and includes a head part and a tail part. The head part is to have an affinity with a surface of a dispersoid which is a material to be dispersed, and the tail part is to have an affinity with a solvent to be dispersed, i.e., a dispersion medium. The dispersant also operates as a barrier to a collision between particles.

Sodium dodecyl benzen sulfonate (NaDDBS) as a water-based dispersant, sodium dodecyl sulfonate), TX-100, polyvinyl pyrrolidone, or the like may be used as the dispersant of the carbon nanotube.

A nutrient protein of a cell may be used as the dispersant of the carbon nanotube.

According to an exemplary embodiment of the present general inventive concept, a nanomaterial is dispersed by using a serum media including FBS, which is a nutrient protein of a cell, not using a general surface chemical treatment. The serum media is sonicated by using a tip sonication at 24% power of a 500-watt sonication machine in a 3-second-on 6-second-off method for every 30 minutes in quadruple. Also, the sonication is performed with dipping all samples into ice in order to prevent proteins from being denaturalized by heat.

Dispersed CNT has a much weaker cohesion degree than the serum media (w/o FBS) and thus is effective in dispersing a nanomaterial. Also, nano toxicity of a pure carbon nanomaterial is researchable without chemical surface coating (COOH, NH2, OH).

A multiwalled carbon nanotube may have a diameter between 10 nm and 50 nm or may have a diameter of 30 nm.

According to an exemplary embodiment of the present general inventive concept, as a diameter of a carbon nanomaterial is small, a proliferation of a brain tumor cell may be further inhibited Also, four types of carbon nanomaterials are used in the exemplary embodiment of the present general inventive concept. The used carbon nanomaterials are shown in Table 1 below.

TABLE 1

| CMMS | mwCNT | phCNF | hbCNF | hlCNF |
| --- | --- | --- | --- | --- |
| Diameter | 30 nm | 150 nm | 250 nm | 250 nm |
| Hydrophilic Property Degree | Partial Hydrophilic Property | Partial Hydrophilic Property | Hydrophobic Property | Partial Hydrophilic Property |

The nanomaterials are treated in neuroma (U373MG) according to concentrations and time, and an MTT analysis is performed. The mwCNT has the strongest cytotoxicity due to its concentration. Also, hlCNF having a surface from which hydrocarbon has been removed (thermal treatment: reaction for 4 hours at a temperature of 400° C.) has considerable toxicity.

Therefore, toxicity of carbon affects a cell division. Also, as the carbon is smaller and is further exposed to a surface, a dispersion degree of the carbon becomes higher, and thus a degree of the toxicity become serious.

A cell train is cultivated with a culture solution including nanomaterials, and a TUNEL analysis is performed to test a correlation with an apoptosis of a tumor cell of a carbon nanomaterial. As a result of the test, the apoptosis of the tumor cell is not observed.

When caspase-3 which is well known as one of main substrates of apoptosis is inspected with western blotting, caspase-3 is not detected from all groups.

According to an exemplary embodiment, according to a result of treating a carbon nanomaterial in cell U373MG and investigating cell migration and division, all carbon nanomaterials used in the test affect cell migration and division.

Also, the carbon nanomaterials affect cell migration and division in a hippocampus original steam cell line (HT22) which is not yet divided into neurons.

However, a carbon nanomaterial used in an exemplary embodiment of the present general inventive concept is not divided, toxicity does not appear in neurons which are completely divided.

As a result, a carbon nanomaterial of the present general inventive concept, in particular, mwCNT, phCNF, hbCNF, and hlCNF, do not cause toxicity in a brain cell which has been completely divided and thus do not proliferate and inhibits cell division and proliferation in a brain tumor cell which continuously proliferates.

Therefore, based on the above fact, the present general inventive concept provides a composite for inhibiting a proliferation of a cancer cell including a carbon nanomaterial as an active component.

Also, the present general inventive concept provides a pharmacological composite for inhibiting a proliferation of a cancer cell including a carbon nanotube as an active component.

A composite of the present general inventive concept inhibits a proliferation and a migration of a cancer cell which specifically proliferates.

The composite may include an effective dose of a carbon nanomaterial of the present general inventive concept, a diluent, a preserved agent, a solubilizer, other adjuvants and/or carriers which is pharmacologically allowable. A pharmacological unit injection type composite may be formulated and used.

The pharmacological unit injection type composite of the present general inventive concept may be formulated according to a general method.

The composite of the present general inventive concept may be manufactured and used as an aqueous injectable solution, a nonaqueous injectable solution, a turbid injectable solution, a suspension injectable solution, or injectable (freeze-dried) powder which is melted and used as sterile injectable water. Various types of dosage forms such as other injectable forms, parenteral injectable forms, etc. may be fabricated according to a technique which is described in books well known in the art or which is commonly used.

An added base includable in the composite may be any based which is commonly used in injections. For example, the base includes distilled water, a sodium chloride solution, a mixture of sodium chloride and sodium organic matter, or a similar mixture, mannitol, lactose, dextran, a solution such as glucose, glycine, an amino acid solution such as arginine, a mixture of an organic acid solution or a salt solution and a glucose solution, a similar solution, etc. Also, the injection may be fabricated as a solution, a suspension solution, or a colloid solution by adding osmolyte, a pHregulator, embalmment such as methyl hydroxybenzoate or propyl hydroxybenzoate, vegetable oil such as sesame oil or soybean oil, lecithin, or a surface-active agent such as a nonionic surface-active agent to the base.

Also, the effective dose refers to a dose indicating a preventive or curative effect when the composite is injected into a patient. A dose of the composite of the present general inventive concept may be appropriately selected according to an injection path, an injected object, age, gender, weight, individual differences, disease state. The selected effective dose may be injected once a day or many times a day.

The composite of the present general inventive concept may vary a content of an effective component according to a degree of a disease.

The composite of the present general inventive concept may be locally injected in an injection form fabricated by the fabricating method into a cancer cell part. Also, the composite may be mixed with another anticancer drug in order to inhibit a division, a proliferation, and a spread of a cancer cell.

An effective dose of a carbon nanomaterial included as an effective component in the composite of the present general inventive concept is not limited and may be between 0.001 ug/ml and 10 ug/ml.

The cancer cell of the present general inventive concept may be all kinds of cancers and thus is not limited.

The cancer cell of the present general inventive concept may be a brain tumor cell.

According to the present general inventive concept, a proliferation of a cancer cell and a migration of a cell may be inhibited by using a carbon nanotube to prevent a cancer disease from being aggravated. Also, the carbon nanotube may be accessarily used with another anticancer drug to ultimately prevent and cure a cancer and thus contribute to the cancer market.

Carbon nanomaterials used in the present general inventive concept are shown in Table 2 below.

TABLE 2

| CMMs | mwCNT | phCNF | hbCNF | hlCNF |
| --- | --- | --- | --- | --- |
| Diameter | 30 nm | 150 nm | 250 nm | 250 nm |
| Hydrophilic Property Degree | Partial Hydrophilic Property | Partial Hydrophilic Property | Hydrophobic Property | Partial Hydrophilic Property |

The carbon nanomaterials mwCNT (SES, TX, USA), phCNFj (PS 24, Pyrograff, USA), hbCNF, and hlCNF (AG-1, Pyrograff, USA), astrocyte sarcoma which is a kind of tumor cell (U373MG: neuroglioma, ATCC, USA), and a brain cell (HT22: a kind of hippocampus original stem cell, Prof. c. Behl, University of Mainz) are used.

A carbon nanomaterial (hlCNF) having an improved hydrophilic property is added through a thermal treatment in order to check an effect of a hydrophilic property of a carbon nanomaterial on a cell.

in order to disperse a carbon nanotube (CNT) having a diameter of 20 nm and carbon nanotube (CNFs) each having diameters between 60 nm and 150 nm and between 100 nm and 300 nm, serum media (including FBS) is dispersed by using a tip sonication. The dispersion is performed at 24% power of a maximum 500-watt sonication machine according to a 3-secone-on and 6-second-off method form every 30 minutes in quadruple. Also, the dispersion is performed with dipping all samples in ice in order to prevent proteins from being denaturalized by heat. A cohesion degree of CNT dispersed into various types of proteins is weaker than that of serum free media (w/o FBS) after a predetermined time and thus is effective in dispersing a nanomaterial. Also, nanotoxicity of a pure carbon nanomaterial is researchable without chemical surface coating (COOH, NH2, OH).

Cell U373MG is suspended in serum media, and every 200000 cells are put on a culture plate of 35 mm Cells are adsorbed on the bottom within 3 hours due to adsorption characteristics of the cells.

In order to investigate an effect of a nanomaterial on a cell adsorption, an MTT analysis method is performed 1 hour and 3 hours after a cell is incubated, to investigate an adsorption rate.

The MTT analysis is performed on a 96-well incubation plate, and a colorimetric analysis is performed based on a principle of returning 3-(4,5-dimethylthiazol-2-yl-2,5-diphenyltetrazolium bromide (MTT) to a blue formazan product. DMSO is added to each 96-well plate 2 hours after MTT (1 mg/ml) incubating at a temperature of 37° C. An absorbance of a fusible MTT formazan product is measured in 570 nm by a spectrophotometry.

Figure 55:
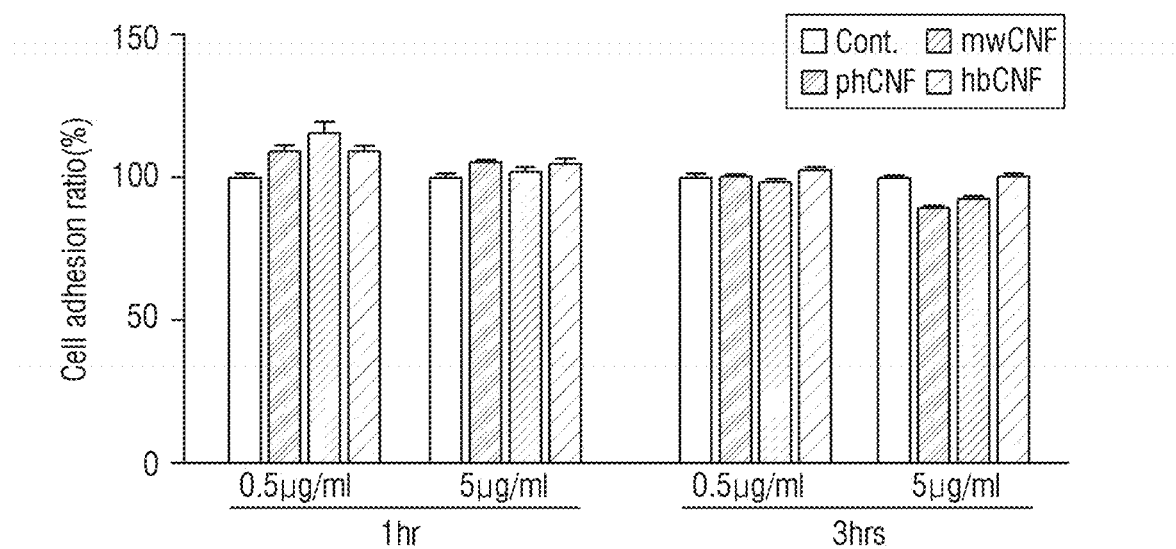
FIG. 55 is a graph illustrating a cell adsorption rate by performing a MTT analysis method in order to check an effect of a carbon nano material on a cell adsorption in U373MG cell.

When showing a result with a cell adhesion ratio, nanomaterials do not affect adsorption of a cell in CNT/CNF concentrations. However, after a nanomaterial of 5 ug/ml is injected after 3 hours, the nanomaterial shows a result as shown in FIG. 55. An increase in concentration affects the cell adhesion ratio. However, in terms of statistical situation (AVOVA analysis), there is no great difference.

Figure 56:
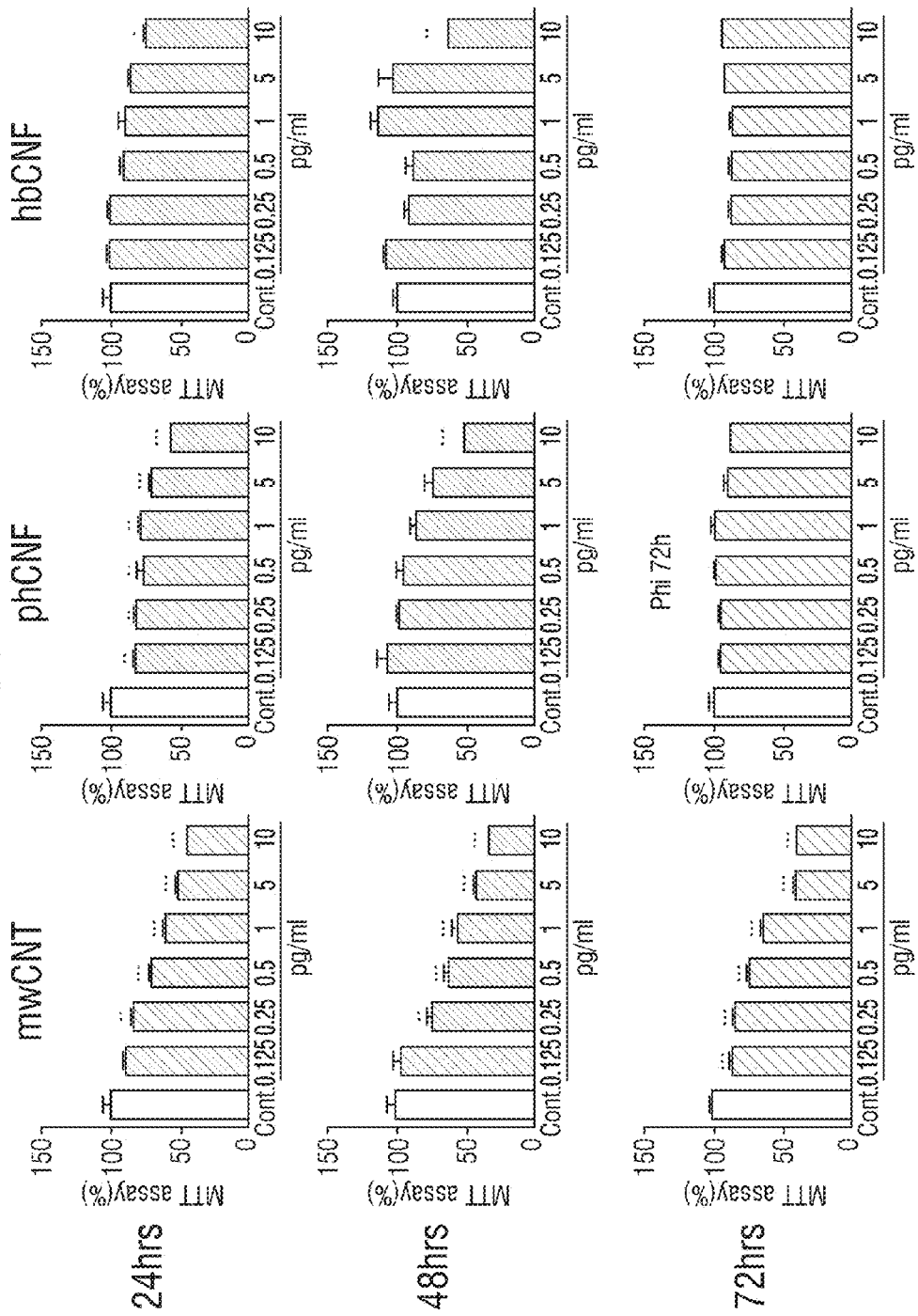
FIG. 56 is a view illustrating a test result of viability obtained by treating nano materials of mwCNT, phCNF, and hbCNF in a neuroblastoma cell according to concentrations and times.

Nanomaterials (mwCNT, phCNF, hbCNF, hlCNF) are treated in cells according to concentrations and time to perform an MTT analysis. mwCNT has the strongest cytotoxicity according to concentrations, and phCNF has weaker cytotoxicity than mwCNT. hbCNF hardly has cytotoxicity (FIG. 56).

Figure 57:
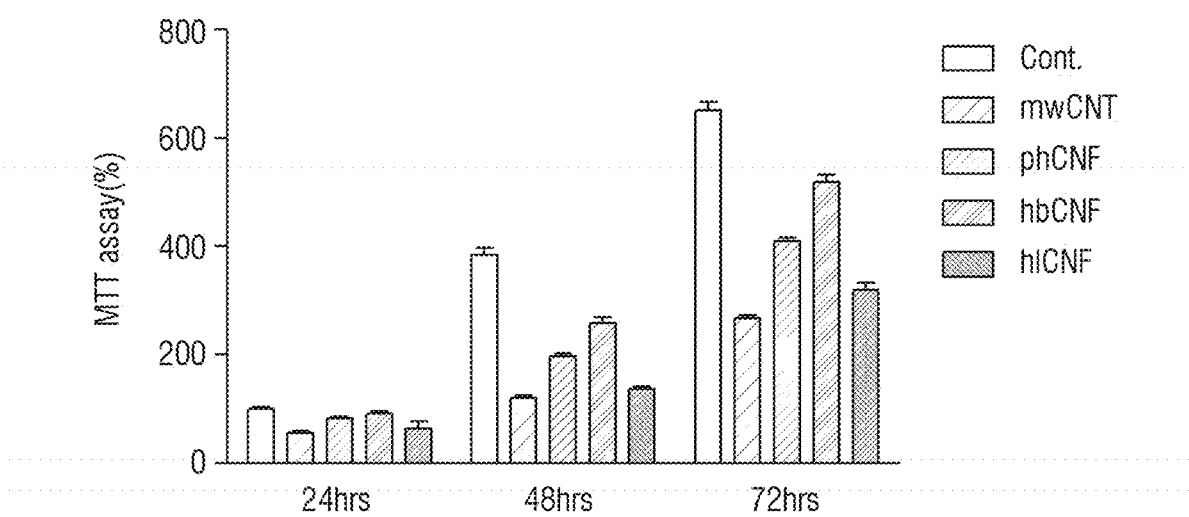
FIG. 57 is a view illustrating a test result of cytotoxicity of carbon nano materials including hlCNF.

Carbon nanomaterials are treated, and then MTT assay is performed according to each time. A cell has a higher MTT value as time goes on through a division. If a carbon nanomaterial is treated, an MTT value is lowered. When 24 hours goes by, mwCNT and hlCNT respectively have values of 40.286% and 37.182% after 24 hours and have values of 81.992% and 118.529% after 72 hours. mwCNT and hlCNF have stronger cytotoxicity than carbon nanomaterials having the same sizes (FIG. 57).

Each 200000 U373MG cell strains are divided on a 6-well plate, incubated for 48 hours in a culture solution including nanomaterial of 5 ug/ml, and undergoes a TUNEL analysis.

The TUNEL analysis is to cleanse centrifugally filtered cells with PBS/BSA and fix the cells with paraformaldehyde for 15 minutes. Also, the cells passes through Triton-X 100. FITC-conjugated dUTP is treated by using an apoptosis detection system kit (Roche, Mannheim, Germany. cat. 11 684 817 910) and observed through a fluorescence microscope.

A TUNEL positive cell appearing in the TUNEL analysis senses a free 3'-OH group when DNA strands are broken into pieces and suggests an apoptosis.

Figure 58:
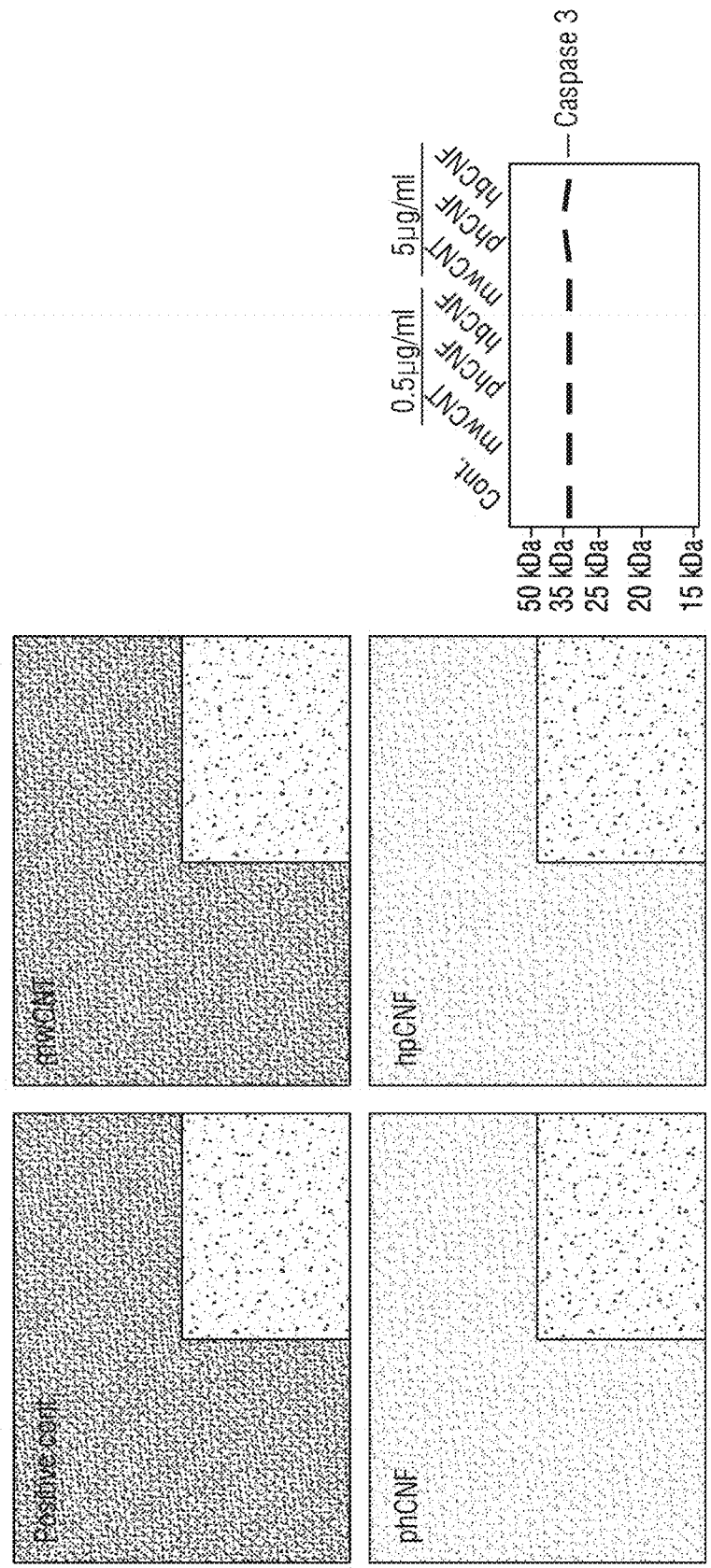
FIG. 58 is a view illustrating a result of treating nano materials in U373MG cell train to perform a TUNEL analysis method a result of performing a western blot to check whether caspase-3 is detected.

As a result, an apoptosis is not observed in any control group (FIG. 58).

Also, a western blot is performed to observe the apoptosis on a protein level.

Cell strains are dissolved with a lysis buffer (25 mM HEPES; pH 7.4, 100 mM NaCl, 1 mM EDTA, 5 mM MgCl2, 0.1 mM DTT and protease inhibitor mixture). Each 15 ug of proteins is put on 12.5% SDS gel per well, and then an electrophoresis is performed for 1 hour 40 minutes at 100 volt. The SDS gel on which the electrophoresis has been completed adheres to a nitrocelluose membrane, and then the proteins delivered to the SDS gel is moved to the nitrocelluose membrane. The nitrocelluose is cleansed with tris buffered saline (TBS), preprocessed with 5% nonfat dry milk, and a caspase-3 (cellsignaling. cat. 9661) antibody having a concentration of 1:1000 is reacted for 16 hours. The nitrocelluose membrane is rinsed with TBS including 0.1% Tween, and a rabbit secondary antibody to which horseradish peroxidase is joined and has a concentration of 1:10000 is reacted for 1 hour. A fluorescence color reaction is caused with an ECL reagent, and an immune reaction is detected with an image analyzing system (LAS-4000, Fujifilm).

The caspase-3 is an apoptosis marker protein which is cut to be 19 kD if an apoptosis occurs.

Cut caspase-3 is not detected from all control groups (FIG. 58).

Figure 59:
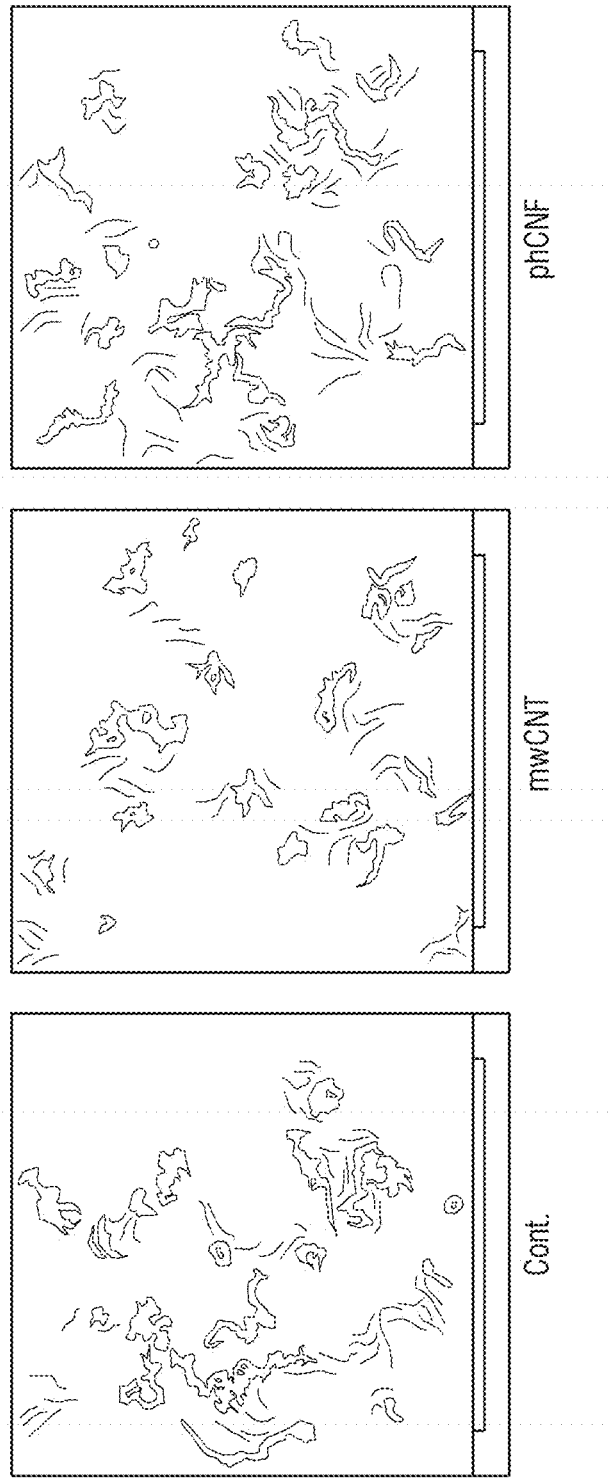
FIG. 59 is a view illustrating a result of checking mobility of a cell in each condition for 7 hours, wherein blue denotes a first start portion of a cell, and black denotes a last position.

5 ug/ml of carbon nanomaterials are treated in U373MG and is observed live by using a cell observer (Carl Zeiss, Germany) to investigate cell migration and division. The cell observer is to satisfy all conditions ($CO_2$, temperature, moisture) for incubating a cell, capture the cell in seconds or minutes, make the cell in to a moving picture, and analyze the result. In the present test, an image is captured and analyzed for 7 hours or 24 hours in every 5 minutes. As shown in FIG. 59, paths of all cells moving from first positions to last positions are measured. A movement speed and a movement distance of a cell are measured through this (FIG. 60), and the number of times of division is measured within the moving picture (FIG. 61).

Figure 60:
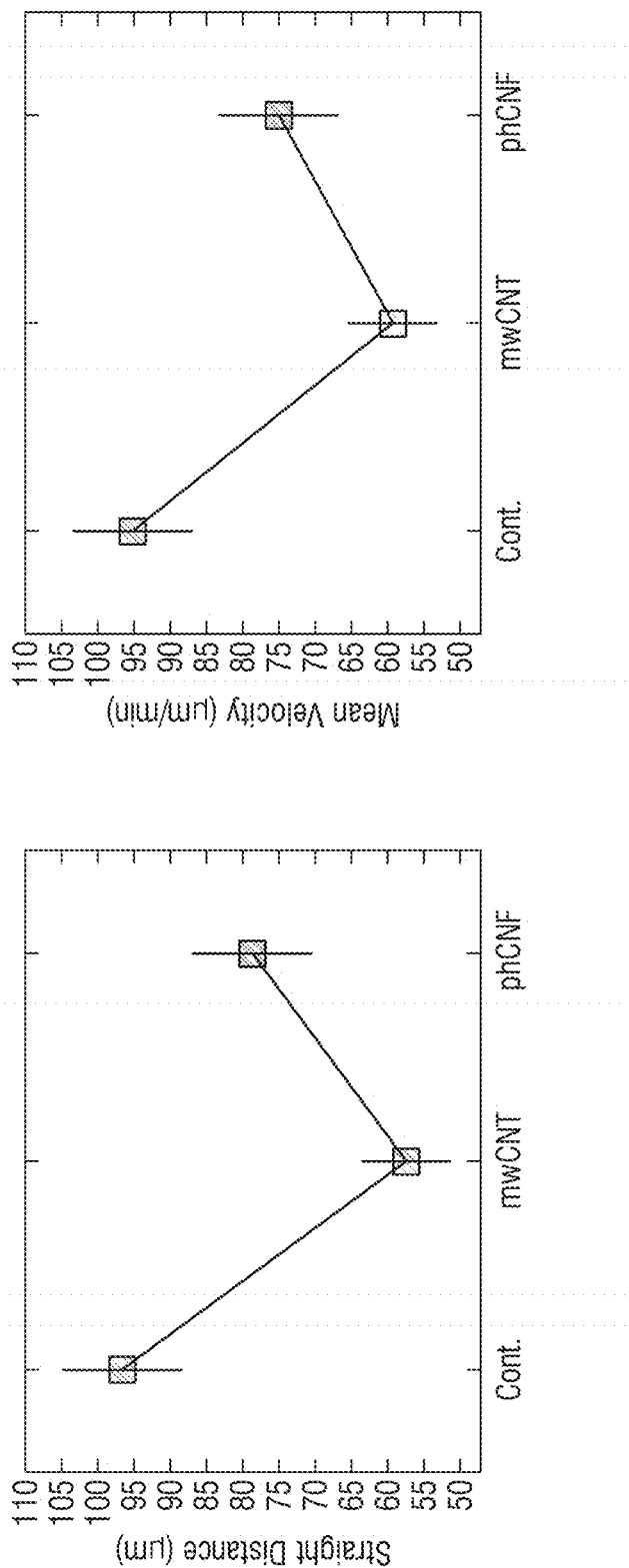
FIG. 60 is a view illustrating a total mobility distance and a speed in each condition.

As a result, as shown in FIG. 60, all types of carbon nanotubes affect a movement distance and a movement speed of a cell.

Figure 61:
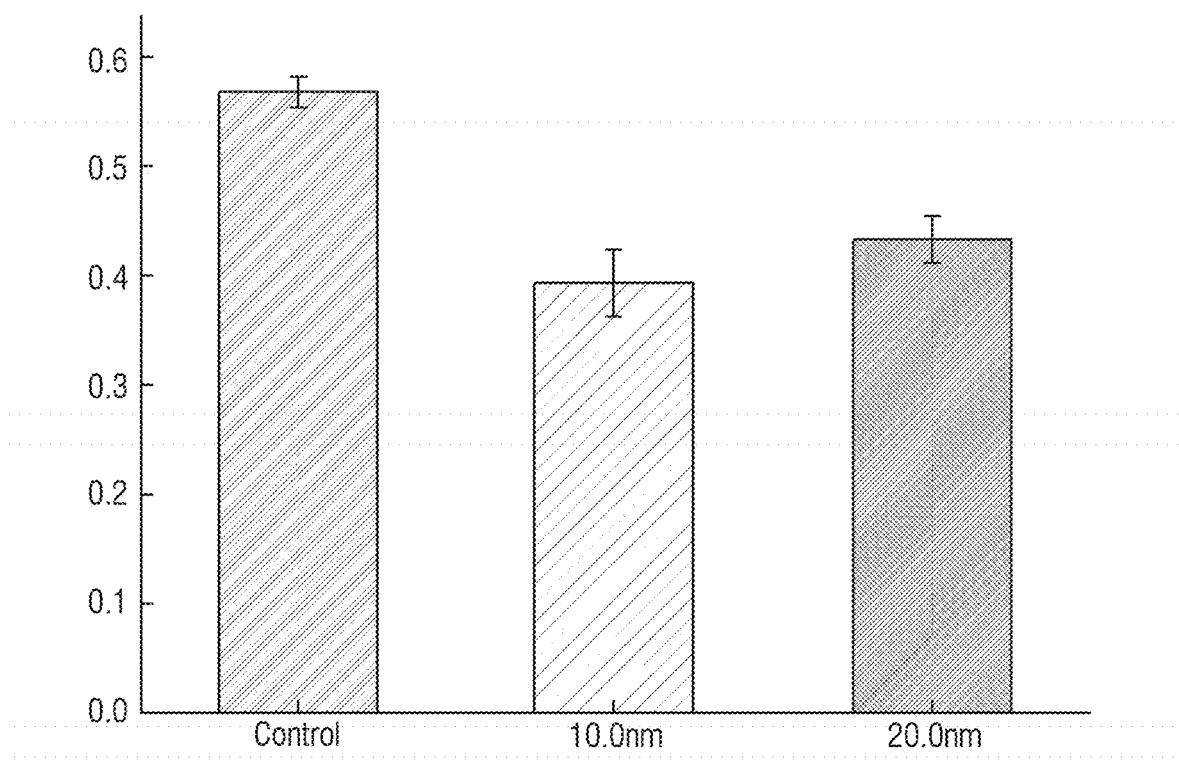
FIG. 61 is a view illustrating a division degree of a cell in each condition.

Also, as shown in FIG. 61, according to a result of analyzing a cell division, a nanomaterial is involved in a proliferation of a cell, and this result is similar to the above MTT result.

5 ug/ml of a carbon nanomaterial is treated in a hippocampus original stem cell line (HT22) which is not divided into neurons, and an MTT analysis is performed.

Figure 62:
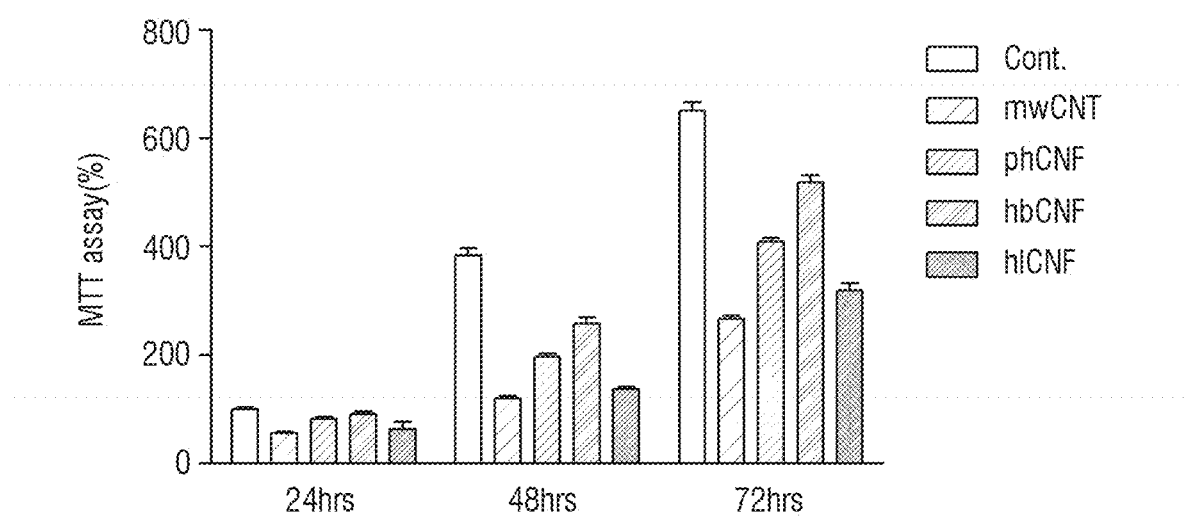
FIG. 62 is a view illustrating a result of treating carbon nano materials in HT22 which is not divided into neurons to perform the MTT analysis method.

As a result, as a result of treating each carbon nanomaterial in HT22 which is not divided into neurons, an aspect such as a nerve tumor cell appears (FIG. 62).

Figure 63:
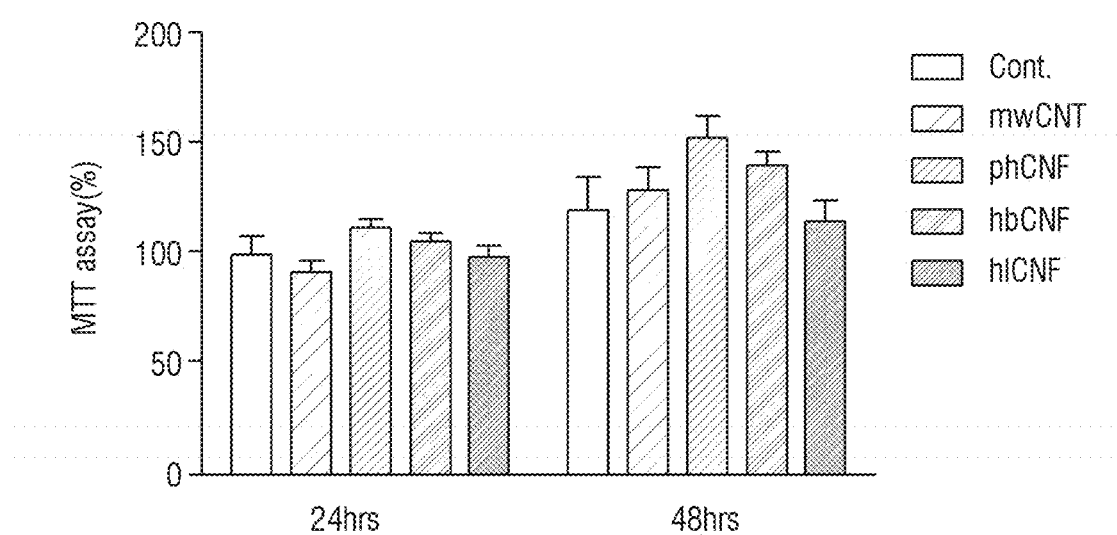
FIG. 63 is a view illustrating a result of treating a carbon nano material in a neuron into which cell HT22 is divided and then is not divided, to perform the MTT analysis method.

However, when HT22 cell is divided, i.e., neurons which are completely divided and thus are not divided any more are treated with carbon nanomaterial, toxicity does not appear. This strongly suggests results that a carbon nanomaterial is not involved in an extinction of a cell but affects a division of the cell (FIG. 63).

[Third Toxicity Treatment]

A stent having a nano-structured surface and a method of fabricating the stent may be applied to a biofuel battery part and to all elements of a battery to be inserted into a living body or an artificial vessel which is exposable to a living body or the blood.

Figure 64:
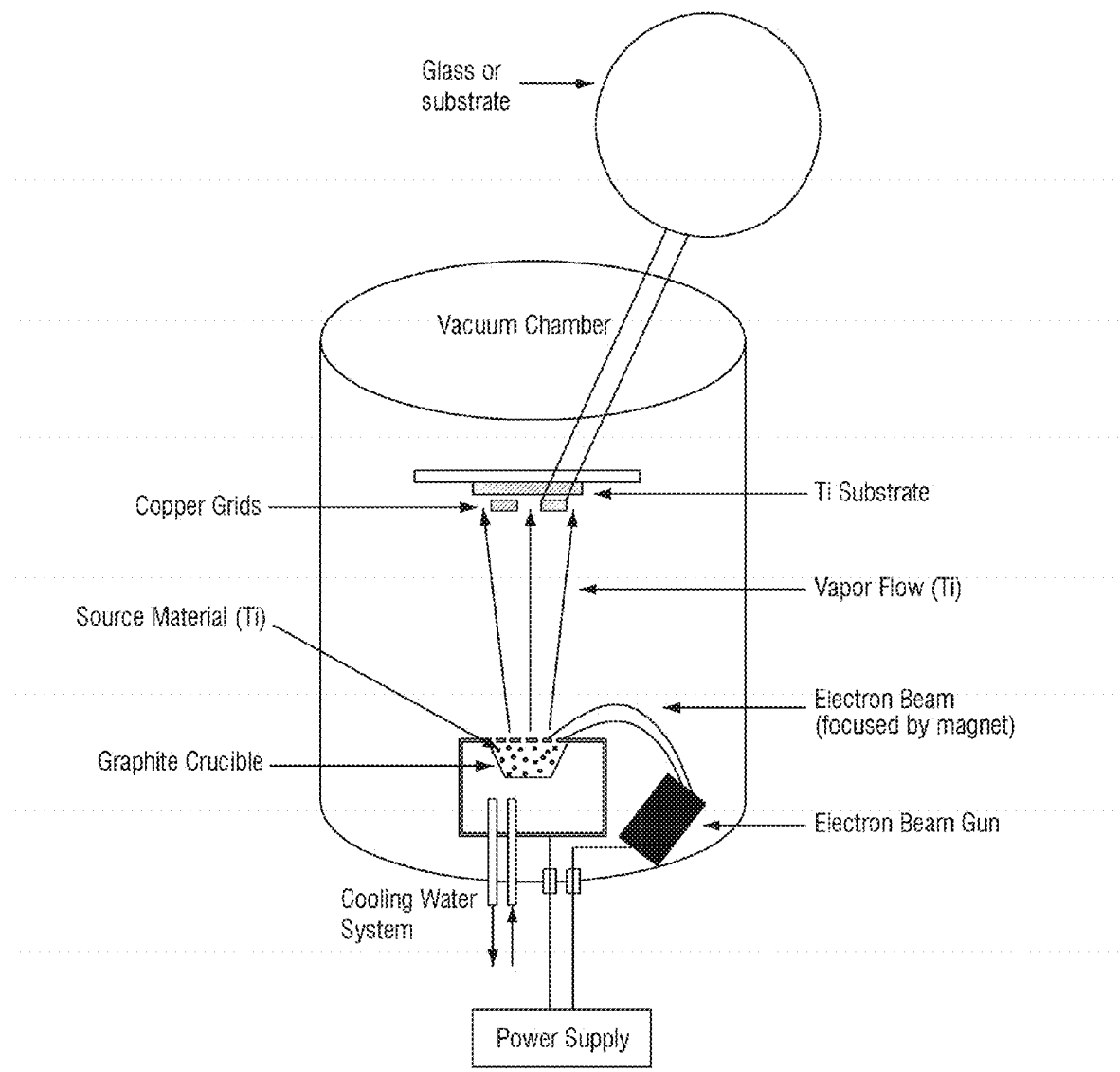
FIG. 64 is a view illustrating a structure of an e-beam evaporator for forming a nano-structure.
Figure 65:
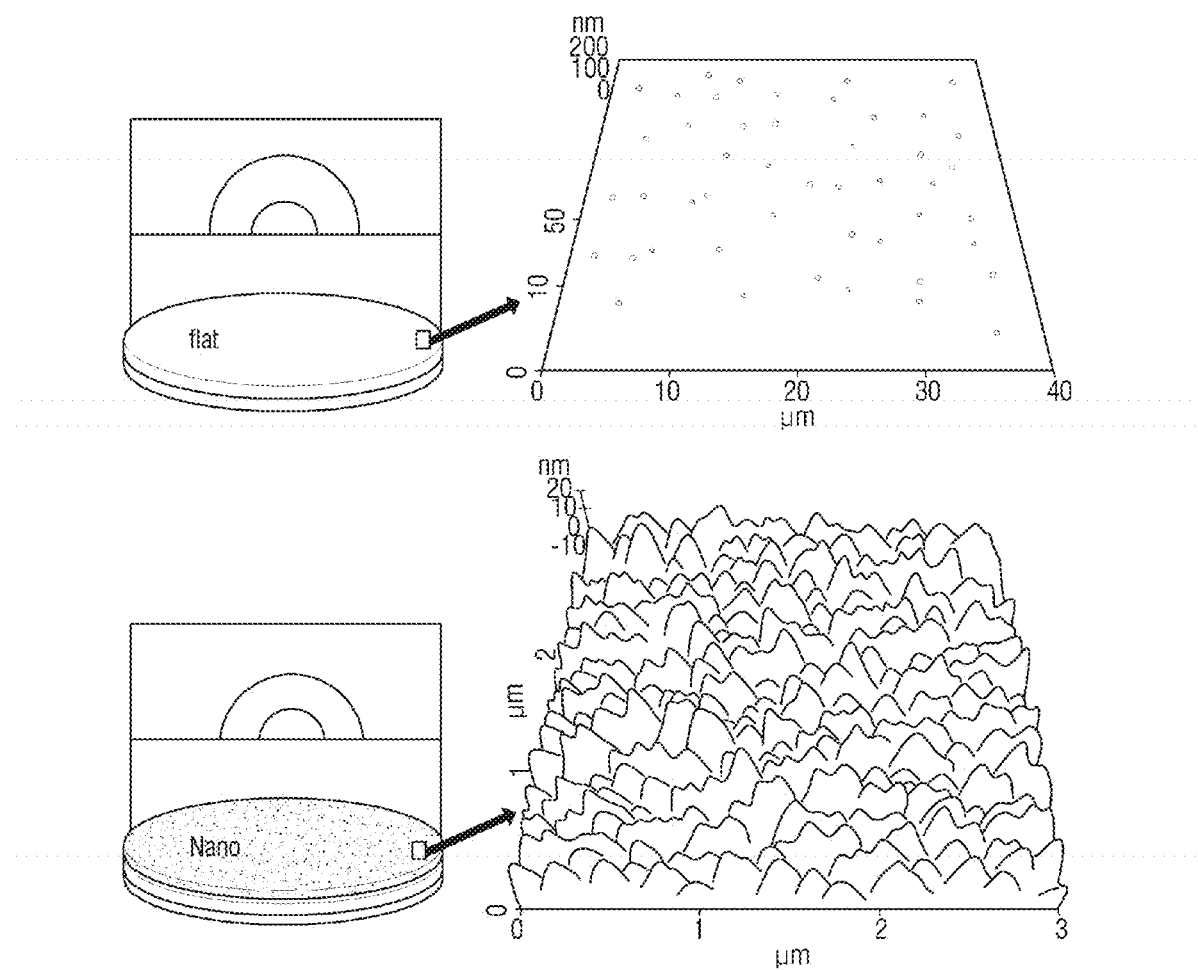
FIG. 65 is a view illustrating a surface of a nano-structure formed by using an e-beam evaporator.

The present general inventive concept relates to a method of fabricating a stent having a nano-structured surface (FIG. 65) and formed of a titanium material, including: (1) depositing titanium on a surface of the stent by using an e-beam evaporator (FIG. 64); and (2) increasing a deposition speed to a range between 35 A°/sec and 45 A°/sec to form a nanostructure on a surface of titanium.

The stent is a general stent which is not coated with polymer and is generally formed of stainless steel or a cobalt-chrome alloy.

The stent is a cylindrical metal screen which is inserted to restore a blood flow when a coronary artery supplying oxygen and nutrition to a cardiac muscle pumping the heart is narrowed or clogged.

A vacuum evaporation of the e-beam is a method of applying a very high voltage to allow thermal electrons emitted from a filament to crash against an evaporation source in order to evaporate a material to be deposited through generated heat and deposit the material on a substrate.

The term "evaporation" used in the present general inventive concept is to heat and evaporate a metal or a compound in a vacuum state and coat steam as a thin film on an surface of an object.

The method of fabricating the stent according to the present general inventive concept is characterized in that a deposition speed is increased to a range between 35 A°/sec and 45 A°/sec by using an e-beam evaporator to fabricate a nano-structured (protrusion-structured) thin stent in an existing method of forming a stent of a titanium material.

The e-beam evaporator may be an ultrahigh vacuum e-beam apparatus (10−8 torr).

The deposition speed of the step (1) may be between 1.5 A°/sec and 2.5 A°/sec, i.e., may be 2 A°/sec.

The deposition speed of the step (2) may be 40 A°/sec, an e-beam current density may be between 165 $mA/cm^2$ and 175 $mA/cm^2$, i.e., may be 170 $mA/cm^2$.

The present general inventive concept also relates to a stent which is formed of a titanium material whose surface has a nano-structure.

A characteristic part of the present general inventive concept relates to a stent structure which is formed of a well-known titanium material and has a nano-structured (protrusion-structured) surface.

The nano-structure of the stent may have a thickness between 1 nm and 50 nm, i.e., 1 nm and 35 nm.

A nano-structure of the present general inventive concept has a thin thickness of 35 nm or less and is transparent and thus is applicable to cell moving picture capturing and microvessel.

The stent of the present general inventive concept may be fabricated by the above-described fabricating method.

A titanium stent having a nano-structure having a thickness of 50 nm, i.e., 35 nm or less, according to the present general inventive concept inhibits a toxicity reaction of macrophagocyte which is one of immune cells, to prevent angiostenosis and restenosis caused by an insertion of an implanted material.

If an existing titanium is inserted into a blood vessel, a recurrence ratio of hemadostenosis recurs is very high. This is because the existing titanium causes a biocompatibility problem and an immune reaction and toxicity of an immunocyte.

However, a titanium stent of the present general inventive concept having a nano-structure having a thickness of 50 nm, i.e., 35 nm or less, less stimulates macrophagocyte which is one of immunocytes and thus does not induce an immune reaction of the macrophagocyte. Titanium of the present general inventive concept having a nano-structure reduces a secretion rate of NO secreted when inducing an infection of an immune reaction of macrophagocyte and reduces a manifestation of iNOS which is an enzyme generating NO.

In other words, the stent of the present general inventive concept inhibits a toxicity reaction and an immune reaction of an immunocyte to prevent a restenosis of a blood vessel when the stent is inserted into the blood vessel.

Therefore, the present general inventive concept provides a method of preventing a restenosis of a blood vessel, including: applying a titanium stent having a nano-structure having a thickness of 50 nm, i.e., 35 nm, to an endangium.

Hereafter, an exemplary embodiment of the present general inventive concept will be described in detail.

<First Exemplary Embodiment of Third Toxicity Treatment> Fabricating of Titanium Nano-Structure A pure titanium material (99.9%: T-2069, Cerac Inc.) is evaporated with an e-beam of an ultrahigh e-beam apparatus (10-8 torr) to be deposited on a surface of a sample titanium nano-structure in order to fabricate a titanium nano-structure. Pure titanium is deposited to a thickness of 50 nm on a cover glass (glass coverslips, 12-550-15, Fisher-Scientific, NH) to form a flat titanium surface. Here, a deposition speed is 2 A°/sec, an e-beam current density is between 60 mA/cm$^2$ and 70 mA/cm$^2$. To form a nano-structure, the deposition speed of the sample is increased to 40 A°/sec, and the e-beam current density is 170 mA/cm$^2$. If the deposition speed of the sample is increased, a particular nano-structure is formed from a part having a thickness of 30 nm. It is determined from this that stability of a connective tissue of deposition atoms forms a nano-structure. A nano-structure of a surface is formed to a thickness of 35 nm or less. Energy of the e-beam of the evaporator used in a test is 7.9 keV.

Figure 66:
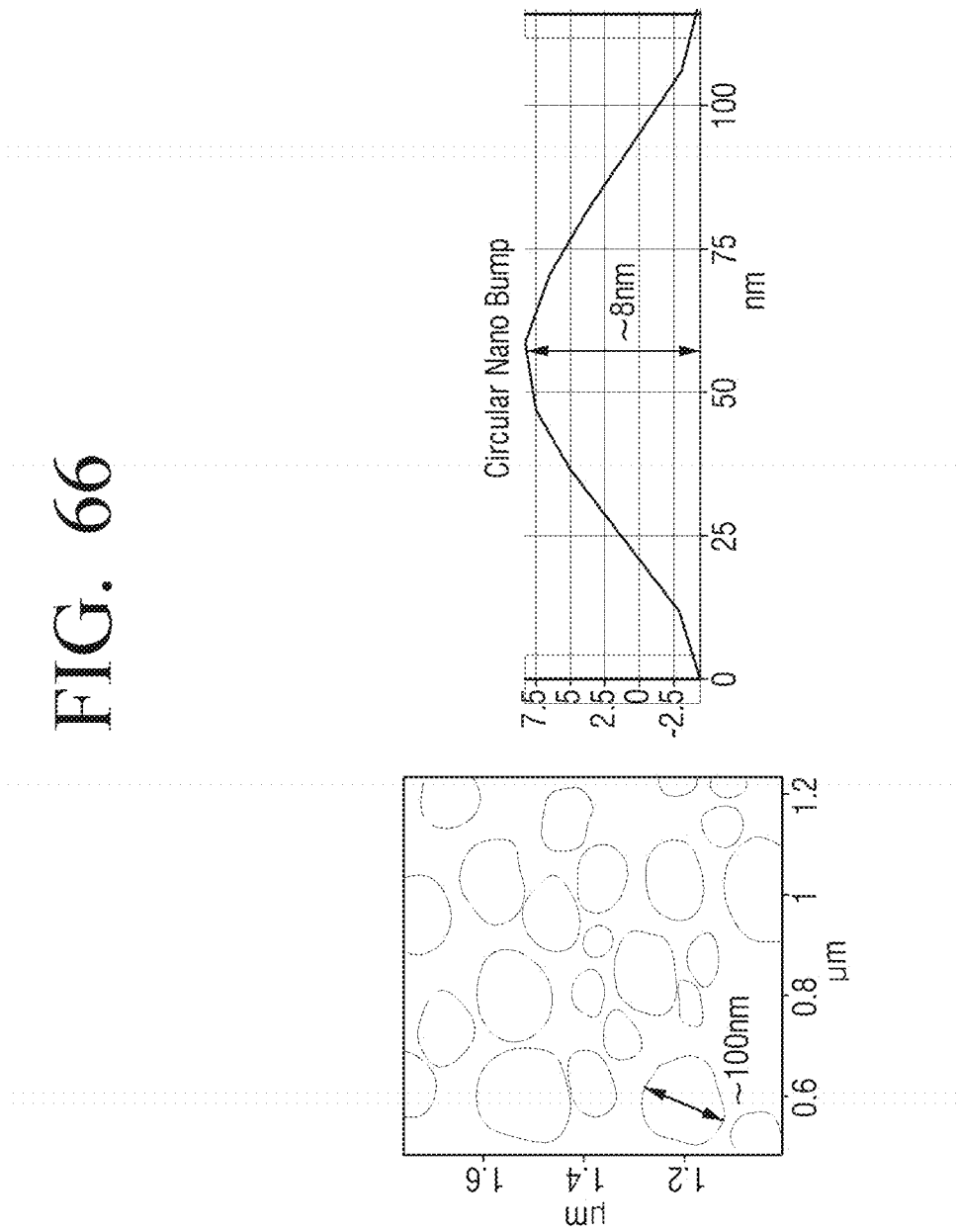
FIG. 66 is a view illustrating a nano-structure having a circular hemisphere and a height between about 8 nm and about 10 nm.

<Second Exemplary Embodiment of Third Toxicity Treatment> Observing Changes of Morphology and Actin of Macrophagocyte A general slide (control), a titanium slide, and a nano slide are fixed on a E-well plate and then sterilized, and then macrophagocyte is put, incubated for 12 hours, and stabilized. A morphology of a cell is observed by using an AE31 inverted microscopes (Motic, Wetzlar, Germany). As a result, the macrophagocyte of the titanium much more stretches than a control group, and the macrophagocyte of the titanium slide much less stretches than the macrophagocyte on the nano slide. It is checked from this that existing titanium less stimulates the macrophagocyte than nano does (FIG. 66).

In order to check a cytoskeleton of the macrophagocyte based on the observation of the morphology of the macrophagocyte, the actin is dyed and observed with a fluorescent material (red-marked with a horizontal line). In more detail, a macrophagocyte is put on a 6-well plate on which a sample is put, incubated for 12 hours, and stabilized. The macrophagocyte is cleansed with PBS two times and fixed by using 3.7 paraformaldehyde. The macrophagocyte is cleansed with PBS and is dyed with a fluorescent phalloidin conjugate solution of 50 ug/ml for 40 minutes.

Figure 67:
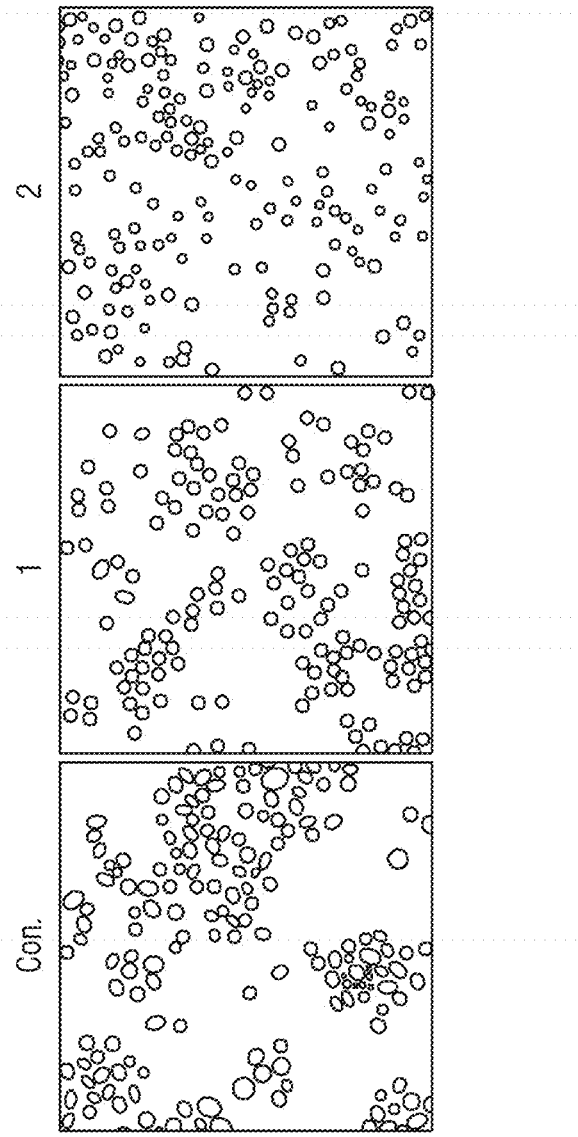
FIG. 67 is a view illustrating a result of observing a shape of macrophagocyte through an optical microscope (Con: control group, 1: when treating titanium, 2: when treating nano-processed titanium)

The macrophagocyte is cleansed with PBS and is dyed with DAPI for 5 minutes. The macrophagocyte is re-cleansed with the PBS one time, the slide is separated from the plate, and the macrophagocyte is mounted on a slide of microscope by using an antifade and observed by using an LSM 5 exciter (Carl Zeiss, Jena, Germany). Like the result of observing the morphology, the actin of the macrophagocyte on the nano slide less stretches than the actin of the macrophagocyte on the titanium slide (FIG. 67).

<Third Exemplary Embodiment of Third Toxicity Treatment> Measuring of Nitric Oxide (NO) and iNOS NO operate as a local controlling element and a nearotransmitter in the body. If a blood oxygen concentration is lowered, an endotheliocyte of a vessel wall generates NO. Also, NO operates in an adjacent myocyte to activate an enzyme loosening muscles. NO is secreted in a macrophagocyte when causing an infection in an immune reaction, and thus NO of the macrophagocyte is measured to check an infection arousing degree.

3-1. NO Analysis

A macrophagocyte is put on a 6-well plate on which a sample is put, incubated for 4 hours, and stabilized. Next, a slide is moved onto a new plate to measure only a cell on the slide, and then the cell is incubated for 20 hours (a total of 24 hours). A media of the cell is collected and reacts with a Griess solution at a ratio of 1:1 in order to measure a chromophoric degree.

As a result of measuring NO of the macrophagocyte, NO much more secreted from titanium than from a control group is reduced in nano (FIG. 68).

3-2. iNOS Western Blotting

A macrophagocyte is put on a 6-well plate on which a sample is put, incubated for 4 hours, and stabilized. Thereafter, a slide is moved onto a new plate to measure only a cell on the slide, and then the cell is incubated for 20 hours (a total of 24 hours). The macrophagocyte is cleansed with PBS and then moved to an E-tube. The cell is melted in an extraction buffer solution (a PBS solution including 1% triton X-100, 0.5% sodium deoxycholate, and 0.1% SDS) including a protease inhibitor.

A protein is quantified by using and a BSA standard and a Bio-Rad protein assay kit. A total protein from 10 ug to 50 ug of a cell undergoes an electrophoresis in a 8% polyacrylamide gel including 0.1% SDS, and a protein existing in the gel is moved to a nitrocelluose (NC) membrane by using an electroblotting method. In order to prevent a nonspecific combination, the NC membrane is dipped into a tris-buffered saline-tween (TBS-tween) solution including 5% nonfat dry milk and is reacted at a room temperature for 1 hour.

The NC membrane is cleansed with the TBS-tween solution one time for 15 minutes and then is cleansed with a new TBS-tween solution two times for 5 minutes. The NC membrane is dipped into a TBS solution including an antibody of a target protein (iNOS), left for 12 hours in a refrigerator, and cleansed according to the above-described method.

A filter is put into a TBS-tween solution including a secondary antibody marked with HRP, left at a room temperature for 1 hour, and cleansed one time for 15 minutes and four times for 5 minutes with a TBS-tween solution. Bands are visualized on a film by using an enhanced chemiluminescence (ECL).

An enzyme generating NO in a macrophagocyte is inducible nitride oxide synthase (iNOS), and iNOS is manifested when causing an infection, to generate NO. In other words, iNOS is directly involved in an infection reaction of the macrohpagocyte and operates when the macrophagocyte is activated to emit an inflammatory cytokine in the blood and then generate NO.

Figure 69:
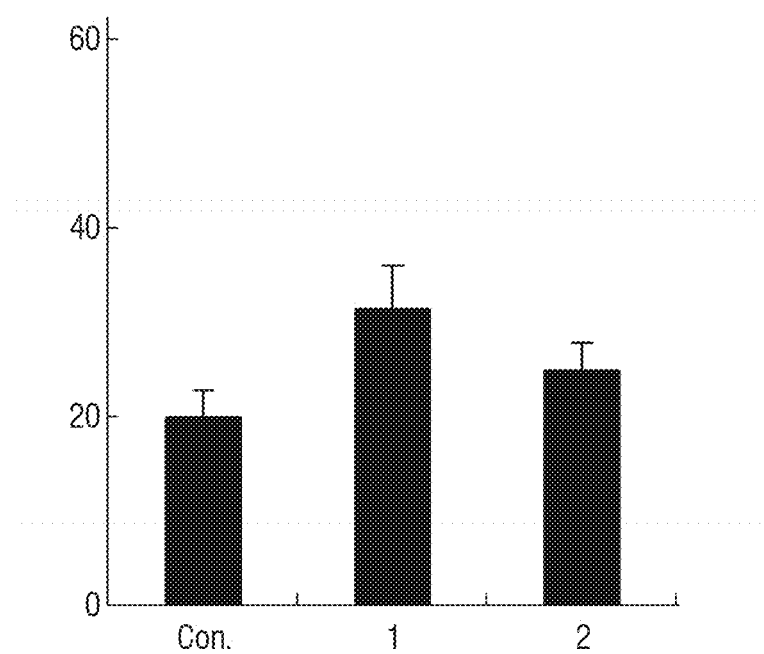
FIG. 69 is a view illustrating a result of measuring NO of macrophagocyte (Con: control group, 1: when treating titanium, and 2: when treating nano-processed titanium)

As a result of testing western blotting in order to check a manifestation degree of an iNOS protein, iNOS more manifested in titanium than in a control group like a result of NO assay is reduced in nano. (FIG. 69).

3-3. Observing of iNOS in Cell

A macrophagocyte is put on a 6-well plate on which a sample is put, incubated for 4 hours, and stabilized. Thereafter, a slide is moved onto a new plate to measure only a cell on the slide, and the cell is incubated for 20 hours (a total of 24 hours). The cell is cleansed with PBS two times and then fixed by using 3.7% paraformaldehyde. The cell is cleansed with PBS, and an antibody of iNOS is put in a concentration of 10 ug/ml, and the cell is allowed to be reacted to the antibody. The cell is cleansed with PBS two times and allowed to be reacted to a secondary antibody marked with a green fluorescent material (marked with a grid line) for 1 hour.

The cell is cleansed with PBS, the slide is separated from the plate, and the cell is mounted on a slide for a microscope by using an antifade and observed by using an LSM 5 exciter (Carl Zeiss, Jena, Germany).

Figure 70:
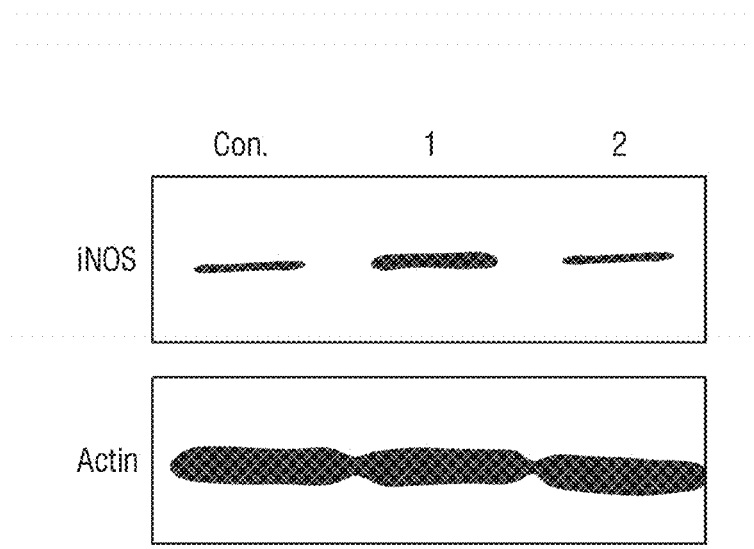
FIG. 70 is a view illustrating a test result of Western blotting for checking an expression degree of protein iNOS of macrophagocyte.

As a result of checking a manifestation degree of iNOS of a macrphagocyte by using a fluorescent material (green-marked with a grid line), the fluorescent material much dyes titanium than a control group. Also, the fluorescent material is more reduced in nano than in the titanium (FIGS. 70 and 71).

[Biocompatible Coating Layer]

Hereinafter, a biocompatible coating layer converting a biofuel battery part or a secondary part contacting the blood or a living body, i.e., a bioprotective layer, will be described in consideration of biocompatibility of a battery to be inserted into a living body. However, the biocompatible coating layer is not limited to the biofuel battery part but may be applied to all elements of the battery or an artificial vessel which is exposable to the living body or the blood.

The term "biocompatible polymer" used in the present general inventive concept refers to polymer which has an affinity with a cell tissue, is not recognized as a foreign material when being applied to the living body, and does not induce undesirable long-term effects such as thrombopoiesis, infection, a change of a matter property, etc. In general, when a polymer material contacts the blood, an adhesion of a blood protein component occurs within several seconds on a surface of the polymer material, and a platelet thrombus reaction and a red thrombus appear. The biocompatible polymer of the present general inventive concept includes polymer having a reformed surface in order to increase blood compatibility. A biocompatible polymer usable in the present general inventive concept includes a polymer material having a high hydrophile property like polyethylene glycol, polyacrylamide, etc. and having a reformed surface. Also, the biocompatible polymer includes polymer having a cell compatibility and polymer which hardly affects or does not affect the number of cells, growths of the cells, maintenance of a cell membrane, a biosynthesis process, or an enzyme activation.

According to the object of the present general inventive concept, a biocompatible polymer of the present general inventive may mean nondegradable polymer and include a polyolefin, polystyrene, polyethylene oxide, polyvinyl chloride, polyamide, polymethylmetacrylate, polyurethane, polyester, or a combination thereof but is not limited thereto. The biocompatible polymer has a high blood compatibility and thus may be polyurethane group widely used an artificial vessel, an artificial heart, etc., polycarbonate group which has a mechanical and thermal resistiveness and thus is applied to the heart, a lung aid, an artificial heart valve switch, etc. The biocompatible polymer may be a polycarbonate urethane (PCU). The PCU is a medical polymer allowed by FDA to be applied to clinical trials such a heart valve, a semilunar valve, or artificial blood. The PCU is not dissolved by oxygen and thus maintain a predetermined mechanical strength in body fluid. The PCU is a matrix and synthesized with a carbon nanotube to show a high dispersibility.

The term "carbon nanotube" used in the present general inventive concept refers to a carbon material which has a tube shape formed through rolling of a hive-shaped flat plate type carbon tube formed through a combination between one carbon atom and three carbon atoms, a diameter between 1 nm and 100 nm, and a high aspect ratio having a length between tens of nm and dozens of μm. The carbon nano tube includes several types of carbon nanotubes and is classified into a multi-walled nanotube (MWCNT) formed of two or more walls according to the number of walls enclosing a longitudinal direction on its axis and a single-walled nanotube (SWCNT) formed of only one wall. The carbon nanotube include all these types in the present general inventive concept but may be a multi-walled carbon nanotube. A diameter of a carbon nanotube useable in the present general inventive concept may be between 1 nm and 100 nm.

The polymer composite coating layer of the present general inventive concept may be used to coat a medical device to be inserted into a living body.

The term "medical device to be inserted into the living body" used in the present general inventive concept may be one selected from the group consisting of a microvessel medical device, an artificial vessel scaffold, a fusion power electrode source or a power supply wire of a blood vessel, a biochip, a nanorobot, an implant, an artificial heart valve, an artificial bladder, an artificial urinary tract, an artificial semilunar valve, an artificial vessel, an artificial heart, a cardiac pacemaker insulator, a catheter, and a stent. However, the medical device is not limited thereto but may be any one to be inserted into a living body.

A content of a biocompatible polymer and a carbon nanotube of a coating layer of the present general inventive concept may be a ratio between 1:1 w % and 1:10 w %. The coating layer may be formed of a polymer-nano composite formed of a synthesis of the biocompatible polymer and the carbon nanotube. In the present general inventive concept, the polymer-nano composite has the characteristics of the coating layer disclosed in the present general inventive concept.

The term "composite" used in the present general inventive concept means a synthesis of two or more individual materials.

The polymer composite coating layer of the present general inventive concept may have a nanometer thickness or a submicron-meter thickness, i.e., a thickness between 30 nm and 200 nm, and is transparent. The nanometer thickness indicates a nanometer and means a thickness of 100 nm or less according to the object of the present general inventive concept. Also, the submicron-meter means a thickness range between 100 nm and 1 μm.

In the present general inventive concept, the biocompatible polymer and the carbon nanotube are adjusted to the nanometer thickness and the submicron-meter thickness, i.e., a thickness of 100 nm or less, to form a coating of a biomedical device which is inserted into a microvessel and a coronary artery. Also, the biocompatible polymer and the carbon nanotube are transparent and thus may be used to analyze an activity of a live cell.

Figure 177:
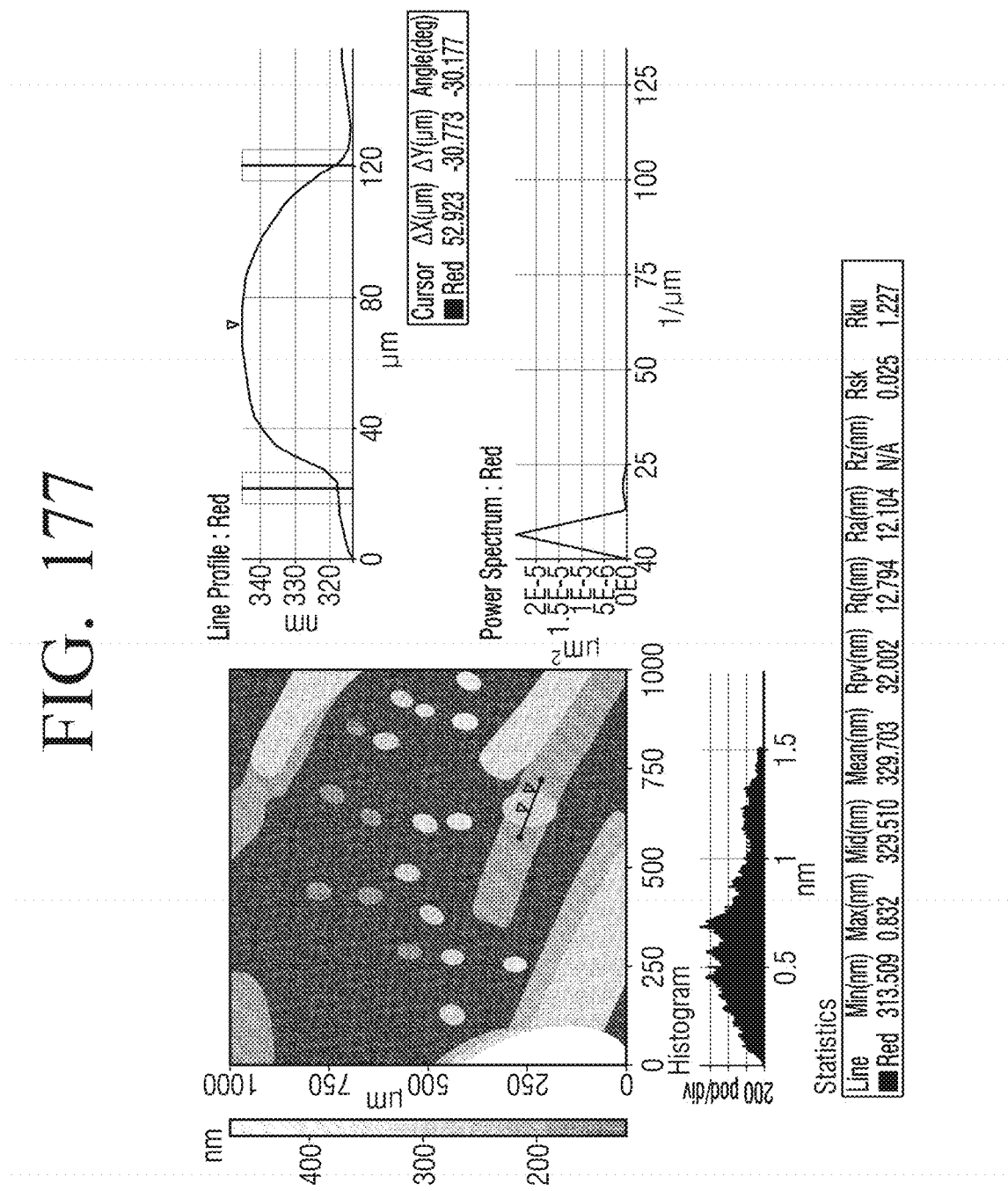
FIG. 177 is a view illustrating a carbon nanotube which is not exposed onto a surface but is covered with a thin film of about 30 nm when it is observed that a polymer sphere is formed on the carbon nanotube when applying heat.

Also, the coating layer has a structure in which a carbon nanotube is not directly exposed to a surface of the biocompatible polymer. Since the carbon nanotube is not directly exposed to the surface, a chemical component of the biocompatible polymer is maintained, a nanostructure formed by a carbon nanotube is formed in the biocompatible polymer to compare biocompatibility and toxicity with an existing biopolymer material in order to improve the biocompatibility and the toxicity and adjust a mechanical strength in a synthesis ratio of carbon nanotubes. As shown in FIG. 177, a polymer sphere formed when heat is applied is formed on a carbon nanotube (to a thickness of 30 nm). Therefore, the carbon nanotube is not exposed to the surface but is covered with an ultrathin film having a thickness of 30 nm.

Also, the coating layer has an insulation differently from a polymer-carbon nanotube composite which is used in a medical information and communication apparatus.

According to another aspect, the present general inventive concept provides a method of fabricating a polymer composite coating layer having a nanometer thickness and a submicronmeter thickness, including: respectively putting a biocompatible polymer and a carbon nanotube into solvents in a ratio between 1:1 w % and 1:10 w % and respectively sonicating the biocompatible polymer and the carbon nanotube; mixing the two sonicated solutions; coating the mixture on glass by using a spin coater; drying the glass coated with the mixture at a room temperature; and irradiating ultraviolet rays to the dried glass to sterilize and disinfect the dried glass.

The contents of the biocompatible polymer in the fabricating method of the present general inventive concept are the same as the above-described contents. The biocompatible polymer may be a polycarbonate or a polycarbonate urethane.

The fabricating method of the present general inventive concept, the solvent of the carbon nanotube may be one or more selected from the group consisting of water, 1,2-dichloroethane, tetrahydrofuran, dimethyl formamide, toluene, ethanol, and a mixture thereof or may be 1,2-dichloroethane.

The solvent of the polycarbonate urethane may be chloroform.

In the sonicating step, tip and bath ultrasonic apparatuses may be used, and a sonication processing time may be 1 hour to 24 hours but is not limited thereto and may be easily selected by those skilled in the art.

According to an exemplary embodiment of the present general inventive concept, a polycarbonate urethane is mixed with chloroform, a carbon nanotube is mixed with 1,2-dichloroethane, and each solution is sonicated, dispersed, and coated on glass by using a spin coater. Thereafter, the glass is dried at a room temperature, and sterilized and disinfected with ultraviolet rays to fabricate a coating layer having a thickness of 100 nm or less.

The coating layer may be used as a coating material of a medical device to be inserted into a living body. The above-described contents are equally applied to the medical device and may be a microvessel medical device, an artificial vessel scaffold, a fusion power electrode source or a power supply wire of a blood vessel, a nanorobot, an implant, an artificial heart valve, an artificial bladder, an artificial urinary tract, an artificial semilunar valve, an artificial vessel, an artificial heart, or a cardiac pacemaker insulator.

The fabricating method of the present general inventive concept may further include: adjusting a synthesis ratio between the biocompatible polymer and the carbon nanotube to adjust a surface strength of the coating layer.

A process technique of a single layer biopolymer-nano composite having high biocompatibility and a nanometer or submicronmeter thickness is not developed. Also, a technique for simultaneously adjusting nano-surface energy and surface strength of a coating layer having a thin film thickness has not been reported. In the present general inventive concept, when a biocompatible polymer and a carbon nanotube are synthesized with each other, a content ratio of w % of the carbon nanotube is increased to define an increase in a mechanical surface strength in order to increase a surface strength of a thin film nano coating layer.

Also, the fabricating method of the present general inventive concept may further included: adjusting a synthesis ratio between the biocompatible polymer and the carbon nanotube to adjust nanoscale roughness of the coating layer in order to check biocompatibility.

In the present general inventive concept, when the biocompatible polymer and the carbon nanotube are synthesized with each other, a content ratio of w % of the carbon nanotube is increased. Therefore, nanoscale roughness of a nano-coating layer, and surface energy is increased to increase surface energy of a polymer-nano composite coating layer having a nanometer or submicronmeter thickness in order to adjust an adhesion of a protein in a living body, thereby increasing biocompatibility.

According to an exemplary embodiment of the present general inventive concept, a biocompatible polymer and a carbon nanotube are synthesized with each other in a ratio between 1:1 and 1:10, and the synthesis ratio is changed to check a tendency of a physical property of a composite. As a result, as 1,2-dichloroethane is added to the polycarbonate urethane, surface energy decreases, and surface strength softens. As the synthesis ratio of the carbon nanotube in the polycarbonate urethane is increased, the surface energy increases, and thus the nanoscale roughness increases, thereby increasing the surface strength (refer to FIG. 179). For this fact, the biocompatible polymer-nano composite having the nanometer or submicron-meter thickness adjusts the synthesis ratio of the polymer and the carbon nanotube in order to adjust the surface energy and the surface strength.

Figure 181:
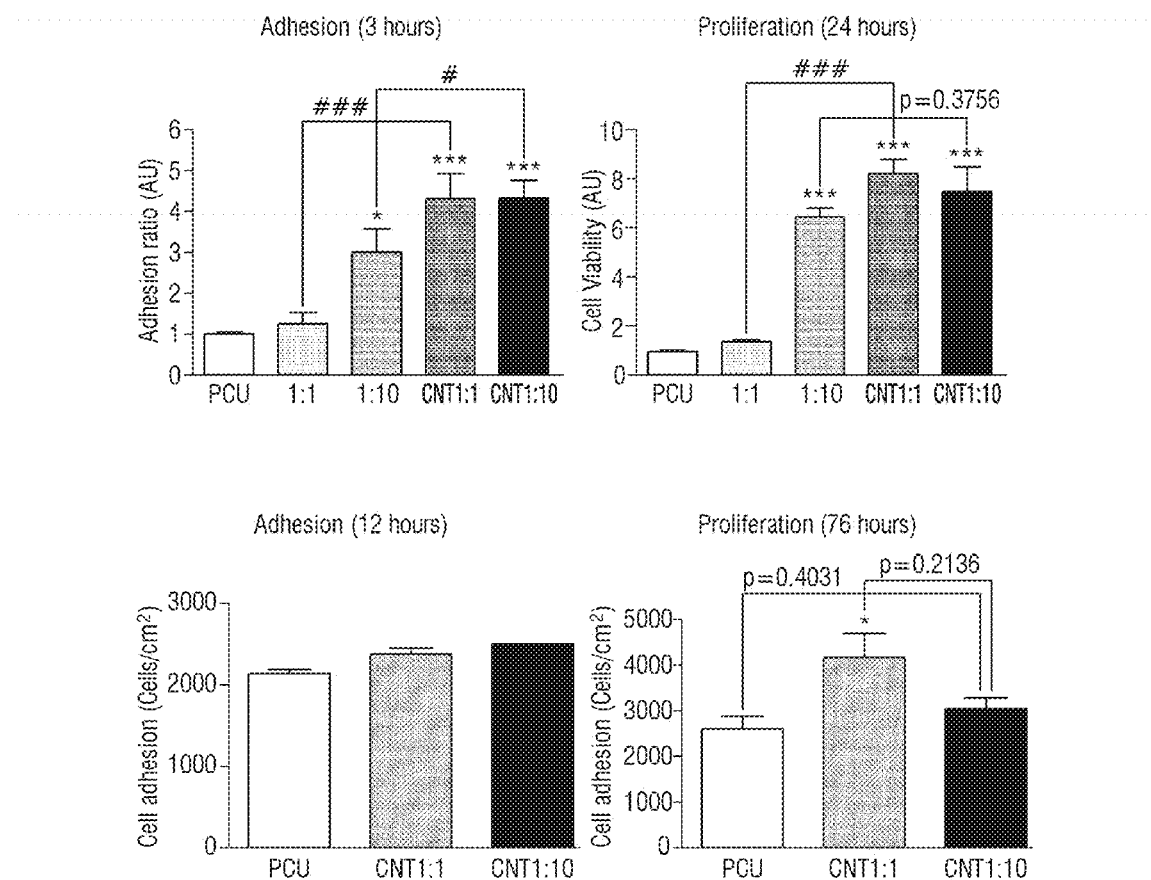
FIG. 181 is a view illustrating adsorption and proliferation (refer to an upper graph) of immunocyte with respect to a synthesis ratio between CNT and PCU in the coating layer of the present general inventive concept, wherein the adsorption of the immunocyte increases for 3 hours with an increase in a surface tension, the proliferation also increases for 24 hours with the increase in the adsorption, a lower graph illustrating adsorption and proliferation of a mesenchymal stem cell, and self-renewal is adjusted according to the increased nano roughness and adsorption of protein

Also, the roughness of the nano-surface may be adjusted through an adhesion of a protein in a living body, and thus a polymer-nano composite may be fabricated to be appropriate for biocompatibility. According to an exemplary embodiment of the present general inventive concept, in order to check an adhesion adjustment effect of a carbon nanotube-polycarbonate urethane composite with respect to a protein of a living body, an adhesion of vitronectin which is a cell adhesive glucoprotein existing in a blood plasma and a serum connective tissue and an adhesion of FBS used as an essential protein of a culture cell beige in an animal blood are investigated. As a result, as a content ratio of the carbon nanotube increases, the vitronectin and the FBS adhere well. As shown in FIG. 180, protein is much adsorbed with an increase in the carbon nanotube, and roughness of a nano-surface more affects the adhesion of the protein than surface energy. Also, the roughness of the nano-surface increases with the increase in the carbon nanotube, and thus surface tension increases (refer to FIG. 178). An adhesion of an immunocyte increases with the increase in the surface tension, and thus a proliferation of the immunocyte increases (refer to FIG. 181).

Through the adjusting method of the present general inventive concept as described above, if biopolymer is coated on an implantable device, a nanotube is synthesized with the biopolymer to form a nanotopo in order to adjust surface tension, thereby improving biocompatibility and toxicity more than an existing biopolymer material. Also, a mechanical strength is adjusted through a synthesis ratio of the nanotube to adjust a dynamic property, and thus the biopolymer may be applied in more implant polymer application fields.

A coating layer which has a nanometer or submicron-meter thickness and is fabricated by the fabricating method, i.e., a nanotube polymer thin film structure, may be used as an artificial vessel scaffold, an artificial bladder, an artificial urinary tract, a fusion power electrode source coating of a blood vessel, or a biocoating material of a power supply wire of a power source. The thin film structure has an effect of inhibiting a human immuno deficiency toxicity. The fabricating method of the present general inventive concept may be a coating method of improving biocompatibility and inhibiting an activity of a macrophagocyte which is a representative an immunoactive cell in order to reduce immunotoxicity. The polymer-nanocomposite or the coating layer may be used in all types of implantable medical devices and may be appropriate for the environments such as insertions of a capillary vessel and a microvessel.

The present general inventive concept relates to a coating layer which is formed by mixing a biocompatible polymer with a carbon nanotube to have a nanometer or submicron-meter thickness and a method of fabricating the coating layer. A synthesis ratio between the biocompatible polymer and the carbon nanotube is adjusted to increase biocompatibility of the coating layer having the thin film thickness and adjust a mechanical strength. Therefore, the coating layer may be applied to a medical device to be inserted into a microvessel of a living body, such as a nano-medical device and a wire coating.

Hereinafter, the present general inventive concept will be described in more detail according to exemplary embodiments. However, these exemplary embodiments is to exemplarily describe the present general inventive concept, and thus the scope of the present general inventive concept is not limited to these exemplary embodiments.

First Exemplary Embodiment of Fourth Toxicity Treatment: Fabricating CNT_PCU Composite Coating Layer 1 g of polycarbonate urethane (Lubrizol, PC-3575A) is injected into 16 ml of chloroform to fabricate a solution. 0.3 g of a carbon nanotube is injected into 60 ml of 1,2-dichloroethane to fabricate a solution. Ultrasonic waves are applied to the polycarbonate urethane for 1 hour and to the carbon nanotube for 24 hours at a room temperature. The two solutions are mixed. Therefore, a content of the carbon nanotube to the polycarbonate urethane and is between 100 w % and 1000 w %. The solutions are coated on glass by using two spin coaters and then dried at a room temperature in a vacuum state. UV rays are irradiated to sterilize and disinfect the glass in order to CNT-PCU. A mixed degree of a chemical solution for forming a particular is as follows.

(1) PCU: 1,2-Dichloroethane (1:1)→2 ml: 25 ml
(2) PCU: 1,2-Dichloroethane (1:10)→0.2 ml: 25 ml
(3) PCU: CNT (1:1)→2 ml: 25 ml
(4) PCU: CNT (1:1)→0.2 ml: 25 ml After sonication (PCU+1,2-Dichloroethane=30 min, PCU+CNT=1 hr), each composite solution is coated on the glass by using a spin coater. The glass is dried (at a room temperature in a vacuum state), and UV rays are irradiated onto the glass to sterilize, disinfect, and keep the glass.

Figure 176:
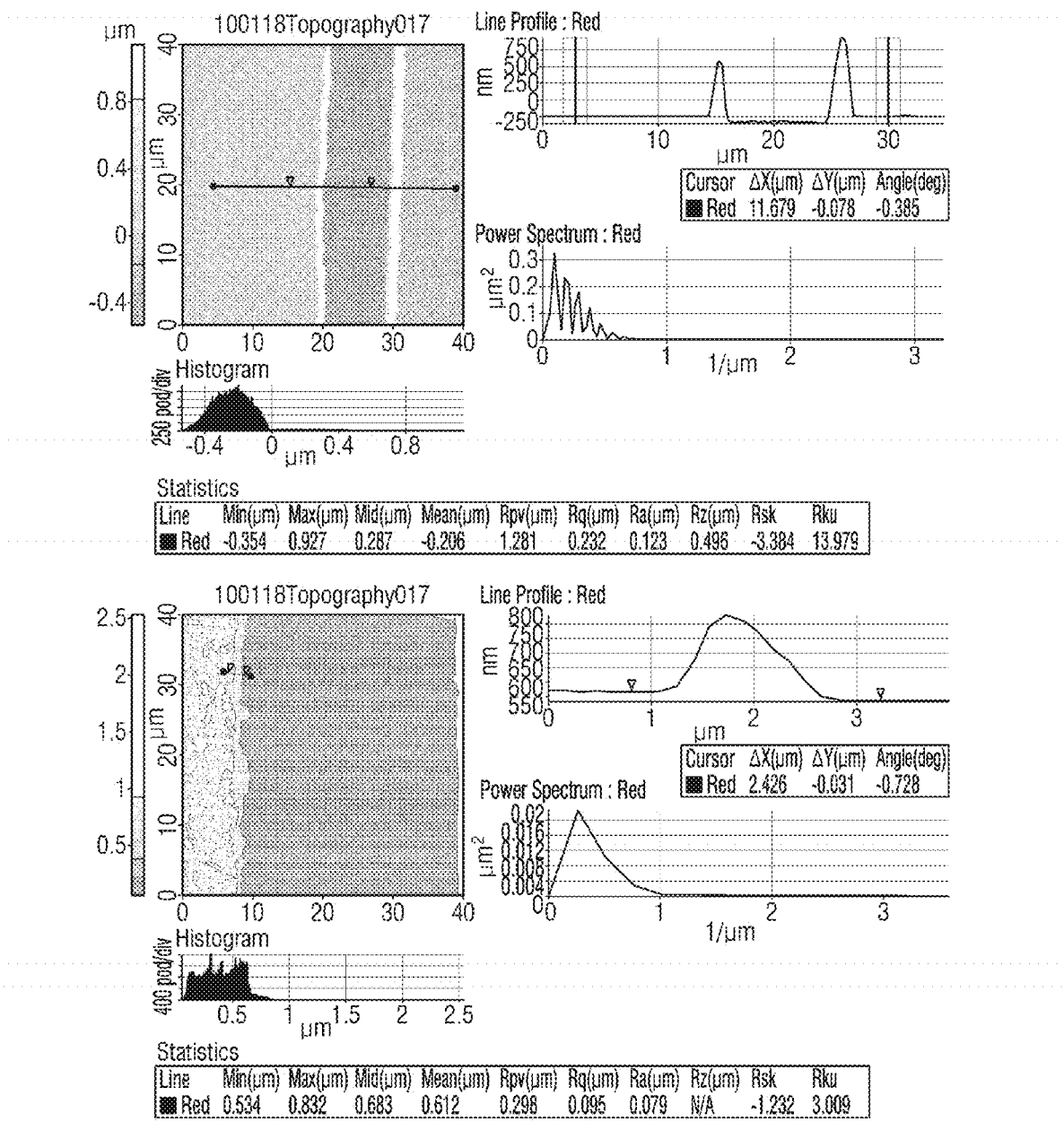
FIG. 176 is a view illustrating a result of measuring a thickness of a polymer coating layer according to an exemplary embodiment of the present general inventive concept, wherein a lower figure illustrates thicknesses (AFM analysis) of a carbon nanotube and a polymer composite, and each of the thicknesses is about 31 nm.

As a result, a coating layer having a nano thin film structure having a thickness of 100 nm or 200 nm or less (refer to FIG. 176).

Figure 175:
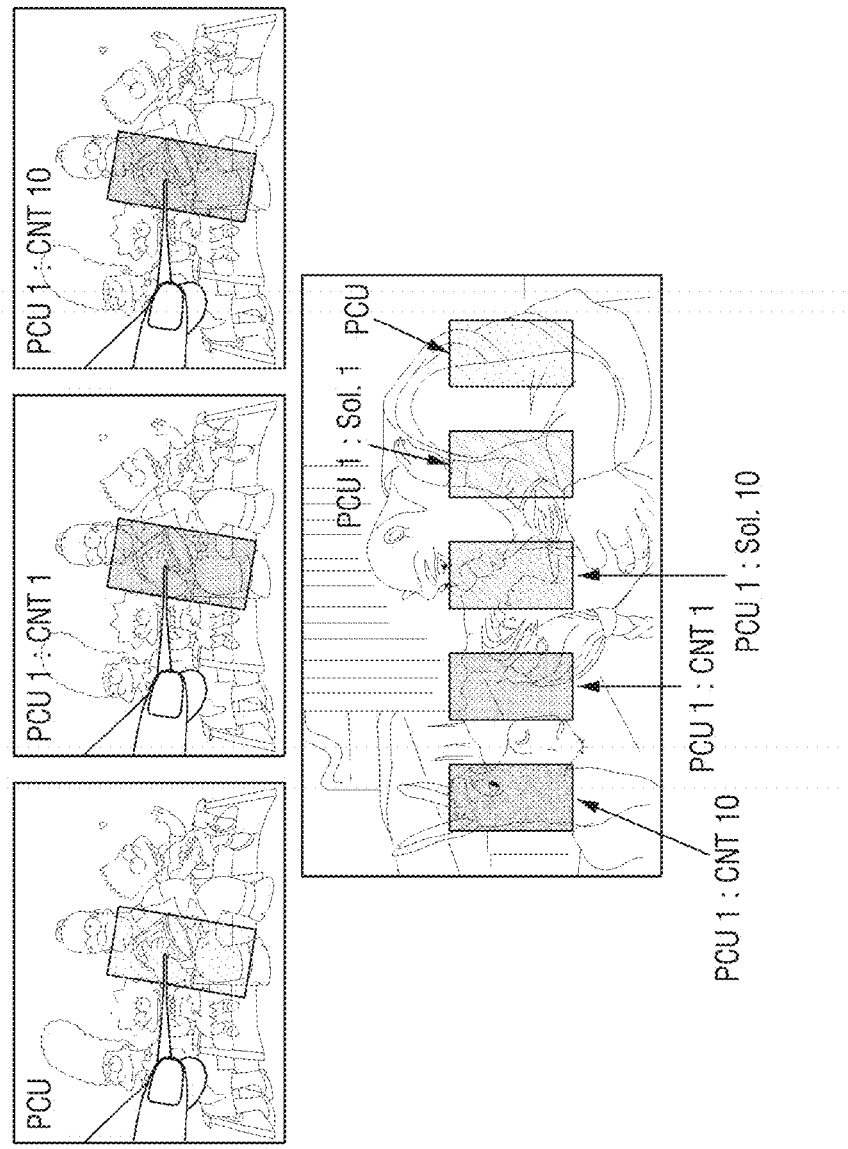
FIG. 175 is a view illustrating an sample of a coating layer fabricated by changing a synthesis ratio between CNT and PCU.

Second Exemplary Embodiment of Fourth Toxicity Treatment: Investigating of Surface Characteristic of CNT-PCU Composite Coating Layer Transparency As a result of investigating a transparent degree of a CNT-PCU composite coating layer of the present general inventive concept, as shown in FIG. 175, a carbon nanotube is coated to a thickness of 100 nm or less and thus keeps a transparent state thereof.

Measuring of Surface Hardness: Dynamic Hardness

A dynamic hardness which is newly defined by JIS is measured as a surface hardness. The dynamic hardness is hardness which is obtained by measuring how much a penetrator penetrates a specimen, i.e., is obtained from test force of a process of pushing the penetrator and an indent depth. In the present general inventive concept, when the indent depth of the test force penetrator P[mN] into the specimen is D[μm], hardness is calculated by using dynamic hardness DH defined in Equation below:

$$DH = \alpha \times P/D^2$$

($\alpha$ denotes an integer by a penetrator shape. 115° triangle pyramidal penetrator: $\alpha = 3.8584$)

Figure 179:
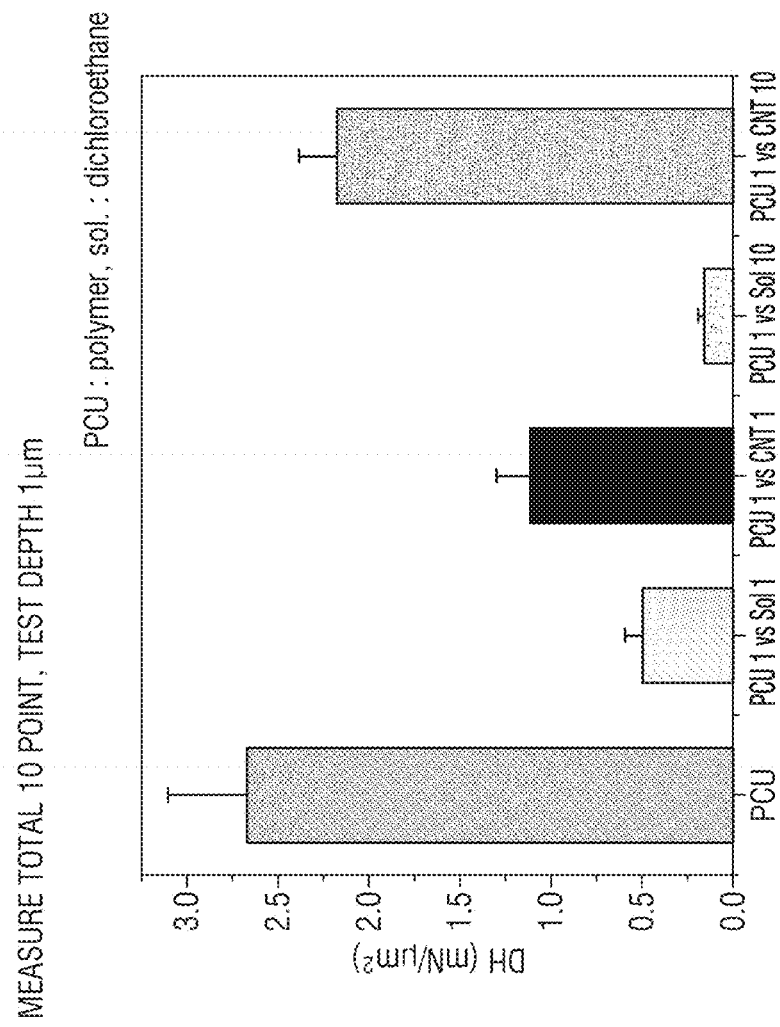
FIG. 179 is a view illustrating a result of measuring dynamic hardness of a coating layer fabricated by changing a synthesis ratio between CNT and PCU, wherein the surface hardness increases with an increase in the carbon nanotube (if a weight of CNT is 10 times increased, the surface hardness value increases two times or more.

As a result, as shown in FIG. 179, the hardness increases with an increase in a synthesis ratio of CNT to PCU. As CNT is added, surface energy increases (nanoscale roughness increases), and surface hardness increases. Also, as 1,2-Dichloroethane is chemically added to PCU, the surface energy decreases, and surface strength is adjusted.

Third Exemplary Embodiment of Fourth Toxicity Treatment: Adjustment Effect of Protein Absorbance of CNT-PCU Coating Layer in Living Body In order to perform a protein adsorption test (ELISA or absorbance KIT) for a CNT-PCU composite coating layer, a protein undiluted solution (FBS, Gibco) used for incubating a cell is diluted to ⅕, and then an adsorption test is performed on a surface of each sample. After 3 hours elapses, a cleanser (SDS1%) is used to take off a protein, and then a protein absorbance is measured by an ELISA reader by using a protein absorbance measuring KIT (coomasie 595 nm, Thermo).

Also, an absorption test is performed by using vitronectin (V 8379, Sigam). After 3 hours elapses, a cleanser (SDS1%) is used to take off a protein, and then a protein absorbance is measured by an ELISA reader by using a protein absorbance measuring KIT (coomasie 595 nm, Thermo).

As a result, a protein absorption degree of the coating layer increases according to a ratio between CNT and PCU. Also, nanoscale surface roughness is very important to the protein absorption, and an adsorption of the vitronectin increases according to the ratio between CNT/PCU. Therefore, if the ratio between CNT and PCU of the coating layer is adjusted to adjust surface energy, an adsorption of a protein in a living body is adjusted, and thus the coating layer is further appropriate for the living body (refer to FIG. 180).

Fourth Exemplary Embodiment of Fourth Toxicity Treatment: Effect of Adhering and Proliferating of CNT-PCU Composite in Cell A macrophagocyte (J774, ATCC) is incubated to 100000/cm$^2$ in each coated sample, and then the number of cells is measured by MTT after 3 hours and 24 hours. Also, a stem cell is incubated to 2500/cm$^2$ in each coated sample, and then the number of cells is measured by using a Dapi (fluorescence microscope) measuring method after 3 hours and 24 hours.

As a result, an adhesion and a proliferation of a coating layer to an immunocyte and a mesenchyma stem cell increase according to a ratio between CNT and PCU. Therefore, an adhesion degree increases in an interactive of the coating layer of the present general inventive concept with the stem cell and the immunocyte, and proliferation increases. Therefore, the ratio between CNT and PCU is adjusted to improve a biocompatibility of the coating layer of the present general inventive concept.

[Initial Driving of Transformer Circuit Part]

Hereinafter, a boost type power conversion system for initial driving will be disclosed as an example of a transformer circuit part of a battery to be inserted into a living body.

Figure 72:
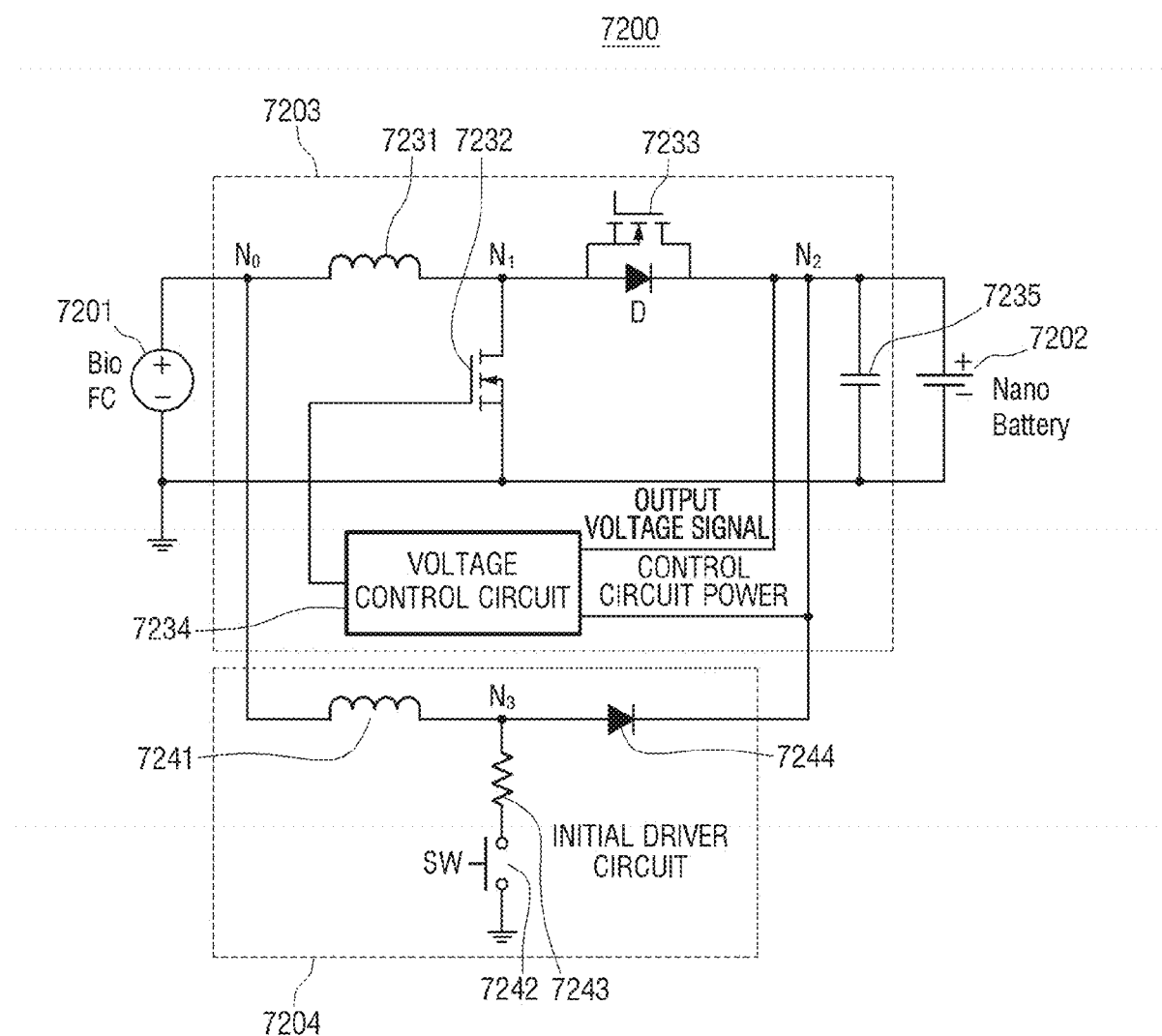
FIG. 72 is a view illustrating a boosting power transforming system according to an exemplary embodiment of the present general inventive concept.

FIG. 72 is a view illustrating a boost type power conversion system according to an exemplary embodiment of the present general inventive concept.

Referring to FIG. 72, a boost type power conversion system 7200 includes a fuel battery part 7201, a secondary battery part 7202, a boost type power converter 7203, and an initial driver circuit 7204.

In the boost type power conversion system 7200, the fuel battery part 7201 and the secondary battery part 7202 are fused into a single body and may be inserted into a living body or a blood vessel.

The fuel battery part 7201 is an energy source which generates a low voltage and may include a battery or a solar battery which outputs a direct current (DC) voltage.

For example, the fuel battery part 7201 may generate a voltage by using a material of a living body such as glucose of the blood. In this case, the generated voltage may have a low voltage value which is difficult to be charged to the secondary battery part 7202.

The secondary battery part 7202 is an element which stores or uses a boosted voltage and may be an electrochemical storage device having a function of storing DC energy or an electronic device using a DC voltage.

The boost type power converter 7203 boots the voltage generated by the fuel battery part 7201 and provides the boosted voltage to the secondary battery part 7202.

The initial driver circuit 7204 controls initial driving of the boost type power converter 7203. In detail, the initial driver circuit 7204 provides control power to the boost type power converter 7203 in initial driving of the boost type power converter 7203. The initial driver circuit 7204 may be a starting circuit which is to drive the boost type power converter 7203.

The boost type power converter 7203 according to an exemplary embodiment of the present general inventive concept includes a first boosting inductor 7231, a first transistor 7232, a second transistor 7233, a voltage control circuit 7234, and an output capacitor 7235.

The first boosting inductor 7231 accumulates energy generated by the fuel battery part 7201. Here or hereinafter, the accumulation of the energy refers to storage of energy.

The first transistor 7232 controls a boosting operation. In detail, the first transistor 7232 controls the energy accumulation of the first boosting inductor 7231.

The second transistor 7233 provides the energy stored in the first boosting inductor 7231 to the output capacitor 7235.

The voltage control circuit 7234 controls an output voltage of the boost type power converter 7203. Also, the voltage control circuit 7234 controls on/off operations of the first transistor 7232.

The output capacitor 7235 receives and stores the energy stored in the first boosting inductor 7231 and generates the output voltage.

A circuit structure of the boost type power converter 7203 will be described in more detail with reference to FIG. 72.

The first boosting inductor 7231 includes an end which is connected to the fuel battery part 7201 and an other end which is connected to a first node $N_1$. The first transistor 7232 includes a drain terminal which is connected to the first node $N_1$, a gate terminal which is connected to the voltage control circuit 7234, and a source terminal which is connected to a ground terminal.

The second transistor 7233 includes a source terminal which is connected to the first node $N_1$ and a drain terminal which is connected to a second node $N_2$. A signal opposite to a gate terminal of the first transistor 7232 is applied to a gate terminal of the second transistor 7233. In detail, a NOT gate (not shown) is connected to an output side of the voltage control circuit 7234, and thus an output signal of the voltage control circuit 7234 is converted by the NOT gate and then provided to the gate terminal of the second transistor 7233.

The voltage control circuit 7234 includes a first terminal which is connected to the gate terminal of the first transistor 7232 and second and third terminals which are connected to the second node $N_2$.

The output capacitor 7235 includes an end which is connected to the second node $N_2$ and an other end which is connected to the ground terminal.

A diode D includes an anode which is connected to the source terminal of the second transistor 7233 and a cathode which is connected to the drain terminal of the second transistor 7233.

The first and second transistors 7232 and 7233 are shown as N-type MOS transistors but may be P-type MOS transistors. Also, the first and second transistors 7232 and 7233 may be bipolar transistors. If the first and second transistors 7232 and 7233 are changed as described above, a part of a circuit structure shown in FIG. 1 may be changed. This change is obvious to those skilled in the art. The first and second transistors 7232 and 7233 may be MOS transistors or bipolar transistors.

The initial driver circuit 7204 according to an exemplary embodiment of the present general inventive concept includes a second boosting inductor 7241, a switch 7242, a resistor 7243, and a diode 7244.

The second boosting inductor 7241 accumulates the energy generated by the fuel battery part 7201.

The switch 7242 controls a boosting operation of an initial driver circuit.

The resistor 7243 limits a current of the second boosting inductor.

The diode 7244 provides the energy stored in the second boosting inductor to the output capacity 235.

A circuit structure of the initial driver circuit 7204 will be described in more detail with reference to FIG. 72.

The initial driver circuit 7204 may further include a ground terminal which is connected to an end of the switch 7242, besides the second boosting inductor 7241, the switch 7242, the resistor 7243, and the diode 7244.

The second boosting inductor 7241 includes an end which is connected to the fuel battery part 7201 and an other end which is connected to a third node $N_3$.

The switch 7242 switches an end of the resistor 7243 and an end of the ground terminal.

The resistor 7243 includes an end which is connected to an other end of the switch 7242 and an other end which is connected to the third node $N_3$.

The diode 7244 includes an anode which is connected to the third node $N_3$ and a cathode which is connected to the output capacitor 7235.

A boost type power conversion system according to another exemplary embodiment of the present general inventive concept includes a boost type power converter 7203 which boots the voltage generated by the fuel battery part 7201 and provides the boosted voltage to the secondary battery part 7202 and an initial driver circuit 7204 which applies the control power to the boost type power converter 7203 to control initial driving of the boost type power converter 7203.

According to another exemplary embodiment of the present general inventive concept, there is provided a boost type power conversion system which boots an energy source providing a low voltage by which a voltage control circuit cannot be driven, by using an initial driver circuit, to store the boosted energy source or use the boosted energy source as power of an electronic circuit.

Figure 73:
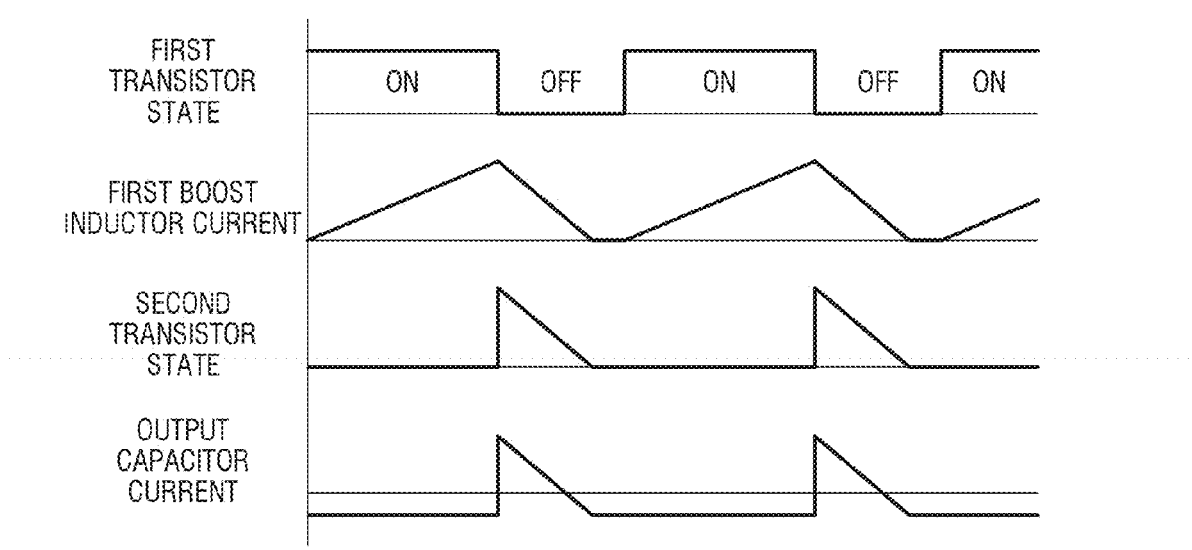
FIG. 73 is a view illustrating waveform for illustrating an operation of a boost power converter.

FIG. 73 is a view illustrating waveforms indicating an operation of a boost type power converter.

The operation of the boost type power converter will be described in more detail with reference to FIGS. 72 and 73.

If the first transistor 7232 is turned on, a current flowing in the first boosting inductor 7231 linearly increases, and energy generated by the fuel battery part 7201 is accumulated in the first boosting inductor 7231.

If the first transistor 7232 is turned off in this condition, the energy accumulated in the first boosting inductor 7231 is transmitted to the output capacitor 7235 through the diode connected to the second transistor 7233. In this case, the diode D includes an anode which is connected to the source terminal of the second transistor 7233 and a cathode which is connected to the drain terminal of the second transistor 7233.

Here, in order to reduce a voltage drop occurring in the diode connected to the second transistor 7233, the voltage control circuit 7234 may operate the second transistor 7233 to turn on the second transistor 7233. In detail, the voltage control circuit 7234 boosts a voltage between the source terminal and the gate terminal of the second transistor 7233 to be equal to or greater than a threshold voltage to operate the second transistor 7233 in order turn on the second transistor 7233.

An output voltage of the boost type power converter 7203 is controlled by a an ON/OFF time ratio of the voltage control circuit 7234 (i.e., a duty ratio). If the ON time increases, the output voltage is higher.

A voltage of the output capacitor 7235 is fed back to control the ON/OFF time ratio in order to obtain an output voltage having a preset value through the boost type power converter 7203.

The voltage control circuit 7234 may be various types of electronic devices, and power having an appropriate level voltage is required to drive the voltage control circuit 7234. This power may be supplied from an energy source such as the fuel battery part 7201.

However, if a voltage of the energy source is low, and thus an appropriate level voltage is not supplied to the voltage control circuit 7234, this power may be supplied from the output capacitor 7235 of the boost type power converter 7203.

If the power of the voltage control circuit 7234 is supplied to the output capacitor 7235, the output capacitor 7235 is to be charged in order to operate the voltage control circuit 7234. If a voltage of the output capacitor 7235 is 0V on an initial stage, the boost type power converter 7203 does not operate.

Therefore, in an initial operation of the boosting type power converter 7203, energy required until the voltage control circuit 7234 normally operates may be stored in the output capacitor 7235.

The initial driver circuit 7204 operates to charge the output capacitor 7235 in the initial operation of the boost type power converter 7203. The detailed operation of the initial driver circuit 7204 will be described in more detail later with reference to FIG. 74.

Figure 74:
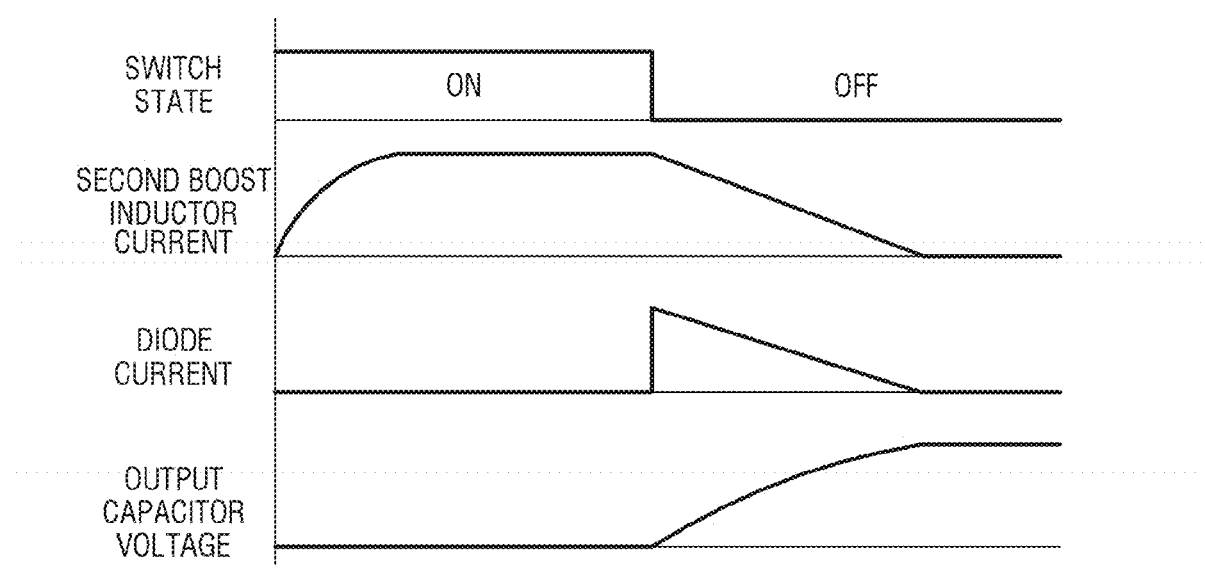
FIG. 74 is a view illustrating a waveform for illustrating an operation of an initial driver circuit.

FIG. 74 is a view illustrating waveforms indicating an operation of an initial driver circuit.

Referring to FIGS. 72 through 74, if the switch 7242 short-circuits in an initial driving of the boost type power converter 7203, a current of the second boosting inductor 7241 linearly increases, and energy generated by the fuel battery part 7201 is accumulated in the second boosting inductor 7241. A level of a current flowing in the second boosting inductor 7241 and a level of the energy accumulated in the second boosting inductor 7241 are limited by the resistor 7243 connected to the switch 7242 in series.

If the switch 7242 is turned off in this condition, the energy accumulated in the second boosting inductor 7241 is stored in the output capacitor 7235 through the diode 7244 in order to supply power necessary for initial driving of the voltage control circuit 7234.

The initial driver circuit 7204 operates only once when the boosting type power converter 7203 operates. After the initial driving, the boosting type power converter 7203 continuously supplies energy to the output capacitor 7235. Therefore, power is continuously supplied to the voltage control circuit 7234.

Figure 75:
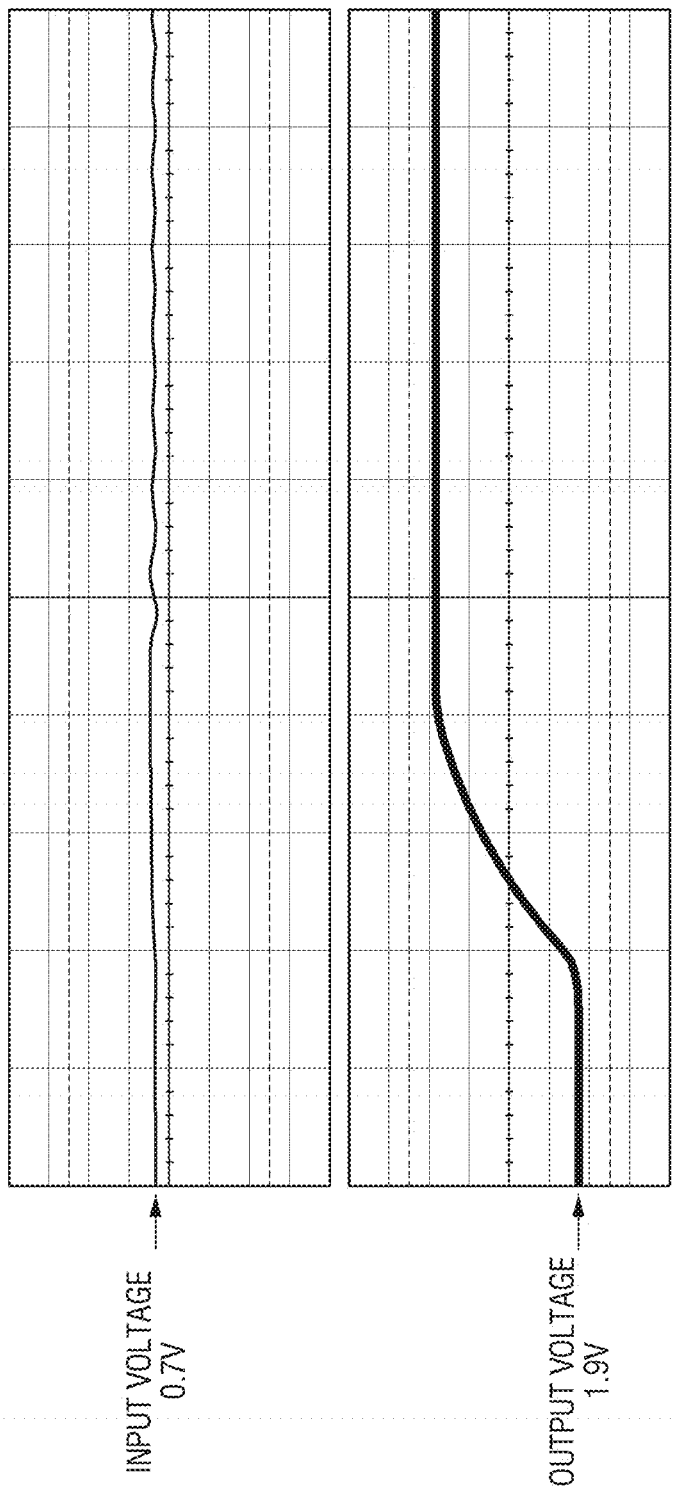
FIGS. 75 and 76 is graphs illustrating operation waveforms of a boost power converter.
Figure 76:
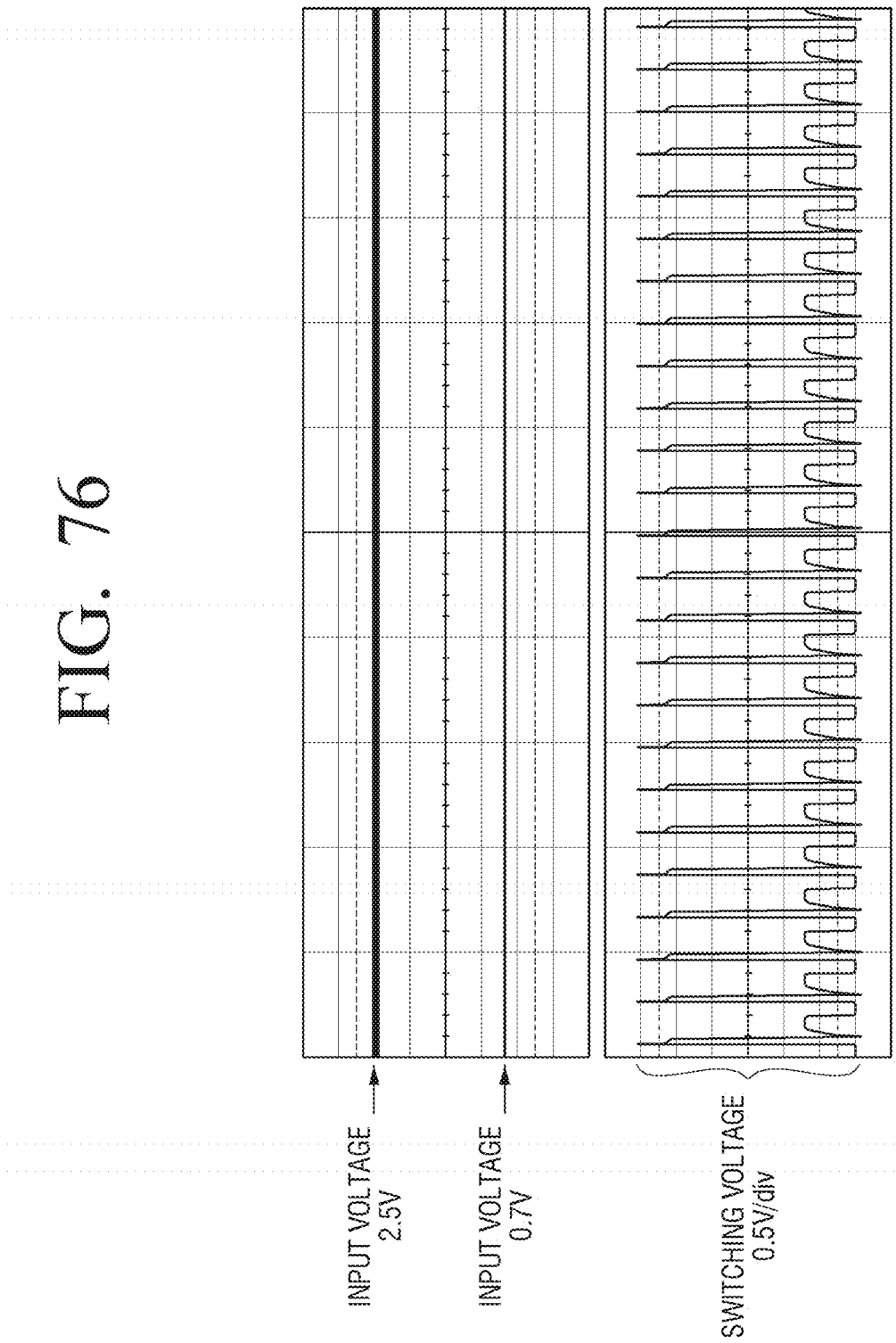

FIGS. 75 and 76 are graphs illustrating operation waveforms of a boosting type power converter according to an exemplary embodiment of the present general inventive concept.

Referring to FIG. 75, due to an operation of the initial driver circuit 7204, a voltage (voltage of node I of FIG. 1) of 0.7V of the fuel battery part 7201 charges the output capacitor 7235 of the boosting type power converter 7203 to a voltage (voltage of node O of FIG. 1) of 1.9V.

Referring to FIG. 76, if the boosting type power converter 7203 normally operates after the operation of the initial driver circuit 7204, and an input voltage (the voltage of the node I of FIG. 1) is 0.7 V, an output voltage (the voltage of the node O of FIG. 1) is boosted to 2.5 V.

[Tracking of Maximum Power Point of Transformer Circuit Part]

Hereinafter, a maximum power point tracking power converting and charging system for tracking a maximum power point in a transformer circuit part of a battery to be inserted into a living body will be disclosed. A maximum power point tracking power converting and charging system 7700 is an example of a transformer circuit part.

Figure 77:
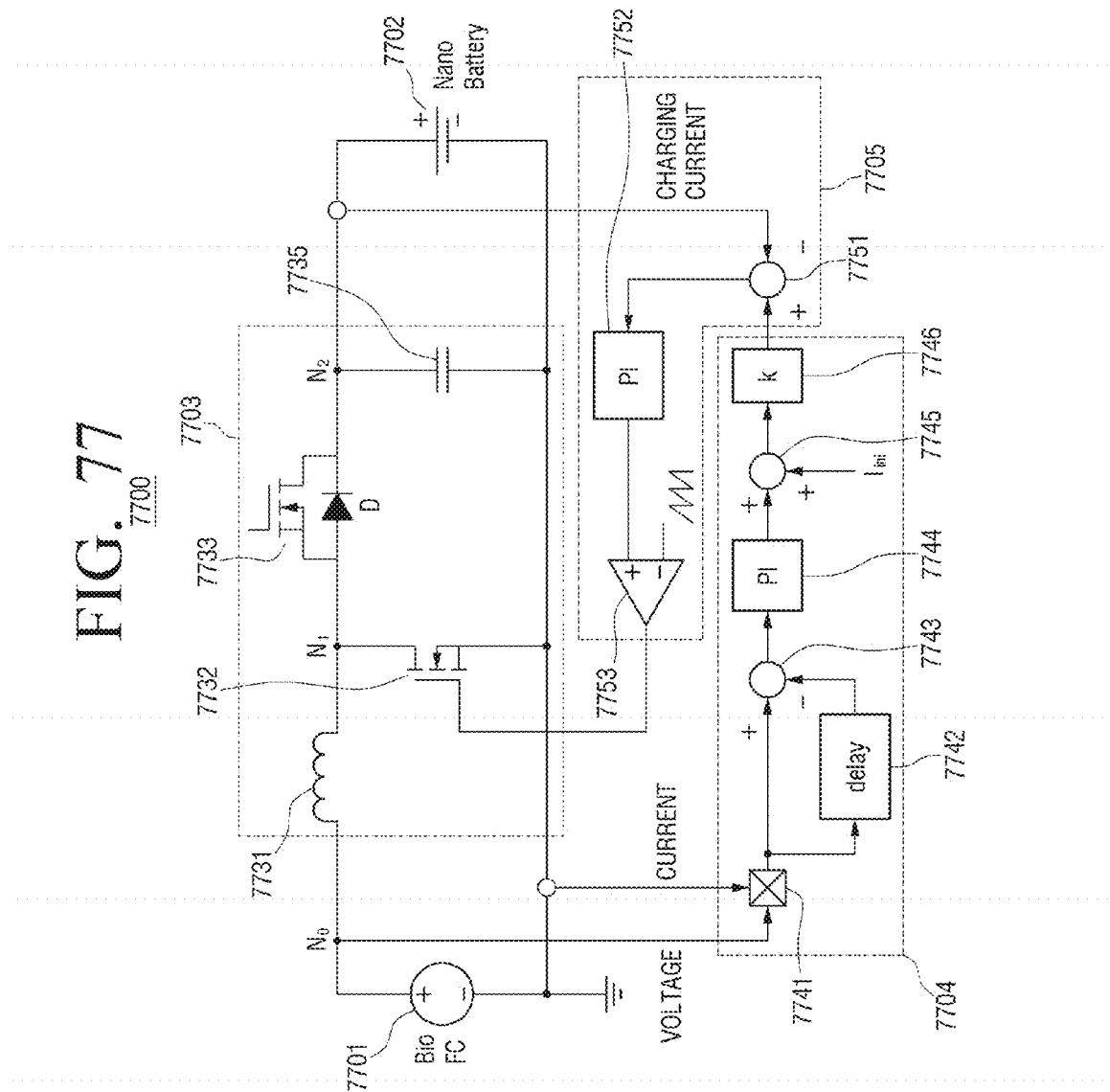
FIG. 77 is a view illustrating a system for converting and charging maximum power point tracking power according to an exemplary embodiment of the present general inventive concept.

FIG. 77 is a view illustrating a maximum power point tracking power converting and charging system according to an exemplary embodiment of the present general inventive concept.

Referring to FIG. 77, the maximum power point tracking power converting and charging system 7700 includes a fuel battery part 7701, a secondary battery part 7702, a boosting type power converter 7703, a maximum power point tracking circuit 7704, and a charging current control circuit 7705.

In the maximum power point tracking power converting and charging system 7700, the fuel battery part 7701 and the secondary battery part 7702 are fused into a single body and may be inserted into a living body or a blood vessel.

The fuel battery part 7701 is an energy source which generates a low voltage and may include a battery or a solar battery which outputs a DC voltage. For example, the fuel battery part 7701 generates a voltage by using a material in the living body such as glucose of the blood. In this case, the generated voltage may have a low voltage value which is difficult to charge the secondary battery part 7702.

The secondary battery part 7702 is an element which stores or uses a boosted voltage and may be an electrochemical storage device having a function of storing DC energy or an electronic device using a DC current.

The boosting type power converter 7703 boosts the voltage generated by the fuel battery part 7701 and supplies the boosted voltage to the secondary battery part 7702.

The maximum power point tracking circuit 7704 calculates a charging current command (or reference command) for tracking a maximum power point by using a voltage and a current of the fuel battery part 7701.

The charging current control circuit 7705 controls the current charging the secondary battery part 7702 to track the charging current command calculated by the maximum power point tracking circuit 7704.

The maximum power point tracking power converting and charging system 7700 uses the maximum power point tracking circuit 7704 and the charging current control circuit 7705 to charge the secondary battery 7702 at a maximum power point generated by the fuel battery part 7701. Therefore, the maximum power point tracking power converting and charging system 7700 uses an energy source such as a fuel battery or a solar battery to increase energy conversion efficiency in order maximize an energy utilization ratio.

The boosting type power converter 7703 according to an exemplary embodiment of the present general inventive concept includes a first boosting inductor 7731, a first transistor 7732, a second transistor 7733, and an output capacitor 7735.

The first boosting inductor 7731 accumulates energy generated by the fuel battery part 7701. Here, or hereinafter, the accumulation of the energy refers to a storage of energy.

The first transistor 7732 controls a boosting operation. In detail, the first transistor 7732 controls the energy accumulation of the first boosting inductor 7731.

The second transistor 7733 supplies the energy stored in the first boosting inductor 7731 to the output capacitor 7735.

The output capacitor 7735 receives and stores the energy stored in the first boosting inductor 7731 and generates an output voltage.

A circuit structure of the boosting type power converter 7703 will be described with reference to FIG. 77.

The first boosting inductor 7731 includes an end which is connected to the fuel battery part 7701 and an other end which is connected to a first node $N_1$. The first transistor 7732 includes a drain terminal which is connected to the first node $N_1$, a gate terminal which is connected to an output terminal of a comparator 7753 of the charging current control circuit 7705 which will be described later, and a source terminal which is connected to a ground terminal.

The second transistor 7733 includes a source terminal which is connected to the first node $N_1$ and a drain terminal which is connected to a second node $N_1$. A signal opposite to the gate terminal of the first transistor 7732 may be applied to a gate terminal of the second transistor 7733. In detail, a NOT gate (not shown) is connected to an output (i.e., an output of the comparator 7753) of the charging current control circuit 7705, the output signal of the comparator 7753 is converted by the NOT gate, and the converted signal is applied to the gate terminal of the second transistor 7733.

The output capacitor 7735 includes an end which is connected to the second node and an other end which is connected to the ground terminal.

The diode D includes an anode which is connected to the source terminal of the second transistor 7733 and a cathode which is connected to the drain terminal of the second transistor 7733.

The first and second transistors 7732 and 7733 are shown as NMOS transistors but may PMOS transistors. Also, the first and second transistors 7732 and 7733 may be bipolar transistors. If the first and second transistors 7732 and 7733 are changed as described above, a part of the circuit structure of FIG. 77 may be changed, and this change is obvious to those skilled in the art. The first and second transistors 7732 and 7733 may be MOS transistors but may bipolar transistors.

An operation principle of the boosting type power converter 7703 will be described in more detail with reference to FIG. 77.

An output voltage and an output current of the boosting type power converter 7703 are controlled by the first transistor 7732. If the first transistor 7732 is turned on, a current flowing in the first boosting inductor 7731 linearly increases, and the energy generated by the fuel battery part 7701 is accumulated in the first boosting inductor 7731. If the first transistor 7732 is turned off in this condition, the energy accumulated in the first boosting inductor 7731 is transmitted to the output capacitor 7735 through the diode D added to the second transistor 7733. Here, the second transistor 7733 may be turned on in order to reduce a voltage drop occurring in the diode D added to the second transistor 7733.

The output voltage of the boosting type power converter 7703 (i.e., a voltage of the second node) is controlled by an ON/OFF time ratio (i.e., a duty ratio) of the first transistor 7732. In detail, if the ON time of the first transistor 7732 increases, the output voltage of the boosting type power converter 7703 rises. Differently from this, if the ON time of the first transistor 7732 decreases, the output voltage of the boosting type power converter 7703 is lowered.

The maximum power point tracking circuit 7704 includes a multiplier 7741, a delay circuit 7742, a first subtractor 7743, a first proportion-integration (PI) controller 7744, an adder 7745, and an amplifier 7746.

The multiplier 7741 multiplies the voltage generated by the fuel battery part 7701 by the current flowing through the fuel battery part 7701 to calculate power $P_k$.

The delay circuit 7742 delays the power $P_k$ for a preset time to calculate delay power $P_{k-1}$.

The first subtractor 7743 calculates a difference $\Delta P$ between the power $P_k$ and the delay power $P_{k-1}$.

The first PI controller 7744 generates an increment value $\Delta I$ of a current command so that the minimal change $\Delta P$ is 0, to track a maximum power point.

The adder 7745 adds the increment value $\Delta I$ of the current command and an initial value $I_{ini}$ of the current command together to generate a current command.

Figure 78:
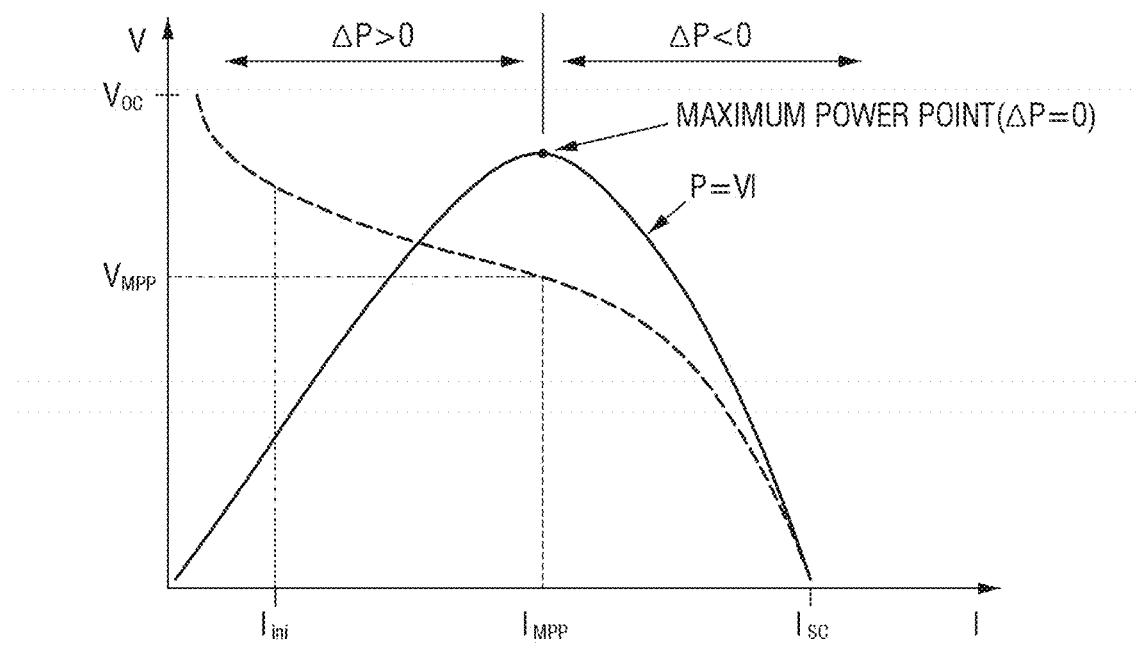
FIG. 78 is a graph illustrating an operation principle of maximum power point tracking.

The current command includes the addition of the initial value and the increment value. Also, since the increment value is 0 on an initial stage, an arbitrary current command is applied on the initial stage, and this is described as the initial value of the current command. The initial value of the current command is an arbitrary value. Also, as shown in FIG. 78, the maximum power point tracking power converting and charging system 7700 controls the maximum power point tracking circuit to track the maximum power point from the initial value of the current command to value $L_{MPP}$.

The amplifier 7746 scales a value (i.e., the generated current command) output from the adder to a predefined gain value k. Therefore, a charging current command for tracking the maximum power point may be calculated from the amplifier 7746.

The charging current control circuit 7705 includes a second subtractor 7751, a second PI controller 7752, and a comparator 7753.

The second subtractor 7751 calculates a current error. In detail, the second subtractor 7751 calculates an error (i.e., a current error) between a current charging the secondary battery part 7702 and a charging current output from the amplifier 7746 and outputs the error.

The second PI controller 7752 controls the charging current to minimize the current error output from the second subtractor 7751.

The comparator 7753 generates a driving pulse of the first transistor 7732. In detail, the comparator 7753 compares a voltage command output from the second PI controller 7752 with a preset saw tooth wave to generate a pulse width modulation (PWM) pulse for controlling the duty ratio of the first transistor 7732 and supplies the generated PWM pulse to the first transistor 7732.

An output current of the first boosting inductor 7731 of the boosting type power converter 7703, i.e., an inductor current, is equal to the generated current of the fuel battery part 7701. A width of a pulse output from the comparator 7753 is adjusted to control the output current of the first boosting inductor 7731. The adjustment of the width of the pulse is equal to a fluctuation of a voltage, and thus an output value of the second PI controller 7752 is a reference voltage changing a pulse width. If the reference voltage is high, the pulse width increases. If the reference voltage is low, the pulse width decreases. Therefore, the inductor current also increases. As a result, the reference voltage is described as a voltage command.

FIG. 78 is a graph illustrating an operation principle of maximum power point tracking.

Referring to FIGS. 77 and 78, operation principles of the maximum power point tracking circuit 7704 and the charging current control circuit 7705 of the maximum power point tracking power converting and charging system 7700 will be described in more detail.

Referring to FIG. 78, a minimal change $\Delta P$ of power at a maximum power point is 0. Here, a voltage and a current generated from the fuel battery part 7701 are respectively a maximum power point voltage $V_{MPP}$ and a maximum power point current $I_{MPP}$. If a current supplied from the fuel battery part 7701 is lower than the maximum power point current $I_{MPP}$, the minimal change ΔP of the power according to a current increase is a positive value. If the current supplied from the fuel battery part 7701 is higher than the maximum power point current $I_{MPP}$, the minimal change ΔP of the power according to the current increase is a negative value.

According to a maximum power point tracking method of the present general inventive concept, a minimal change ΔP of power may be calculated to be 0 in order to control a charging current amount.

A voltage and a current of the fuel battery part 7701 of FIG. 77 may be detected to calculate an instantaneous value $P_k$ from the multiplier 7741. If the first subtractor 7743 calculates a difference between the calculated instantaneous power $P_k$ and an instantaneous power value $P_{k-1}$ delayed for a preset time, the minimal change ΔP of the power may be obtained as in Equation 1 below:

$$\Delta P = P_k - P_{k-1}$$

wherein k denotes a natural number having a size equal to or greater than 1.

The first PI controller 7744 of FIG. 77 generates an increment value ΔI of a current command so that the minimal change ΔP of the power is 0.

Here, the first PI controller 7744 has a function of allowing the minimal change ΔP of the power to be 0. For example, the first PI controller 7744 may include a controller having a similar function to a lead-lag compensator and a proportion-integration-differentiation (PID) controller.

The adder 7745 adds the increment value ΔI of the current command and an initial value $I_{ini}$ of the current command together to generate the current command and multiplies the current command and a gain k of the amplifier 7746 together to calculate a charging current command for maximum power point tracking.

Here, the current command denotes a reference current for the maximum power point tracking. Therefore, if the maximum power point tracking power converting and charging system 7700 is in a normal state, the current command is a value equal to the maximum power point current $I_{MPP}$. The maximum power point tracking power converting and charging system 7700 does not calculate the maximum power point current $I_{MPP}$ but increases (the increment value of the current command) the reference current so that the second PI controller 7752 gradually converges the current value of the fuel battery part 7701 in the maximum power point current $I_{MPP}$ by using the increment value of the power. If the increment value of the current command is added to the initial value $I_{ini}$ of the current command, the fuel battery part 7701 may calculate a current value which is to be generated for the maximum power point tracking. Therefore, if the second PI controller 7752 normally operates, the current generated by the fuel battery part 7701 may be equal to the calculated current value.

The charging current control circuit 7705 controls the current charging the secondary battery part 7702 to track the charging current command output from the amplifier 7746.

Here, If the calculated current command is multiplied by the gain k of the amplifier 7746, a current to charge the secondary battery part 7702 is calculated. Here, the calculated current value is the charging current command. If a voltage is boosted by the boosting type power converter 7703, the current generated by the fuel battery part 7701 and the current charging the secondary battery part 7702 may have different levels. Therefore, if the second PI controller 7752 normally operates, the current charging the secondary battery part 7702 may be equal to the current generated by the fuel battery part 7701.

The second subtractor 7751 of FIG. 77 calculates an error between the charging current command and a battery charging current, and the second PI controller 7752 generates a voltage command to minimize the error.

Here, the second PI controller 7752 has a function of minimizing a charging current error. For example, the second PI controller 7752 may include a controller having a function similar to a lead-lag compensator and a PID controller.

The comparator 7753 generates and outputs a PWM pulse which is to control an ON/OFF time of the first transistor 7732 operating in a high frequency, by using the voltage command generated and output from the second PI controller 7752.

According to the above-described method, the maximum power point tracking power converting and charging system 7700 may control the ON/OFF time of the first transistor 7732. Therefore, the secondary battery part 7702 is charged at the maximum power point generated by the fuel battery part 7701. As a result, an energy source such as a fuel battery or a solar battery may be used to improve energy conversion efficiency in order to maximize an energy utilization ratio.

Also, compared to a conventional complicated maximum power point tracking circuit and system, the maximum power point tracking circuit 7704 and the charging current control circuit 7705 may be realized by using a simple analog circuit. Therefore, the maximum power point tracking circuit 7704 and the charging current control circuit 7705 may be made small. Also, the maximum power point tracking power converting and charging system 7700 may be made small.

A maximum power point tracking power converting and charging system according to another exemplary embodiment of the present general inventive concept includes a boosting type power converter, a maximum power point tracking circuit, and a charging current control circuit.

The maximum power point tracking power converting and charging system includes the boosting type power converter 7703 which boots a voltage generated by the fuel battery part 7701 and supplies the boosted voltage to the secondary battery part 7702, the maximum power point tracking circuit 7704 which calculates a charging current command for maximum power point tracking by using a current flowing into the fuel battery part 7701 and a voltage generated by the fuel battery part 7701, and the charging current control circuit 7705 which controls the boosting type power converter 7703 so that the current charging the secondary battery part 7702 tracks the charging current command.

The maximum power point tracking power converting and charging system charges the secondary battery part 7702 at the maximum power point of the fuel battery part 7701.

[Various Exemplary Embodiments of Secondary Battery Part]

Hereinafter, a secondary battery part of a battery to be inserted into a living body will be described in detail according to types and shapes of an electrode and a current collector. However, for the descriptive convenience, various exemplary embodiments of the secondary battery part will be classified into first through seventh exemplary embodiments and then described. An electrode, a current collector, a nanostructure, etc. which will be described in the various exemplary embodiments of the secondary battery part may be equally applied to a biofuel battery part.

[First Exemplary Embodiment of Secondary Battery Part]

The first exemplary embodiment of the secondary battery part relates to a positive electrode or a negative electrode and may be applied to a lithium-based or alkali-based battery. However, the first exemplary embodiment is not limited thereto.

Figure 79:
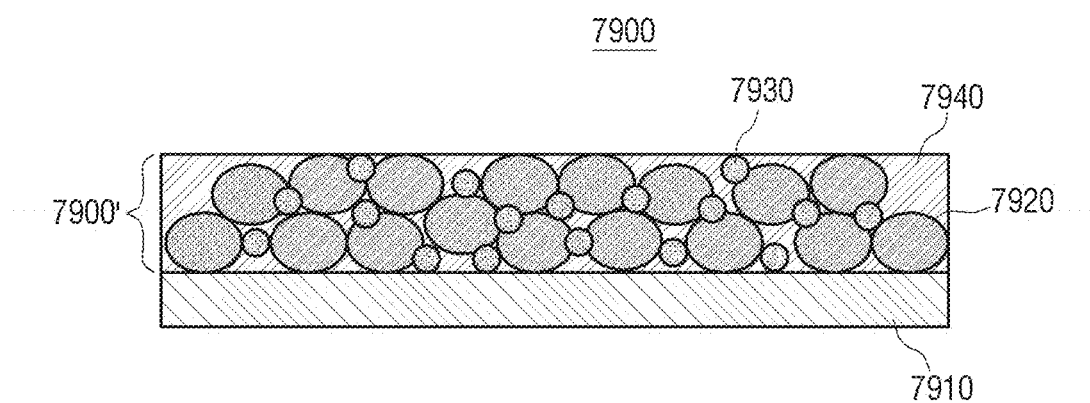
FIGS. 79 and 80 are cross-sectional views illustrating a structure of an electrode of a battery according to an exemplary embodiment of the present general inventive concept.
Figure 80:
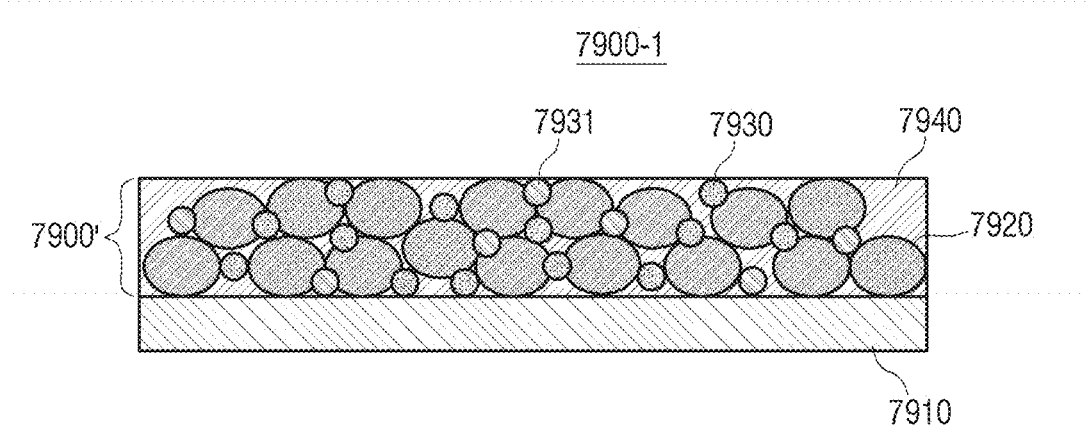

FIGS. 79 and 80 are cross-sectional views illustrating an electrode structure according to an exemplary embodiment of the present general inventive concept.

Referring to FIG. 79, an electrode 7900 includes a current collector 7910, an active material 7920, a conductive material 7930, and a binder 7940.

The electrode 7900 may be used in a primary or secondary battery. Also, the electrode 7900 may be used as a lithium-based battery, an alkali-based battery, and an acid-based battery. Here, the alkali-based battery refers to a battery using 1-family and 2-family alkali metals. For example, the alkali-based battery may be a battery using 1-family elements including H, Na, K, Rb, Cs, Fr, etc., 2-family elements including Be, Mg, Ca, Sr, Ba, Ra, etc., or Ni, Pb, or the like. Lithium is alkali metal, but the lithium-based battery is generally referred to as a lithium-based battery, and thus the present general inventive concept complies with this. The acid electrode may be a lead accumulator.

For the descriptive convenience, the electrode 7900 will be used in the lithium-based battery. However, the contents will be described later may be equally applied except for an element varying according to properties of metals used in the lithium-based battery and a battery using the above-mentioned metals.

The current collector 7910 operates to form an electron flow between an electrode active material, and any current collector which does not causes a chemical change and has a high conductivity may be used as the current collector 7910.

The current collector 7910 may be formed of one selected from the group consisting of copper, nickel, stainless steel, titanium, aluminum, carbon-coated aluminum, nickel foam, copper foam, a polymer substrate coated with a conductive metal, and combinations thereof. The materials may be processed as a foam type, a mesh type, a conductive material-coated type, a bored type, or the like but is not limited thereto. Alternatively, a surface of one of the materials may be coated with another material and then may be used.

The active material particle (or powder) 7920, the conductive material particle (or powder) 7930, and the binder 7940 may be mixed in a slurry form to constitute an electrode layer 7900'. The electrode layer 7900' may be constituted by using the active material particle 7920 and the conductive particle 7930 except for the binder 7940. This will be described later.

The active material 7920 may be any material which causes a reversible reaction of lithium.

If the electrode 7900 is used as a negative electrode of a battery, a material causing a reversible reaction of lithium, the active material 7920 may be one selected from the group consisting of a material reversibly forming a compound along with lithium, C, Na, K, Rb, Cs, Fr, Be, Mg, Ca, Sr, Ba, Ra, Ti, Ag, Zn, Cd, Al, Ga, In, Si, Ge, Sn, Pb, Sb, Ni, Bi, combinations thereof, an oxide thereof, and a nitride thereof. The active material 7920 may be formed of a negative electrode active material including the above materials and a lithium alloy. A material having a secession (decomposition) reaction of 2.5 V (Li/Li+) with respect to a lithium electrode may be used.

The material causing the reversible reaction of lithium may be a carbon material. In other words, any carbon negative electrode active material generally used in a lithium secondary battery may be used. Representative examples of the carbon negative active material include crystalline carbon, amorphous carbon, and a combination thereof.

If the electrode 7900 is used as a positive electrode of the battery, a positive electrode active material may be any compound causing a reversible reaction of lithium. For example, the positive electrode active material may be one selected from $Ni_3Si_2$, $LiMn_2$, $LiCoO_2$, $LiNiO_2$, $V_2O_5$, $LiFePO_4$, metal sulfide, sulfur, etc.

An active material having a surface on which a coating layer is formed may be used, or compounds having an active material and a coating layer may be mixed and used. The coating layer may include at least one coating element compound selected from the group consisting of oxide of a coating element, hydroxide, oxyhydroxide of the coating element, oxycarbonate of the coating element, and hydroxycarbonate of the coating element. A compound forming these coating layers may be amorphous or crystalline. Also, a coating element coating the coating layer may be one selected from the group consisting of Li, Mg, Al, Co, K, Na, Ca, Si, Ti, V, Sn, Ge, Ga, B, As, Zr, and combinations thereof, an oxide thereof, or a nitride thereof.

A process of forming the coating layer may be any method of using these elements not to have a bad effect on a physical property of a positive electrode active material, e.g., a chemical vapor deposition, a physical vapor deposition, spray coating, a immersing method. This will be well understood by those skilled in the art, and thus its detailed description will be omitted.

The active material may be included not to lower its combination strength with a current collector due to a capacity decrease with a total weight of an electrode layer or a relative decrease in an amount of a binder.

The conductive material 7930 adds conductivity to the electrode (easily moves an electron necessary for an electrochemical reaction) and operates as a lubricant between active material particles to improve plate element expansion and life characteristics.

Here, the conductive material 7930 is generally a carbon material or may be a shape memory alloy-based metal to inhibit volume changes of an electrode active material.

A Ti—Ni binary alloy, e.g., nitinol, may be representatively used.

Alternatively, a shape memory alloy of a third-family alloy or more, which is formed by adding third family (e.g., V, Cr, Mn, Co, Hf, Zr, Pd, Pt, Nb, Cu, Fe, or the like) to the Ti—Ni binary alloy, may be used.

If necessary, the conductive material 7930 may be greatly classified into Ni-based, Cu-based, and Fe-based materials. In detail, dozens of types of shape memory alloys, such as Cu—Zn—Ni, Cu—Al—Ni, Ag—Ni, Au—Cd, may be used.

The shape memory alloy refers to a material whose phase is changed due to external energy (i.e., heat, magnetism, stress). In particular, the shape memory alloy may show from a hard physical property to a soft physical property according to phase transformations of Austenite and Martensite. Also, if external stress is applied, a stress organic Martensite is formed. If the external stress is removed, Austenite re-appears.

In other words, if the shape memory alloy is used as a conductive material, a phase change occurs due to stress generated by a volume change of the electrode, and the stress is absorbed to minimize a damage to the electrode.

Also, a shape in which Martensite or two phases (Austenite and Martensite) coexists from the start according to a use temperature may be used as an additive (or a conductive material).

The shape memory alloy may be formed by using a dissolution method (an atomizing method, arc melting method), an explosion method (dry, wet), a sintering method, a pressure-assisted current sintering method, or the like. This is obvious to those skilled in the art, and thus its detailed description will be omitted.

Besides the above-described shape memory alloy, a material having no shape memory alloy effect may be additionally used as the conductive material 7930. This will be described in detail with reference to FIG. 80.

A shape of the conductive material 7930 is not limited, and thus the conductive material 7930 may have various shapes such as a standing shape, a scaly shape, a fiber shape, or the like.

The binder 7940 well attaches active material particles to one another and well attaches an active material to a current collector.

The binder 7940 may be formed of polyvinyl alcohol, carboxymethylcelluose, hydroxypropylcelluose, diacetylcelluose, polyvinylchloride, carboxylated polyvinylchloride, polyvinyldifluoride, polymer including ethylene oxide, polyvinylpyrrolidone, polyurethane, polytetrafluoroethylene, polyvinylidene fluoride, polyethylene, polypropylene, styrene-butadiene rubber, acrylated styrene-butadiene rubber, epoxy resin, nylon, or the like but is not limited thereto.

The binder 7940 may be mixed in an appropriate capacity with respect to a total weight of an electrode layer without causing an adhesive strength and a capacity.

Also, particles constituting the electrode layer 7900' may be grinded or seived to adjust a grain size.

The electrode layer 7900' may include pores.

The stoma of the electrode layer may be formed according to a general pore forming method. If the pores are formed by using a pore former, sizes, distribution, and porosity of the pores formed in the electrode layer may be adjusted according to a size, a content, and a processing method of the pore former. Here, the pore former may be any pore former which is used to form pores. In detail, the pore former may be (NH4)2CO3, NH4HCO3, (NH4)2C2O4, which is volatile-removed by a thermal treatment to form pores in an electrode layer, a mixture thereof, a polymer material such as poly (alkylenecarbonate) poly(alkyleneoxide), poly(dialkylsiloxane), acrylate-based polymer, or the like, which is dissolved in a nonaqueous organic solvent to be eluted, or alkali metal containing carbonate, such as Li2CO3, K2CO3, Na(CO3)2, or the like, which is dissolved in an acid to be eluted.

Here, the porosity of the electrode layer 7900' may be a degree not to badly affect a volume expansion inhibition and an energy density.

Alternatively, a high intensity binder layer (not shown) may be positioned on the electrode layer 7900'. Here, the high intensity binder layer may include a high intensity binder and a filler.

The high intensity binder may be a high intensity binder which has a low melting point and thus is highly crystallized at a low temperature to improve a mechanical strength.

The high intensity binder may be formed of one selected from the group consisting of acrylate-based polymer, vinyl-based polymer, fluorine-based polymer, imide-based polymer, cellulose-based polymer, amide imide-based polymer, sulfon-based polymer, alkyleneoxide-based polymer, copolymer thereof, and a mixture thereof. In detail, the high intensity binder may be formed of one selected from the group consisting of polyvinylchloride, polyvinylidene fluoride, polyvinylidene fluoride-hexafluoropropylene copolymer, polyvinyl alcohol, polyimide, carboxymethylcellulose, and a mixture thereof.

Also, the high intensity binder layer may further include an acrylic binder along with the high intensity binder. The high intensity binder improves infinity with electrolyte when the electrolyte invades into the high intensity binder to increase lithium ion conductivity.

The high intensity binder may further include lithium salt as an adhesive for improving a battery characteristic at a high rate besides the high intensity binder and the filler.

An appropriate amount of the lithium salt may be mixed in consideration of ionic conductivity, viscocity, and liquidity of an electrolyte layer.

Also, the high intensity binder layer may be formed to an appropriate thickness in consideration of ionic conductivity and electric conductivity.

If the high intensity binder layer is formed, a volume expansion in an electrode layer and an interface reaction with an electrolyte on a pole plate are inhibited, and thus the high intensity binder layer shows a long life characteristic.

Referring to FIG. 80, an electrode 7900-1 includes a current collector 7910, an active material 7920, conductive materials 7930 and 7931, and a binder 7940.

As shown in FIG. 79, a material having a shape memory alloy effect may be used as the conductive material 7930, and a material having no shape memory alloy effect may be used as the conductive material 7931. For example, conductive polymer may be used as a conductive material having no shape memory alloy effect. Poly(sulfumitrile), polypyrrole, poly(p-phenylene), poly(phenylenesulfide), polyaniline, poly(p-phenylenevinylene), or the like may be realized as polymer having electric conductivity.

In other words, the conductive materials 7930 and 7931 may be a form in which the conductive material 7930 having a shape memory alloy effect and the conductive material 7931 having no shape memory alloy effect are mixed.

The structure of the electrode 7900-1 of FIG. 80 is equal to the structure of FIG. 79 except that the conductive material 7930 having the shape memory alloy effect and the conductive material 7931 having no shape memory alloy effect are mixed, and thus its detailed description will be omitted.

Figure 81:
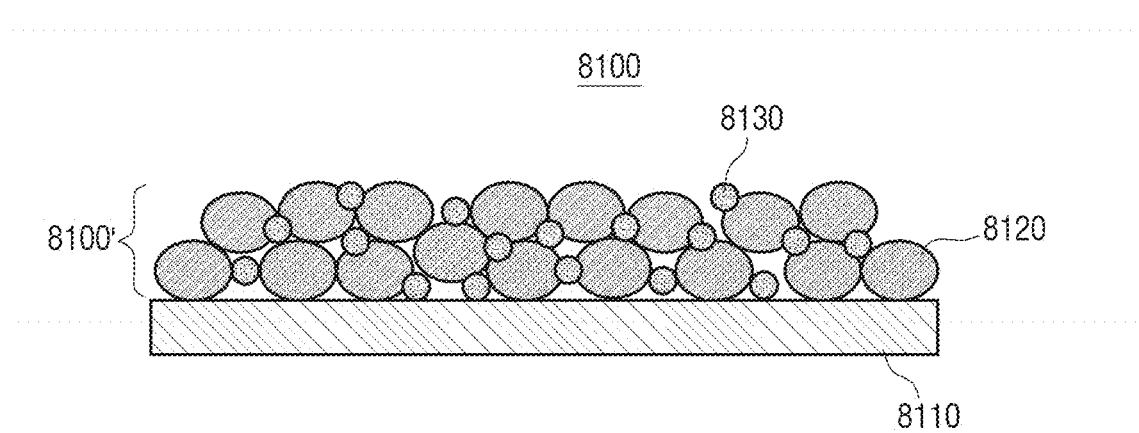
FIGS. 81 and 82 are cross-sectional views illustrating a structure of an electrode of a battery according to another exemplary embodiment of the present general inventive concept.
Figure 82:
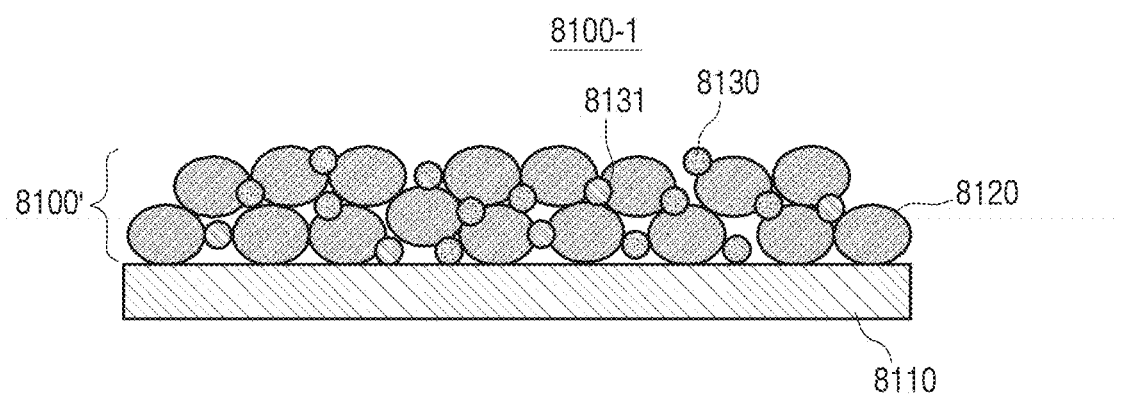

FIGS. 81 and 82 are cross-sectional views illustrating an electrode structure according to another exemplary embodiment of the present general inventive concept.

Referring to FIG. 81, an electrode 8100 includes a current collector 8110, an active material 8120, and a conductive material 8130.

The structure of FIG. 81 may have a form which is coated with an electrode layer 8100' formed of a mixture of the active material particle 8120 and the conductive material 8130 on the current collector 8110.

A shape memory alloy-based metal may be used as the conductive material 8130. A Ti—Ni binary alloy (e.g., nitinol) may be representatively used as the conductive material 8130.

Alternatively, the conductive material 8130 may be a shape memory alloy having a ternary or more alloy shape in which a ternary element (e.g., V, Cr, Mn, Co, Hf, Zr, Pd, Pt, Nb, Cu, or the like) is added to the Ti—Ni binary alloy.

The shape memory alloy may be greatly classified into NI-based, Cu-based, and Fe-based alloys. In detail, dozens of types of shape memory alloys, such as Cu—Zn—Ni, Cu—Al—Ni, Ag—Ni, Au—Cd, may be used.

Referring to FIG. 82, an electrode 8100-1 includes a current collector 8110, an active material 8120, and conductive materials 8130 and 8131.

A material having a shape memory alloy effect may be used as the conductive material 8130, and a material having no shape memory alloy effect may be used as the conductive material 8131.

In other words, the conductive materials 8130 and 8131 may have a form in which the conductive material 8130 having the shape memory alloy effect and the conductive material 8131 having no shape memory alloy effect are mixed.

The structure of the electrode 8100-1 of FIG. 82 is equal to the structure of FIG. 81 except that the conductive material 8130 having the shape memory alloy effect and the conductive material 8131 having no shape memory alloy effect are mixed, and thus its detailed description will be omitted.

Figure 90:
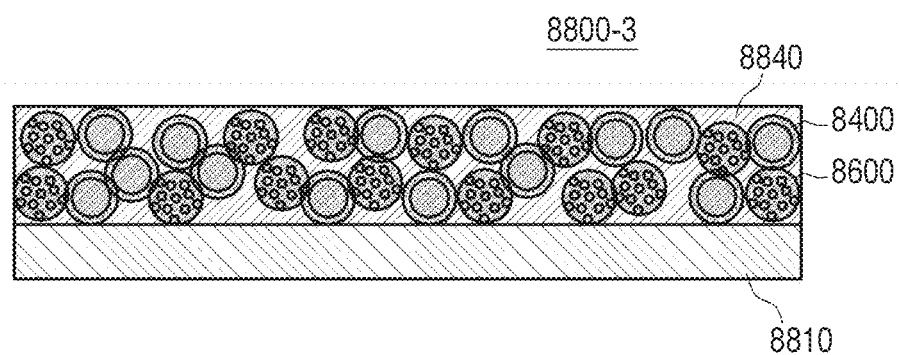

The structures of FIGS. 81 and 82 are equal to the structures of FIGS. 79 and 90 except that the structures of FIGS. 79 and 80 have no binders, and thus their detailed descriptions will be omitted.

Figure 83:
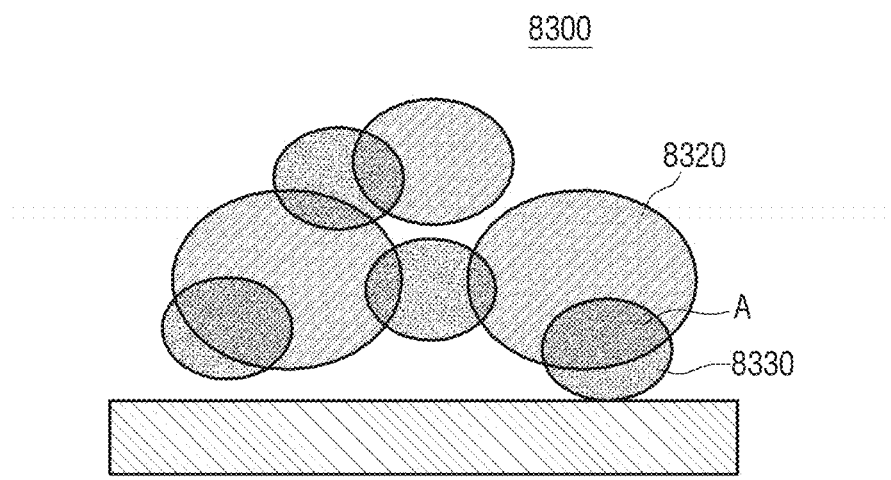
FIG. 83 is a view illustrating a structure of an electrode layer composition according to an exemplary embodiment of the present general inventive concept.

FIG. 83 is a view illustrating a structure of an electrode layer composite according to an exemplary embodiment of the present general inventive concept.

Referring to FIG. 83, part A in which an active material 8320 and a conductive material 8330 overlap with each other may form a composite unreactive to lithium or a composite having a low reaction to lithium in order to an electrode damage.

For example, if the active material 8320 is formed of $Ni_3Si_2$, and the conductive material 8330 is formed TiNi, the part A in which the active material 8320 and the conductive material 8330 overlap with each other forms a Ti—Si-based composite. Here, the Ti—Si-based composite has a low reaction to lithium and reduces the electrode damage.

Figure 84:
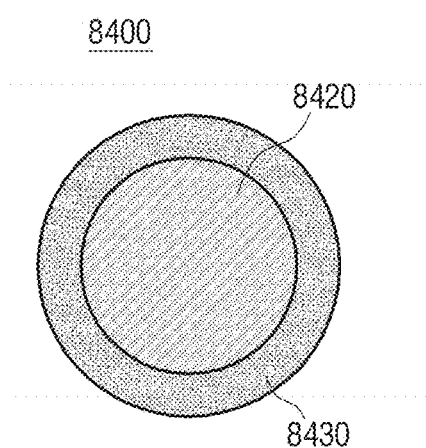
FIGS. 84 and 85 are views illustrating a structure of an electrode layer composition according to another exemplary embodiment of the present general inventive concept.
Figure 85:
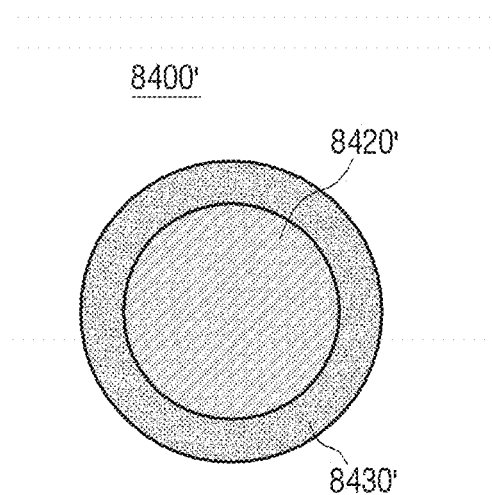

FIGS. 84 and 85 are views illustrating a structure of an electrode layer composite according to another exemplary embodiment of the present general inventive concept.

Referring to FIG. 84, in the electrode layer composite coated on a current collector, a conductive material 8430 coats an active material particle (or powder) 8420. Here, a shape memory alloy-based metal may be used as the conductive material 8430. A Ti—Ni binary alloy (e.g., nitinol) may be representatively used.

Alternatively, the conductive material 8430 may be a ternary or more alloy in which a ternary element (e.g., V, Cr, Mn, Co, Hf, Zr, Pd, Pt, Nb, Cu, Fe, or the like) is added to the Ti—Ni binary alloy.

The shape memory alloy may be greatly classified into NI-based, Cu-based, and Fe-based alloys. In detail, dozens of types of shape memory alloys, such as Cu—Zn—Ni, Cu—Al—Ni, Ag—Ni, Au—Cd, may be used.

Also, the active material composite 8420 may be a material causing a reversible reaction of lithium, a material capable of reversibly forming a composite along with lithium metal, or the like as described above. The detailed example is as described above, and thus its detailed description will be omitted.

Referring to FIG. 85, differently from the form of FIG. 84, an electrode layer composite coated on a current collector may have a form in which an active material 8420 coats a conductive material particle (or powder) 8430. Here, materials of the conductive material 8430 and the active material 8420 are as described above, and thus their detailed descriptions will be omitted.

Also, the electrode layer composite may further include a conductive material having no shape memory alloy effect besides the conductive material 8430 and the active material 8420.

Figure 86:
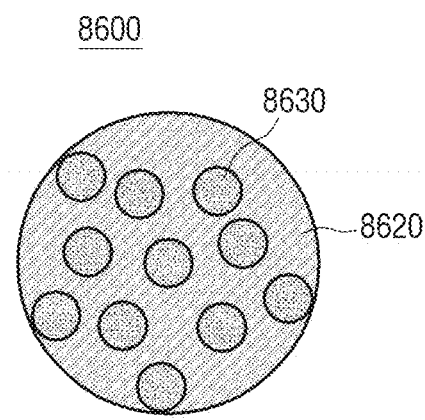
FIGS. 86 and 87 are views illustrating a structure of an electrode layer composition according to another exemplary embodiment of the present general inventive concept.
Figure 87:
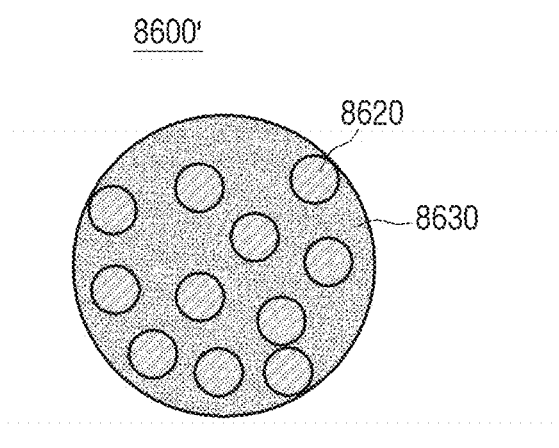

FIGS. 86 and 87 are views illustrating a structure of an electrode layer composite according to another exemplary embodiment of the present general inventive concept.

Referring to FIG. 86, an electrode layer composite 8600 coated on a current collector may have a form in which conductive material particles (or powder) 8630 are dispersed in active material particles (or powder) 8620.

Referring to FIG. 87, differently from the form of FIG. 86, an electrode layer composite 8600' may have a form in which active material particles 8620 are dispersed in conductive material particles 860.

The electrode layer composite 8600 or 8600' may further include a conductive material having no shape memory alloy effect besides the conductive material 8630 and the active material 8620.

Also, a conductive material having no shape memory alloy effect may be further included besides the conductive material 8630 and the active material 8620 illustrated in FIGS. 86 and 87.

Figure 88:
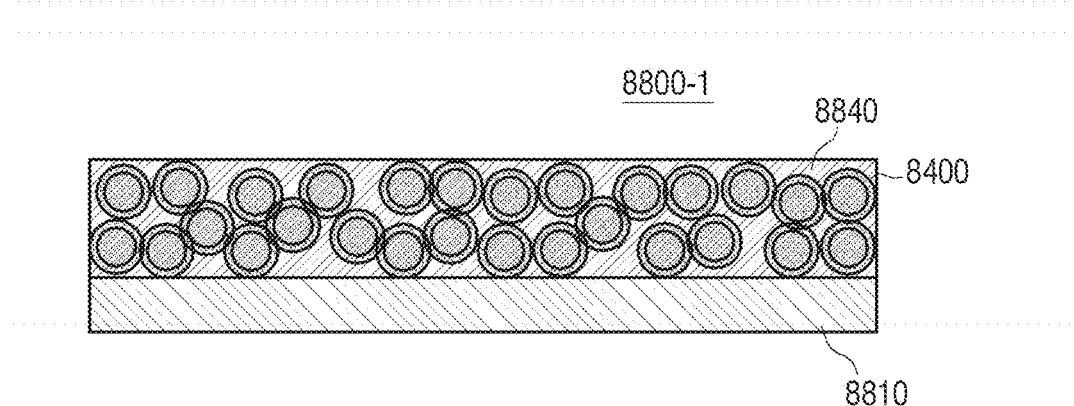
FIGS. 88 through 90 are views illustrating an electrode structure of a battery according to various exemplary embodiments of the present general inventive concept.
Figure 89:
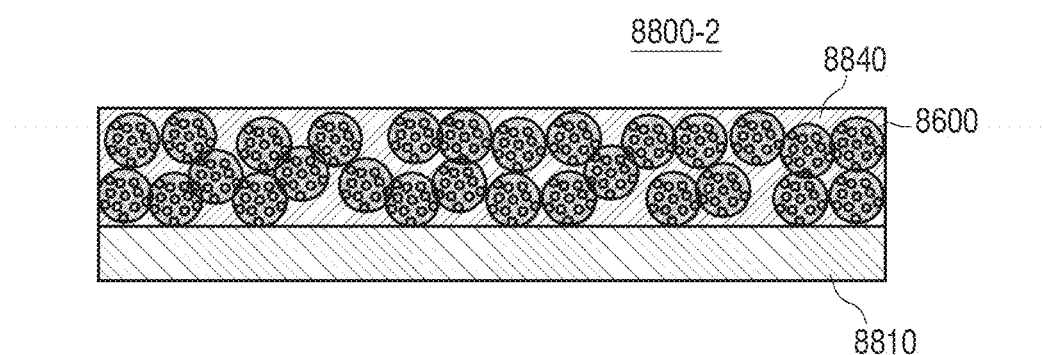

FIGS. 88 through 90 are views illustrating an electrode structure according to various exemplary embodiments of the present general inventive concept.

Referring to FIG. 88, a lithium battery electrode 8800-1 includes a current collector 8810, an active material particle 8400, and a binder 8840.

Here, the active material particle 8400 may be at least one of the forms of FIGS. 84 and 85.

An electrode layer is formed of only one form (an active material form of FIG. 84) in FIG. 88 but is only exemplary. Therefore, the electrode layer may be formed of a form in which active material particles of FIGS. 84 and 85 are mixed.

Also, the lithium battery electrode 8800-1 includes the binder 8840 in the present exemplar embodiment but is only exemplary. Therefore, the lithium battery electrode 8800-1 may be formed in a form in which only the active material particle 8400 is coated on the current collector 8810 except for a binder.

Referring to FIG. 89, an electrode 8800-2 includes a current collector 8810, an active material particle 8600, and a binder 8840.

Here, the active material particle 8600 may be at least one of the forms of FIGS. 86 and 87.

Also, an electrode layer may be formed in only a form (an active material form of FIG. 86) but is only exemplary. Therefore, the electrode layer may be formed in a form which active material particles of FIGS. 86 and 87 are mixed.

The electrode 8800-2 includes the binder 8840 in the present exemplary embodiment but is only exemplary. Therefore, the electrode 8800-2 may be formed in a form in which only the active material particle 8600 is coated on the current collector 8810 except for a binder.

Referring to FIG. 90, an electrode 8800-3 includes a current collector 8810, active material particles 8400 and 8600, and a binder 8840.

Here, the active material particles 8400 and 8600 may be constituted by mixing at least one of the forms of FIGS. 84 and 85 with at least one of the forms of FIGS. 86 and 87.

Although not shown in the drawings, active materials and conductive materials of FIGS. 79, 80, 81, and 82, at least one of active material particles of FIGS. 84 and 85, and at least one of active material particles of FIGS. 86 and 87 are mixed to constitute an electrode layer.

The electrode 8800-3 includes the binder 8840 in the present exemplary embodiment but is only exemplary. Therefore, the electrode 8800-3 may have a form in which only the active material particles 8400 and 8600 are coated on the current collector 8810 except for a binder.

As described with reference to FIGS. 79 through 87, an electrode layer of FIGS. 88 through 6C may additionally include a conductive material having no shape memory alloy effect.

The forms of FIGS. 86, 87, and 88 through 90 are only exemplary, and thus an electrode active material and conductive polymer may be mixed by using various polymerizing methods, synthesizing methods, and substituting methods besides this method.

Figure 91:
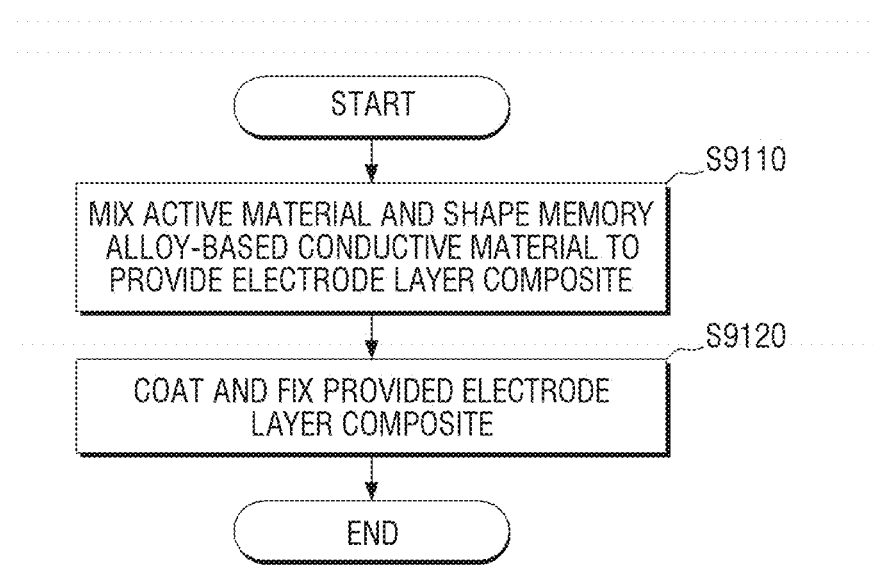
FIG. 91 is a flowchart illustrating a process of fabricating an electrode according to an exemplary embodiment of the present general inventive concept.

FIG. 91 is a flowchart illustrating a process of fabricating an electrode according to an exemplary embodiment of the present general inventive concept.

Referring to FIG. 91, in operation S9110, an active material and a shape memory alloy-based conductive material are mixed to form an electrode layer composite. Here, the shape memory alloy-based conductive material may be representatively TiNi-based metal. This is as described above, and thus its detailed description will be omitted.

Also, a binder may be additionally mixed to form the electrode layer composite. Here, the active material and the conductive material may be power forms. In detail, a form of the electrode layer composite may be at least one of the electrode layer composites of FIGS. 79 through 90.

A conductive material having no shape memory alloy effect may be additionally included to fabricate the electrode layer composite.

In operation S9120, the electrode layer composite is coated on a current collector and the fixed. Also, a thermal treatment process may be added.

Here, a coating process may be performed by one selected from the group consisting of a screen printing method, a spray coating method, a coating method using a doctor blade, a gravure coating method, a deep coating method, a silk screen method, a painting method, a slot die method, an aerosol deposition method, and combinations thereof but is not limited thereto.

Also, the fixing process is to fix a mixed material on the current collector by using a sintering method or a hot pressing method but is not limited thereto. Here, the sintering method refers to a method of heating press formed materials to firmly adhere the press formed materials to each other in order to sinter the press formed materials. The hot pressing method refers to a heating and pressurizing method.

The fixing process may be used as a thermal treating process of the active material and the conductive material, and a stacking process and the fixing process may be realized as one process.

Also, a drying process may be performed. Here, the drying process may be performed by a general method such as natural drying, hot air drying, or the like.

Pores may be formed in an electrode layer.

A process of forming the pores may be performed by thermally treating an electrode in which an electrode layer is coated on a current collector. In other words, the electrode may be thermally treated to evaporate a binder having a low melting point in order to appropriately form the pores.

The pores may be formed by a pore former. Here, the pore former may be a pore former which is volatilized by thermal treatment in the electrode layer, a pore former which is eluted by a nonaqueous organic solvent or an acid, or the like but is not limited thereto. In this case, an appropriate removing process may be performed according to a kind of pore former.

Figure 92:
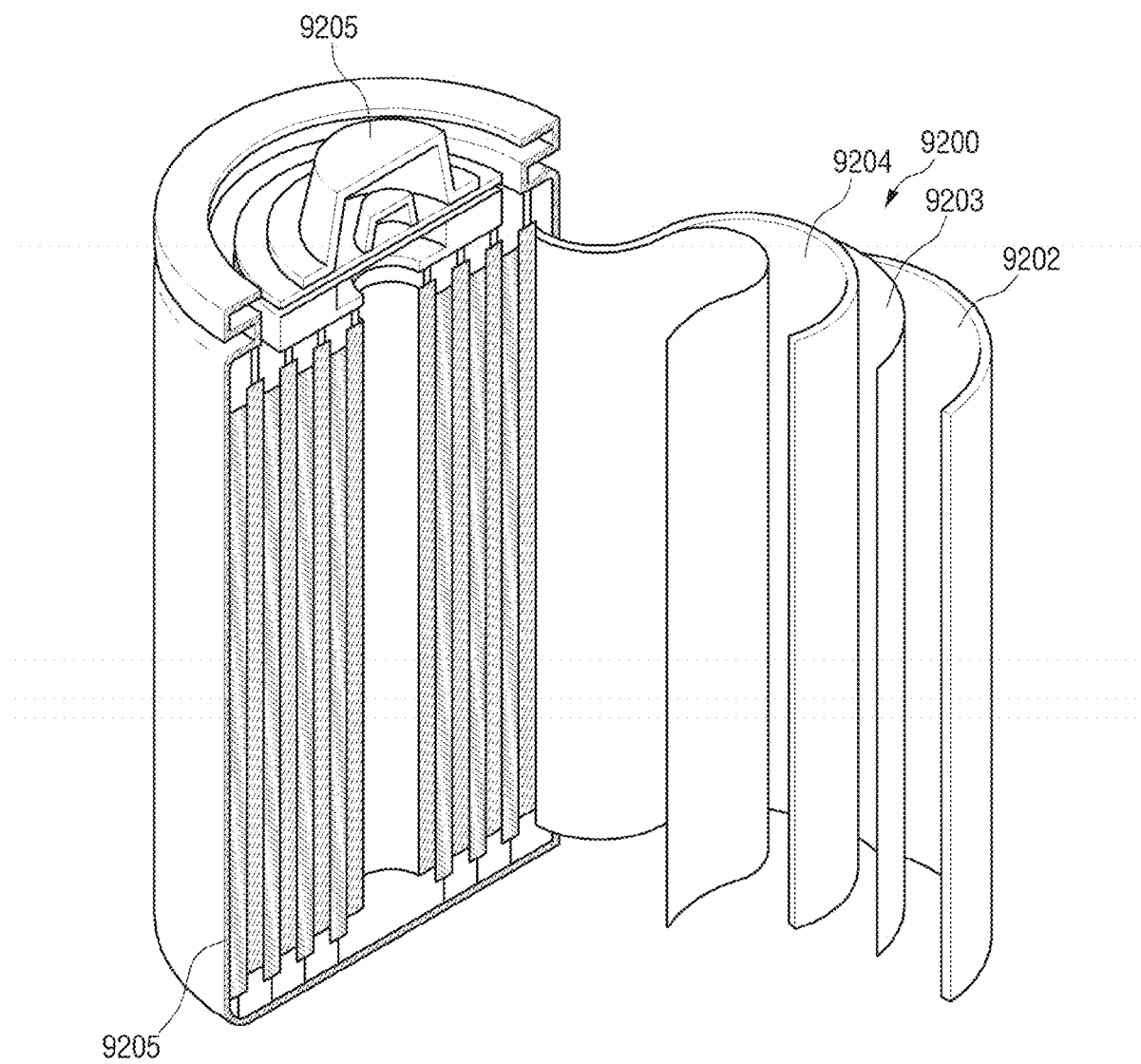
FIG. 92 is a view illustrating a structure of a battery according to an exemplary embodiment of the present general inventive concept.

FIG. 92 is a view illustrating a structure of a battery according to an exemplary embodiment of the present general inventive concept.

Referring to FIG. 92, a battery 9200 according to the present exemplary embodiment includes a cathode 9202, an anode 9204, a battery vessel 9205 including an electrolyte impregnated into a separator 9203 positioned between the cathode 9202 and the anode 9204, and an enclosing member 806 enclosing the battery vessel 9205. In this case, the battery 9200 may be a lithium secondary battery but is not limited thereto. The battery 800 may be a battery using 1-family, 2-family alkali-based metals. However, for the descriptive convenience, the battery 800 will be described as a lithium battery.

Here, the above-described electrodes may be used as the cathode 9202 and the anode 9204.

The battery 9200 of FIG. 92 includes the separator 9203. However, if a negative electrode includes a high intensity binder layer, the battery 9200 may not include the separator 9203.

The battery 9200 may be classified into a lithium ion battery, a lithium ion polymer battery, and a lithium polymer battery according to types of separator and electrolyte, may be classified into cylindrical, square, coin, and pouch types according to its shapes, and may be classified into bulk and thin film types according to its sizes.

The cathode 9202 and the anode 9204 are as described above, and thus their detailed descriptions will be omitted A thin film type or bulk type material may be used as the electrolyte. In a really used apparatus, a solid inorganic electrolyte or an organic polymer electrolyte is generally used, but a liquid electrolyte may be used for a test.

The electrolyte may include lithium salt and a nonaqueous organic solvent.

The lithium salt is a material which is dissolved in an organic solvent to operate as a supply source of lithium ion to enable a basic operation of the lithium secondary battery and promotes a movement of the lithium ion between an anode and a cathode.

The lithium salt may be one selected from the group consisting of $LiPF_6$, $LiFB_4$, $LiSbF_6$, $LiAsF_6$, $LiClO_4$, $LiCF_3SO_3$, $LiC_4F_0SO_3$, $LiN(CF_3SO_2)_2$, $LiN(C_2F_5SO_2)_2$, $LiAlO_2$, $LiAlCl_4$, $LiN(C_pF_{2p+1}SO_2)(C_qF_{2q+1}SO_2)$ (here, p and q are natural numbers), $LiSO_3CF_3$, LiCl, LiL, lithium bisoxalate borate, and a mixture thereof but is not limited thereto.

The nonaqueous organic solvent operates as a medium to which ions involved in an electrochemical reaction of a battery are moved. A carbonate-based solvent, an ester-based solvent, a keton-based solvent, an alcohol-based solvent, or a nonprotonic solvent may be used as the nonaqueous organic solvent.

One or more nonaqueous organic solvents may be mixed and used. If one or more nonaqueous organic solvents are mixed and used, a mixture ratio may be appropriately adjusted according to a target battery performance. This is a content which can be understood by those skilled in the art, and thus its detailed description will be omitted.

The separator 9203 may exist between an anode and a cathode according to a type of lithium battery. The separator 9203 separates the cathode 9202 and the anode 9204 from each other and provides a movement path of lithium ions. Any separator which is generally used in the lithium battery may be used. In particular, a separator having a low resistance to the movement of ions of the electrolyte and a high moisturization capability of the electrolyte may be used. For example, polyethylene, polyester, polypropylene, polyvinylidene fluoride, or a multilayer which is a dual layer or more thereof may be used. A mixture multilayer, such as polyethylene/polypropylene dual layer separator, a polyethylene/polypropylene/polyethylene three-layer separator, a polypropylene/polyethylene/polypropylene three-layer separator, or the like, may be used.

A secondary battery of FIG. 92 has a cylindrical shape but is only exemplary. Therefore, the secondary battery may have various shapes such as a cylindrical shape, a square shape, a coin shape, a pouch shape, or a shift shape.

As described above, a separator is disposed between an anode pore plate and a cathode pore plate to form a battery structure. This battery structure is winded or folded to be inserted into a cylindrical battery case or a square battery case, and then an organic electrolyte of the present general inventive concept is injected in order to complete a lithium ion battery. Also, the battery structure is stacked in a bicell structure and then immersed into the organic electrolyte, and an obtained resultant is put into a pouch and sealed to complete a lithium ion polymer battery.

Therefore, an electrode damage caused by a volume change of an electrode may be minimized by using a composite unreactive to lithium or a composite having a low reaction to lithium as an electrode layer. In detail, a phase is changed and stress is absorbed due to stress generated by the volume change of the electrode by using a shape memory alloy as a conductive material in order to minimize the electrode damage. Therefore, a damage to an electrode of a lithium battery may be minimized, thereby increase a life of the electrode.

However, as mentioned above, using an electrode of the present general inventive concept in a lithium battery is only exemplary. Therefore, the electrode of the present general inventive concept may be used as an electrode of a battery using another alkali-based metal. For example, the electrode of the present general inventive concept may be used as an electrode of a battery using a 1-family element such as H, Na, K, Rb, Cs, Fr, or the like, a 2-family element such as Be, Mg, Ca, Sr, Ba, Ra, or the like, NI, Pb, or the like.

[Second Exemplary Embodiment of Secondary Battery Part]

The second exemplary embodiment of the secondary battery part relates to a positive or negative pole electrode which may be applied to a lithium-based battery but is not limited thereto.

Figure 93:
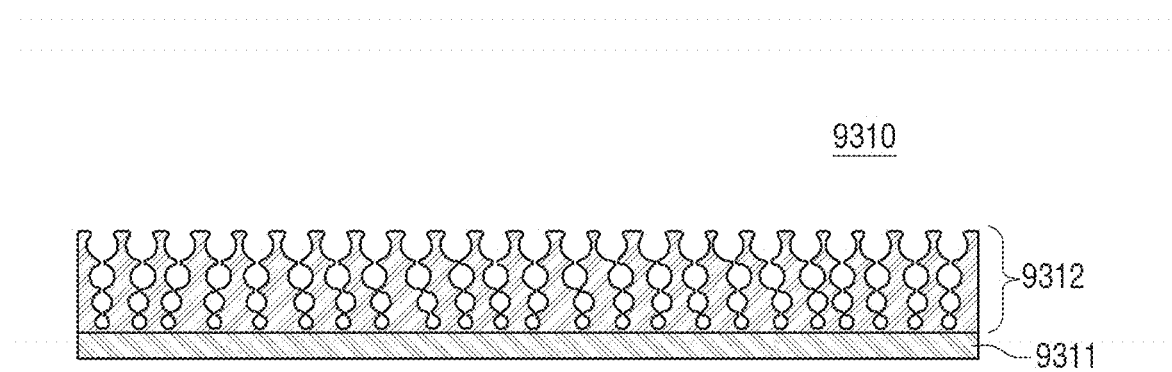
FIG. 93 is a cross-sectional view illustrating a structure of a current collector according to an exemplary embodiment of the present general inventive concept.

FIG. 93 is a cross-sectional view illustrating a structure of a porous current collector according to an exemplary embodiment of the present general inventive concept.

Referring to FIG. 93, a current collector 9310 includes a pad part 9311 and a current collector part 9312.

The pad part 9310 is a part which is to be connected to an external terminal and may have a plate shape having no pores.

The current collector part 9312 is a part which contacts an electrode active material and may include a plurality of pores 10.

A porosity rate of the current collector part 9312 may vary according to a distance from the pad part 9310. In detail, the porosity rate of the current collector part 9312 increase in proportion to the distance from the pad part 9310. Therefore, a contact area with an electrode layer (not shown) formed on the current collector 9312 increases.

Also, an active material constituting an electrode is positioned in the pores of the current collector part 9312, and thus a total size of the electrode may decrease.

The current collector 9310 operates to form a flow of electrons between the electrode active material and a battery terminal. Any one which does not cause a chemical change in the battery and has a high conductivity may be used as the current collector 9310.

The current collector 9310 may be formed of one selected from the group consisting of Co, Ni, stainless steel, Ti, Al, carbon-coated Al, Ni foam, Co foam, a polymer substrate coated with conductive metal, and combinations thereof but is not limited thereto. One of a material which coats at least one surface of the above-described materials may be used.

A shape memory binary alloy or a Ti—Ni—X-based shape memory ternary ally may be used as the current collector 9310. A Ti sulfide and an NI sulfide may be generated on a surface of the current collector 9310 by using an internal sulfuration method to be used as positive pole active materials. Therefore, the Ti and NI sulfides have shape memory characteristics and simultaneously perform roles of a current collector and an anode of a battery through one device.

The current collector 9310 may be etched to increase a surface area.

Figure 94:
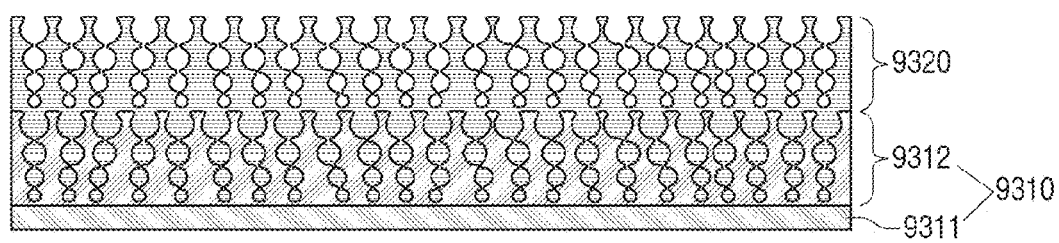
FIG. 94 is a cross-sectional view illustrating an electrode structure using a current collector of FIG. 1.
Figure 95:
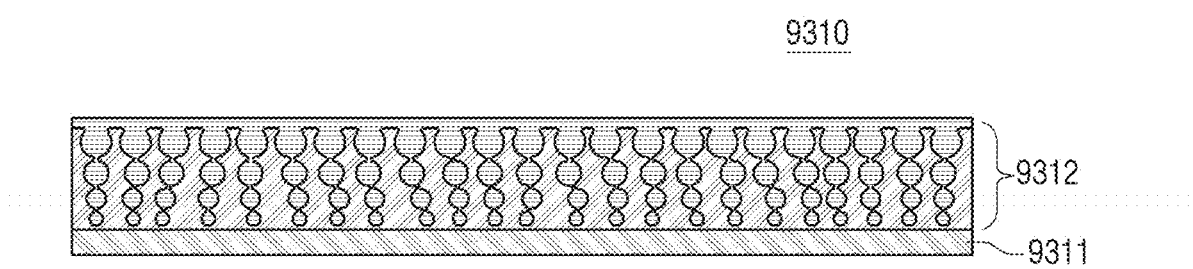
FIG. 95 is a cross-sectional view illustrating an electrode according to an exemplary embodiment of the present general inventive concept.

FIGS. 94 and 95 are cross-sectional views illustrating an electrode structure using a current collector of FIG. 93.

Referring to FIGS. 94 and 95, an electrode 9300 includes a current collector 9310 and an electrode layer 9320.

The current collector 9310 is as shown in FIG. 93, and thus its detailed description will be omitted.

The electrode layer 9320 may be formed of a material which an electrochemical reaction to an electrolyte of a battery may have a slurry shape in which active material and a conductive material are mixed. The electrode layer 9320 may further include a binder.

The electrode layer 9320 includes a plurality of pores 20, and a porosity rate of the electrode layer 9320 varies in proportion to a distance from the current collector 9310. In detail, the porosity of the electrode layer 9320 increases in proportion to the distance from the current collector 9310.

The electrode layer 9320 may be formed and pressed on the porous current collector 9310 or a method (CVD method) of coating a liquid state electrode layer 9320 on the porous current collector 9310 may be used to allow the electrode layer 9320 to contact the porous current collector 9310. In this case, the electrode 9300 may be an electrode all-in-one device in which an active material constituting the electrode layer 9320 is inserted into the poles of the current collector 9310.

In FIG. 94, the porous electrode layer 9320 is formed on the porous current collector 9310 to insert a part of the porous electrode layer into the pores of the porous current collector 9310. However, as shown in FIG. 95, most of the porous electrode layer 9320 may be inserted into the pores 10 of the porous current collector 9300 to form a single body device.

Figure 96:
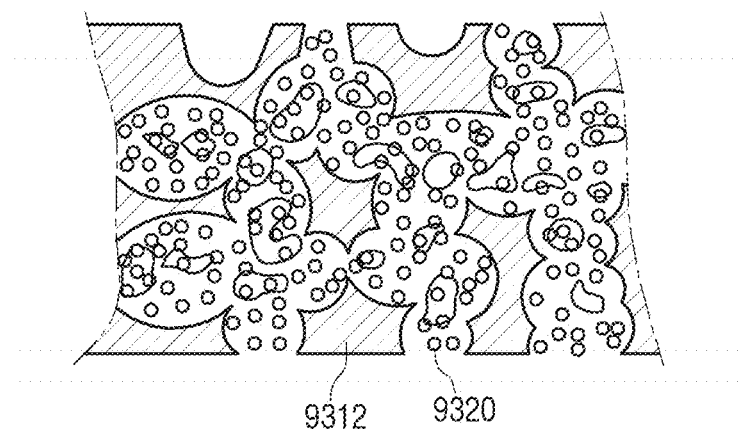
FIG. 96 is a cross-sectional view illustrating a porous electrode according to an exemplary embodiment of the present general inventive concept.
Figure 97:
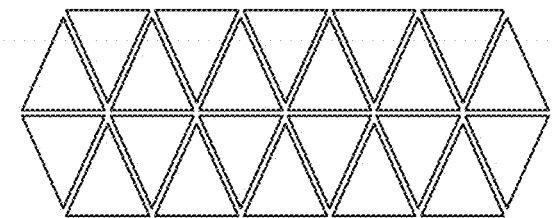
FIGS. 97 through 100 are views illustrating stomata according to various exemplary embodiments of the present general inventive concept.
Figure 98:
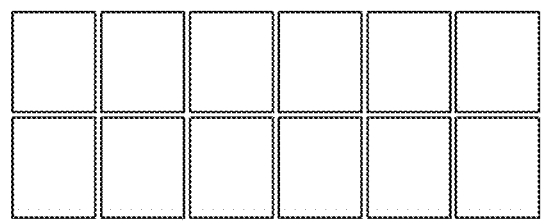
Figure 99:
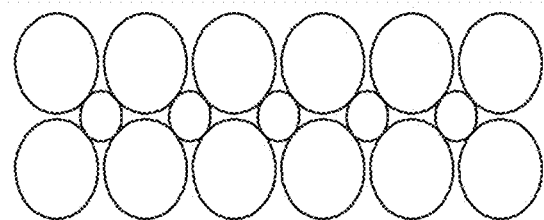
Figure 100:
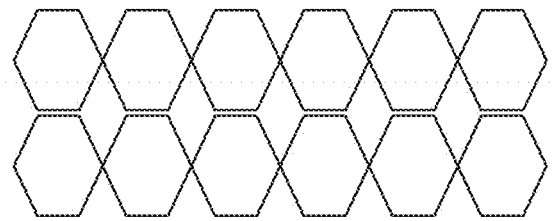

FIG. 96 is a cross-sectional view of a porous electrode according to an exemplary embodiment of the present general inventive concept.

Referring to FIG. 96, a cross-section of the porous electrode 9300 may be a form in which a slurry constituting the electrode layer 9320 is charged into the pores of the porous current collector 9310.

If the electrode 9300 is used as a lithium battery, an active material may be formed of a material reversibly intercalating lithium ions, a material reversibly forming a composite along with lithium metal, or a cathode material including lithium metal or a lithium alloy. A lithium-aluminum alloy or a lithium-tin alloy may be used as the lithium alloy.

The material reversibly reacting the lithium ions may be a carbon material or any carbon cathode active material which is generally used in a lithium ion secondary battery. A representative example of the material include crystalline carbon, amorphous carbon, or both them. A representative example of the material reversibly forming the composite along with the lithium metal may be a titanium nitrate but is not limited thereto.

A metal-based active material may be used or one selected from the group consisting of lithium metal, a metal material alloyed with lithium, and a mixture thereof may be used. In detail, the metal material alloyed with the lithium may be one selected from the group consisting of Na, K, Rb, Cs, Fr, Be, Mg, Ca, Sr, Ba, Ra, Ti, Ag, Zn, Cd, Al, Ga, In, Si, Ge, Sn, Pb, Sb, Ni, Bi, and a mixture thereof.

If the electrode 9300 is used as an anode of the lithium battery, any composite generating a reversible reaction of lithium may be used as an anode active material. For example, $Ni_3Si_2$, $LiMn_2O_4$, $LiCoO_2$, $LiNiO_2$, $LiFePO_4$, $V_2O_5$, TiS, MoS, or the like or at least one selected from them may be used as the anode active material.

A coating layer may be formed on a surface of an active material or a composite including an active material and a coating layer may be mixed and used. The coating layer may include at least one coating element composite selected from the group consisting of oxide of a coating element, hydroxide, oxyhydroxide of the coating element, oxycarbonate of the coating element, and hydroxycarbonate of the coating element. These composites forming the coating layer may be amorphous or crystalline. The coating element included in the coating layer may be one selected from the group consisting of Mg, Al, Co, K, Na, Ca, Si, Ti, V, Sn, Ge, Ga, B, As, Zr, and a combination thereof.

A process of forming the coating layer may be performed by using any coating method (e.g., a spray coating method, a dip coating method, or the like) which does not badly affect a physical property of the anode active material by using these elements in the composite and is well understood by those skilled in the art. Therefore, a detailed description thereof will be omitted.

The active material may be included not to lower a combination force with a current collector due to a capacity drop with respect to a total weight of an active material layer or a relative decrease in a binder amount.

The conductive material may be formed of conductive polymer. The conductive material may be formed of polymer having electrical conductivity, poly(sulfurnitrile), polypyrrole, poly(p-phenylene), poly(phenylenesulfide), polyaniline, poly(p-phenylenevinylene), or the like.

The electrode active material and the conductive polymer may be mixed before being stacked on the current collector 9310. In detail, the electrode active material and the conductive polymer may be realized in power forms, and thus power may be mixed to form a composite, and the conductive polymer may be coated on a surface of the electrode active material to be mixed in a polymer form. A polymerization of the electrode active material and the conductive polymer may be formed by using various polymerizing methods, a substituting method, or the like. The electrode active material may be added in a process of fabricating the conductive polymer to form the polymer of the electrode active material and the conductive material.

A shape of the conductive material is not particularly limited and may a standing shape, a scaly shape, a fiber shape, or the like.

The binder operates to well attach cathode active material particles to one another and well attach a cathode active material to a current collector.

For example, the binder may be formed of polyvinyl alcohol, carboxymethyl celluose, hydroxypropyl cellulose, diacetyl cellulose, polyvinyl chloride, carboxyl polyvinyl chloride, polyvinyl fluoride, polymer including ethylene oxide, polyvinyl pyrolidone, polyurethane, polytetrafluorethylene, polyvinyliden fluoride, polyethylene, polypropylene, styrene-butadiene rubber, acrylated styrene-butadiene rubber, epoxy resin, nylon, or the like but is not limited thereto.

Also, a water system binder may be used as the binder. If a battery is fabricated by using the electrode 9310, an electrolyte may be well infiltrated into the water system binder.

For example, the water system binder may be formed of one or two or more selected from the group consisting of acrylonitrile butadiene rubber, styrene-butadiene rubber, acryl rubber, hydroxyethyl cellulose, carboxymethyl cellulose, and polyvinylidene fluoride.

Also, particles constituting the electrode layer 9320 grinded and sieved to adjust a particle size.

The pores in the current collector 9310 and the electrode layer 9320 may be formed according to a general pore forming method. If the pores are formed by using a pore former, sizes, distribution, and porosity of the pores formed in the electrode active material layer may be adjusted according to a size, a content, and a processing method of the pore former. Here, the pore former may be any pore former which is generally used to form pores. In detail, the pore former may be $(NH_4)_2CO_3$, $NH_4HCO_3$, $(NH_4)_2C_2O_4$, and a mixture thereof, poly(alkylenecarbonate) which is melted in a non-aqueous organic solvent to be eluted, poly(alkylene oxide), poly(dialkyl siloxane), a polymer material such as acrylate-based polymer, or alkali metal containing carbonate such as $Li_2CO_3$, $K_2CO_3$, $Na(CO_3)_2$, or the like which is melted in an acid to be eluted. Here, the porosity of the active material layer may be a degree which does not badly affect a volume expansion and energy density.

The pores 10 and 20 in the current collector 9310 and the electrode layer 9320 may be formed by an aerosol method. A detailed description thereof will be described later.

As the current collector 9310 becomes distant from a part contacting the electrode layer 9320, a porosity in the current collector 9310 decreases. As the electrode layer 9320 becomes distant from a part contacting the current collector 9310, the porosity in the electrode layer 9320 increases. Therefore, a contact area between the current collector 9310 and the electrode layer 9320 and a contact area between the electrode layer 9320 and an electrolyte constituting the battery may increase.

According to a method of realizing the above-described structure, a slurry in which an electrode active material and a conductive material (or including a binder) are mixed may be gradually stacked on a current collector with gradually adjusting an amount of conductive material.

Alternatively, an electrode layer may be grown on the current collector with reducing the number of electrode active materials or reducing an amount of conductive material by using an aerosol method. If the aerosol method is used, a binder may not be necessary, an electrode may be fabricated at a room temperature, and a thermal treatment is not necessary.

An electrode layer may be grown on a current collector by using a sintering method. Here, the sintering method refers to a method of pressurizing powder in an appropriate size, heating the pressurized powder, adhering the powder to one another, and sintering the powder. The sintering method may be widely understood by those skilled in the art, and this its detailed description will be omitted.

FIGS. 97 through 100 are views illustrating pore shapes according to various exemplary embodiments of the present general inventive concept.

Referring to FIGS. 97 through 100, pores formed in at least one of a current collector and an electrode layer may have various shapes such as a triangular shape, a square shape, a circular shape, a hexagonal shape, etc.

Figure 101:
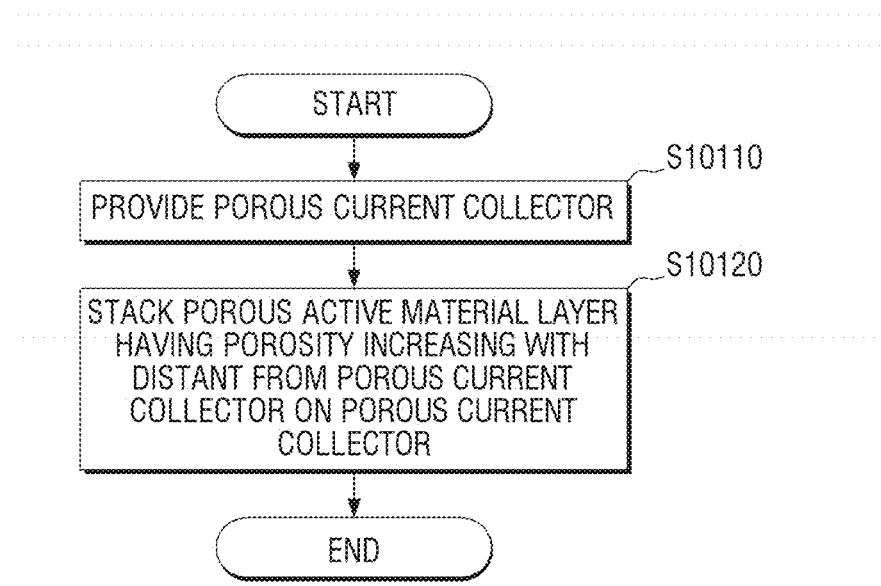
FIG. 101 is a flowchart illustrating a method of fabricating an electrode according to an exemplary embodiment of the present general inventive concept.

FIG. 101 is a flowchart illustrating a method of fabricating an electrode according to an exemplary embodiment of the present general inventive concept.

Referring to FIG. 101, in operation S10110, a porous current collector is provided.

In operation S10120, a porous electrode layer having a porosity increasing in a direction distant from the porous current collector is stacked on the porous current collector.

In this case, the pores in the porous current collector and the porous electrode layer may be formed by using general pore former or an aerosol method. A structure forming pores by using an aerosol method according to various exemplary embodiments of the present general inventive concept will be described with reference to FIGS. 102 and 103.

Figure 102:
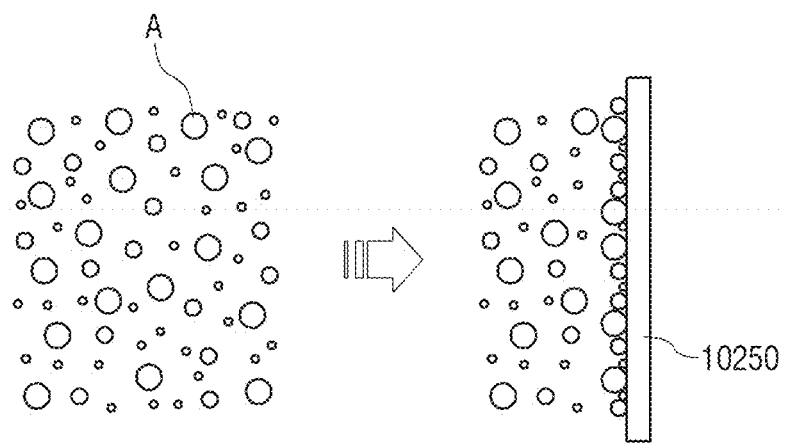
FIGS. 102 through 107 are views illustrating an aerosol method according to various exemplary embodiments of the present general inventive concept.
Figure 103:
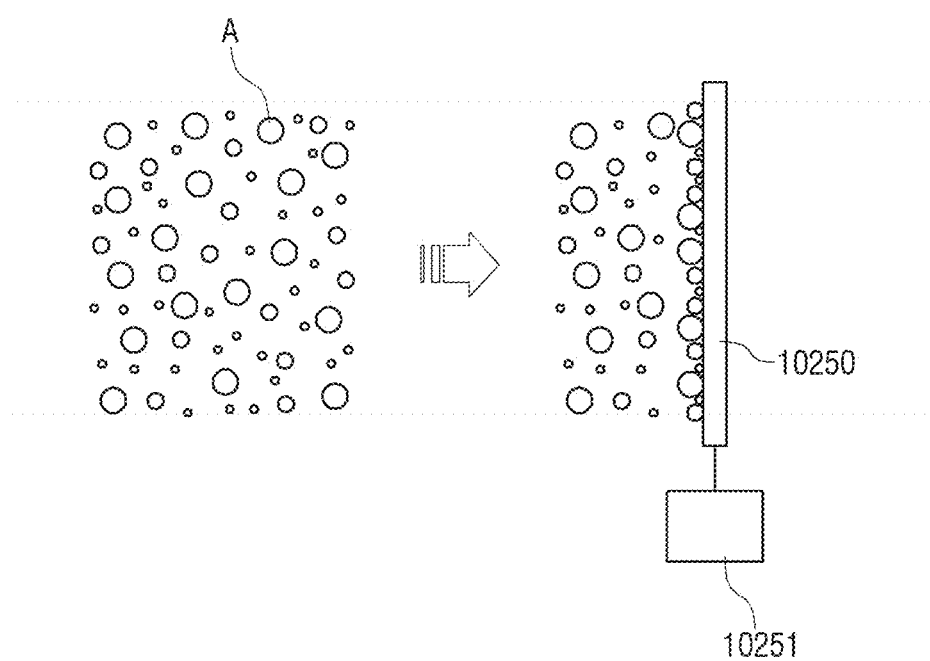

FIGS. 102 and 103 are views illustrating an aerosol method according to an exemplary embodiment of the present general inventive concept.

Referring to FIG. 102, a method of fixing aerosol particles to a body to be fixed by using a collision fixing method may be used. In other words, the aerosol method may be a method of forcing aerosol particles A to collide with a body 10250 to be fixed to fix the aerosol particles A to the body 10250. Here, the aerosol particles A may be moved according to a flow of an inert gas or nitrogen and thus naturally collide or may collide with the body 10250 by an external wind force.

The aerosol particles A may be particles constituting the current collector 9310 and the active material layer 9320.

The body 10250 to be fixed may be the pad part 9311 if the current collector 9310 is formed or may be the current collector 9300 if the active material layer 9320 is formed.

The above definitions of the aerosol particles A and the body 10250 may be equally applied hereinafter.

If the body 10250 is a porous substrate, the aerosol particles A are fixed to the body 10250 through a colliding, blocking, and diffusing, and a gaseous component such as the inert gas or the nitrogen may be separated to the outside through pores of the substrate.

Referring to FIG. 103, particles may be fixed by using a thermophoretic phenomenon. In other words, a temperature of the body 10250 is adjusted to be lower than a temperature of the aerosol particles A through a thermostat 10251 to automatically move the aerosol particles A to the body 10250 in order to fix the aerosol particles A to the body 10250.

In this case, the number of aerosol particles A may be gradually adjusted to adjust a porosity.

Figure 104:
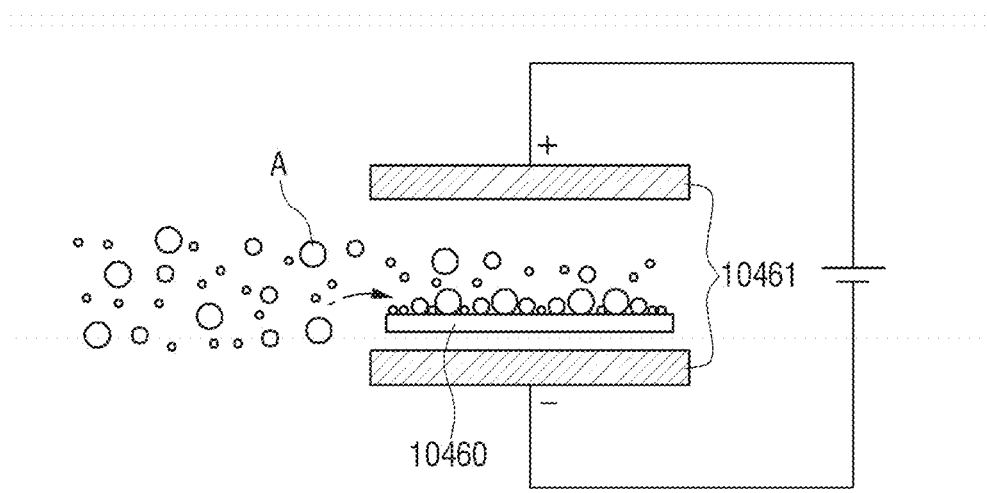
Figure 105:
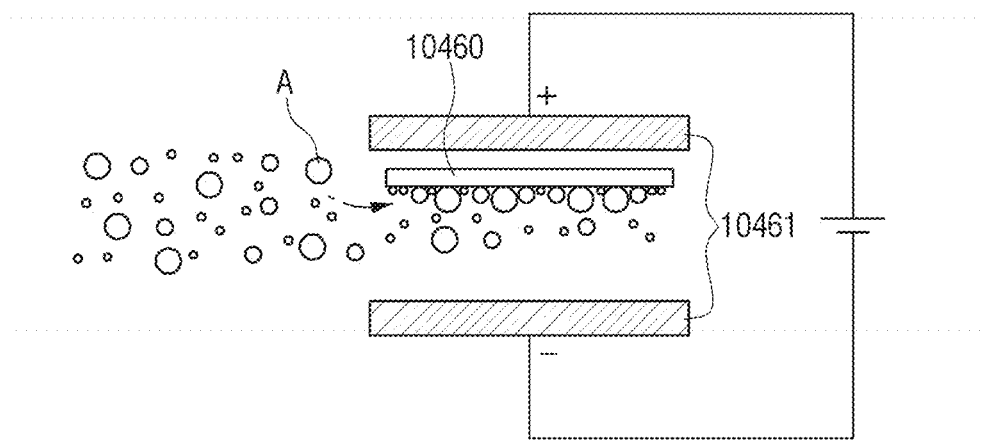

FIGS. 104 and 105 are views illustrating an aerosol method according to another exemplary embodiment of the present general inventive concept.

Referring to FIGS. 104 and 105, a porous current collector and a porous active material may be formed by using an electric field.

The electric field formed on an electrode plate 10461 may be used. In other words, aerosol particles A are electrified with positive charge (in the case of FIG. 104) or negative charge (in the case of FIG. 105), moved to a body 10460 to be fixed between positive electrode plates 10461 to which power is applied, in order to move the aerosol particles A to the body 10460 by using an influence gravity between one of the positive electrode plates 10461 and the positive charge (in the case of FIG. 104) or the negative charge (in the case of FIG. 105), thereby fixing the aerosol particles A to the body 10460.

A surface of a body to be fixed may be processed to reinforce fixing efficiency of the aerosol particles A.

In other words, a part of a surface of the body peels off by performing a surface treatment with respect to the body which is an object to be plated or coating chemicals on the body, thereby generating an uneven part. Also, a fixing force and fixing efficiency of the aerosol particles may increase through colliding, blocking, and diffusing by the uneven part.

Here, the chemicals may be a material having a strong acid or alkali property, e.g., may be NaOH, HNO3, HCL, H2SO4, or the like.

The surface treatment of the body to be fixed may be applied at any time before the aerosol particles are fixed to the body.

According to the present general inventive concept, if the aerosol particles A are fixed to the body, a step of treating an adhesion improver for improving the fixing strength, i.e., adhesion, may be further included.

For example, a method of mixing and spraying aerosol particles with an adhesive liquid, a method of coating an adhesive liquid on a body to be fixed before aerosol particles are fixed, a method of coating an adhesive liquid on the body to which aerosol particles adhere and are fixed after the aerosol particles are fixed may be used.

According to the present general inventive concept, a step of hot-pressing the bodies 10250 and 10460 through a rolling method using a pressing roll may be further included after the metal aerosol nano-particles are fixed.

Here, a temperature condition for the hot-pressing may be a temperature higher than or equal to a room temperature. A top limit of the temperature condition may vary according to types of the bodies 10250 and 10460. In other words, a temperature at which the bodies 10250 and 10460 are not deformed may be used. A temperature at which properties of the adhesive improver and the aerosol particles A besides the types of the bodies 10250 and 10460 are not deformed may be used.

According to the step of hot-pressing the body to be fixed, the fixing strength of the fixed aerosol particles A may further increase, and various foreign matters such as moisture, etc. are volatilized and removed due to heat generated by heating.

Figure 106:
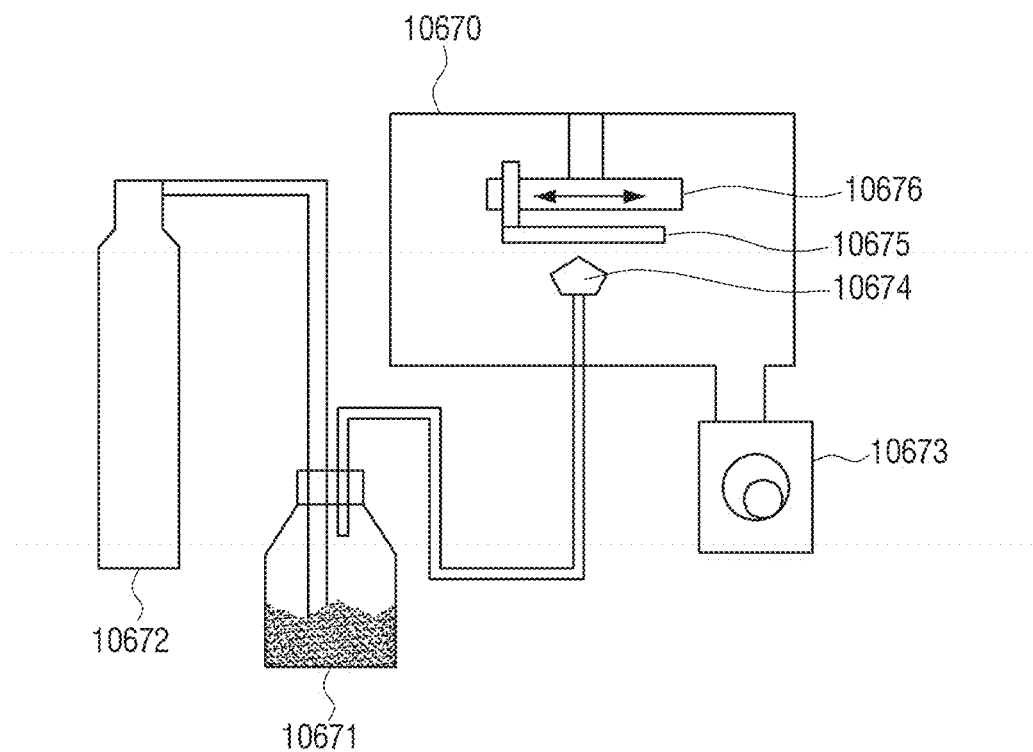

FIG. 106 is a view illustrating an aerosol method according to another exemplary embodiment of the present general inventive concept.

According to an aerosol deposition apparatus of FIG. 106, a carrier gas 10672 flows into an aerosol chamber 10671 containing powder, and minute powder floating in the aerosol chamber 10671 is sprayed to a substrate 10676 of a deposition chamber in a vacuum state through a nozzle 10674. The substrate 10676 may move on X and Y axes, and a mask M may be positioned on the substrate 10676.

Figure 107:
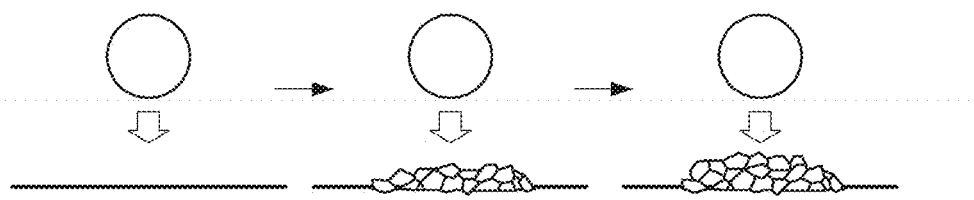

FIG. 107 is a view illustrating a process of coating aerosol particles.

A process of fabricating an LiFePO4 thin film will be exemplarily described. As shown in FIG. 107, if dispersed particles LiFePO4 collided with the substrate, the particles are grinded, and some pieces are stacked in the substrate or are strongly combined, and next particles collide thereon. The collided particles are grinded and thus form a layer having a strong combination strength, and then next particles collided thereon.

Figure 108:
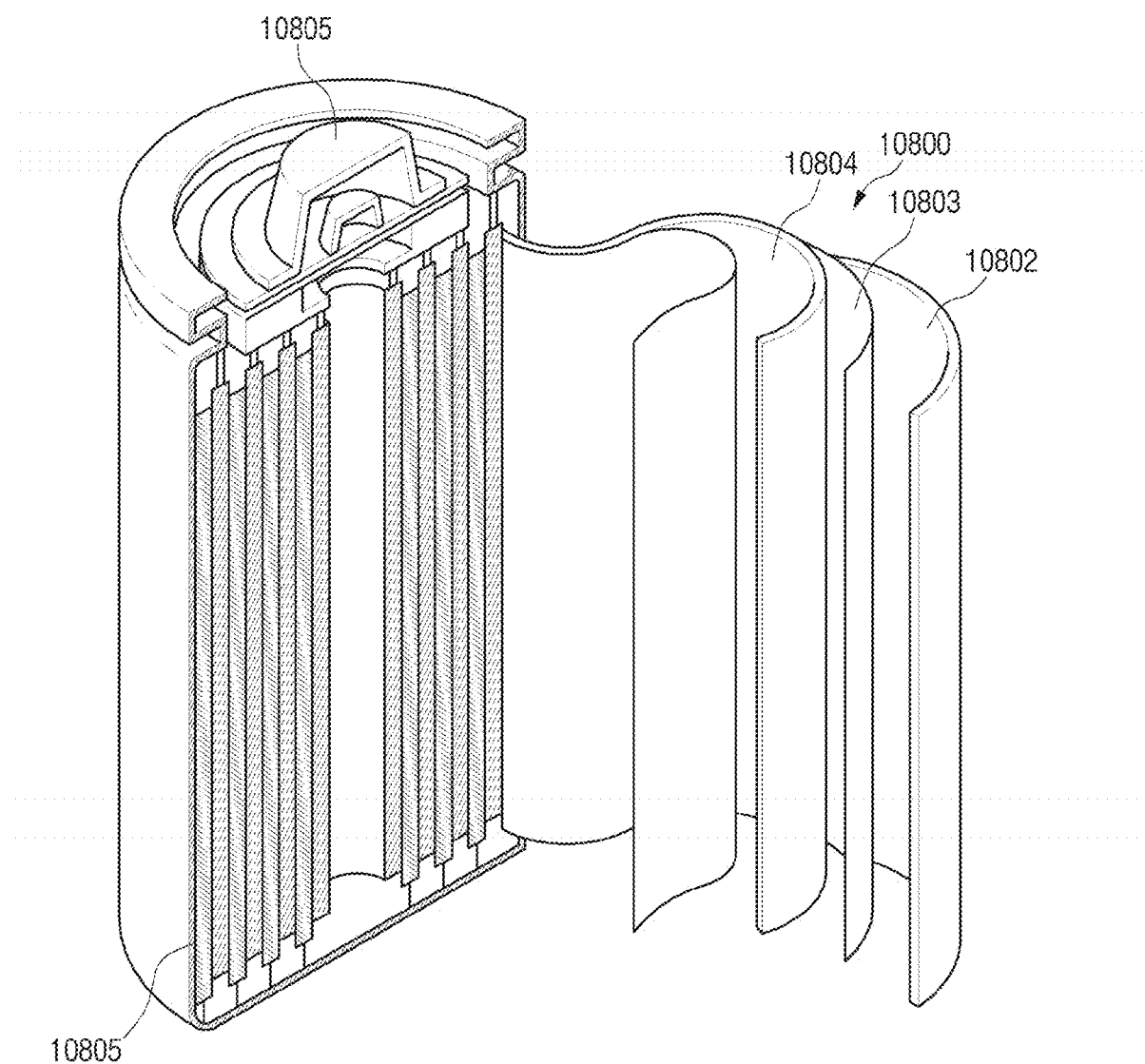
FIG. 108 is a view illustrating a structure of a lithium battery according to an exemplary embodiment of the present general inventive concept.

FIG. 108 is a view illustrating a structure of a lithium battery according to an exemplary embodiment of the present general inventive concept.

Referring to FIG. 108, a lithium battery 10800 includes a cathode 10802, an anode 10804, a battery vessel 10805 including an electrolyte immersed into a separator 10803 existing between the cathode 10802 and the anode 10804, and an enclosing member 10806 which encloses the battery vessel 10805. Here, be above-described porous electrodes may be used as the cathode 10802 and the anode 10804.

The lithium battery 10800 of FIG. 108 includes the separator 10803. However, if at least one of a cathode and an anode includes a high intensity binder layer, the lithium battery 1800 may not include the separator 10803.

A lithium secondary battery may be classified into a lithium ion battery, a lithium ion polymer battery, and a lithium polymer battery according to types of separator and electrolyte, may be classified into cylindrical, square, coin, and pouch types according to its shapes, and may be classified into a bulk type and a thin film type according to its sizes.

The cathode 10802 and the anode 10804 are as described above, and their detailed descriptions will be omitted.

A thin film type or a bulk type material may be used as the electrolyte. However, a solid inorganic electrolyte or an organic polymer electrolyte is generally used in an actually used apparatus, but a liquid electrolyte is generally used for a test.

The electrolyte may include lithium salt and a nonaqueous organic solvent.

The lithium salt is melted in an organic solvent to operate as a supply source of lithium ions n a battery in order to enable a basic operation of the lithium secondary battery and promote movements of lithium ions between an anode and a cathode.

The lithium salt may be one selected from the group consisting of $LiPF_6$, $LiBF_4$, $LiSbF_6$, $LiAsF_6$, $LiClO_4$, $LiCF_3SO_3$, $LiC_4F_9SO_3$, $LiN(CF_3SO_2)_2$, $LiN(C_2F_5SO_2)_2$, $LiAlO_2$, $LiAlCl_4$, $LiN(C_pF_{2p+1}SO_2)(C_qF_{2q+1}SO_2)$ (here, p and q are natural numbers), $LiSO_3CF_3$, $LiCl$, $LiI$, lithium bisoxalate borate, and a mixture thereof but is not limited thereto.

The nonaqueous organic solvent operates as a medium to which ions involved in an electrochemical reaction of the battery may be moved. A carbonate-based, ester-based, ketone-based, alcohol-based, or nonprotonic solvent may be used as the nonaqueous organic solvent.

The nonaqueous organic solvent may be independently used or one or more nonaqueous organic solvents may be mixed and used. If one or more nonaqueous organic solvents are mixed and used, a mixture ratio may be appropriately adjusted according to a target battery performance. This will be understood by those skilled in the art, and thus a detailed description thereof will be omitted.

The separator 10803 may exist between a cathode and an anode according to a type of lithium secondary battery. The separator 10803 separates the cathode 10802 and the anode 10804 from each other and provides a movement path of lithium ions. Such a separator may be any separator which is generally used in a lithium battery. In particular, a separator having a low resistance to the movement of ions of the electrolyte and a high moisturization capability of the electrolyte may be used. For example, polyethylene, polyester, polypropylene, polyvinylidene fluoride, or a multilayer which is a dual layer or more thereof may be used. A mixture multilayer, such as polyethylene/polypropylene dual layer separator, a polyethylene/polypropylene/polyethylene three-layer separator, a polypropylene/polyethylene/polypropylene three-layer separator, or the like, may be used.

The lithium secondary battery of FIG. 108 has a cylindrical shape but is only exemplary. Therefore, the lithium secondary battery may have various shapes such as cylindrical, square, coin, pouch, or shift shapes.

As described above, a separator is disposed between a positive pore plate and a negative pore plate to form a battery structure. The battery structure is winded or folded to be inserted into a cylindrical battery case or a square battery case, and then an organic electrolyte is injected to complete a lithium ion battery. Also, the battery structure is stacked in a bicell structure and then immersed into an organic electrolyte, and a resultant structure is put into a pouch and then sealed to complete a lithium ion polymer battery.

Therefore, a contact area between a current collector and an active material layer may increase in an electrode, and a contact area between the electrode and an electrolyte may increase in a battery. Therefore, efficiency of the battery (e.g., an energy storage performance of a secondary battery) may be improved.

Also, a size of the battery may be minimized.

[Third Exemplary Embodiment of Secondary Battery Part]

The third exemplary embodiment of the secondary battery part relates to a device in which an electrode and a current collector form a single body. The single body device may be applied to a positive or negative pore electrode and a lithium-based battery but is not limited thereto.

Figure 109:
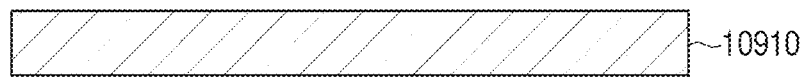
FIGS. 109 through 111 are cross-sectional views illustrating a process of forming a current collector-electrode all-in-one device according to an exemplary embodiment of the present general inventive concept.
Figure 110:
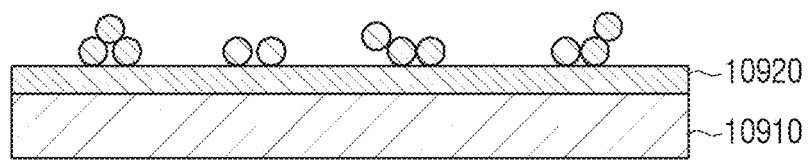
Figure 111:
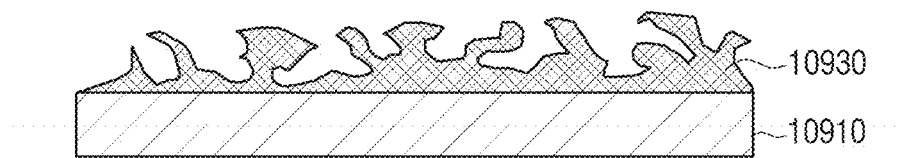

FIGS. 109 through 111 are cross-sectional views illustrating a process of fabricating an all-in-one current collector and electrode device according to an exemplary embodiment of the present general inventive concept.

FIG. 109 is a cross-sectional view of an current collector 11810 used in the all-in-one current collector and electrode device.

A current collector 10910 is formed of a conductive material. In the present exemplary embodiment, the current collector 10910 may be formed of a copper plate having a thickness of 20 μm.

FIG. 110 is a cross-sectional view illustrating a plated metal lay 10920 formed on the current collector 10910. The plated metal layer 10920 is formed by electroless nickel plating. In the present exemplary embodiment, The electroless nickel plating is used as a method for forming Ni and $Ni_3P$ plating on the current collector 10910. Also, $NiCl_2 \cdot 6H_2O$, $NaPO_2H_2 \cdot H_2O$, $NaH_3C_6H_5O_7 \cdot 2H_2O$, and $NH_4Cl$ may be used as an original material of Ni and $Ni_3P$ plating.

The electroless nickel plating is a method of autocatalytically returning metal ions in a metallic salt aqueous solution through a force of a reducing agent without receiving electric energy from an external source to extract metal on a surface of an object to be processed and is referred to as chemical plating or autocatalytic plating.

Before the plated metal layer 10920 is formed on the current collector 10910, a copper plate having the same size as the current collector 10910 may contact an other side on which the plated metal layer 10920 will not be formed, in order to form the plated metal layer 10920 only on a side of the current collector 10910.

A plating solution is fabricated to form the plated metal layer 10920. In the present exemplary embodiment, in order to fabricate the plating solution, the original material of Ni and $Ni_3P$, i.e., $NiCl_2 \cdot 6H_2O$, $NaPO_2H_2 \cdot H_2O$, $NaH_3C_6H_5O_7 \cdot 2H_2O$, and $NH_4Cl$, are added to distilled water, and then, a temperature of the solution increases to reach a preset plating temperature. If the solution reaches the preset plating temperature, the solution is adjusted in a strong alkali atmosphere by using sodium hydroxide. Here, the preset plating temperature may be 90°.

Here, the original material of Ni and $Ni_3P$ may be 45 g/l of $NiCl_2 \cdot 6H_2O$, 22 g/l of $NaPO_2H_2 \cdot H_2O$, 100 g/l of $NaH_3C_6H_5O_7 \cdot 2H_2O$, and 50 g/l of $NH_4Cl$ based on 1 L of distilled water.

If the plating solution is completely fabricated, the current collector 10910 is immersed into the plating solution for a preset plating time. Here, the current collector 10910 may contact a copper plate having the same size on the other side in order to form the plated metal layer 10920 on the side. Here, the preset plating time may be 30 minutes.

If the current collector 10910 is immersed into the plating solution and the preset plating time, e.g., 30 minutes, elapsed, the plated metal layer 10920 is formed on the current collector 10910 in a shape as shown in FIG. 110. Therefore, one side of the current collector 10910 is plated with Ni and $Ni_3P$. Referring to FIG. 110, spherical particles having a size between 2 μm an 3 μm are formed on a surface of the plated metal layer 10920 formed on the current collector 10910.

When a plated metal layer is formed on the current collector 10910 by using electroless plating, a material, such as Zn, Fe, Cd, Co, Ni, Sn, Pb, Cu, and Ag, may be used as a raw material.

FIG. 111 is a cross-sectional view illustrating a metal sulfide layer 30 formed by sulfurating the current collector 10910 on which the plated metal layer 10920 is formed. In the present exemplary embodiment, a raw material for sulfurating may be $(NH_4)_2Sx$ and $Na_2S$.

In order to sulfurate the current collector 10910 on which the plated metal layer 10920 is formed, a sulfurating solution is fabricated. In order to fabricate the sulfurating solution, $(NH_4)_2Sx$ and $Na_2S$ may be added to distilled water to form a solution, and a temperature of this solution increases until the temperature of the this solution reaches a preset sulfuration temperature. Here, the preset sulfuration temperature may be 80°. Also, when increasing the temperature to fabricate the sulfurating solution, sodium sulfide may be agitated at a predetermined speed when the sodium sulfide is completely melted. When fabricating the sulfurating solution, 200 ml of $(NH_4)_2Sx$ and 0.47 g of $Na_2S$ may be used based on 250 ml of distilled water.

If the sulfurating solution is completely fabricated, the sulfurating solution is coated on the current collector 10910 on which the plated metal layer 10920 is formed, dried for a predetermined time, and heated at a predetermined temperature, i.e., 60°.

As described above, if a predetermined time elapses when the sulfurating solution is coated on the current collector 10910 on which the plated metal layer 10920 is formed and heated at the predetermined temperature, sulfurating is completed. If the sulfurating is completed, an all-in one current collector and electrode device having a structure of FIG. 111 is completed.

As shown in FIG. 111, as $NH_3$ is evaporated due to thermal treatment in a process of sulfurating the current collector 10910 on which the plated metal layer 10920 is formed, many pores are formed in a surface of the all-in one current collector and electrode device. The pores assists a liquid electrolyte in easily penetrating the all-in-one current collector and electrode device when the all-in-one current collector and electrode device is applied to a lithium secondary battery.

Figure 112:
FIGS. 112 through 114 are views illustrating a surface shape of FIGS. 109 through 111.
Figure 113:
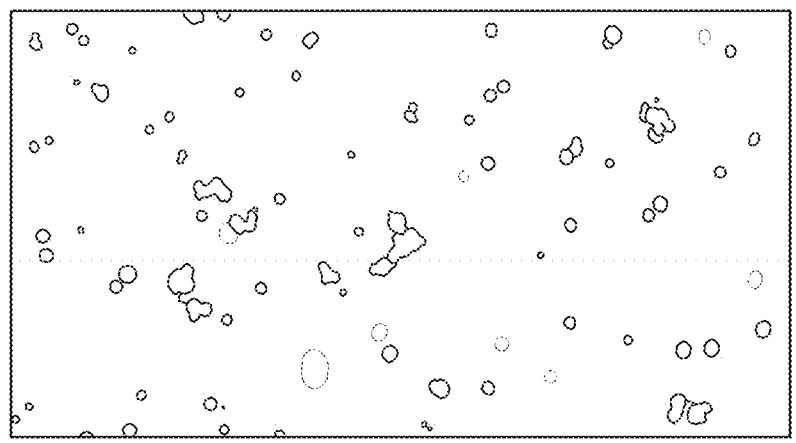
Figure 114:
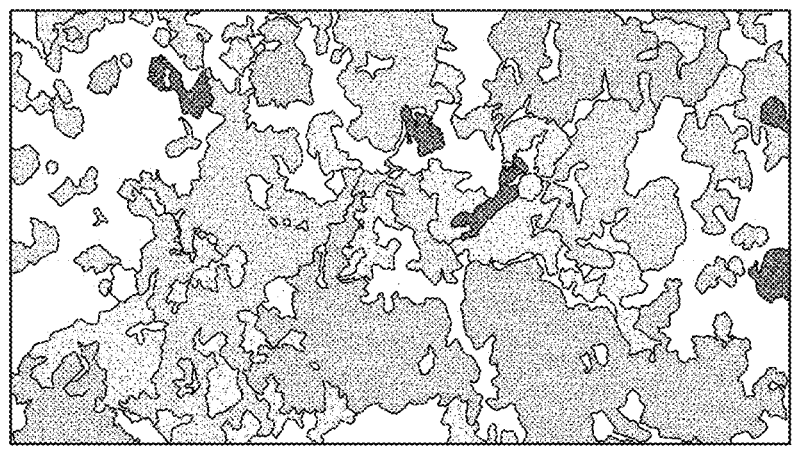

FIGS. 112 through 114 are views illustrating surface shapes of FIGS. 109 through 111.

FIG. 112 illustrates a shape of a surface of the current collector 10910 of FIG. 109 observed through a scanning electron microscope (SEM). As shown in FIG. 112, curves appears on the surface of the current collector 10910 when processing the current collector 10910. However, the curves on the surface of the current collector 10910 do not affect the fabrication of the all-in-one current collector and electrode device.

FIG. 113 illustrates a shape of the surface of the current collector 10910 on which the plated metal layer 10920 is formed, observed through a SEM. Particles appearing in the plated metal layer 10920 of FIG. 113 correspond to the spherical particles of FIG. 110. The spherical particles are $Ni_3P$ or $Ni_2P$. Also, the curves on the surface of the current collector 10910 of FIG. 112 disappear in FIG. 113.

FIG. 114 illustrates a shape of the surface of the current collector 10910 on which the metal sulfide layer 10930 of FIG. 111 is formed, observed through an SEM. If the current collector 10910 on which the plated metal layer 10920 of FIG. 113 is formed is sulfurated, $NH_3$ ad moisture are evaporated in the thermal treatment of the sulfurating, and thus many pores are formed on the surface of the current collector 10910. Here, a penetrating area of an electrolyte is secured due to the pores formed through the evaporation of $NH_3$ ad moisture.

Figure 115:
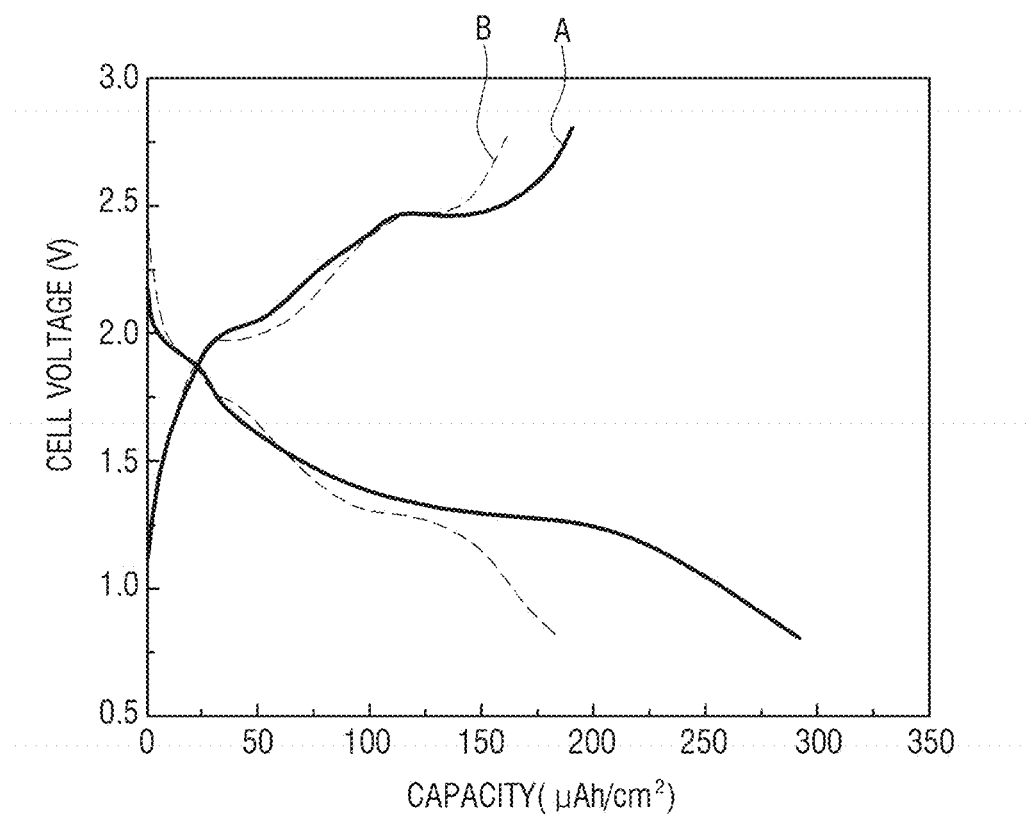
FIG. 115 is a graph illustrating charging/discharging according to a constant current test of a current collector all-in-one device according to an exemplary embodiment of the present general inventive concept.

FIG. 115 is a graph illustrating charge/discharge with respect to a constant current test of an all-in-one current collector and electrode device according to an exemplary embodiment of the present general inventive concept.

According to charge/discharge curves of FIG. 115, the all-in-one current collector and electrode device is stacked on a stainless steel cell along with a liquid electrolyte and lithium ions to constitute a battery. Also, the battery is tested at a constant current of 50 μA in a voltage range between 0.8 V and 2.8 V. On the graph of FIG. 115, A denotes a charge/discharge curve in a first cycle, and B denotes a charge/discharge curve in a second cycle.

As shown in FIG. 115, the all-in-one current collector and electrode device shows a reaction section between 1.98V and 1.3V in a discharge process and a reaction section between 1.9V and 2.45V in a charge process. 1.98V of the discharge process and 2.45V of the charge process refers to an oxidation-reduction process of $Ni_3P$, and 1.3V of the discharge process and 1.9V of the charge process refers to an oidation-reduction process of nickel sulfide.

Figure 116:
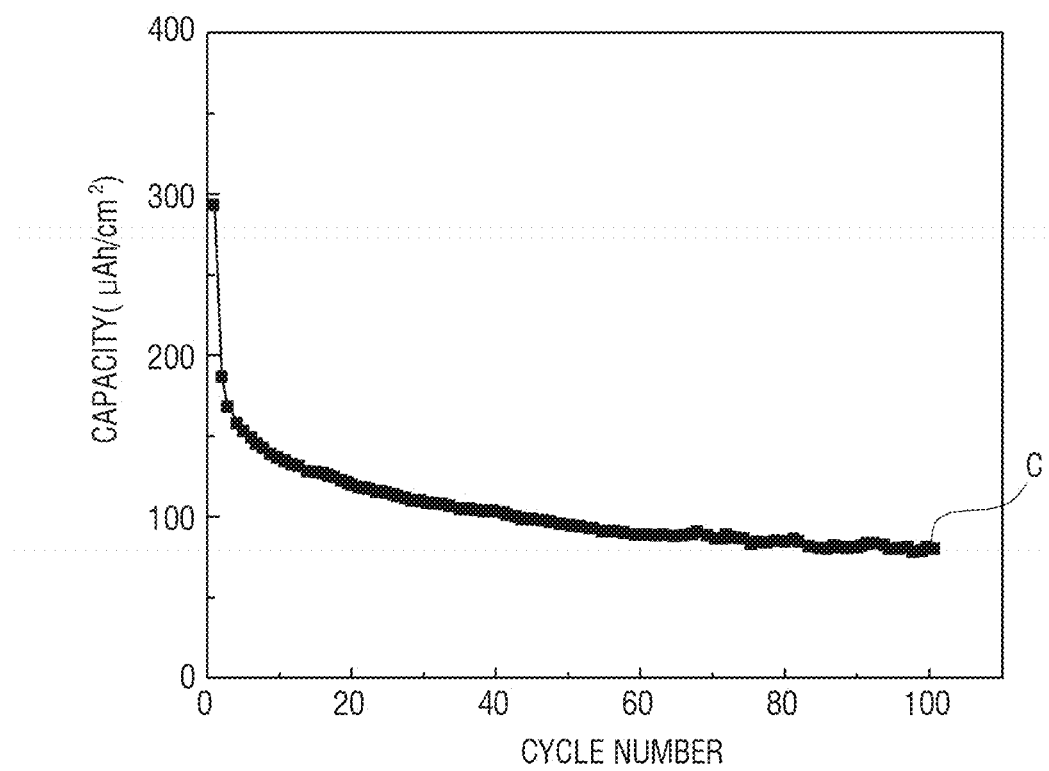
FIG. 116 is a graph illustrating a discharge capacity according to a cycle number of a current collector all-in-one device according to an exemplary embodiment of the present general inventive concept.

FIG. 116 is a graph illustrating a discharge capacity with respect to a cycle number of an all-in-one current collector and electrode device according to an exemplary embodiment of the present general inventive concept.

FIG. 116 illustrates a graph C illustrating a discharge capacity with respect to the cycle number of the all-in-one current collector and electrode device in the same conditions as those of FIG. 115. The discharge capacity decreases with an increase in the cycle number.

Figure 117:
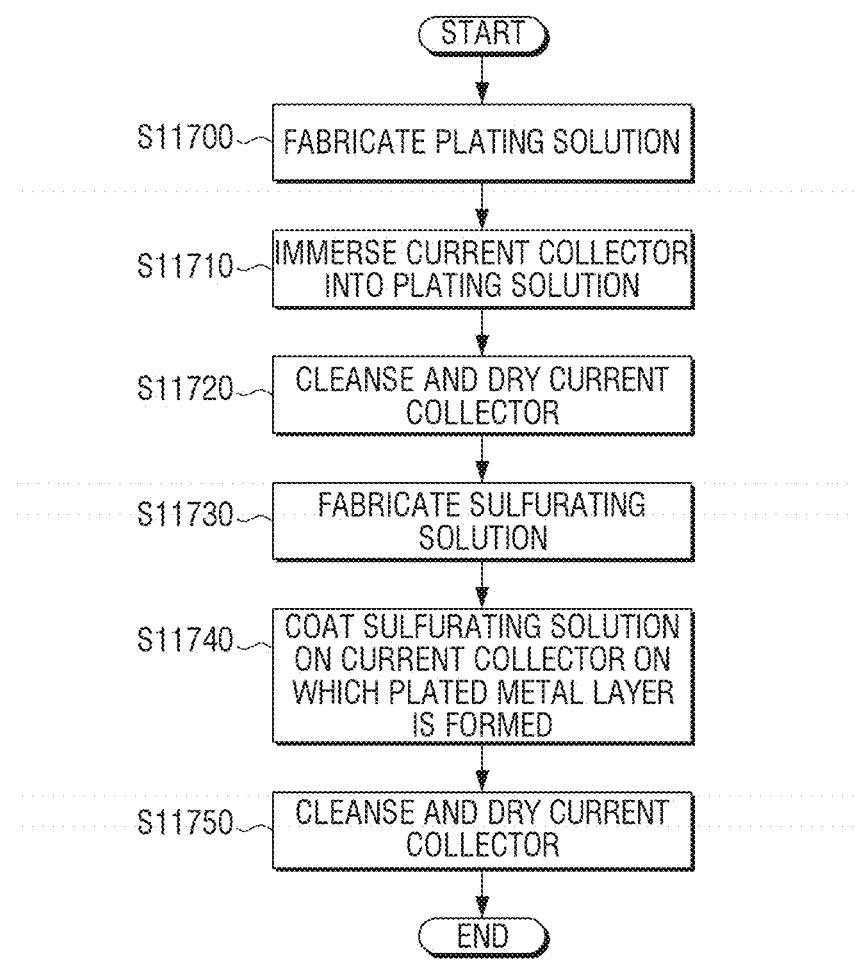
FIG. 117 is a flowchart illustrating a method of fabricating a current collector all-in-one device according to an exemplary embodiment of the present general inventive concept.

FIG. 117 is a flowchart illustrating a method of fabricating an all-in-one current collector and electrode device according to an exemplary embodiment of the present general inventive concept.

In operation S11700, a plating solution for electroless plating is fabricated. Here, the plating solution may be a solution which is fabricated by adding $NiCl_2.6H_2O$, $NaPO_2H_2.H_2O$, $NaH_3C_6H_5O_7.2H_2O$, and $NH_4Cl$ to distilled water to fabricate a solution and adjusting the solution in a strong alkali atmosphere by using sodium hydroxide when the solution reaches a preset plating temperature, e.g., 90°.

If the plating solution is completely fabricated, the current collector 10910 of FIG. 112 is immersed into the plating solution for a preset plating time, e.g., 30 minutes, in operation S11710. Here, only a side of the current collector 10910 is to be plated.

If the current collector 10910 is immersed into the plating solution, and then the preset plating time elapses, the plated metal layer 10920 is formed on the side of the current collector 10910. In operation S11720, the current collector 10910 on which the plated metal layer 10920 is formed is cleansed by using distilled water, and remaining moisture is removed through a drying process.

If the plated metal layer 10920 is completely formed by using the electroless plating, a sulfurating solution for sulfurating is fabricated in operation S11730. Here, the sulfurating solution may be a solution which is fabricated by adding $(NH_4)_2Sx$ and $Na_2S$ to distilled water to fabricate a solution and increasing a temperature of the solution until the temperature of the solution reaches a preset sulfuration temperature, e.g., 80°. Here, $Na_2S$ which is one of raw materials of the sulfurating solution is to be completely melted.

If the sulfurating solution is completely fabricated, a pre-fabricated sulfurating solution is coated on the current collector 10910 on which the plated metal layer 10920 is formed, dried for a predetermined time, e.g., 3 hours, at a room temperature, and sulfurated at a predetermined temperature, i.e., 60°, for 12 hours in operation S11740.

If the sulfurating is completed, a metal sulfide layer 10930 is formed on the current collector 10910. The metal sulfide layer 10930 is cleansed with distilled water, and remaining moisture is removed through a drying process in operation S11750.

Operations S11700 through S11720 correspond to a process of forming the plated metal layer 10920 by using the electroless plating, and operations S11730 through S11750 correspond to a process of forming the metal sulfide layer 10930 by sulfurating. The all-in-one current collector and electrode device is fabricated through this process.

An active material layer of an electrode is formed through the above-described process. As described above, the active material layer of the electrode formed through electroless plating and sulfurating is thinner than a conventional electrode. Therefore, electrons are easily moved in a battery reaction, and thus a performance of the battery is improved.

The all-in-one current collector and electrode device is stacked on a stainless steel cell along with a liquid electrolyte and lithium ions to constitute the battery. If the battery constituted by using the all-in-one current collector and electrode device, a reaction area of the lithium ions increases due to an easy penetration of the liquid electrolyte.

Figure 118:
FIGS. 118 through 120 are cross-sectional views illustrating a process of fabricating a 3-dimensional (3D) nano-structure according to another exemplary embodiment of the present general inventive concept.
Figure 119:
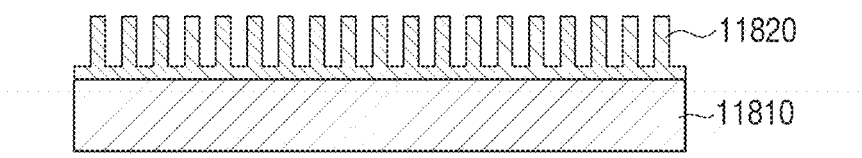
Figure 120:
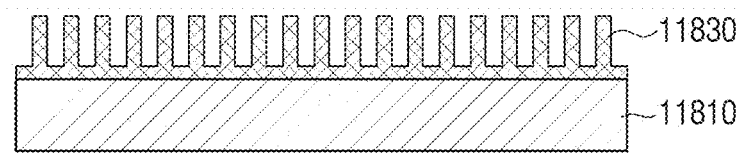

FIGS. 118 through 120 are cross-sectional views illustrating a process of fabricating a 3-dimensional (3D) nanostructure according to another exemplary embodiment of the present general inventive concept. For the descriptive convenience, detailed descriptions of the same elements of FIGS. 118 through 120 as those of FIGS. 109 through 117 will be omitted.

FIG. 118 is a cross-sectional view of a current collector 11810 used in the 3D nanostructure.

The current collector 11810 operates to form a flow of electrons between an electrode active material and a battery terminal and may be any current collector which does not cause a chemical change in the battery and has a high conductivity.

The current collector 11810 may be formed of one selected from the group consisting of Co, Ni, stainless steel, Ti, Al, carbon-coated Al, Ni foam, Cu foam, a polymer substrate coated with conductive metal, and combinations thereof. The material may be processed in foam, mesh, conductive material coating, punch types, etc. but is not limited thereto. At least one of the above-described materials whose surface is coated with another material may be used.

FIG. 119 is a cross-sectional view illustrating a metal layer 1820 which is formed on the current collector 11810 and has a 3D nanostructure. The metal layer 11820 may be formed by electroplating or pattern type thin film deposition method.

A plurality of nanostructures constituting the metal layer 11820 may be formed at enough distances to interpose an electrolyte therebetween.

Here, the metal layer 11820 may be formed of carbon. If the metal layer 11820 is formed of the carbon, a 3D structure may be formed through etching the carbon layer. Metal is plated on the carbon of the 3D structure, and a metal sulfide (sulfuration thermal treatment) or metal oxide (oxidation) layer may be formed as will be described later. Therefore, a contact area between the carbon of the 3D structure and a metal sulfide or metal oxide having low electric conductivity increases. As a result, a whole pillar has a lower electrode resistance than a structure in which a metal sulfide or metal oxide is formed, and an area capable of supplying electrons increases, thereby improving the performance of the battery.

The metal layer 11820 may be formed of Zn, Fe, Cd, Co, Ni, Sn, Pb, Cu, and Ag.

Electroplating refers to a method of covering a surface of an object with another thin metal thin by using a principle of electrolysis, i.e., is referred to as electric plating.

A method of forming a 3D nano-structured metal layer through the pattern type thin film deposition method will now be described. For the descriptive convenience, hereafter, a nanotemplete will be formed of anodic aluminum oxide (AAO), and a nanostructure will be formed of Ru.

In order to form the AAO nanotemplate on the current collector 11810, a voltage of predetermined volt is applied in an oxalic acid solution having a predetermined condition to perform a primary anodic oxidation process in order to form a template (not shown) having a porous pattern. An irregularly formed surface part is removes, and a secondary anodic oxidation is performed to improve an alignment. If the removal of the surface part and the anodic oxidation are performed three time and fourth time, a nanotemplate (not shown) having higher alignment may be formed. The nanotemplate is immersed into a phosphoric acid solution of a predetermined condition to perform a pore extending process in order to adjust a size of a pore. Through this process, a nanotemplate (not shown) in which a pore having a nanosize is formed in a vertical direction may be formed on the current collector 11810.

If a condition of the anodic oxidation process is changed, sizes, depths, and distances of the pores may be adjusted.

In order to deposit Ru 11820, a cycle is repeated in 5 steps in an atomic layer deposition apparatus [Ru(DMPD) (EtCp), (DER)] in which a liquid injection apparatus is installed, by using a precursor and an $O_2$ to perform 1000 or more cycles to a nanometer thickness of 0.5 per one cycle in order to form a high-quality Ru thin film having no nucleation, low roughness, and nonresistance, thereby filling the AAO nanotemplate pores with the Ru 11820.

Next, through BC13 plasma etching, a resistive layer formed in the anodic oxidation process may be removed.

The nanotemplate filled with the Ru 11820 is immersed into a mixture of a chromic acid and a phosphoric acid to selectively remove an aluminum oxide template (not shown).

Therefore, a metal layer 11820 including a plurality of nanostructures protruding from the surface of the current collector 11810 may be fabricated.

Here, the metal layer 11820 may have a nano-tube, a nano-wire, nano-rod, or nano-fiber shape or may have at least one of nano-ring and nano-horn shapes.

Alternatively, nano-particles each having a smaller diameter than an empty space between the nano-structures may be included between the plurality of nano-structures (or between tubes). Here, the nanoparticles may be formed in spherical, tube, rod, or tubular shapes.

Catalyst metal (not shown) may be formed at ends of the nanostructures. The catalyst metal may be any catalyst metal which shows a self-assembly characteristic according to a temperate rise. For example, the catalyst metal may be Au, Ag, Pt, Pd, Cu, or the like but is not limited thereto. Here, the catalyst metal operates as a catalyst for growing the nanostructures. A method of distributing the catalyst metal is not particularly limited, i.e., may be performed as follows.

A solution in which salt of the catalyst metal is melted in a solvent is dispersed on the current collector 11810, and the solvent is removed to distribute the catalyst metal. Here, the solvent may be an alcohol-based solvent such as ethanol, methanol, isopropyl alcohol, butyl alcohol an organic solvent such as DMAc, dimethyl formamide, DMSO, N-methylpyrrolidone, or tetrahydrofuran but is not limited thereto.

The catalyst metal may be Au, Ag, Pt, Pd, Cu, or the like or chloride, nitrate, ammonium salt, or the like of these catalyst metals may be dispersed, melted, and used.

In the present exemplary embodiment, the metal layer 11820 is separately formed on the current collector 11810. However, if a substrate is not required, a material which may be used as the metal layer 11820 may be directly etched to form the metal layer 11820.

For convenience, a plurality of nanostructures having nano-rod shapes are shown in FIG. 119, but the number of nanostructures formed on the current collector 11810 may vary according to distances of the nanostructures. Also, the nanostructures are aligned in one direction in FIG. 119 but may irregularly aligned. In addition, the nanostructures are formed in a direction perpendicular to a surface of the substrate, but the direction in which the nanostructures are formed is not limited.

FIG. 120 is a cross-sectional view illustrating a metal composite layer 11830 formed on the current collector 11810 on which the metal layer 11820 having the 3D nanostructure is formed.

Here, the metal composite layer 11830 may be a metal sulfide or a metal oxide 11830 which is formed by sulfurating or oxidation treating the metal layer 11820.

The metal sulfide layer 11830 may be formed by coating the current collector 11810 on which the metal layer 11820 having the 3D nanostructure is formed with a sulfurating solution. This is as described above, and thus a detailed description thereof will be omitted.

The metal oxide layer 11830 may be formed through an oxidation thermal treatment or a thermal treatment using a precursor.

Figure 121:
FIGS. 121 through 124 are cross-sectional views illustrating a process of fabricating a 3D nano-structure according to another exemplary embodiment of the present general inventive concept.
Figure 122:
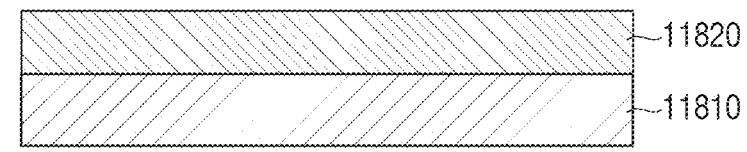
Figure 123:
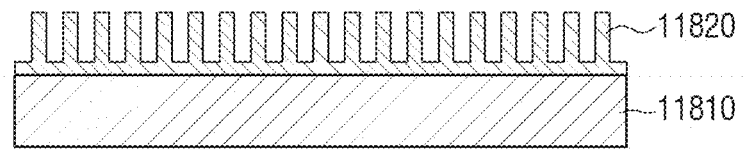

FIGS. 121 through 123 are cross-sectional views illustrating a process of fabricating a 3D nanostructure according to another exemplary embodiment of the present general inventive concept.

FIG. 121 is a cross-sectional view of the current collector 11810 used in the 3D nanostructure.

The current collector 11830 may be any current collector having high conductivity as described above.

FIG. 122 is a cross-sectional view illustrating the metal layer 11820 which is to form the 3D nanostructure and is deposited on the current collector 11810. The metal layer 11820 may be deposited to a uniform thickness on the current collector 11810 by using a sputtering method, an evaporation method, a plating method, or the like. A mask (not shown) in which patterns are formed is coated on the deposited metal layer 11820 to fabricate the 3D nanostructure by using an etching method such as dry etching or wet etching. For example, ammonia and hydrogen gases may be used as etch materials.

An etching process is greatly classified into wet etching and dry etching. The wet etching is to melt an exposed part (having no PR patterns) by using acid chemicals which reacts with metal or the like to corrode the metal. The dry etching is to accelerate ions to take a material of an exposed part off in order to form patterns.

A method of forming mask patterns used in etching for forming the 3D nanostructure will now be described in brief.

Patterns of masks (not shown) may be formed through a lithographic process.

Lithography refers to a process of changing masks by using photons, electrons, ions, or the like having passed through the masks and chemically processing a denaturalized part to form desired patterns. The lithographic process may be divided into 3 steps. First, a photosensitive polymer material (resist) is uniformly coated to a uniform thickness on a material in which patterns are to be formed. Next, photons, electrons, ions, or the like having passed through masks in which desired patterns are engraved are radiated onto a photosensitive layer. The denaturalized photosensitive layer is appropriately developed to form patterns.

Lithography and processing may be repeated several times to form a more complicated and minute shape.

The metal layer 11820 is etched by using the masks in which the patterns are formed to fabricate a 3D nanostructure protruding the surface of the current collector 11810.

In this case, an etching, re-growth, doping, or lift-off process may be applied, and its detailed description will be omitted.

Besides the method of FIGS. 118 through 123, various methods may be used to fabricate a nanostructure. For example, a method of using a 3D template may be used. An oxidation inorganic material, such as SiO, TiO, Al2O3, or the like, may be coated by using physical/chemical vapor deposition, physical/chemical vapor deposition using a 3D template, atomic layer deposition (ALD), molecular beam epitaxy, thermal or electron beam evaporation, pulsed laser deposition, porous metal sputtering, spray pyrolysis, casting, spin coating, sol-gel, monomer evaporation, water casting, langmuirBlodgett, electro/electroless plating, or the like, to form a 3D nanostructure. A surface area per unit area may vary according to the used template, and a physical/chemical characteristic may vary according to a characteristic of used polymer or inorganic material.

FIG. 123 is cross-sectional view illustrating the metal layer 11820 which is formed on the current collector 11810 and has the 3D nanostructure.

A plurality of nanostructures constituting the metal layer 11820 may be formed at enough distances to interpose an electrolyte between the plurality of nanostructures.

Here, the metal layer 11820 may be formed of carbon. If the metal layer 11820 is formed of the carbon, the carbon layer may be etched to form a 3D structure. Metal is coated on the carbon having the 3D structure to form a metal sulfide layer (sulfutrating) or a metal oxide layer (thermal treating). According to this method, an area between the carbon having the 3D structure and the metal sulfide or metal oxide having low electric conductivity increases. Therefore, a whole pillar has lower electrode resistance than a structure in which metal sulfide or metal oxide is formed, and an area capable of supplying electrons increases, thereby improving a performance of a battery.

The metal layer 11820 may be formed of Zn, Fe, Cd, Co, Ni, Sn, Pb, Cu, Ag, or the like The metal layer 11820 may have a nano-tube, nano-wire, nano-rod, nano-fiber shape or may have at least one of nano-ring and nano-horn shapes.

Alternatively, nano-particles each having a smaller diameter than an empty space between the nano-structures may be included between the plurality of nano-structures (or between tubes). Here, the nanoparticles may be formed in spherical, tube, rod, or tubular shapes.

A plurality of nanostructures having nano-rod shapes are shown in FIG. 123, but the number of nanostructures formed on the current collector 110 may vary according to distances of the nanostructures. Also, the nanostructures are aligned in one direction in FIG. 123 but may be irregularly aligned. In addition, the nanostructures are formed in a direction perpendicular to a surface of the substrate, but the direction in which the nanostructures are formed is not limited.

Figure 124:
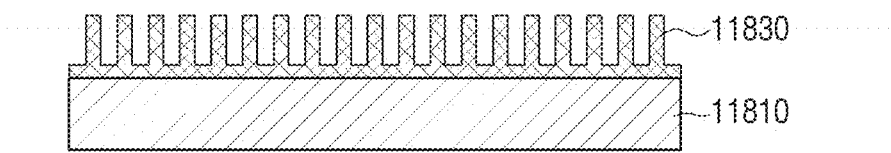

FIG. 124 is a cross-sectional view illustrating the metal composite layer 11830 formed on the current collector 11810 on which the metal layer 11820 having the 3D nanostructure.

Here, the metal composite layer 11830 may be a metal sulfide or a metal oxide 11830 which is formed by sulfurating or oxidation treating the metal layer 11820 having the nanostructure.

The metal sulfide layer 11830 may be formed by coating the current collector 11810 on which the metal layer 11820 having the 3D nanostructure is formed with a sulfurating solution. This is as described with reference to FIG. 11, and thus a detailed description thereof will be omitted.

The metal oxide layer 11830 may be formed by performing an oxidation thermal treatment or a thermal treatment using a precursor with respect to the current collector 11810 on which the metal layer 11820 having the 3D nanostructure is formed.

FIGS. 125 through 130 are cross-sectional views illustrating a process of fabricating a 3D nanostructure according to another exemplary embodiment of the present general inventive concept. For the descriptive convenience, detailed description of the same elements of FIGS. 125 through 130 as those of FIGS. 109 through 117 will be omitted hereinafter.

Figure 125:
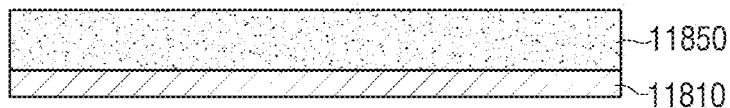
FIGS. 125 through 130 are cross-sectional views illustrating a process of fabricating a 3D nano-structure according to another exemplary embodiment of the present general inventive concept.

FIG. 125 is a cross-sectional view illustrating a carbon layer 11850 formed on the current collector 11810 used in the 3D nanostructure.

The current collector 11810 operates to form a flow of electrons between an electrode active material and a battery terminal and may be any current collector which does not cause a chemical change in a battery and has high conductivity.

The carbon layer 11850 may be formed of amorphous carbon.

Figure 126:
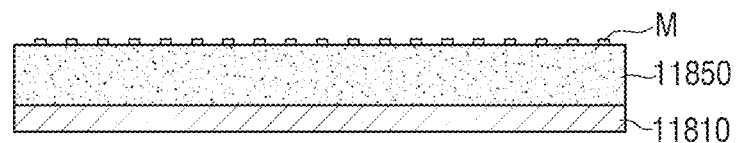

FIG. 126 is a cross-sectional view illustrating the carbon layer 11850 which is coated with a mask in which patterns are formed to etch the carbon layer 11850 in a 3D nanostructure.

An etching process for etching the carbon layer 11850 to form the 3D nanostructure will now be described.

The etching process is greatly classified into wet etching and drying etching. The wet etching is to melt an exposed part (having no PR patterns) by using acid chemicals which reacts with metal or the like to corrode the metal. The dry etching is to accelerate ions to take a material of an exposed part off in order to form patterns.

Each of the wet etching and the dry etching is classified into selective and nonselective etching. The selective etching refers to etching which reacts to a layer on a surface without affecting other layers among several layers. The nonselective etching refers to etching which reacts to the other layers to simultaneously etch several layers.

The selective etching of the wet etching is possible by combining some chemicals to react to a particular material to form and use an etchant. The dry etching is possible by injecting a reactive gas reacting to a particular material. In particular, ion beam etching (IBE) or sputtering using ion acceleration and sputtering etching using magnetron correspond to the nonselective etching of the dry etching. Reactive ion etching using a reactive gas in ion acceleration corresponds to the selective etching of the dry etching.

Both wet etching and dry etching may be used as etching of the carbon layer 11850 according to the present general inventive concept. Among them, the selective etching may be used. Detailed descriptions thereof are as described above and thus will be omitted herein.

As shown in FIG. 126, the carbon lay 11850 is etched by a mask M in which patterns are formed. Here, the above-described dry etching or wet etching may be used as an etching method.

As shown in FIG. 123, a mask remaining on the etched carbon layer 11850 is removed. Here, an organic solvent, such as alcohol class, glycol class, ether class, ester class, or the like, may be used as a removing solution.

Figure 127:
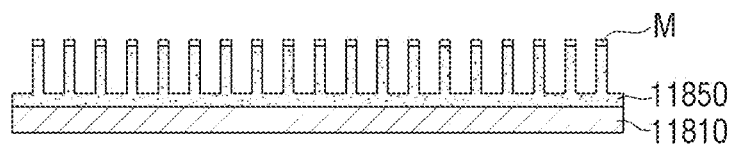
Figure 128:
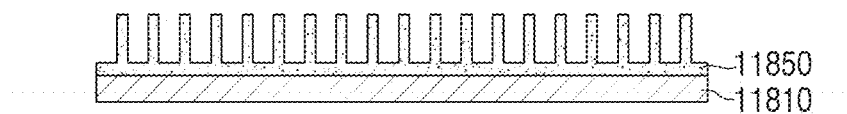

According to method described with reference to FIGS. 125 through 127, a structure in the carbon layer 11850 having the 3D nanostructure is formed on the current collector 110 may be fabricated as shown in FIG. 128. Here, a plurality of nanostructures constituting the 3D nanostructure may be formed at enough distances to interpose an electrolyte between the plurality of nanostructures.

Here, the nanostructures may have a nano-tube, nano-wire, nano-rod, nano-fiber shape or may have at least one of nano-ring and nano-horn shapes.

Alternatively, nano-particles each having a smaller diameter than an empty space between the nano-structures may be included between the plurality of nano-structures (or between tubes). Here, the nanoparticles may be formed in spherical, tube, rod, or tubular shapes.

Figure 129:
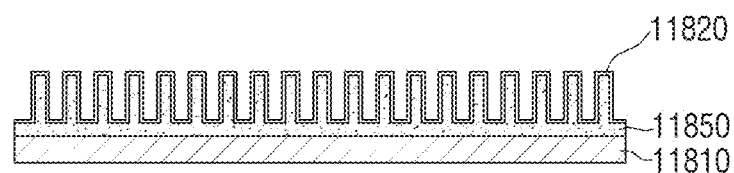

FIG. 129 is a cross-sectional view illustrating the metal layer 11820 formed on the carbon layer 11850 etched in the 3D nanostructure. The metal layer 120 may be formed by wet etching such as electroless plating, electroplating, or the like or dry etching such as sputtering, evaporation, or the like.

Here, the electroless plating is a method of autocatalytically returning metal ions in a metallic salt aqueous solution through a force of a reducing agent without receiving electric energy from an external source to extract metal on a surface of an object to be processed and is referred to as chemical plating or autocatalytic plating. The electroplating refers to a method of covering a surface of an object with another thin metal thin by using a principle of electrolysis, i.e., is referred to as electric plating.

The sputtering refers to a method of attaching ions generated in plasma to wafer by using a thin film apparatus. The evaporation refers to a method of heating a boat in a high vacuum ($5 \times 10^{-5} - 1 \times 10^{-7}$ torr) by using an e-beam or a filament to melt and distill metal on the boat to condense the distilled metal on a cold surface of the wafer in order to deposit a metal material.

Here, the metal layer 11820 may be formed of Zn, Fe, Cd, Co, Ni, Sn, Pb, Cu, Ag, or the like.

Figure 130:
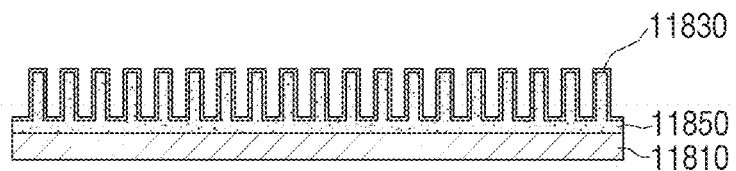

FIG. 130 is a cross-sectional view illustrating the metal composite layer 11830 formed on the carbon layer 150 which has the 3D nanostructure and is plated with the metal layer 11820.

Here, the metal composite layer 11830 may be a metal sulfide or a metal oxide 11830 which is formed by sulfurating or oxidizing the carbon layer 11850 which has the nanostructure and is plated with the metal layer 11820.

The metal sulfide layer 11830 may be formed by coating a sulfurating solution on the current collector 11850 which has the 3D nanostructure and is plated with the metal layer 11820. This is as described with reference to FIG. 111, and a detailed description thereof will be omitted.

The metal oxide layer 11830 may be formed by performing an oxidation treatment or a thermal treatment using a precursor with respect to the current collector 11810 which has the 3D nanostructure and is plated with the metal layer 11820.

According to this method, a contact area between the carbon of the 3D structure and a metal sulfide or metal oxide having low electric conductivity increases. As a result, a whole pillar has a lower electrode resistance than a structure in which a metal sulfide or metal oxide is formed, and an area capable of supplying electrons increases, thereby improving the performance of the battery.

For the convenience, a plurality of nanostructures having nano-rod shapes are shown in FIGS. 127 through 130, but the number of nanostructures formed on the current collector 11810 may vary according to distances of the nanostructures. The nanostructures are aligned in one direction in FIG. 127 but may irregularly aligned.

Figure 131:
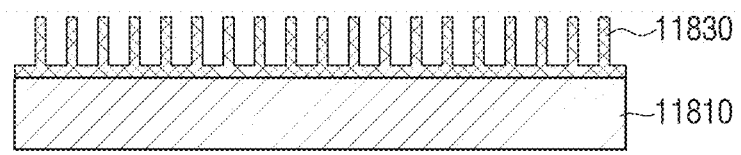
FIGS. 131 and 132 are cross-sectional views illustrating a 3D nano-structure according to various exemplary embodiments of the present general inventive concept.
Figure 132:
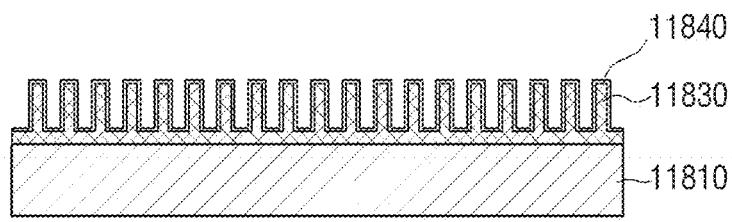

FIGS. 131 and 132 are cross-sectional views of a 3D nanostructure according to various exemplary embodiments of the present general inventive concept.

Referring to FIG. 131, a 3D nanostructure according to an exemplary embodiment of the present general inventive concept includes the current collector 11810 and the metal layer 11830 which has been sulfurated.

The current collector 11810 may be etched in a 3D nanostructure, e.g., may be etched according to the method described with reference to FIGS. 119 and 123.

The metal layer 11830 which has been sulfurated may be treated by sulfurating the metal layer 11820 etched in the 3D nanostructure in an active material form, e.g., may be treated by the method described with reference to FIGS. 120 and 124.

Referring to FIG. 132, a 3D nanostructure according to another exemplary embodiment of the present general inventive concept includes the current collector 11810, the sulfurated metal layer 11830, and the coating layer 11840.

The coating layer 11840 may be formed by coating and thermally treating polymer, oil, sugars, liquid silicon, or the like.

FIGS. 133 through 136 are plan views illustrating a structure of a 3D nanostructure according to various exemplary embodiments of the present general inventive concept.

Figure 133:
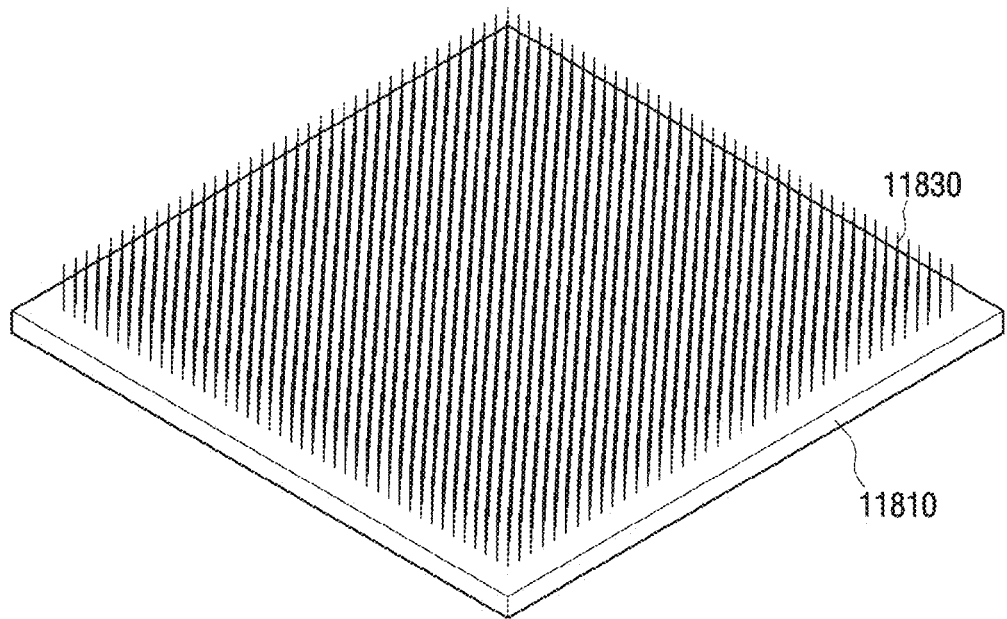
FIGS. 133 through 136 are plan views illustrating a 3D nano-structure according to various exemplary embodiments of the present general inventive concept.

Referring to FIG. 133, a plurality of nanostructures are vertically formed on the current collector 11810 at enough distances to interpose an electrolyte between the nanostructures. The nanostructures are aligned in both directions in FIG. 131 but may irregularly aligned.

Figure 134:
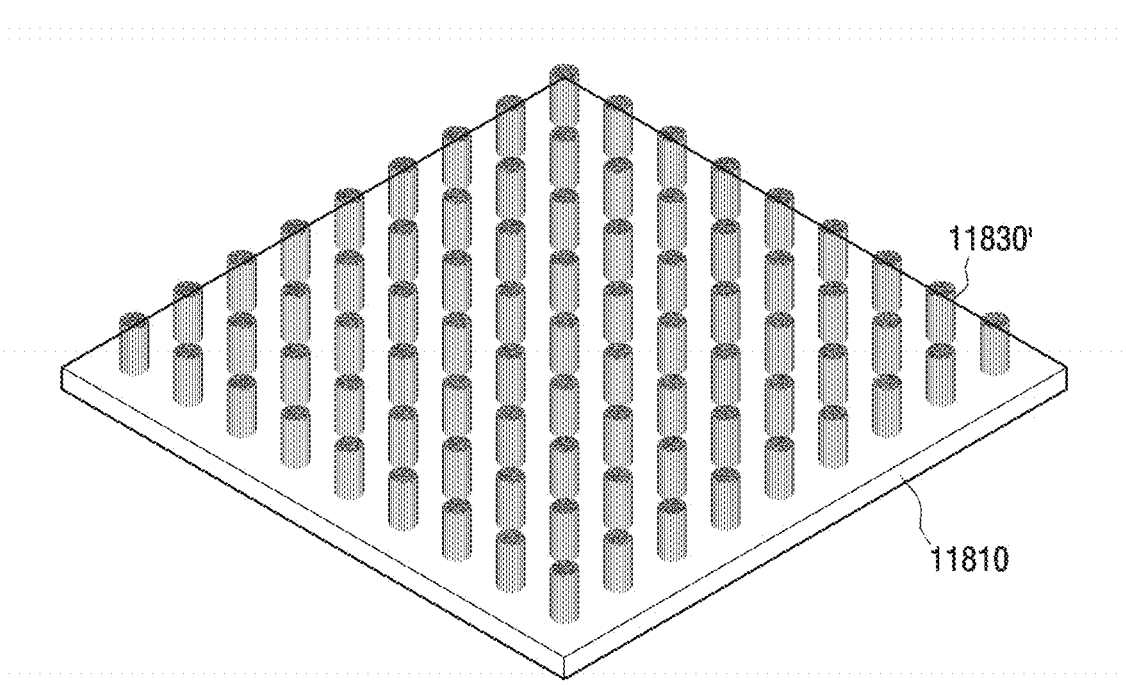

Referring to FIG. 134, the plurality of nanostructures vertically formed on the current collector form groups, and the groups are formed at enough distances to interpose the electrolyte between the groups. The nanostructures forming the nanostructure groups may be formed at enough distances to interpose the electrolyte between the nanostructures.

Figure 136:
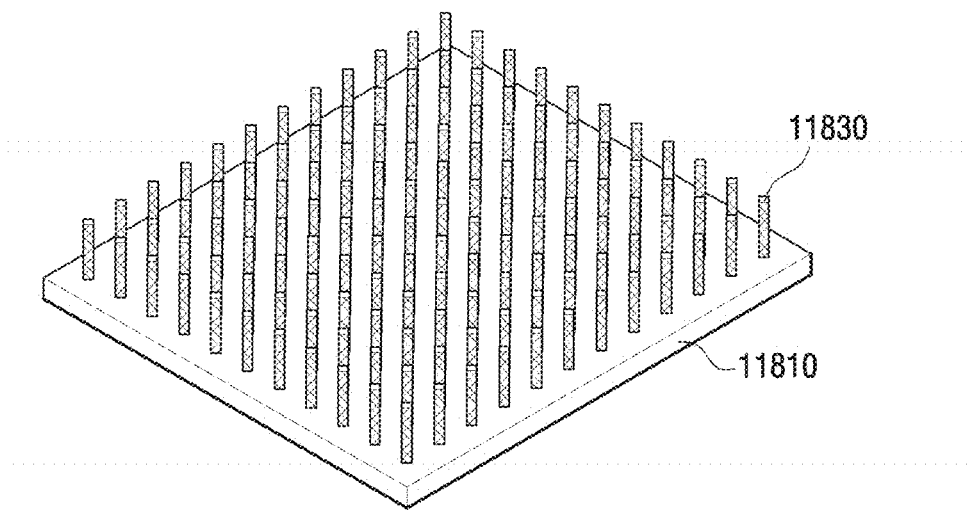

FIGS. 134 and 136, the nanostructures vertically formed on the current collector 11810 may have triangular or diamond cross-sections or polygonal cross-sections but are not limited thereto.

For the descriptive convenience, nanostructures 11830 are vertically formed from the surface of the current collector 11810, but this is only exemplary. Therefore, a direction in which the nanostructures 11830 are formed is not limited.

Figure 137:
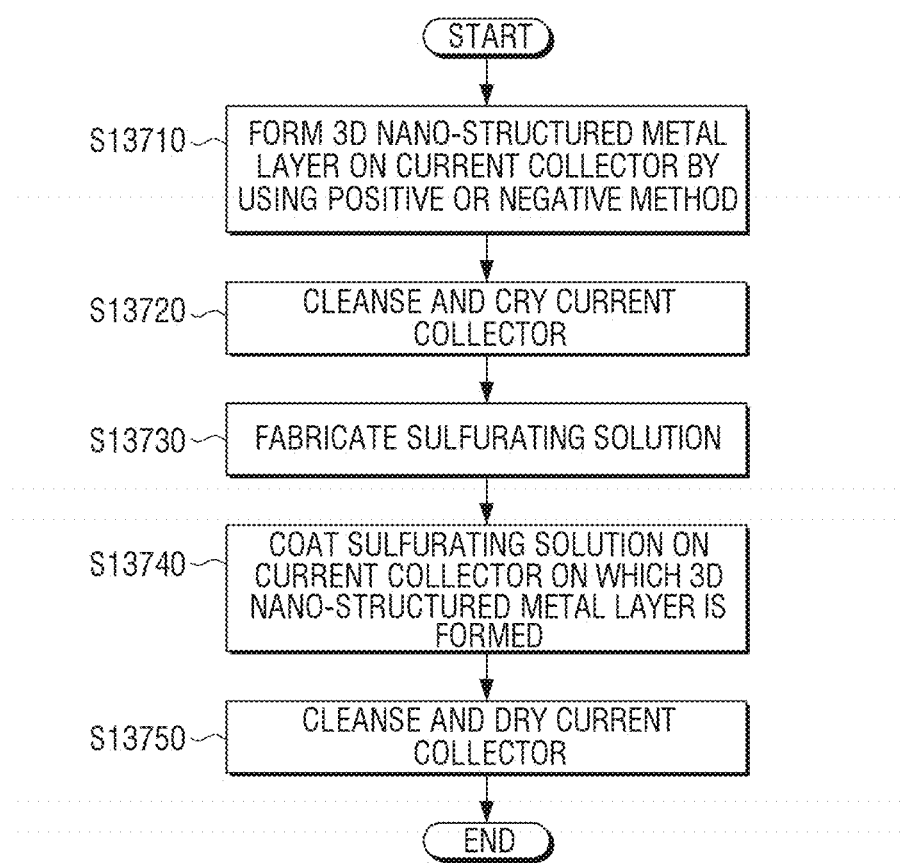
FIG. 137 is a flowchart illustrating a method of forming a 3D nano-structure according to an exemplary embodiment of the present general inventive concept.

FIG. 137 is a flowchart illustrating a method of forming a 3D nanostructure according to an exemplary embodiment of the present general inventive concept.

Referring to FIG. 137, in operation S13710, the metal layer 11820 having the 3D nanostructure is formed on the current collector by using a positive or negative method.

In operation S13720, the current collector 11810 on which the metal layer 11820 is formed is cleansed by using distilled water, and remaining moisture is removed through a drying process.

If the metal layer 11820 having the 3D nanostructure is completely formed, a sulfurating solution for sulfurating is fabricated in operation S13730. Here, in order to fabricate the sulfurating solution, $(NH_4)_2Sx$ and $Na_2S$ may be added to distilled water to form a solution, and a temperature of this solution increases until the temperature of the this solution reaches a preset sulfuration temperature, e.g., 80°. Here, $Na_2S$ which is one of raw materials of the sulfurating solution is to be completely melted.

In operation S13740, the sulfurating solution fabricated in operation S13730 is coated on the current collector 11810 on which the metal layer 11820 is formed, is dried at a room temperature for a predetermined time, e.g., 3 hours, and sulfurated at a predetermined temperature for a preset time.

The metal layer 11820 on which the current collector 11810 is formed may be the metal sulfide layer 11830. In operation S13750, the metal sulfide layer 11830 is cleansed by using distilled water, and remaining moisture is removed through a drying process.

Figure 138:
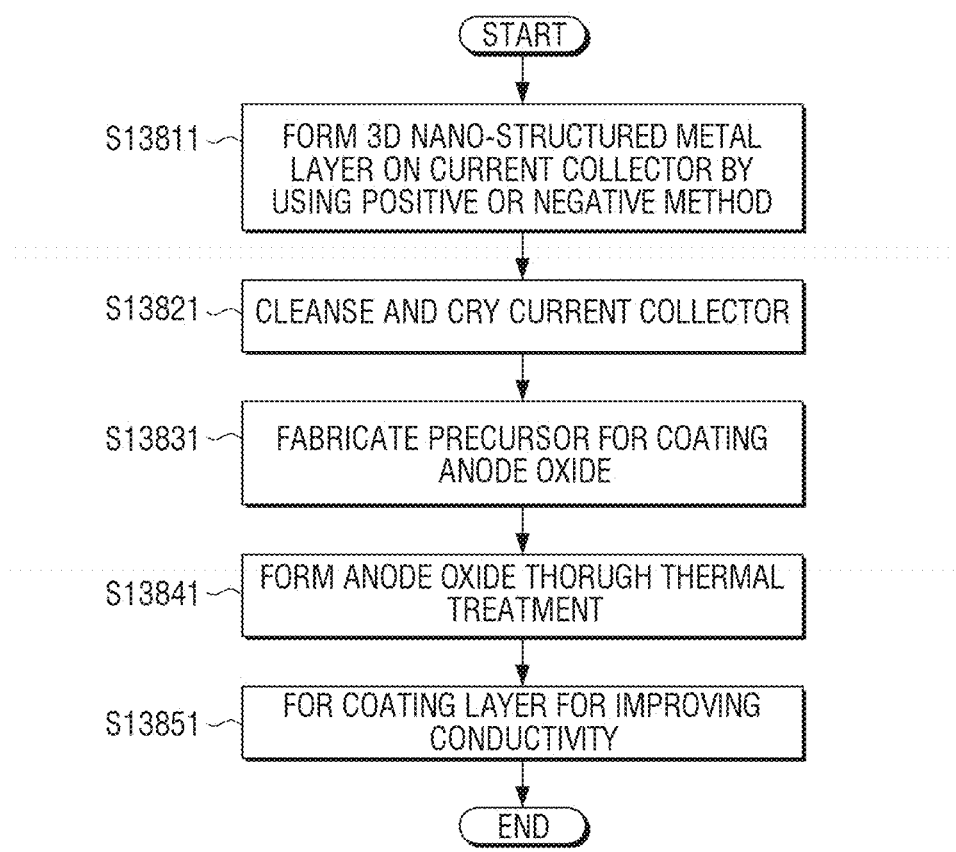
FIG. 138 is a flowchart illustrating a method of forming a 3D nano-structure according to another exemplary embodiment of the present general inventive concept.

FIG. 138 is a flowchart illustrating a method of forming a 3D nanostructure according to another exemplary embodiment of the present general inventive concept.

Referring to FIG. 138, in operation S13811, the metal layer 11820 having the 3D structure is formed on the current collector by using a positive or negative method.

In operation S13820, the current collector 11810 on which the metal layer 11820 is formed is cleansed by using distilled water, and remaining moisture is removed through a drying process.

A precursor solution is fabricated to form the metal oxide layer 11830 on the metal layer 11820. Here, an oxide layer may be formed of an anode oxide, a cathode oxide, a metal sulfide, or the like.

The precursor solution may be fabricated by melting a metal oxide or metal hydroxide precursor in a solvent. For example, the metal oxide or metal hydroxide precursor may be metal salt such as Ni, Cu, Cr, Co, Zn, or Fe. In detail, the metal oxide or metal hydroxide precursor may be nickel nitrate, nickel acetate, nickel chloride, nickel carbonate, nickel sulfate, ferrous sulfate, cobalt sulfate, cobalt nitrate, cobalt chloride, zinc chloride, zinc sulfate, copper sulfate, cuprous chloride, potassium bichromate, or the like. However, the exemplified precursor is only exemplary, and thus metal salt capable of generating hydroxide or oxide according to pH changes of the precursor may be limitlessly used in the present general inventive concept.

A type of the solvent in which the metal oxide or metal hydroxide precursor is melted is not limited. For example, an organic solvent having a high mixture property with respect to water may be used. As this solvent is used, a solvent in which water and an organic solvent are uniformly mixed may be fabricated, and the metal oxide or metal hydroxide is completely melted in the mixture solvent to enable a uniform solution to be fabricated. For example, the organic solvent may be an alcohol-based solvent such as methanol, ethanol, propanol, or butanol.

When the metal oxide or metal hydroxide precursor is put into the solvent to fabricate the solution, a concentration of the solution is appropriately set according to a thickness of a targeted metal oxide or metal hydroxide coating layer and is not particularly limited.

In operation S13841, the precursor generated in operation S13831 is coated on the metal layer 11820 and thermally treated to form the metal oxide layer 11830.

Alternatively, the coating layer 11840 may be formed on the metal oxide layer 11830 to improve conductivity. The coating layer 11840 may be formed by coating and thermally treating polymer, oil, sugars, liquid silicon, or the like.

The 3D nanostructure according to the present general inventive concept may be used as an electrode of a battery.

In detail, the 3D nanostructure may be used as an electrode of a secondary battery, a polymer battery, or an electrochemical (e.g., an electric dual layer capacitor, a pseudo capacitor, or the like).

Also, the 3D nanostructure according to the present general inventive concept ma include an electrode active material formed by sulfurated to provide a smooth electron moving path and include a porous carbon nanotube to increase an electrolyte immersing and reaction system areas. A battery including the 3D nanostructure of the present general inventive concept as the electrode active material, other elements of a capacitor, and a structure are not particularly limited. Therefore, general materials and structures may be limitlessly applied.

[Fourth Exemplary Embodiment of Secondary Battery Part]

The fourth exemplary embodiment of the secondary battery part relates a 3D nanostructure of an all-in-one electrode and current collector device constituting the secondary battery part. The 3D nanostructure of the all-in-one electrode and current collector may be applied a positive or negative pore electrode and a lithium-based battery but is not limited thereto.

The contents of FIGS. 109 through 117 and FIGS. 133 through 136 relating to the third exemplary embodiment of the secondary battery part may be equally applied to the fourth exemplary embodiment of the secondary battery part.

FIGS. 139 through 144 are cross-sectional views illustrating a process of fabricating a 3D nanostructure according to another exemplary embodiment of the present general inventive concept. For the descriptive convenience, detailed descriptions of the same elements of FIGS. 139 through 133 as those of FIGS. 109 through 117 will be omitted hereinafter.

Figure 139:
FIGS. 139 through 144 are cross-sectional views illustrating a process of forming a 3D nano-structure according to another exemplary embodiment of the present general inventive concept.

FIG. 139 is a cross-sectional view of a current collector 13910 used in the 3D nanostructure.

The current collector 13910 operates to form a flow of electrons between an electrode active material and a battery terminal. Any one which does not cause a chemical change in the battery and has a high conductivity may be used as the current collector 9310.

The current collector 13910 may be formed of one selected from the group consisting of Cu, Ni, stainless steel, Ti, Al, carbon-coated Al, Ni foam, Cu foam, a polymer substrate coated with conductive metal, and combinations thereof. The materials may be processed and used in foam, mesh, conductive material coating, or punch forms but are not limited thereto. One of a material which coats at least one surface of the above-described materials may be used.

Figure 140:
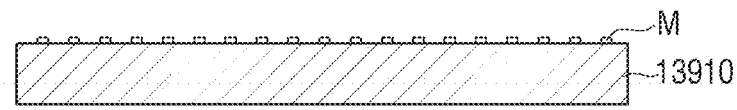

FIG. 140 is a cross-sectional view illustrating the current collector 13910 which is coated with masks in which patterns are formed to etch an upper part of the current collector 13910 in a 3D nanostructure.

An etching process for etching the upper part of the current collector 13910 to form a 3D nanostructure will now be described.

The etching process is greatly classified into wet etching and drying etching. The wet etching is to melt an exposed part (having no PR patterns) by using acid chemicals which reacts with metal or the like to corrode the metal. The dry etching is to accelerate ions to take a material of an exposed part off in order to form patterns.

Each of the wet etching and the dry etching is classified into selective and nonselective etching. The selective etching refers to etching which reacts to a layer on a surface without affecting other layers among several layers. The nonselective etching refers to etching which reacts to the other layers to simultaneously etch several layers.

The selective etching of the wet etching is possible by combining some chemicals to react to a particular material to form and use an etchant. The dry etching is possible by injecting a reactive gas reacting to a particular material. In particular, ion beam etching (IBE) or sputtering using ion acceleration and sputtering etching using magnetron correspond to the nonselective etching of the dry etching. Reactive ion etching using a reactive gas in ion acceleration corresponds to the selective etching of the dry etching.

Both wet etching and dry etching may be used as etching of the current collector 13910 according to the present general inventive concept. Among them, the selective etching may be used.

A method of forming mask patterns used for etching will be described in brief.

Patterns of masks (not shown) may be formed by a lithographic process.

Lithography refers to a process of changing masks by using photons, electrons, ions, or the like having passed through the masks and chemically processing a denaturalized part to form desired patterns. The lithographic process may be divided into 3 steps. First, a photosensitive polymer material (resist) is uniformly coated to a uniform thickness on a material in which patterns are to be formed. Next, photons, electrons, ions, or the like having passed through masks in which desired patterns are engraved are radiated onto a photosensitive layer. The denaturalized photosensitive layer is appropriately developed to form patterns.

Lithography and processing may be repeated several times to form a more complicated and minute shape.

As shown in FIG. 140, the current collector 13910 is etched by using the masks M in which the patterns are formed. Here, the above-described dry etching or wet etching may be used as an etching method.

Figure 141:
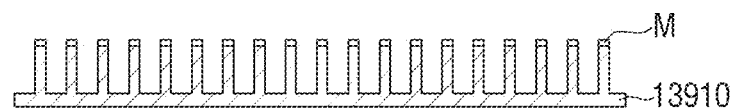

As shown in FIG. 141, masks remaining on the etched current collector are moved. Here, a mask removing solution may be an organic solvent such as an alcohol class, a glycol class, an ether class, an ester class, a ketone class, or the like.

Figure 142:

According to the method described with reference to FIGS. 139 through 141, as shown in FIG. 142, the current collector 13910 whose upper surface is etched in a 3D nanostructure may be fabricated. Here, a plurality of nanostructures constituting the 3D nanostructure may be formed at enough distances to interpose an electrolyte therebetween.

Here, the 3D nanostructure may have a nano-tube, a nano-wire, nano-rod, or nano-fiber shape or may have at least one of nano-ring and nano-horn shapes.

Alternatively, nano-particles each having a smaller diameter than an empty space between the nano-structures may be included between the plurality of nano-structures (or between tubes). Here, the nanoparticles may be formed in spherical, tube, rod, or tubular shapes.

Figure 144:
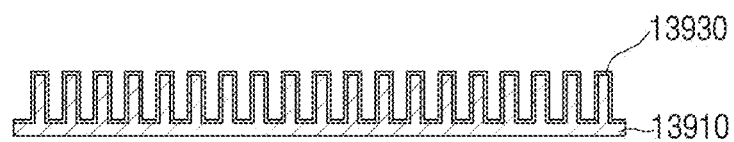

FIG. 144 is a cross-sectional view illustrating a metal layer 13920 formed on the current collector 13910 etched in the 3D nanostructure. The metal layer 13920 may be formed by wet etching such as electroless plating, electroplating, or the like or dry etching such as sputtering, evaporation, or the like.

Here, the electroless plating is a method of autocatalytically returning metal ions in a metallic salt aqueous solution through a force of a reducing agent without receiving electric energy from an external source to extract metal on a surface of an object to be processed and is referred to as chemical plating or autocatalytic plating. The electroplating refers to a method of covering a surface of an object with another thin metal thin by using a principle of electrolysis, i.e., is referred to as electric plating.

The sputtering refers to a method of attaching ions generated in plasma to wafer by using a thin film apparatus. The evaporation refers to a method of heating a boat in a high vacuum ($5 \times 10^{-5}$–$1 \times 10^{-7}$ torr) by using an e-beam or a filament to melt and distill metal on the boat to condense the distilled metal on a cold surface of the wafer in order to deposit a metal material.

Here, the metal layer 13920 may be formed of carbon. In this case, metal is plated on the carbon, and a metal sulfide (sulfuration thermal treatment) or metal oxide (oxidation) layer may be formed as will be described later. Therefore, a contact area between the carbon of the 3D structure and a metal sulfide or metal oxide having low electric conductivity increases. As a result, a whole pillar has a lower electrode resistance than a structure in which a metal sulfide or metal oxide is formed, and an area capable of supplying electrons increases, thereby improving the performance of the battery.

The metal layer 13920 may be formed of Zn, Fe, Cd, Co, Ni, Sn, Pb, Cu, Ag, or the like.

Figure 143:
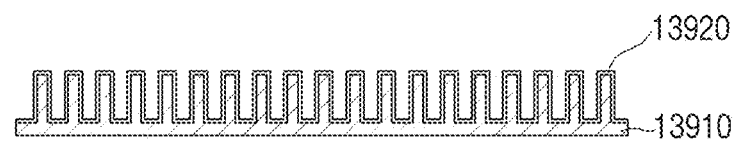

FIG. 143 is a cross-sectional view illustrating a metal composite layer 13930 formed on the current collector 13910 which has the 3D nanostructure and is plated with the metal layer 13920.

Here, the metal composite layer 13930 may be metal sulfide or metal oxide 13930 which is formed by sulfurating or oxidizing the current collector 13910 which has a nanostructure and is plated with the metal layer 13920.

The metal sulfide layer 13930 may be formed by coating a sulfurating solution on the current collector 13910 which has the 3D nanostructure and is plated with the metal layer 13920. This is as described with reference to FIG. 11, and thus a detailed description thereof will be omitted.

The metal oxide layer 13930 may be formed by performing an oxidation treatment or a thermal treatment using a precursor with respect to the current collector 13910 which has the 3D nanostructure and is plated with the metal layer 13920.

For convenience, a plurality of nanostructures having nano-rod shapes are shown in FIGS. 141 through 144, but the number of nanostructures formed on the current collector 11810 may vary according to distances of the nanostructures. Also, the nanostructures are aligned in one direction in FIG. 140 but may irregularly aligned.

Figure 145:
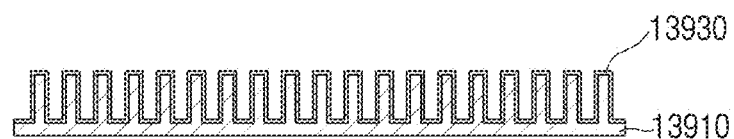
FIGS. 145 and 146 are cross-sectional views illustrating a 3D nano-structure according to various exemplary embodiments of the present general inventive concept.
Figure 146:
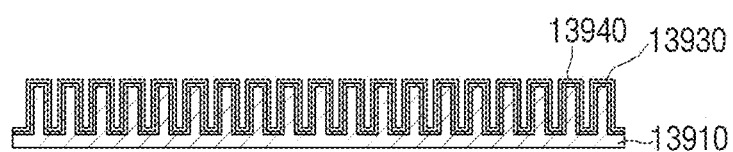

FIGS. 145 and 146 are cross-sectional views of a 3D nanostructure according to various exemplary embodiments of the present general inventive concept.

Referring to FIG. 145, a 3D nanostructure according to an exemplary embodiment of the present general inventive concept includes the current collector 13910 and the sulfurated metal layer 13930.

An upper area of the current collector 13910 is etched in a 3D nanostructure, e.g., may be etched according to the method described with reference to FIGS. 139 through 142.

The sulfurated metal layer 13930 may be fabricated in an active material form by sulfurating the metal layer 13920 plated on the current collector 13910 etched in the 3D nanostructure, e.g., according to the method described with reference to FIGS. 6E and 6F.

Referring to FIG. 146, a 3D structure electrode according to another exemplary embodiment of the present general inventive concept includes the current collector 13910, the sulfurated metal layer 13930, and the coating layer 13940.

The coating layer 13940 may be formed by coating and thermally treating polymer, oil, sugars, liquid silicon, or the like.

A structure of the 3D nanostructure of FIGS. 139 through 146 is mostly equal to the structure of the 3D nanostructure of FIGS. 133 through 136. However, referring to FIG. 133, nanostructures formed by etching the current collector 13910 may be plated with a metal layer (not shown) and sulfurated to be structures on which the sulfurated metal layer 130 is plated.

Referring to FIG. 134, a plurality of nanostructures formed by etching the current collector 13910 may be plated with a metal layer (not shown) as described above and sulfurated to be structures plated with the sulfurated metal layer 130 is plated.

Reference numerals 11810 and 11830 of FIGS. 133 through 136 may respectively correspond to reference numerals 13910 and 13930. Descriptions of parts overlapping with FIGS. 133 through 136 will be omitted hereinafter.

FIGS. 147 through 150 are cross-sectional views illustrating a structure of an energy converting apparatus according to various exemplary embodiments of the present general inventive concept.

Figure 147:
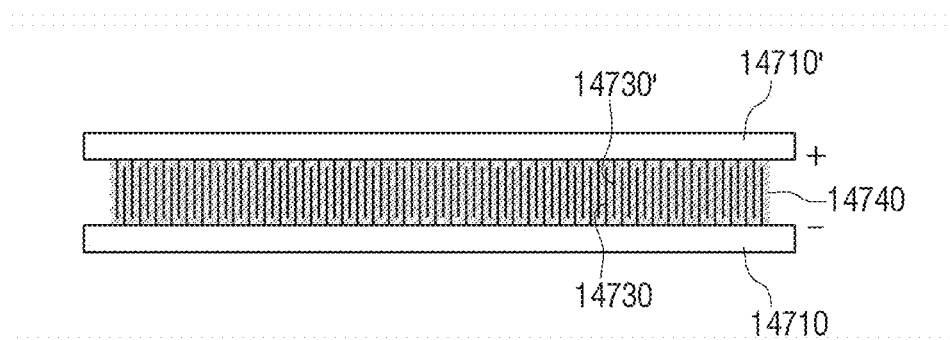
FIGS. 147 through 150 are cross-sectional views illustrating a structure of an energy converting apparatus according to various exemplary embodiments of the present general inventive concept.

Referring to FIG. 147, the energy converting apparatus includes a first current collector 14710, a first electrode part 14730, a second current collector 14710', a second electrode part 14730', and an electrolyte part 14740.

The first electrode part 14730 includes a plurality of nanostructures which are formed by etching an upper area of the first current collector 14710.

The second electrode part 14730' is positioned opposite to the first electrode part 14730 and includes a plurality of nanostructures which are alternately arranged with the plurality of nanostructures of the first electrode part 14730.

Here, the nanostructures constituting the first and second electrode parts 14730 and 14730' may have forms in which a sulfurated metal layer is plated on the first and second current collector 14710 and 14710' etched in the 3D nanostructure.

The electrolyte part 14740 is interposed between the first and second electrode parts 14730 and 14730'. Here, a liquid electrolyte or a solid electrolyte may be used as the electrolyte part 14740.

A hydrochloride acid, a sulfuric acid, a nitric acid, sodium chloride, hydrogen chloride, copper sulfate, natrium sodium chloride, sodium hydroxide, or the like may be used as the liquid electrolyte.

$ZrO2$, $NaAluOl7$, $AgI$, $RbAg4I5$, Nafion, Asahi film, or the like may be used as the solid electrolyte. However, the above-described materials are only exemplary and are not limited thereto.

In FIG. 147, the nanostructures constituting the first and second electrode parts 14730 and 14730' are formed in nano-rod shapes and are vertically formed from a surface of a substrate. However, shapes and directions of the nanostructures are not limited thereto.

Figure 148:
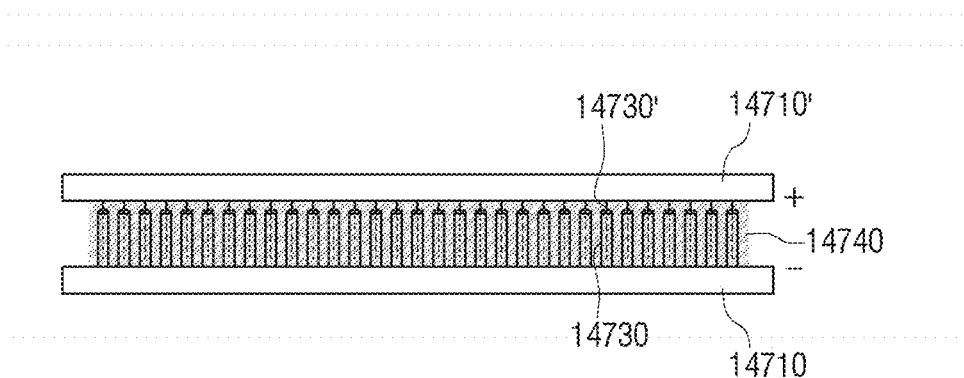

FIG. 148 is a cross-sectional view illustrating a structure of an energy converting apparatus according to another exemplary embodiment of the present general inventive concept.

Referring to FIG. 148, the nanostructures constituting the first electrode part 14730 are formed in nano-tube shapes, and the nanostructures constituting the second electrode part 14730' are formed in nano-wire shapes.

In this case, in the energy converting apparatus, the nano-wires constituting the second electrode part 14730' may be formed to insert the first electrode part 14730 into nano-tubes. In this case, the nano-tubes constituting the first electrode part 14730 may have enough diameters to allow the electrolyte 14740 to penetrate although the nano-wires constituting the second electrode part 14730' are inserted.

Here, the nanostructures constituting the first and second electrode parts 14730 and 14730' may have forms in which a sulfurated metal layer is plated on the first and second current collectors 14710 and 14710' etched in the 3D nanostructures.

Even in this case, as shown in FIG. 147, the nano-tubes constituting the first electrode part 14730 and the nano-wires constituting the second electrode part 14730' may be alternately arranged.

Figure 135:
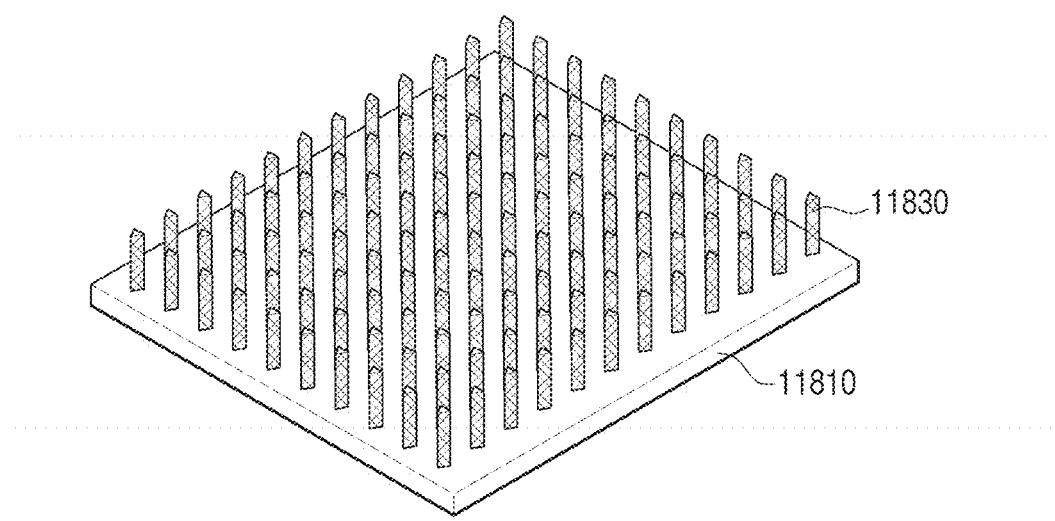

The structures of the energy converting apparatuses of FIGS. 147 and 148 may be structures in which the 3D nanostructures of FIGS. 133, 135, and 136 arranged so that the nanostructures face one another.

Figure 149:
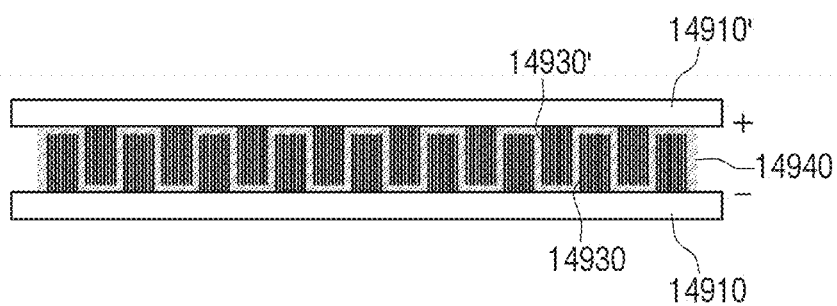

Referring to FIG. 149, the first electrode part 14930 formed on the first current collector 14910 may include a plurality of nanostructure groups formed of a plurality of nanostructures.

The second electrode part 14930' formed on the second current collector 14910' may include a plurality of nanostructure groups formed of a plurality of nanostructures.

Here, the nanostructures constituting the first and second electrode parts 14930 and 14930' may have forms in which a sulfurated metal layer is plated on the first and second current collectors 14910 and 14910' etched in the 3D nanostructures.

Here, distances of the nanostructure groups constituting the first and second electrode parts 14930 and 14930' may be longer than distances of a plurality of nanomaterials constituting each of the nanostructure groups to form each of the nanostructure groups in an island shape.

Also, the nanostructure groups constituting the first and second electrode parts 14930 and 14930' may be alternately arranged.

In this case, sufficient gaps between the nanostructure groups 14930 and 14930' constituting the first and second electrode parts 14930 and 14930' may allow the electrolyte part 14940 to penetrate between the nanostructure groups.

Figure 150:
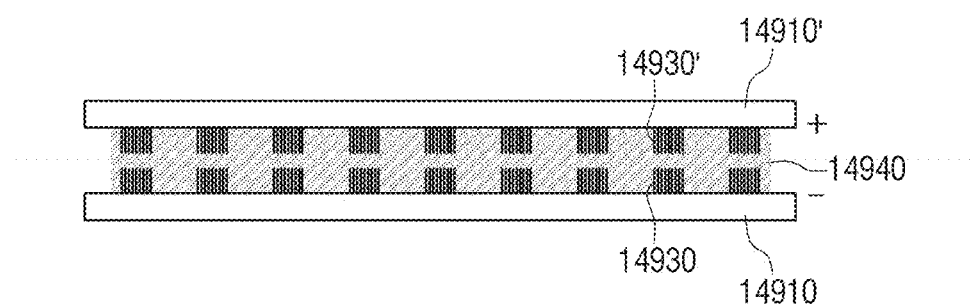

Referring to FIG. 150, the nanostructure groups constituting the first and second electrode parts 14930 and 14930' may face one another in corresponding positions. Even in this case, sufficient gaps between the nanostructure groups 14930 and 14930' constituting the first and second electrode parts 14930 and 14930' may allow the electrolyte part 14940 to penetrate between the nanostructure groups.

According to the exemplary embodiments of FIGS. 149 and 150, the electrolyte 14940 sufficiently penetrates between the nanostructure groups constituting the first and second electrode parts 14930 and 14930'. Therefore, a contact surface area of the electrolyte 14940 increases to improve battery efficiency.

The structures of the energy converting apparatuses of FIGS. 149 and 150 may be structures in which the electrode of FIG. 134 is arranged so that the nanostructures face one another.

Figure 151:
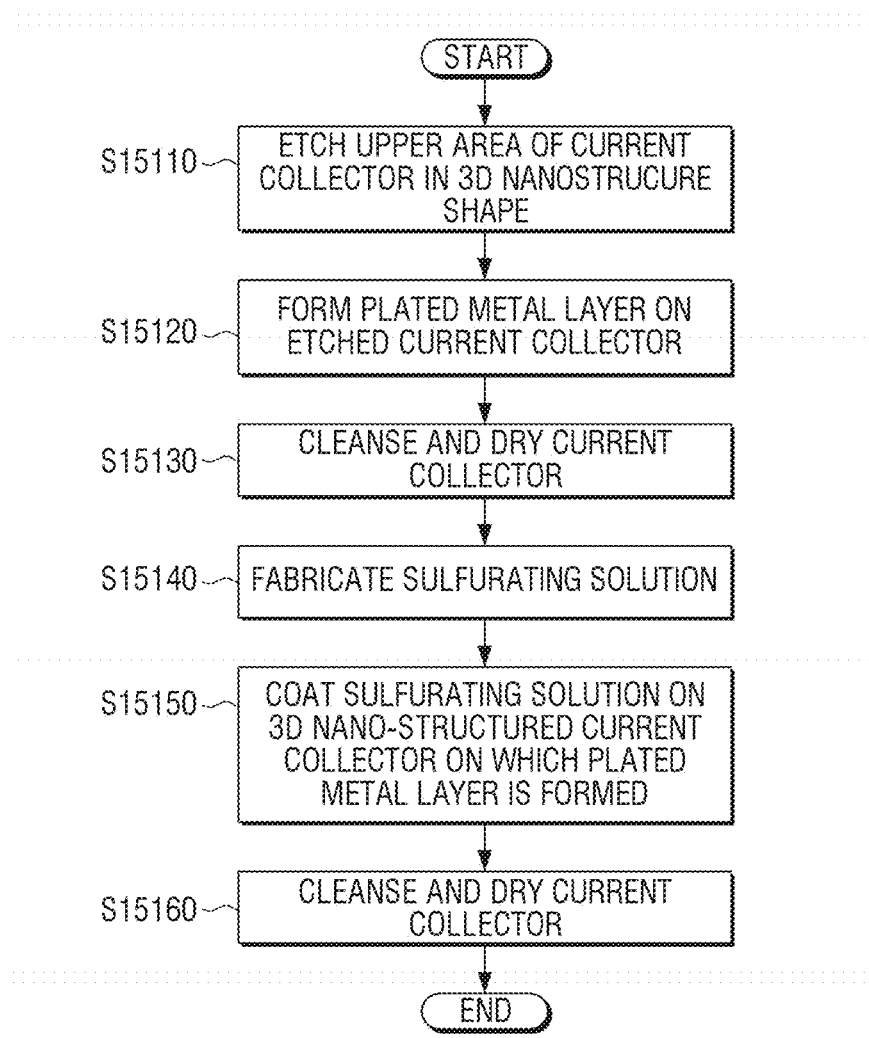
FIG. 151 is a flowchart illustrating a method of forming a 3D nano-structure according to an exemplary embodiment of the present general inventive concept.

FIG. 151 is a flowchart illustrating a method of forming a 3D nanostructure according to an exemplary embodiment of the present general inventive concept.

Referring to FIG. 151, in operation S15110, an upper area of the current collector 13910 is etched in a 3D nanostructure. A plurality of nanostructures forming the 3D nanostructure may have nano-tube, nano-wire, nano-rod, or nano-fiber shapes or may have at least one of nano-ring and nano-horn shapes.

Also, the plurality of nanostructures may have circular, square, triangular, diamond cross-sections or may have polygonal cross-sections, and shapes of cross-sections of the nanostructures are not limited thereto.

Also, the nanostructures 13930 may be etched to be vertically formed. This is only exemplary, and a direction in which the nanostructures 13930 are formed is not limited.

In operation S15120, the plated metal layer 13920 is formed on the current collector 13910 etched in the 3D nanostructure.

Cleaning and drying operations may be selectively added before operation S15120.

In operation S15130, the current collector 13910 etched in the 3D nanostructure in which the metal layer 13920 is formed is cleansed by using distilled water, and remaining moisture is removed through a drying process.

If the metal layer 13920 having the 3D structure is completely formed, a sulfurating solution for sulfurating is fabricated in operation S15140. Here, the sulfurating solution may be a solution which is fabricated by adding $(NH_4)_2Sx$ and $Na_2S$ to distilled water to fabricate a solution and increasing a temperature of the solution until the temperature of the solution reaches a preset sulfuration temperature, e.g., 80°. Here, $Na_2S$ which is one of raw materials of the sulfurating solution is to be completely melted.

If the sulfurating solution is completely fabricated, the sulfurating solution fabricated in operation S15130 is coated on the current collector 13910 having the 3D nanostructure in which the metal layer 13920 is formed, is dried at a room temperature for a predetermined time, e.g., 3 hours or more, and sulfurated at a predetermined temperature for a preset time in operation S15150.

The metal layer 13920 formed on the current collector 13910 having the 3D nanostructure may be a metal sulfide layer 13930. In operation S15160, the metal sulfide layer 13930 is cleansed by using distilled water, and remaining moisture is removed through a drying process.

Figure 152:
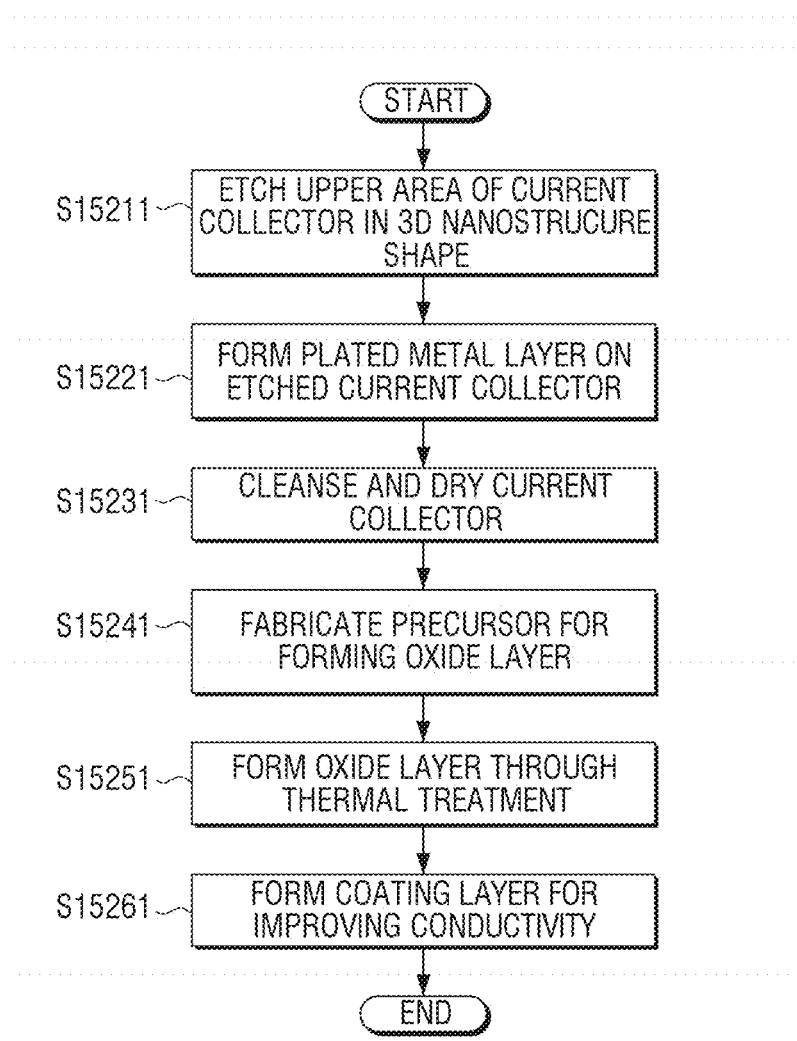
FIG. 152 is a flowchart illustrating a method of forming a 3D nano-structure according to another exemplary embodiment of the present general inventive concept.

FIG. 152 is a flowchart illustrating a method of forming a 3D nanostructure according to another exemplary embodiment of the present general inventive concept.

Referring to FIG. 152, in operation S15211, the upper are of the current collector 13910 is etched in the 3D nanostructure. A plurality of nanostructures forming the 3D nanostructure may have nano-tube, nano-wire, nano-rod, or nano-fiber shapes or may have at least one of nano-ring and nano-horn shapes.

Also, the plurality of nanostructures may have circular, square, triangular, diamond cross-sections or may have polygonal cross-sections, and shapes of cross-sections of the nanostructures are not limited thereto.

In operation S15221, a plated metal layer is formed on the current collector having the 3D nanostructure.

Cleaning and drying operations may be selectively added before operation S15221.

In operation S15231, the current collector 13910 etched in the 3D nanostructure in which the plated metal layer 13920 is formed is cleansed by suing distilled water, and remaining moisture is removed through a drying process.

In operation S15241, a precursor for forming an oxide coating layer on the plated metal layer 13920 is fabricated. Here, the oxide coating layer may be formed of an anode oxide, a cathode oxide, metal sulfide, or the like.

The precursor may be fabricated by melting a metal oxide or metal hydroxide precursor in a solvent. For example, the metal oxide or metal hydroxide precursor may be metal salt such as Ni, Cu, Cr, Co, Zn, or Fe. In detail, the metal oxide or metal hydroxide precursor may be nickel nitrate, nickel acetate, nickel chloride, nickel carbonate, nickel sulfate, ferrous sulfate, cobalt sulfate, cobalt nitrate, cobalt chloride, zinc chloride, zinc sulfate, copper sulfate, cuprous chloride, potassium bichromate, or the like. However, the exemplified precursor is only exemplary, and thus metal salt capable of generating hydroxide or oxide according to pH changes of the precursor may be limitlessly used in the present general inventive concept.

A type of the solvent in which the metal oxide or metal hydroxide precursor is melted is not limited. For example, an organic solvent having a high mixture property with respect to water may be used. As this solvent is used, a solvent in which water and an organic solvent are uniformly mixed may be fabricated, and the metal oxide or metal hydroxide is completely melted in the mixture solvent to enable a uniform solution to be fabricated. For example, the organic solvent may be an alcohol-based solvent such as methanol, ethanol, propanol, or butanol.

When the metal oxide or metal hydroxide precursor is put into the solvent to fabricate the solution, a concentration of the solution is appropriately set according to a thickness of a targeted metal oxide or metal hydroxide coating layer and is not particularly limited.

In operation S15251, the precursor generated in operation S15241 is thermally treated to form an oxide layer (not shown) on the plated metal layer 13920.

Alternatively, a coating layer for improving conductivity may be formed on the oxide layer. The coating layer may be formed by coating and thermally treating polymer, oil, sugars, liquid silicon, or the like.

[Fifth Exemplary Embodiment of Secondary Battery Part]

The fifth exemplary embodiment of the secondary battery part relates to a positive or negative pore electrode constituting the secondary battery part and may be applied to a natrium-based battery but is not limited thereto.

Figure 153:
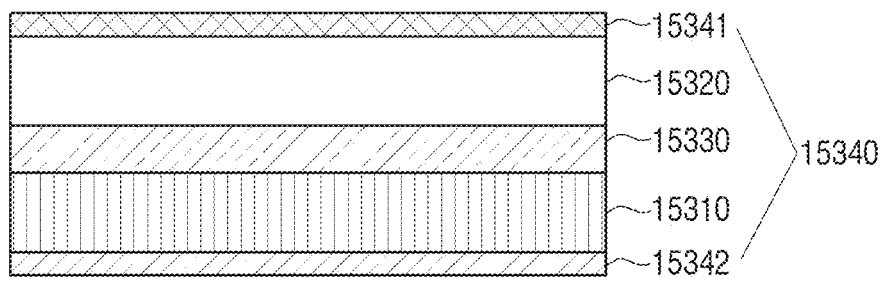
FIG. 153 is a view illustrating a structure of a sodium solid battery according to an exemplary embodiment of the present general inventive concept.

FIG. 153 is a view illustrating a structure of a solid natrium battery 15300 according to an exemplary embodiment of the present general inventive concept.

Referring to FIG. 153, the solid natrium battery 15300 includes a first solid electrode layer 15310, a second solid electrode layer 15320, a solid electrolyte layer 15330, and a current collector layer 15340.

The first solid electrode layer 15310 operates as an anode or a cathode and may be formed of various materials according to a type of the solid electrolyte layer 15330. In detail, the first solid electrode layer 15310 operates as the cathode, the first solid electrode layer 15310 may be formed of Na, an Na alloy, $Zn+ZnCl_2+NaBF_4$, or the like. If the second solid electrode layer 15310 operates as the anode, the first solid electrode layer 15310 may be formed of $Cu+CuCl_2+NaBF_4$, C+S, C+MS (metal sulfide, e.g., NiS, $Ni_3S_2$, $NiS_2$, FeS, $FeS_2$, $Cu_2S$, CuS), $S+Na_2S$—$SiS_2$, $MS+Na_2S$—$SiS_2$, $S+Na_2S$—$P_2S_5$, $MS+Na_2S$—$O_2S_5$, S or $MS+C+PEO+NaClO_3$, or the like.

The second solid electrode layer 15320 has an opposite polarity to the first solid electrode layer 15310 and may be formed of various materials according to a type of the solid electrolyte layer 15330. In detail, if the first solid electrode layer 15310 operates as the cathode, the second solid electrode layer 15320 operates as the anode and may be formed of $Cu+CuCl_2+NaBF_4$, C+S, C+MS (metal sulfide, e.g., NiS, $Ni_3S_2$, $NiS_2$, FeS, $FeS_2$, $Cu_2S$, CuS), $S+Na_2S$—$SiS_2$, $MS+Na_2S$—$SiS_2$, $S+Na_2S$—$P_2S_5$, $MS+Na_2S$—$O_2S_5$, S or $MS+C+PEO+NaClO_3$, or the like. If the first solid electrode layer 15310 operates as the anode, the second solid electrode layer 15320 operates as the cathode and may be formed of Na, an Na alloy, $Zn+ZnCl_2+NaBF_4$, or the like.

The solid electrolyte layer 15330 physically isolates the first and second electrode layers 15310 and 15320 from each other and exchanges ions between two electrodes. The solid electrolyte layer 15330 may be formed of a material such as a solid electrolyte such as β"-alumina having high ion conductivity of natrium ions, NASICON, a sulfide glass electrolyte, or the like.

Table 3 below shows examples of first and second solid electrode materials which may be combined according to a type of the solid electrolyte layer 15330.

TABLE 3

| First Solid Electrode Layer (Cathode) | Solid Electrolyte Layer | Second Solid Electrode Layer (Anode) |
|---|---|---|
| $Zn + ZnCl_2 + NaBF_4$, | β"-alumina | $Cu + CuCl_2 + NaBF_4$ |
| Na | β"-alumina | C + S |
| Na | β"-alumina | C + MS |
| Na or Na alloy | $Na_2S$—$SiS_2$ | $S + Na_2S$—$SiS_2$ |
| Na or Na alloy | $Na_2S$—$SiS_2$ | $MS + Na_2S$—$SiS_2$ |
| Na or Na alloy | $Na_2S$—$P_2S_5$ | $S + Na_2S$—$P_2S_5$ |
| Na or Na alloy | $Na_2S$—$P_2S_5$ | $MS + Na_2S$—$P_2S_5$ |
| Na or Na alloy | $Na_4GeS_4$—$Na_3PS_4$ | $S + Na_2S$—$P_2S_5$, |
| Na or Na alloy | $Na_4GeS_4$—$Na_3PS_4$ | $MS + Na_2S$—$P_2S_5$ |
| Na or Na alloy | $PEO + NaClO3$ | S or MS + C + PEO + NaCl |
| Na or Na alloy | PEO + glass | S or MS + C + PEO + NaCl |
| Na or Na alloy | PVA + NaF | S or MS + C + PEO + NaCl |
| Na or Na alloy | $PVA + NaClO_4$ | S or MS + C + PEO + NaCl |

The current collector layer 15340 may be formed of a material which does not cause a chemical change in the present battery and has conductivity. For example, the current collector 15340 may be formed of Cu, stainless steel, Al, Ni, Ti, baked carbon, carbon on a surface of Cu or stainless steel, a material whose surface is treated with Ni, Ti, Al or the like, an Al—Cd alloy, or the like. A plurality of holes may be formed in a surface of the current collector 15340, and the surface of the current collector 15340 is 3-dimensionally formed to improve an adhesive force between the first and second solid electrode layers 15310 and 15320. The current collector 15340 may be formed in various shapes such as film, sheet, foil, net, porous structure, foam, felt shapes.

The current collector 15340 is formed after the first and second solid electrodes 15310 and 15320 are formed in FIG. 153. However, the solid natrium battery may be realized by using an all-in-on electrode and current collector device.

All elements of the solid natrium battery of the present general inventive concept as described above are realized as solid components. Therefore, the solid natrium battery may solve problems such as a leakage and a volatilization of a liquid electrolyte, a formation of a positive state due to a reaction with a lithium cathode, a formation of dendrite, etc.

A method of fabricating a solid natrium battery as described above will now be described with reference to FIGS. 154 through 156.

Figure 154:
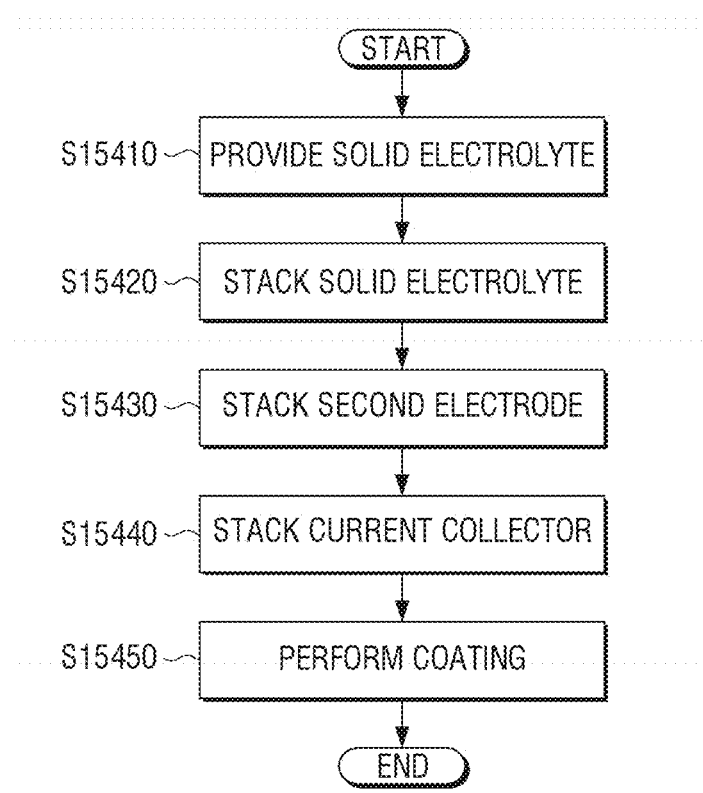
FIG. 154 is a flowchart illustrating a method of fabricating a sodium solid battery according to an exemplary embodiment of the present general inventive concept.

FIG. 154 is a flowchart illustrating a method of fabricating a solid natrium battery according to an exemplary embodiment of the present general inventive concept.

In operation S210, a solid electrolyte such as β"-alumina, nasicon, a sulfide glass electrolyte, or the like is provided. In detail, a method of including β"-alumina of the solid electrolytes will be described later with reference to FIG. 155.

In operation S15420, a solid electrolyte layer 15330 is formed on the first solid electrode layer 15310. In detail, a solid electrolyte is deposited on the first solid electrode layer 1530 to stack the solid electrolyte layer 1530 by using a pressurizing, casting, thin film deposition method, or the like.

In operation S15430, the second solid electrode layer 15320 is formed on the stacked solid electrolyte layer 15330. In detail, a second solid electrode is stacked on the first solid electrode layer 15310 and the solid electrolyte layer 15330 which are sequentially stacked, i.e., on the solid electrolyte layer 15330, to stack the second solid electrode layer 15330 by using a pressurizing method.

In operation S15440, the current collector layer 15340 is formed on the second solid electrode layer 15330 and underneath the first solid electrode layer 15310. In detail, a current collector is stacked on/underneath the first solid electrode layer 15310, the solid electrolyte layer 15330, and the second solid electrode layer 15320 which are sequentially stacked, i.e., underneath the first solid electrode layer 15310 and on the second solid electrode layer 15320 to stack first and second current collectors 15341 and 15342 by using a pressurizing method.

In operation S15450, outer surfaces of the first solid electrode layer 15310, the solid electrolyte layer 15330, and the second solid electrode layer 15320 are coated. In detail, the outer surfaces of the first solid electrode layer 15310, the solid electrolyte layer 15330, and the second solid electrode layer 15320 which are sequentially stacked may be coated with a coating material in order to prevent a solid electrolyte from being exposed to air and thus being polluted. Only the outer surfaces of the solid electrolyte layer 130, the first electrode layer 15310, and the second solid electrode layer 15320 may be coated but may be coated along with the current collector 15340.

A polycarbonate tube may be used as the coating material used for coating or a general polymer resin may be used. For example, PVC, HDPE, epoxy resin, or the like may be used. Also, any material capable of preventing a damage to the solid natrium battery may be used as a coating part.

A first solid electrode layer, a solid electrolyte layer, a second solid electrode layer, and a current collector layer are sequentially stacked as described with reference to FIG. 154. Materials respectively corresponding to the first solid electrode layer, the solid electrolyte layer, the second solid electrode layer, and the current collector layer may be stacked at a time, and only one-time pressurizing may be performed to fabricate the solid natrium battery. Also, the solid natrium battery may be fabricated by using an all-in-one electrode and current collector device.

Figure 155:
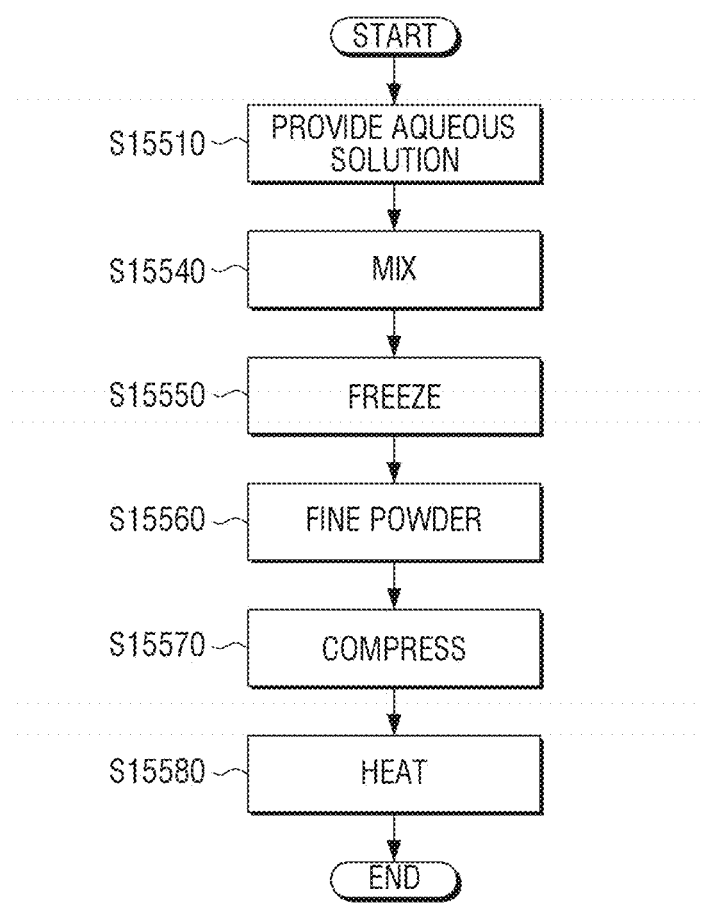
FIG. 155 is a flowchart illustrating a method of fabricating P'''-alumina of solid electrolyte according to an exemplary embodiment of the present general inventive concept.

FIG. 155 is a flowchart illustrating a method of fabricating β"-alumina of a solid electrolyte of the present general inventive concept.

Referring to FIG. 154, in operation S15510, water-soluble solutions of Al, Mg, and Na are provided. In operation S155440, the water-soluble solutions are uniformly mixed.

In operation S155550, the mixed water-soluble solution is frozen. In operation S15560, fine powder is generated. In operation S15570, the fine powder is compressed to generate disk type solid. In operation S15580, the disk type solid is heated at a particular temperature to generate β"-alumina.

As described above, powder type β"-alumina is compressed to fabricate a solid electrolyte, and thus electric conductivity of the solid natrium battery is improved.

FIGS. 156 through 160 are views illustrating a method of fabricating a solid natrium battery according to another exemplary embodiment of the present general inventive concept.

Figure 156:
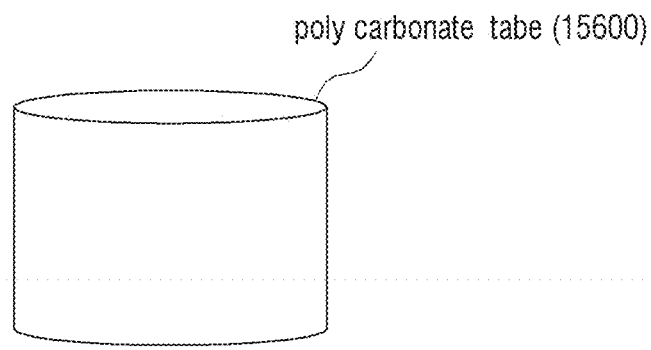
FIGS. 156 through 160 are views illustrating a method of fabricating a sodium solid battery according to another exemplary embodiment of the present general inventive concept.

Referring to FIG. 156, a polycarbonate tube 15600 is provided. Here, the polycarbonate tube 15600 refers to polymer which is formed by combining carbonic acid ester with a molecular main chain and is also referred to as polycarbonate ester. The polycarbonate tube is used as a coating material in the present exemplary embodiment but another polymer material may be used.

Figure 157:
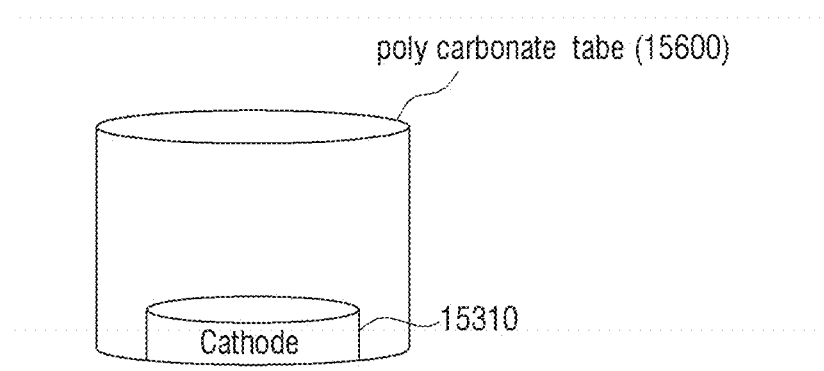

Referring to FIG. 157, a first solid electrode layer 115310 is formed in the polycarbonate tube 15600. In detail, a first solid electrode is processed to be appropriate for a diameter of the polycarbonate tube, and then the processed first solid electrode is inserted into the polycarbonate to stack the first solid electrode layer 15310, A first solid electrode material may be stacked in the polycarbonate tube by using a casting method.

Figure 158:
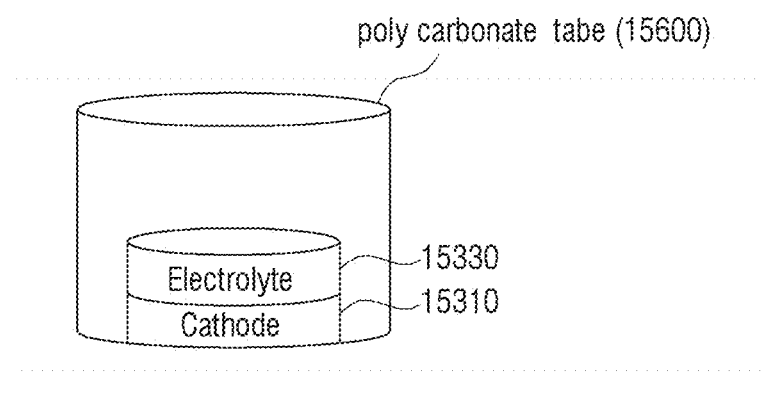

Referring to FIG. 158, the solid electrolyte layer 15330 is formed on the first solid electrode layer 15310. In detail, a solid electrolyte may be processed to be appropriate for a diameter of the polycarbonate tube, and the processed solid electrolyte may be inserted into the polycarbonate to stack the solid electrolyte on the first solid electrode layer 15310. Alternatively, the solid electrolyte may be stacked by using sputtering, chemical deposition, a thin film deposition process such as vacuum deposition, or a method such as plating. The first solid electrode layer 15310 and the processed solid electrolyte are compressed to stack the solid electrolyte layer 15330. The solid electrode material may be stacked on the first solid electrode layer 15310 by using a casting method. Also, solid electrolyte power may be compressed and used.

If β"-alumina is used as the solid electrode material, powder type β"-alumina may be injected into the polycarbonate tube, and compressing and heating may be performed in this state to form the solid electrolyte layer 15330.

Figure 159:
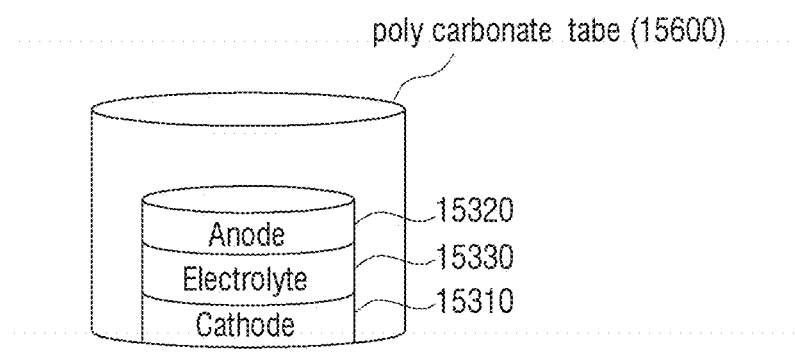

Referring to FIG. 159, the second solid electrode layer 15320 is formed on the solid electrolyte layer 15330. In detail, a second solid electrode material may be processed to be appropriate for the diameter of the polycarbonate tube and then inserted into the polycarbonate tube to stack a second electrode on the solid electrolyte layer 15330. Also, the first solid electrode layer 15310, the solid electrolyte layer 15330, and the processed second solid electrode may be compressed to form the second solid electrode on the solid electrolyte layer 15330. The second solid electrode material may be formed on the solid electrolyte layer 15330 by using a casting method or a thin film deposition method.

Figure 160:
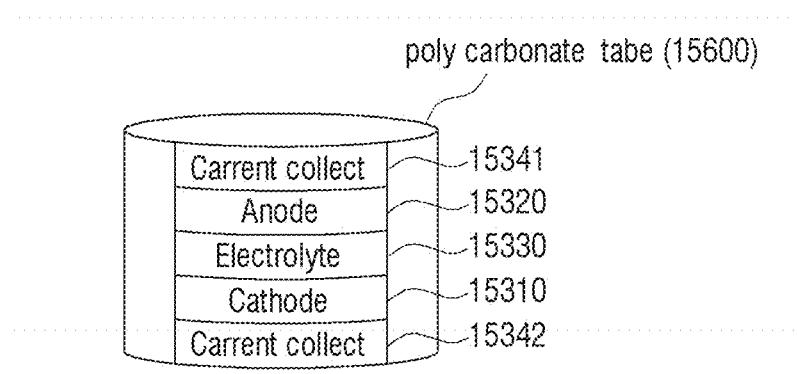

Referring to FIG. 160, a current collector is formed on the second solid electrode layer 15320 and underneath the first solid electrode layer 15310. In detail, a current collector material may be processed to be appropriate for the diameter of the polycarbonate tube, positioned on the second solid electrode layer and underneath the first solid electrode layer positioned in the polycarbonate tube, and stacked by using a compressing method. The current collector material may be formed on and underneath the second solid electrode layer by using a casting method.

If a height of the polycarbonate tube is greater than that of a sequentially stacked solid natrium battery, the polycarbonate tube may be cut to be appropriate to a size. If an empty space exists between the polycarbonate tube and the solid natrium battery, the polycarbonate tube may be contracted by using a vacuum apparatus, and a material which does not cause an electrical and chemical reactions with the solid natrium battery may be filled between the solid natrium battery and the polycarbonate tube in order to seal the solid natrium battery.

As described with reference to FIGS. 156 through 160, a first solid electrode layer, a sold electrolyte layer, a second solid electrode layer, and a current collector layer are sequentially formed. However, materials respectively corresponding to the first solid electrode layer, the sold electrolyte layer, the second solid electrode layer, and the current collector layer may be stacked at a time, and then one-time compressing may be performed to fabricate the solid natrium battery. The solid natrium battery may be fabricated by using an all-in-one electrode and current collector device instead of the second solid electrode layer. Therefore, the solid natrium battery may solve problems such as a leakage and a volatilization of a liquid electrolyte, a formation of a positive state due to a reaction with a lithium cathode, a formation of dendrite, etc.

[Sixth Exemplary Embodiment of Secondary Battery Part]

The sixth exemplary embodiment of the secondary battery part relates to a positive pore electrode constituting the secondary battery part and may be applied to a natrium-based battery but is not limited thereto.

Figure 161:
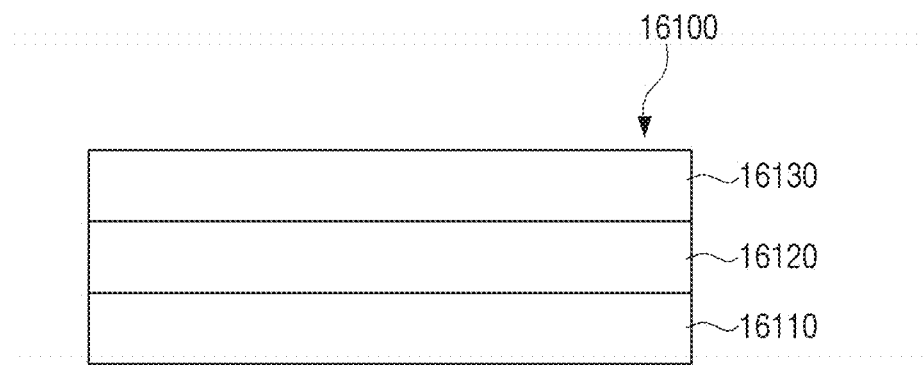
FIG. 161 is a view illustrating a structure of a battery according to an exemplary embodiment of the present general inventive concept.

FIG. 161 is a view illustrating a structure of a battery according to an exemplary embodiment of the present general inventive concept.

Referring to FIG. 161, a battery 16100 includes a positive pore electrode 16110, an electrolyte 16120, and a negative pore electrode 16130. The negative pore electrode 16130 used in the battery 16100 may be formed of Na. Therefore, the battery 16100 corresponds to a Na battery. In detail, the battery 16100 corresponds to a Na—S battery.

The electrolyte 16120 operates to transmit ions between the positive pore electrode 16110 and the negative pore electrode 16130. The electrolyte 16120 may be formed of a solid electrolyte or a liquid electrolyte. TEGDME may be used as an example of the electrolyte 16120 in the battery 16100 but is not limited thereto. In general, the electrolyte 16120 may be formed of another generally used electrolyte.

The positive pore electrode 16110, the electrolyte 16120, and the negative pore electrode 16130 are respectively formed in layer forms and sequentially stacked in FIG. 161, but this is only exemplary. Shapes and positions of the positive pore electrode 16110, the electrolyte 16120, and the negative pore electrode 16130

All elements of the solid natrium battery fabricated by the above-described fabricating method may be realized as solid components are not necessarily limited to FIG. 161. In other words, The positive pore electrode 16110, the electrolyte 16120, and the negative pore electrode 16130 may be formed in thread forms not the layer forms. For example, if the positive pore electrode 16110 or the negative pore electrode 16130 is fabricated in the thread form, the electrolyte 16120 covers a surface thereof. Also, the other electrode (16130 or 16110) may cover the surface of the electrolyte 16120 to realize a thread type battery.

The positive pore electrode 16110 of FIG. 161 includes an additive and a metal sulfide. The additive is mixed with the metal sulfide to form the positive pore electrode 16110 in order to inhibit an overcharge phenomenon and a discharge capacity reduction phenomenon.

A transition metal or a catalyst may be used as the additive.

Transition metals shown in the periodic table Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, and Uub, and thus one of them may be used as the additive.

Examples of the catalyst include PtCo, Ag/C, CuO, NiO, FeO, $Co(OH)_2$, PT, Pt/C, etc., and thus one of them may be used as the additive 16111.

In the present specification below, Ni will be used. As a result of a test which will be described later shows a result of using Ni as the additive 16111 but is not limited thereto.

The metal sulfide may be formed of a general electrode material including sulfur. For example, one of various metal sulfides, such as $Ag_2S$, $As_2S_3$, CdS, CuS, $Cu_2S$, FeS, $FeS_2$, HgS, $MoS_2$, $Ni_3S_2$, NiS, $NiS_2$, PbS, $TiS_2$, MnS, $Sb_2S_3$, etc., may be used as the metal sulfide. $Ni_3S_2$ of them is used in the present specification below but is not limited thereto. The overcharge and discharge capacity reduction inhibiting performance will be described later.

Figure 162:
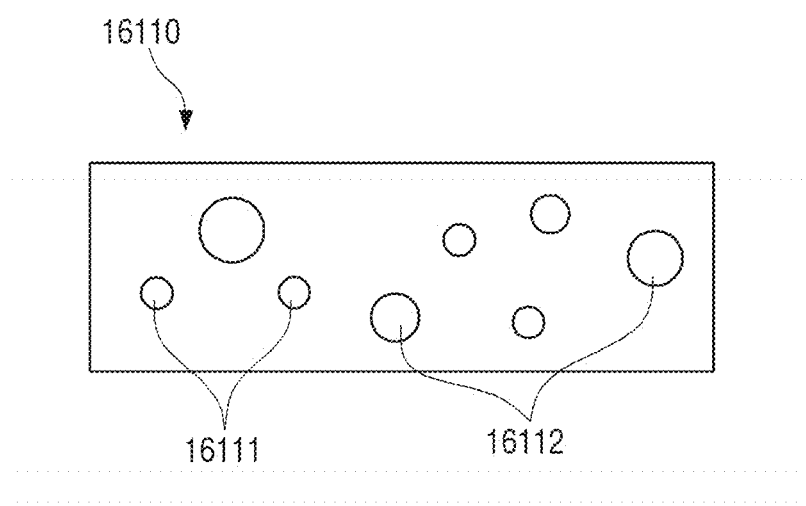
FIGS. 162 through 164 are views illustrating a structure of an anode electrode according to various exemplary embodiments of the present general inventive concept.

FIG. 162 is a view illustrating a structure of a positive pore electrode according to an exemplary embodiment of the present general inventive concept. Referring to FIG. 162, the positive pore electrode 16110 may include the additive 16111 and the metal sulfide 16112 which are mixed. The additive 16111 of FIG. 162 may be Ni, and the metal sulfide 16112 may be $Ni_3S_2$. As shown in FIG. 162, particles of the additive 16111 and the metal sulfide 16112 may be mixed to be separated from one another in the positive pore electrode 16110.

The additive 16111 and the metal sulfide 16112 may be mixed by using a ball milling method or an electroless plating method.

The ball milling method refers to a method of mixing materials by using a ball milling apparatus to fabricate an electrode. In detail, a conductive material, a binding material, a solvent, etc. are put into the ball milling apparatus along with the additive 16111 and the metal sulfide 16112 to be mixed. The mixed resultant material is dried in a particular condition to fabricate the positive pore electrode 16110 in which the additive 16111 and the metal sulfide 16112 are mixed. The drying condition may be variously determined. For example, the drying condition may be a condition of performing drying for one day at a room temperature in a vacuum state.

The electroless plating method refers to a surface treating method of generating a chemical reduction reaction on a surface of the metal sulfide 16112 by using an electroless plating solution to extract the additive 16111. In detail, the metal sulfide 16112 is put into the electroless plating solution including the additive 16111 and stirred in a particular condition. If the resultant material is cleansed and dried, the additive 16111 is extracted on the metal sulfide 16112 to obtain the coated metal sulfide 16112. The positive pore electrode 16110 may be fabricated by using this.

Figure 163:
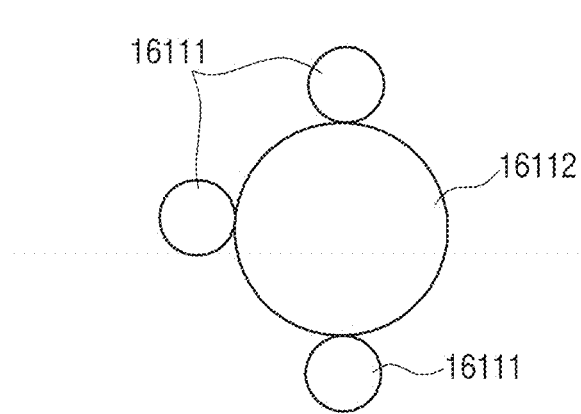

FIG. 163 is a view illustrating a type of the metal sulfide 16112 to which the additive 16111 sticks through the electroless plating method. As shown in FIG. 163, at least one or more additive 16111, i.e., Ni, may be attached onto a surface of the metal sulfide 16112, i.e., $Ni_3S_2$. If the positive pore electrode 16110 is fabricated in this state, the positive pore electrode 16110 may have a type shown in FIG. 164.

Figure 164:
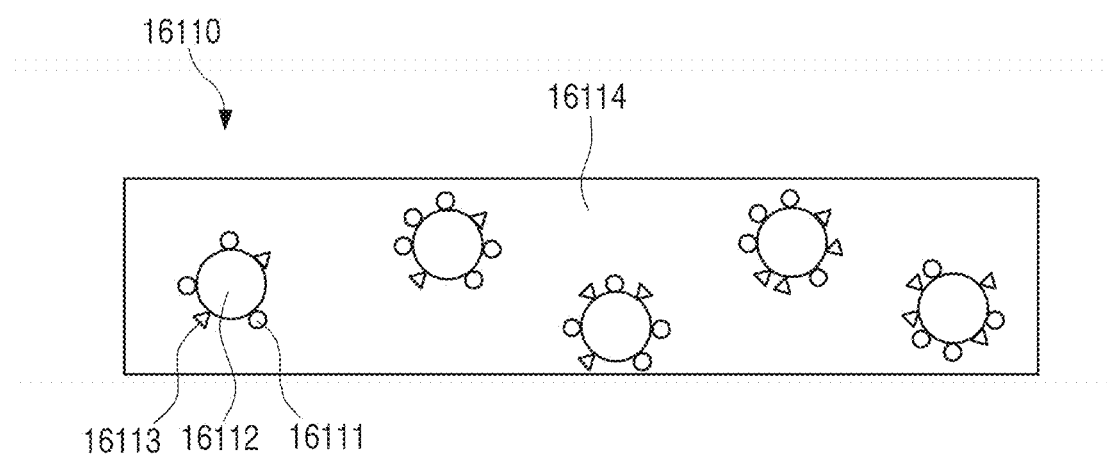

FIG. 164 is a view illustrating a type of the positive pore electrode 16110 according to another exemplary embodiment of the present general inventive concept. Referring to FIG. 164, the positive pore electrode 16110 may include the metal sulfide 16112, the additive 16111, a conductive material 16113, and a binding material 16114. The additive 16111 and the conductive material 16113 may be attached on a surface of the metal sulfide 16112, and the binding material 16114 binds the metal sulfides 16112. A distance between the metal sulfides 16112 may be a predetermined distance in FIG. 164, but this is for the descriptive convenience, and the metal sulfides 16112 may be densely combined with one another. The type of the positive pore electrode 16110 as shown in FIG. 164 may be fabricated through an electroless plating method.

The ball milling method or the electroless plating method is a well-known technique, and this a detailed description thereof will be omitted.

A mixture ratio between the additive 16111 and the metal sulfide 16112 may be adaptively set in consideration of a battery characteristic. For example, the mixture ratio may be set to 1:4, 1:1, 4:1, or the like and but is not limited thereto. Therefore, an another undescribed mixture ratio may be adopted. As an inclusion ratio of the additive 16111 increases, an inclusion ratio of the metal sulfide 16112 is relatively lowered instead of further weakening an overcharge phenomenon, thereby reducing a capacity with respect to a volume. Therefore, the mixture ratio may be appropriately set in consideration of an overcharge phenomenon inhibition degree and the capacity to the volume.

Figure 165:
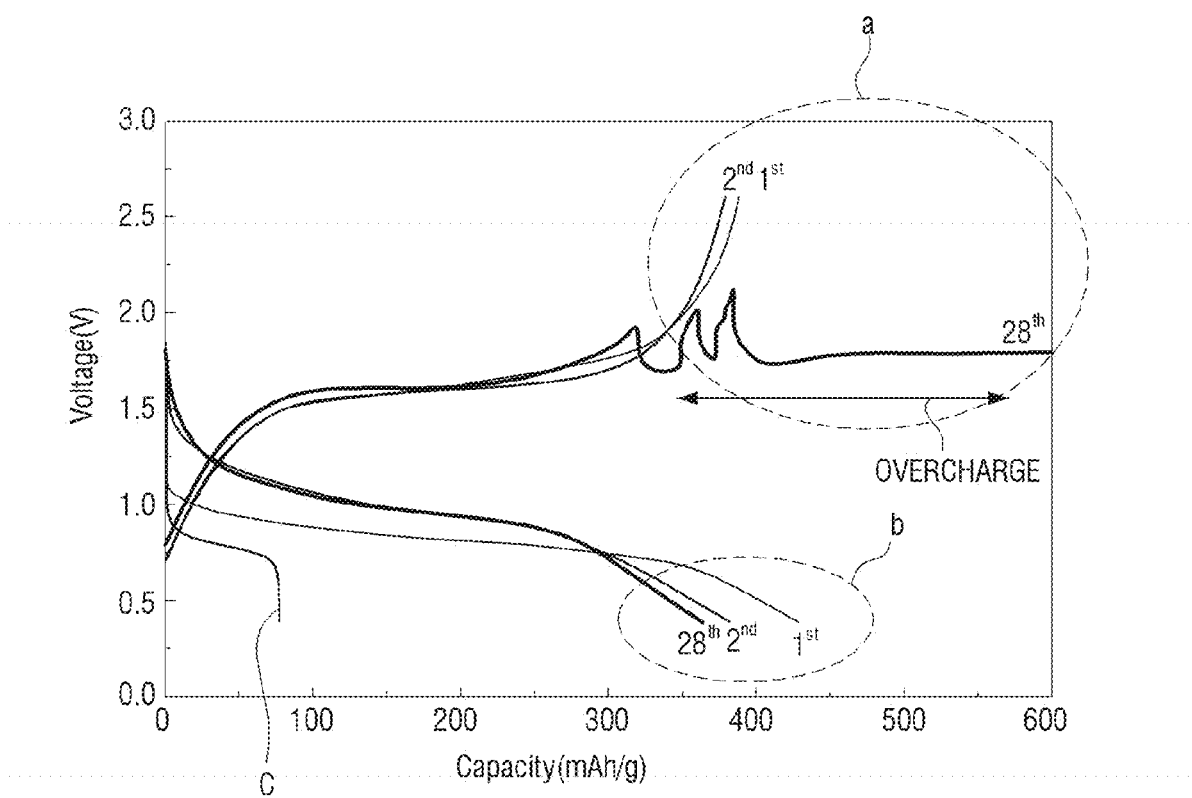
FIG. 165 is a view illustrating charging and discharging characteristics of a conventional sodium battery.

FIG. 165 is a graph illustrating charge and discharge characteristics of a battery which uses $Ni_3S_2$ as a cathode material and Na as a cathode material. Upper graphs (a) of FIG. 165 are charge curves showing voltage changes when being charged at a constant current density, and lower graphs (b) are discharge curves corresponding to discharges. In detail, the graphs (a) and (b) illustrate a discharge capacity of a conventional battery when a current is applied at a current density of 450 mA/g and at an 1C discharge speed. The 1C discharge speed refers to a speed at which charging is performed for 1 hour and discharging is performed one time.

When a charge finishing voltage is set to 2.6V, and a discharge finishing voltage is set to 0.4V, an appropriate capacity is charged in charges and discharges of one time and two times, and then the charge finishing voltage reaches 2.6V to complete charges. However, the charge finishing voltage does not reach 2.6V in charges and discharges of 28 times, and an overcharge state in which charges continues occurs. A capacity when the charges and discharges of 28 times are achieved is about 360 mAh/g.

Graph c of FIG. 165 illustrates an initial discharge characteristic measured at a 2C discharge speed. When a current is applied at the 2C discharge speed, a capacity is about 70 mAh/g. Therefore, the capacity more rapidly decreases than the capacity of 450 mAh/g when the current is applied at a 1C speed.

As described above, a current structure of a natrium battery generates an overcharge phenomenon in a state in which charges and discharges do not occur several times.

Figure 166:
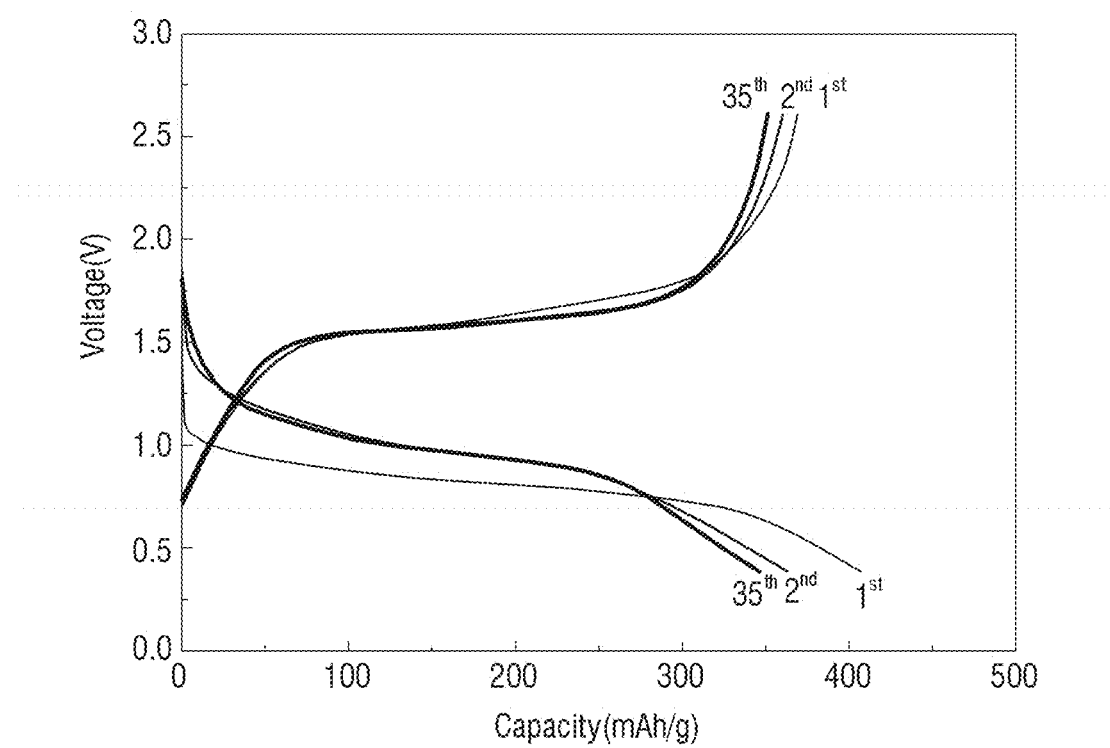
FIGS. 166 through 170 are views illustrating measuring of charging and discharging characteristics of a battery using an anode electrode in various conditions.

FIG. 166 is a graph illustrating charge and discharge characteristics measured in the same condition as that of FIG. 165 with respect to a battery using a positive pore electrode according to an exemplary embodiment of the present general inventive concept. In the positive pore electrode of FIG. 166, Ni is used as the additive 16111, and $Ni_3S_2$ is used as the metal sulfide 16112. A mixture of the additive 16111 and the metal sulfide 16112 is set to $Ni_3S_2$:Ni=4:1, and a current density of a 1C discharge speed is used.

Referring to FIG. 166, charging is achieved to 2.6V in $35^{th}$ charge and discharge, and thus an overcharge does not occur. As described above, the additive 16111 is added to the electrode to improve the overcharge phenomenon.

Figure 167:
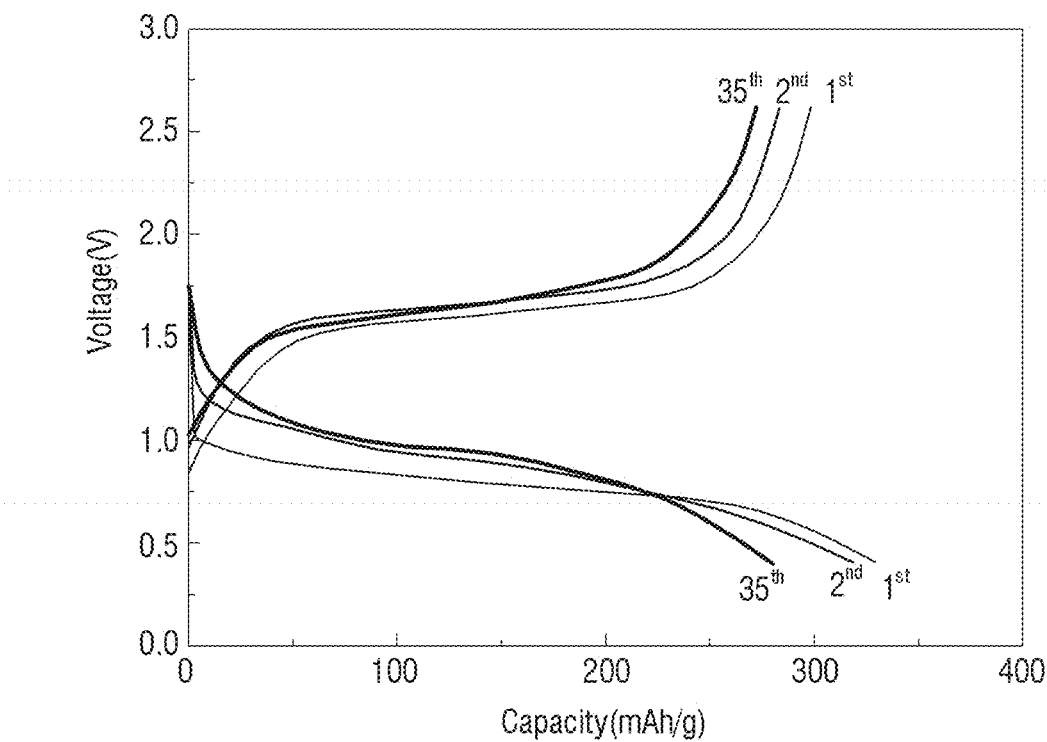

FIG. 167 is a graph illustrating charges and discharges performed at a 2C charge and discharge speed with respect to a battery using a positive pore electrode fabricated in a mixture ratio of $Ni_3S_2$:Ni=4:1. As in FIG. 166, although $35^{th}$ charge and discharge are performed, an overcharge phenomenon does not occur in FIG. 167. In particular, a discharge capacity in an initial discharge at a 2C discharge speed is about 330 mAh/g and this is very higher than the discharge capacity of 70 mAh/g of the graph c of FIG. 165. In other words, in the 2C high speed charge and discharge, a much higher performance than the conventional natrium battery may be obtained. This performance is not limited to the 2C high speed charge and discharge and may be obtained in a higher charge and discharge.

Figure 168:
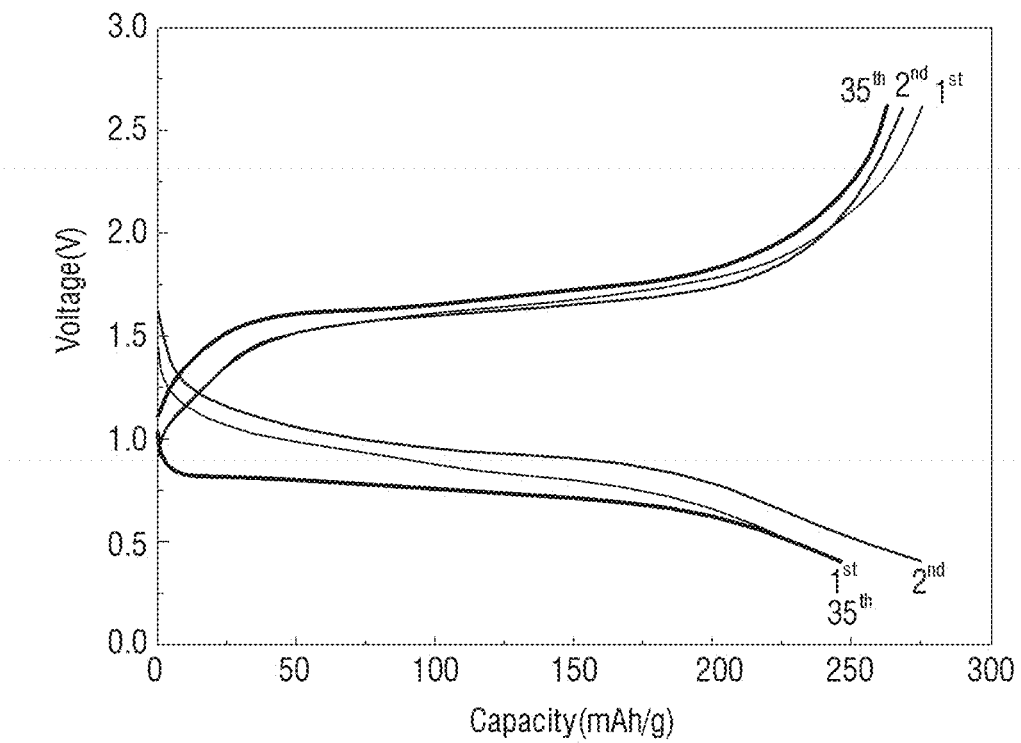

FIG. 168 is a graph illustrating charge and discharge characteristics measured at a current density of a 3C charge and discharge speed with respect to a battery using a positive pore electrode fabricated in a mixture ratio of $Ni_3S_2$:Ni=4:1. As in FIG. 168, although $35^{th}$ charge and discharge are performed, an overcharge phenomenon does not occur.

Figure 169:
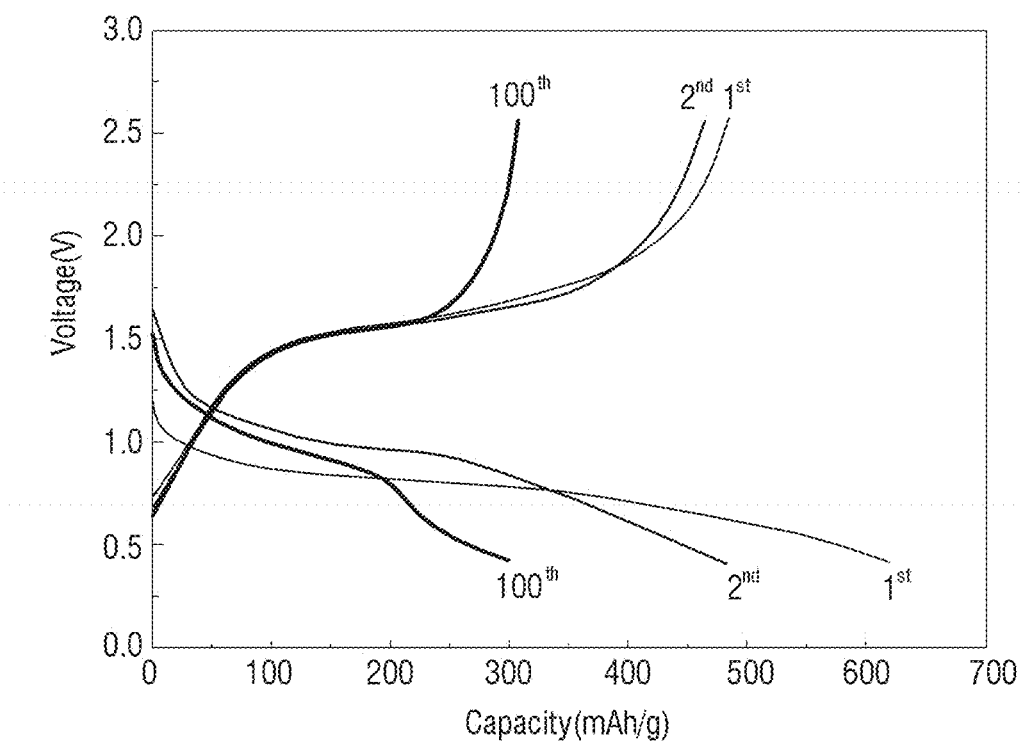

FIG. 169 is a graph illustrating charge and discharge characteristics measured at a current density of a 3C charge and discharge speed when an inclusion ratio of NI increases compared to FIGS. 166 through 168. In detail, FIG. 169 illustrates a result of measuring a battery using a positive pore electrode fabricated in a mixture ratio of $Ni_3S_2$:Ni=4:1. Referring to FIG. 169, an overcharge phenomenon does not occur until 100 times charge and discharges continue.

As described above, various charge and discharge characteristics may be obtained according to a mixture ratio between the additive 16111 and the metal sulfide 16112.

Therefore, the mixture ration may be set to be appropriate for a use purpose of the battery to fabricate the positive pore electrode 16110. In the above-described drawings, the number of times of charges and discharges in which an overcharge phenomenon does not occur are mentioned. However, this is only a numerical value provided for the descriptive convenience, and an overcharge does not occur only to the number of times.

Figure 170:
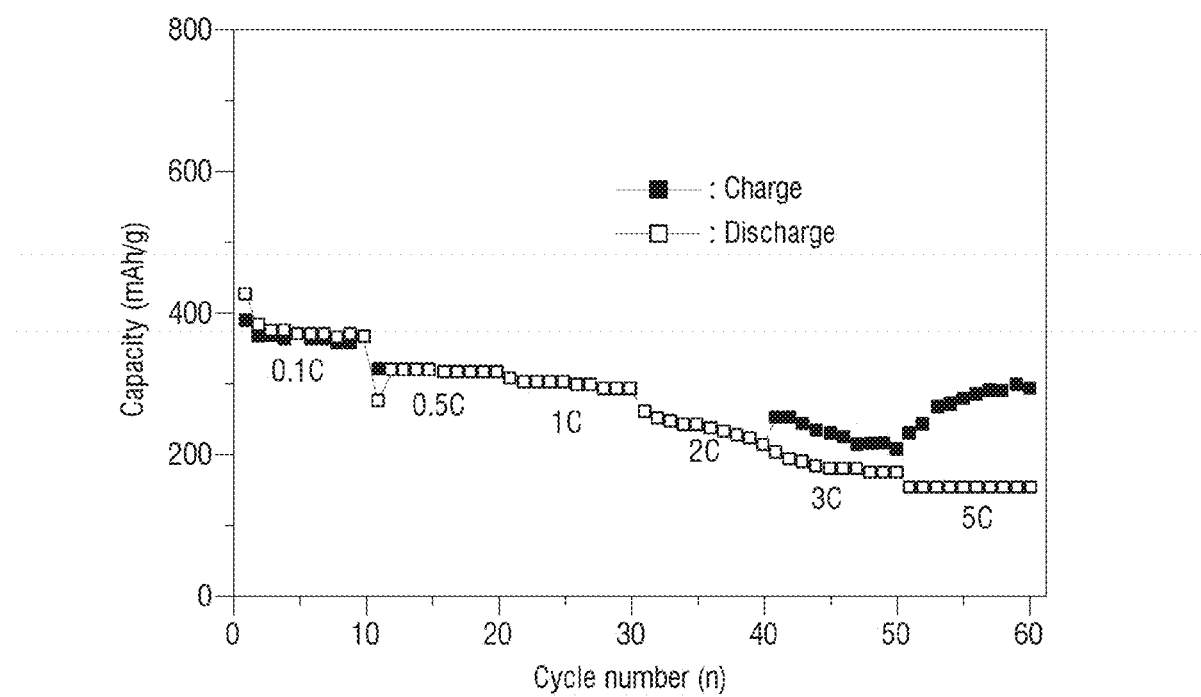

FIG. 170 is a graph illustrating charge and discharge characteristics with respect to a cycle number. Referring to FIG. 170, Ni is added as the additive 16111, and charge and discharge repeating characteristics are checked with respect to a C-rate of the positive pore electrode 16110 having the metal sulfide ($Ni_3S_2$) 16112. In other words, although a high voltage is applied, charge and discharge characteristics of the positive pore electrode 16110 are high (2C).

Figure 171:
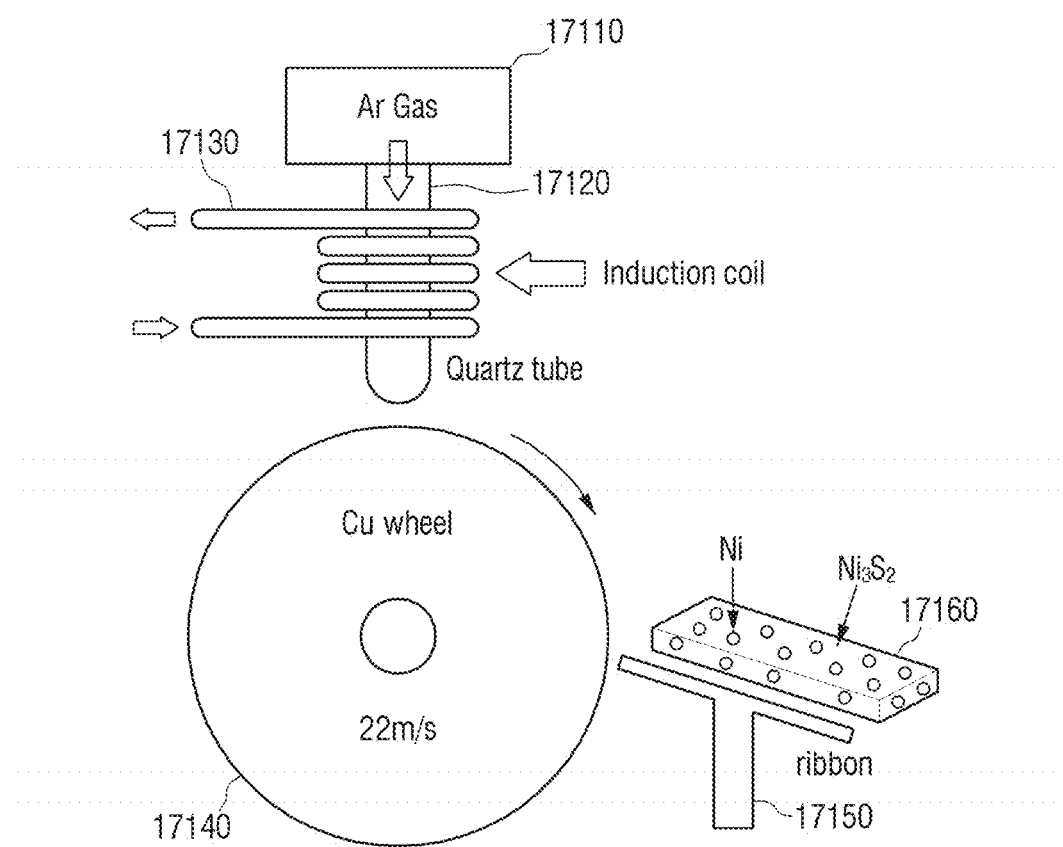
FIGS. 171 and 172 are views illustrating a method of fabricating an anode electrode by using a rapid solidification.
Figure 172:
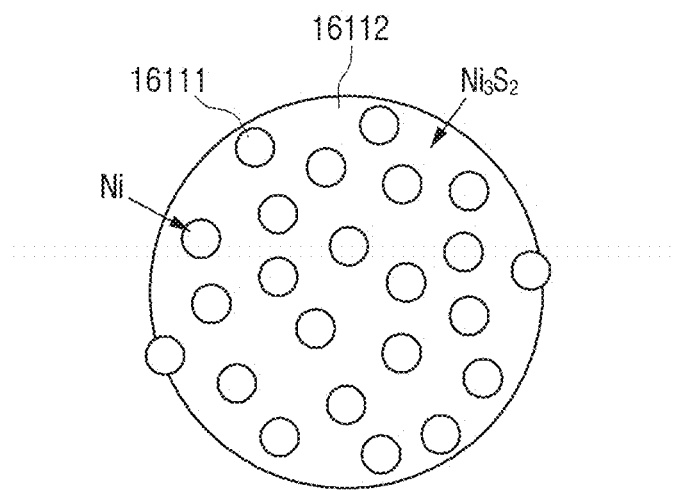
Figure 173:
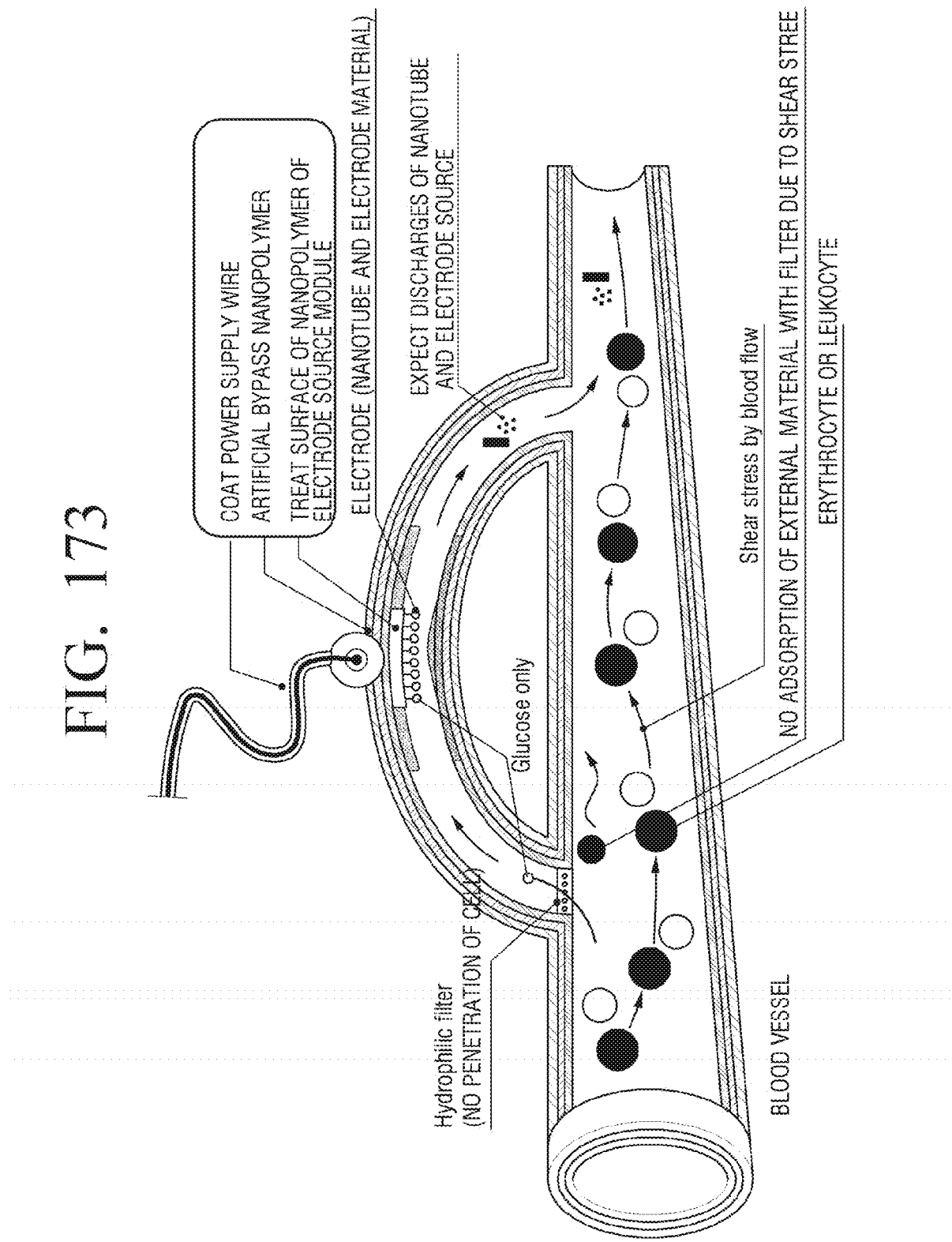
FIG. 173 is a view illustrating coated surfaces of a power supply wire and an electrode source module as a coating layer according to an exemplary embodiment of the present general inventive concept.
Figure 174:
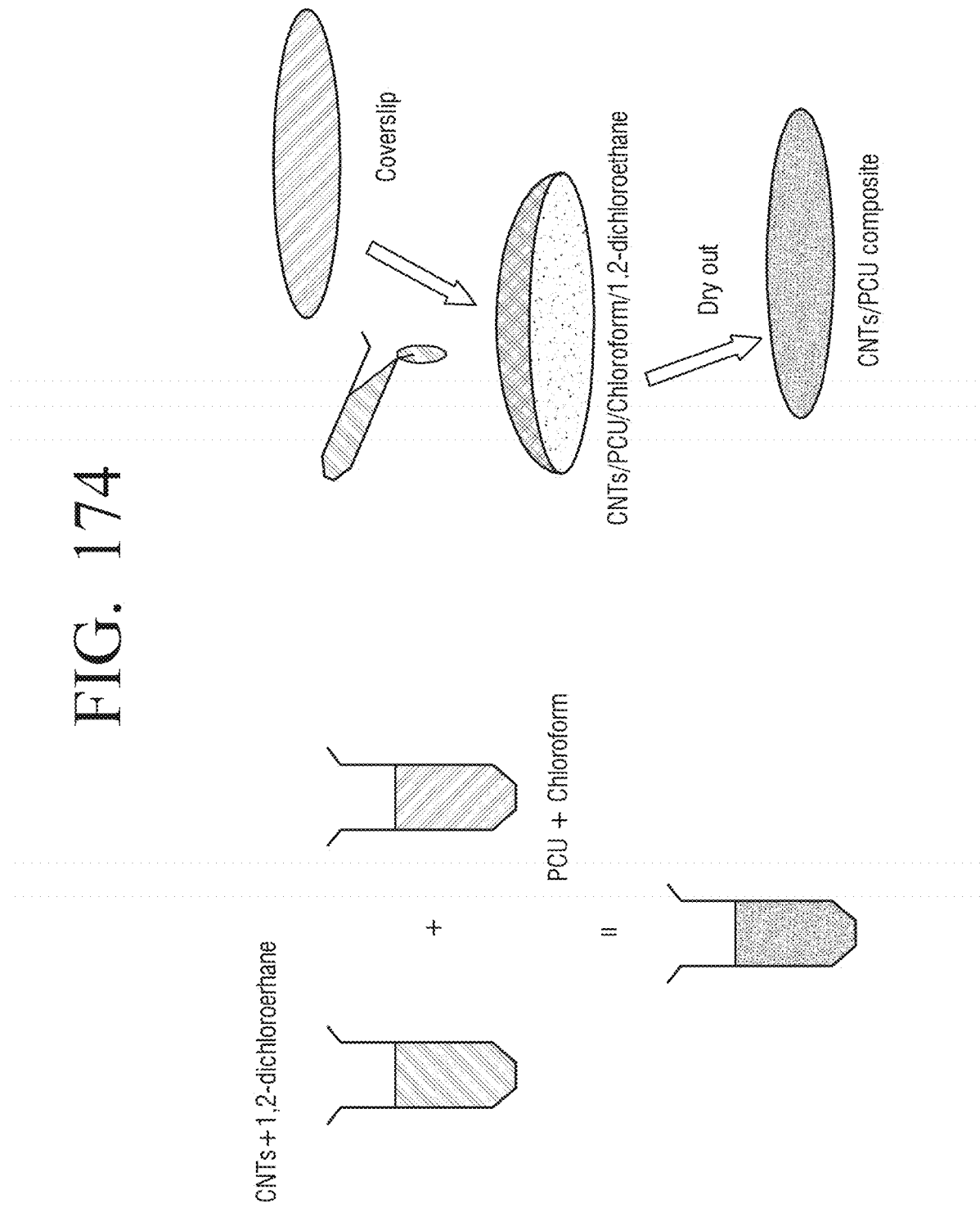
FIG. 174 is a schematic view illustrating a process of fabricating a coating layer according to an exemplary embodiment of the present general inventive concept.

FIGS. 171 and 172 are views illustrating a method of fabricating a positive pore electrode by using a rapid solidification process. Referring to FIG. 171, the additive 16111 is mixed with the metal sulfide 16112 by using the rapid solidification process.

In detail, Ni which is the additive 1611 and $Ni_3S_2$ which is the metal sulfide 16112 are injected into a chamber 17110. The additive 16111 and the metal sulfide 16112 may be melted due to an induction coil 17130 heated according to electricity applied when the additive 16111 and the metal sulfide 16112 move to the bottom of a tube 17120. In this case, the additive 16111 and the metal sulfide 16112 are heated at a melting point or more.

The additive 16111 and the metal sulfide 16112 which are melted through the bottom of the tube 17120 are sprayed onto a surface of a rotating body 17140 which is cooled. As a result, the melted additive 16111 and metal sulfide 16112 may be cooled at a high speed. Also, when the rotating body 17140 rotates, the additive 16111 and the metal sulfide 17140 cooled on the surface of the rotating body 17140 may separate from the rotating body 17140 by using a ribbon 17150. Therefore, a mixture 17160 having a thin plate shape may be generated on a surface of the ribbon 17150.

As shown, the mixture 17160 has a structure in which the additive 16111 is added to the metal sulfide 16112. Here, the additive 16111 and the metal sulfide 16112 may be mixed at a weight ratio of 20:80 but is not limited thereto. Also, the rotating body 17140 may be formed of a Cu wheel and may rotate at 22 m/s.

The mixture of the additive 16111 and the metal sulfide 16112 is grinded to fabricate powder, and the power is fabricated in an electrode form as shown in FIG. 172. In detail, the metal sulfide 112 may be grinded by ball milling to fabricate an electrode material in which Ni powder is formed in and outside powder $Ni_3S_2$.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:
1. A tube-structured battery to be inserted into a living body, comprising:
 a biofuel battery part which generates electric energy by using biofuel in the blood passing through an internal space of the tube structure;
 a transformer circuit part which adjusts a voltage or current density by using the generated electric energy; and a secondary battery part which is charged with the electric energy by using the adjusted voltage or current density to store the electric energy, wherein the tube-structured battery is inserted into the living body or a blood vessel of the living body, wherein the biofuel battery part, the transformer circuit part and the secondary battery part are contained within a single tube-shaped housing.

2. The tube-structured battery of claim 1, wherein the biofuel battery part, the transformer circuit part, and the secondary battery part constitute a fusion battery part, wherein the tube-structured battery comprises a support part which has the tube structure and supports the fusion battery part.

3. The tube-structured battery of claim 1, further comprising:

a transreflective layer which encloses a surface of the biofuel battery part and selectively passes the biofuel of the blood.

4. The tube-structured battery of claim 1, further comprising:

a biocompatible coating layer which encloses at least an area of the tube-structured battery contacting the blood or the living body.

5. The tube-structured battery of claim 1, further comprising:

a fixing part which comprises at least one fixing member for fixing the tube-structured battery into the blood or the living body.

6. The tube-structured battery of claim 1, wherein the biofuel battery part comprises:

an electrode; and an enzymatic area in which at least one enzyme is fixed on a side of the electrode.

7. The tube-structured battery of claim 6, wherein if the biofuel of the blood is attached to the at least one enzyme, the biofuel battery part generates the electric energy.

8. The tube-structured battery of claim 6, wherein the electrode forms a 3-dimensional (3D) nanostructure.

9. The tube-structured battery of claim 6, wherein the biofuel battery part further comprises a current collector, wherein the electrode forms a 3D nanostructure along with the current collector.

10. The tube-structured battery of claim 6, wherein the biofuel battery part further comprises a current collector, wherein the electrode forms a single body along with the current collector.

11. The tube-structured battery of claim 6, wherein the enzymatic area comprises a plurality of enzymatic layers forming a multilayered structure.

12. The tube-structured battery of claim 1, wherein the transformer circuit part comprises:

a coil which, if a current is applied, generates a magnetic field;

a rigid body which increases the generated magnetic field; and a controller which adjusts a current applied to the coil, wherein the rigid body has a tube structure whose both ends are opened, and the coil encloses the rigid body having the tube structure.

13. The tube-structured battery of claim 1, wherein the transformer circuit part comprises:

a boost type power converter which boosts a voltage generated by the biofuel battery part and supplies the boosted voltage to the secondary battery part; and an initial driver circuit which applies control power to the boost type power converter to control initial driving of the boost type power converter.

14. The tube-structured battery of claim 1, wherein the transformer circuit part comprises:

a boost type power converter which boots a voltage generated by the biofuel battery part and supplies the boosted voltage to the secondary battery part;

a maximum power point tracking circuit which calculates a charging current command for maximum power point tracking by using a current flowing into the biofuel battery part and the generated voltage; and a charging current control circuit which controls the boost type power converter to track the charging current command charging the secondary battery part.

15. The tube-structured battery of claim 1, wherein the tube-structured battery performs a toxicity treatment or a biocompatibility treatment with respect to at least one area of the tube-structured battery contacting the blood or the living body.

16. The tube-structured battery of claim 2, wherein the fusion battery part has a flat plate structure, wherein a side of the flat plate structure and an other side of the flat plate structure facing the side are fixed by the support part.

17. The tube=structured battery of claim 2, wherein the support part comprises an opening formed in an area of a side of the tube structure, and the fusion battery part is inserted into the opening.

18. The tube-structured battery of claim 2, wherein the support part has a polygonal pillar shape whose internal cross-section is circular and outer cross-section is polygonal, wherein at least one of the biofuel battery part, the transformer circuit part, and the secondary battery part constituting the fusion battery part is disposed on a side of the polygonal pillar.

19. The tube-structured battery of claim 1, wherein the biofuel battery part is disposed in the blood vessel, and at least one of the transformer circuit part and the secondary battery part is disposed outside the blood vessel.

20. A tube-structured artificial vessel comprising:

a biofuel battery part which generates electric energy by using biofuel of the blood passing through an internal space of the tube structure;

a transformer circuit part which adjusts a voltage or current density by using the generated electric energy; and a secondary battery part which is charged with the electric energy by using the adjusted voltage or current, wherein the biofuel battery part, the transformer circuit part and the secondary battery part are contained within a single tube-shaped housing.

* * * * *